United States Patent
Freier et al.

(10) Patent No.: US 12,281,305 B2
(45) Date of Patent: Apr. 22, 2025

(54) COMPOUNDS AND METHODS FOR REDUCING PRION EXPRESSION

(71) Applicant: Ionis Pharmaceuticals, Inc., Carlsbad, CA (US)

(72) Inventors: Susan M. Freier, San Diego, CA (US); Huynh-Hoa Bui, San Diego, CA (US); Hien Thuy Zhao, San Diego, CA (US)

(73) Assignee: Ionis Pharmaceuticals, Inc., Carlsbad, CA (US)

(*) Notice: Subject to any disclaimer, the term of this patent is extended or adjusted under 35 U.S.C. 154(b) by 815 days.

(21) Appl. No.: 17/294,859

(22) PCT Filed: Nov. 21, 2019

(86) PCT No.: PCT/US2019/062681
§ 371 (c)(1),
(2) Date: May 18, 2021

(87) PCT Pub. No.: WO2020/106996
PCT Pub. Date: May 28, 2020

(65) Prior Publication Data
US 2022/0025366 A1    Jan. 27, 2022

Related U.S. Application Data

(60) Provisional application No. 62/770,386, filed on Nov. 21, 2018.

(51) Int. Cl.
*C12N 15/113*    (2010.01)
*A61K 31/7088*    (2006.01)

(52) U.S. Cl.
CPC ........ *C12N 15/113* (2013.01); *A61K 31/7088* (2013.01); *C12N 2310/14* (2013.01); *C12N 2310/31* (2013.01); *C12N 2310/315* (2013.01); *C12N 2310/321* (2013.01); *C12N 2310/322* (2013.01); *C12N 2310/3231* (2013.01); *C12N 2310/3341* (2013.01); *C12N 2310/34* (2013.01); *C12N 2310/341* (2013.01); *C12N 2310/351* (2013.01); *C12N 2320/35* (2013.01)

(58) Field of Classification Search
CPC .............. C12N 15/113; C12N 2310/14; A61K 31/7088
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |

(Continued)

FOREIGN PATENT DOCUMENTS

| | | |
|---|---|---|
| CN | 103255142 A | 8/2013 |
| JP | 2007-252288 A | 10/2007 |

(Continued)

OTHER PUBLICATIONS

NC_000020.11, Start: 4686151, Stop: 4701588, PRNP, NCBI *Homo sapiens* Annotation Release 108, Jun. 7, 2016 (Year: 2016).*
Ostergaard et al., 2020, "Understanding the effect of controlling phosphorothioate chirality in the DNA gap on the potency and safety of gapmer antisense oligonucleotides" Nucleic Acids Research, 2020, 48(4), p. 1691-1700 (Year: 2020).*
Wan et al., 2014, "Synthesis, biophysical properties and biological activity of second generation antisense oligonucleotides containing chiral phosphorothioate linkages" Nucleic Acids Research, 42(22), p. 13456-13468 (Year: 2014).*
Wozniak and Brezinski, 2023, "Biological Catalysis and Information Storage Have Relied on N-Glycosyl Derivatives of—D-Ribofuranose since the Origins of Life" Biomolecules, 13(5), 782, p. 1-21 (Year: 2023).*

(Continued)

*Primary Examiner* — Jennifer Dunston
*Assistant Examiner* — Jenna L Persons
(74) *Attorney, Agent, or Firm* — Banner & Witcoff, LTD

(57) ABSTRACT

Provided are compounds, methods, and pharmaceutical compositions for reducing the amount or activity of PRNP RNA in a cell or animal, and in certain instances reducing the amount of PrP protein in a cell or animal. Such compounds, methods, and pharmaceutical compositions are useful to ameliorate at least one symptom or hallmark of a neurodegenerative disease. Such symptoms and hallmarks spongiform changes in the brain, development of abnormal protein aggregates, neuronal loss, markers of neuronal loss, rapidly progressing dementia, and death. Such neurodegenerative diseases include prion diseases, Creutzfeldt-Jakob disease (CJD), variant Creutzfeldt-Jakob Disease (vCJD), familial Creutzfeldt-Jakob Disease (fCJD), Gerstmann-Straussler-Scheinker syndrome, fatal familial insomnia, kuru, Alzheimer's disease, or Parkinson's disease.

29 Claims, No Drawings
Specification includes a Sequence Listing.

(56) References Cited

U.S. PATENT DOCUMENTS

| | | | |
|---|---|---|---|
| 5,220,007 | A | 6/1993 | Pederson et al. |
| 5,223,618 | A | 6/1993 | Cook et al. |
| 5,235,033 | A | 8/1993 | Summerton et al. |
| 5,256,775 | A | 10/1993 | Froehler |
| 5,264,423 | A | 11/1993 | Cohen et al. |
| 5,264,562 | A | 11/1993 | Matteucci |
| 5,264,564 | A | 11/1993 | Matteucci |
| 5,185,444 | A | 12/1993 | Summerton et al. |
| 5,276,019 | A | 1/1994 | Cohen et al. |
| 5,286,717 | A | 2/1994 | Cohen et al. |
| 5,319,080 | A | 6/1994 | Leumann |
| 5,321,131 | A | 6/1994 | Agrawal et al. |
| 5,359,044 | A | 10/1994 | Cook et al. |
| 5,366,878 | A | 11/1994 | Pederson et al. |
| 5,367,066 | A | 11/1994 | Urdea et al. |
| 5,378,825 | A | 1/1995 | Cook et al. |
| 5,386,023 | A | 1/1995 | Sanghvi et al. |
| 5,393,878 | A | 2/1995 | Leumann |
| 5,399,676 | A | 3/1995 | Froehler |
| 5,403,711 | A | 4/1995 | Walder et al. |
| 5,405,938 | A | 4/1995 | Sumerton et al. |
| 5,405,939 | A | 4/1995 | Suhadolnik et al. |
| 5,432,272 | A | 7/1995 | Benner |
| 5,434,257 | A | 7/1995 | Matteucci |
| 5,446,137 | A | 8/1995 | Maag et al. |
| 5,453,496 | A | 9/1995 | Caruthers et al. |
| 5,455,233 | A | 10/1995 | Spielvogel et al. |
| 5,457,187 | A | 10/1995 | Gmelner et al. |
| 5,457,191 | A | 10/1995 | Cook et al. |
| 5,459,255 | A | 10/1995 | Cook et al. |
| 5,466,677 | A | 11/1995 | Baxter et al. |
| 5,466,786 | A | 11/1995 | Burh et al. |
| 5,470,967 | A | 11/1995 | Huie et al. |
| 5,476,925 | A | 12/1995 | Letsinger et al. |
| 5,484,908 | A | 1/1996 | Froehler et al. |
| 5,489,677 | A | 2/1996 | Sanghvi et al. |
| 5,491,133 | A | 2/1996 | Walder et al. |
| 5,502,177 | A | 3/1996 | Matteucci et al. |
| 5,508,270 | A | 4/1996 | Baxter et al. |
| 5,514,785 | A | 5/1996 | Van Ness et al. |
| 5,519,126 | A | 5/1996 | Hecht |
| 5,519,134 | A | 5/1996 | Acevedo et al. |
| 5,525,711 | A | 6/1996 | Hawkins et al. |
| 5,527,899 | A | 6/1996 | Froehler |
| 5,536,821 | A | 7/1996 | Agrawal et al. |
| 5,541,306 | A | 7/1996 | Agrawal et al. |
| 5,541,307 | A | 7/1996 | Cook et al. |
| 5,550,111 | A | 8/1996 | Suhadolnik et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,350 | A | 10/1996 | Kmiec |
| 5,565,555 | A | 10/1996 | Froehler et al. |
| 5,567,811 | A | 10/1996 | Mistura et al. |
| 5,571,799 | A | 11/1996 | Tkachuk et al. |
| 5,576,427 | A | 11/1996 | Cook et al. |
| 5,587,361 | A | 12/1996 | Cook et al. |
| 5,587,469 | A | 12/1996 | Cook et al. |
| 5,587,470 | A | 12/1996 | Cook et al. |
| 5,591,722 | A | 1/1997 | Montgomery et al. |
| 5,594,121 | A | 1/1997 | Froehler et al. |
| 5,596,086 | A | 1/1997 | Matteucci |
| 5,596,091 | A | 1/1997 | Switzer |
| 5,597,909 | A | 1/1997 | Urdea et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,610,300 | A | 3/1997 | Altmann et al. |
| 5,614,617 | A | 3/1997 | Cook et al. |
| 5,618,704 | A | 4/1997 | Sanghvi et al. |
| 5,623,065 | A | 4/1997 | Cook et al. |
| 5,623,070 | A | 4/1997 | Cook et al. |
| 5,625,050 | A | 4/1997 | Beaton et al. |
| 5,627,053 | A | 5/1997 | Usman et al. |
| 5,633,360 | A | 5/1997 | Bishofberger et al. |
| 5,639,873 | A | 6/1997 | Barascut et al. |
| 5,645,985 | A | 7/1997 | Froehler et al. |
| 5,646,265 | A | 7/1997 | McGee |
| 5,646,269 | A | 7/1997 | Matteucci |
| 5,652,355 | A | 7/1997 | Metelev et al. |
| 5,652,356 | A | 7/1997 | Agrawal |
| 5,663,312 | A | 9/1997 | Chaturvedula |
| 5,670,633 | A | 9/1997 | Cook et al. |
| 5,672,697 | A | 9/1997 | Buhr et al. |
| 5,677,437 | A | 10/1997 | Teng et al. |
| 5,677,439 | A | 10/1997 | Weis et al. |
| 5,681,941 | A | 10/1997 | Cook et al. |
| 5,698,685 | A | 12/1997 | Summerton et al. |
| 5,700,920 | A | 12/1997 | Altmann et al. |
| 5,700,922 | A | 12/1997 | Cook |
| 5,721,218 | A | 2/1998 | Froehler |
| 5,750,692 | A | 5/1998 | Cook et al. |
| 5,763,588 | A | 6/1998 | Matteucci et al. |
| 5,792,608 | A | 8/1998 | Swaminathan et al. |
| 5,792,847 | A | 8/1998 | Burh et al. |
| 5,801,154 | A | 9/1998 | Baracchini et al. |
| 5,808,027 | A | 9/1998 | Cook et al. |
| 5,830,653 | A | 11/1998 | Froehler et al. |
| 5,859,221 | A | 1/1999 | Cook et al. |
| 5,948,903 | A | 9/1999 | Cook et al. |
| 5,994,517 | A | 11/1999 | Ts'O |
| 6,005,087 | A | 12/1999 | Cook et al. |
| 6,005,096 | A | 12/1999 | Matteucci et al. |
| 6,166,199 | A | 12/2000 | Cook et al. |
| 6,300,319 | B1 | 10/2001 | Manoharan |
| 6,426,220 | B1 | 7/2002 | Bennett et al. |
| 6,525,191 | B1 | 2/2003 | Ramasamy |
| 6,531,584 | B1 | 3/2003 | Cook et al. |
| 6,582,908 | B2 | 6/2003 | Fodor et al. |
| 6,600,032 | B1 | 7/2003 | Manoharan et al. |
| 6,660,720 | B2 | 12/2003 | Manoharan |
| 6,770,748 | B2 | 8/2004 | Imanishi et al. |
| 7,015,315 | B1 | 3/2006 | Cook et al. |
| 7,053,207 | B2 | 5/2006 | Wengel et al. |
| 7,101,993 | B1 | 9/2006 | Cook et al. |
| 7,250,289 | B2 | 7/2007 | Zhou |
| 7,262,177 | B2 | 8/2007 | Ts'o et al. |
| 7,399,845 | B2 | 7/2008 | Seth et al. |
| 7,427,672 | B2 | 9/2008 | Imanishi et al. |
| 7,491,805 | B2 | 2/2009 | Vargeese et al. |
| 7,547,684 | B2 | 6/2009 | Seth et al. |
| 7,569,686 | B1 | 8/2009 | Bhat et al. |
| 7,666,854 | B2 | 2/2010 | Seth et al. |
| 7,696,345 | B2 | 4/2010 | Allerson et al. |
| 7,723,509 | B2 | 5/2010 | Manoharan et al. |
| 7,741,457 | B2 | 6/2010 | Swayze et al. |
| 7,750,131 | B2 | 7/2010 | Seth et al. |
| 7,875,733 | B2 | 1/2011 | Bhat et al. |
| 7,939,677 | B2 | 5/2011 | Bhat et al. |
| 8,022,193 | B2 | 9/2011 | Swayze et al. |
| 8,030,467 | B2 | 10/2011 | Seth et al. |
| 8,080,644 | B2 | 12/2011 | Wengel et al. |
| 8,088,746 | B2 | 1/2012 | Seth et al. |
| 8,088,904 | B2 | 1/2012 | Swayze et al. |
| 8,106,022 | B2 | 1/2012 | Manoharan et al. |
| 8,124,745 | B2 | 2/2012 | Allerson et al. |
| 8,153,365 | B2 | 4/2012 | Wengel et al. |
| 8,268,980 | B2 | 9/2012 | Seth et al. |
| 8,278,283 | B2 | 10/2012 | Seth et al. |
| 8,278,425 | B2 | 10/2012 | Prakash et al. |
| 8,278,426 | B2 | 10/2012 | Seth et al. |
| 8,440,803 | B2 | 5/2013 | Swayze et al. |
| 8,501,805 | B2 | 8/2013 | Seth et al. |
| 8,530,640 | B2 | 9/2013 | Seth et al. |
| 8,546,556 | B2 | 10/2013 | Seth et al. |
| RE44,779 | E | 2/2014 | Imanishi et al. |
| 8,669,102 | B2 * | 3/2014 | Bennett ............... A61P 25/28 435/325 |
| 8,828,956 | B2 | 9/2014 | Manoharan et al. |
| 9,005,906 | B2 | 4/2015 | Swayze et al. |
| 9,012,421 | B2 | 4/2015 | Migawa et al. |
| 9,127,276 | B2 | 8/2015 | Prakash et al. |
| 9,290,760 | B2 | 3/2016 | Rajeev et al. |
| 2001/0053519 | A1 | 12/2001 | Fodor et al. |

(56) References Cited

U.S. PATENT DOCUMENTS

| | | |
|---|---|---|
| 2002/0081645 A1 | 6/2002 | Collinge |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0014048 A1 | 1/2004 | Monia et al. |
| 2004/0171570 A1 | 9/2004 | Allerson et al. |
| 2005/0053583 A1 | 3/2005 | Sakaguchi et al. |
| 2005/0130923 A1 | 6/2005 | Bhat et al. |
| 2005/0255487 A1 | 11/2005 | Khvorova et al. |
| 2006/0148740 A1 | 7/2006 | Platenburg |
| 2006/0280745 A1 | 12/2006 | Collinge et al. |
| 2007/0031844 A1 | 2/2007 | Khvorova et al. |
| 2007/0123480 A1 | 5/2007 | Juteau et al. |
| 2008/0039618 A1 | 2/2008 | Allerson et al. |
| 2008/0085269 A1 | 4/2008 | Eisenbach-Schwartz |
| 2010/0190837 A1 | 7/2010 | Migawa et al. |
| 2010/0197762 A1 | 8/2010 | Swayze et al. |
| 2011/0269818 A1 | 11/2011 | Bennett et al. |
| 2013/0130378 A1 | 5/2013 | Manoharan et al. |
| 2014/0107330 A1 | 4/2014 | Freier et al. |
| 2015/0018540 A1 | 1/2015 | Prakash et al. |
| 2015/0184153 A1 | 7/2015 | Freier et al. |
| 2015/0191727 A1 | 7/2015 | Migawa et al. |
| 2015/0267195 A1 | 9/2015 | Seth et al. |
| 2015/0275212 A1 | 10/2015 | Albaek et al. |
| 2016/0304871 A1* | 10/2016 | Rigo ....................... A61P 25/02 |
| 2019/0381007 A1 | 12/2019 | Maccecchini |

FOREIGN PATENT DOCUMENTS

| | | |
|---|---|---|
| WO | 2005078093 A1 | 8/2005 |
| WO | WO 2010/019270 | 2/2010 |
| WO | WO 2018/007980 | 1/2018 |
| WO | WO 2020/106996 | 5/2020 |
| WO | 2023164696 A2 | 8/2023 |

OTHER PUBLICATIONS

*Homo sapiens* prion protein (PRNP), RefSeqGene on chromosome 20, NCBI Reference Sequence: NG_009087.1, Dec. 1, 2017 (Year: 2017).*

Minikel et al., Jun. 26, 2020, "Prion protein lowering is a disease-modifying therapy across prion disease stages, strains, and endpoints" bioRxiv, doi: 10.1101/2020.03.27.011940 (Year: 2020).*

Raymond et al., Jul. 30, 2019, "Antisense oligonucleotides extend survival of prion-infected mice" JCI Insight, 2019;4(16):e131175 (Year: 2019).*

Barbieri et al., "Silencing of cellular prion protein (PrPC) expression by DNA-antisense oligonucleotides induces autophagy-dependent cell death in glioma cells" Autophagy (2011) 7: 840-853.

Branch et al., "A good antisense molecule is hard to find," TIBS (1998) 23:45-50.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Crooke, St., et al., "Antisense Drug Technology" Second Edition, CRC Press (2008) Chapters 1-28.

Daude et al., "Specific inhibition of pathological prion protein accumulation by small interfering RNAs" Journal of Cell Science (2003) 116(13):2775-2779.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Erana et al., "Prion-like disorders and Transmissible Spongiform Encephalopathies: An overview of the mechanistic features that are shared by the various disease-related misfolded proteins" Biochem. And Biophys. Res. Comm. (2017) 483: 1125-1136.

Ferreira et al., "α-synuclein interacts with PrPC to induce cognitive impairment through mGluR5 and NMDAR2B" *Nature Neuroscience* (2017) 20: 1569-1579.

Friberg et al., "Intracerebral Infusion of Antisense Oligonucleotides Into Prion-infected Mice" Mol The Nucl Acids (2012) 1-12.

Gautschi et al., "Activity of a novel bcl-2/bcl-xLbispecific antisense oligonucleotide against tumors of diverse histologic origins" J. Natl. Cancer Inst. (2001) 93:463-471.

Golding et al., "Suppression of prion protein in livestock by RNA interference" PNAS (2006) 103(14): 5285-5290.

International Search Report for PCT/US19/062681 dated Apr. 7, 2020.

International Search Report for application PCT/US2009/004680 dated Oct. 13, 2009.

Kapuj et al., "Phosphorothioate Oligonucleotides Reduce PrPsc Levels and Prion Infectivity in Cultured Cells" Mol Med (2007) 13(3-4): 190-198.

Maher et al., "Comparative hybrid arrest by tandem antisense oligodeoxyribonucleotides or oligodeoxyribonucleoside methylphosphonates in a cell-free system" Nucl. Acid. Res. (1998) 16(8):3341-3358.

Mastrianni"The genetics of prion diseases" *Genetic Med.* (2010) 12(4): 187-195.

New England Biolabs 1998/1999 Catalog (cover page and pp. 121 and 284).

Ohnishi et al., "Enhancement of Allele Discrimination by Introduction of Nucleotide Mismatches into siRNA in Allele-Specific Gene Silencing by RNAi" PLoS One (2008) 3(5):e2248.

Olie et al., "Analysis of ribosyl-modified, mixed backbone analogs of a bcl-2/bcl-xL antisense oligonucleotide" Biochemica et Biophysica Acta (2002) 1576: 101-109.

Orru et. al., "Rapid and sensitive RT-QuIC detection of human Creutzfeldt-Jakob disease using cerebrospinal fluid" mBio (2015) 6(1): e02451-14.

Pfeifer et al., "Lentivector-mediated RNAi efficiently suppresses prion protein and prolongs survival of scrapie-infected mice" J. Clin. Invest. (2006) 116(12):3204-3210.

Purro et al., "Prion Protein as a Toxic Acceptor of Amyloid-β Oligomers" Biol Psychoatry (2018) 83: 358-368.

Raymond et al., "Antisense oligonucleotides extend survival of prion-infected mice" JCI Insight (2019) 1-13.

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Senesi et al., "In vivo prion models and the disconnection between transmissibility and neurotoxicity" *Ageing Research Reviews* (2017) 36: 156-164.

Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.

Sutou et al., "Knockdown of the bovine prion gene PRNP by RNA interference (RNAi) technology" BMC Biotechnology (2007) 7:44 1-10.

Tilly et al., "Efficient and specific down-regulation of prion protein expression by RNAi" Biochemical and Biophysical Research Communications (2003) 305:548-551.

Vallabh "Developing an antisense drug for prion disease" downloaded from: http://www.prionalliance.org/2018/07/09/developing-an-antisense-drug-for-prion-disease/ (2018) by scientist at Broad Institute.

Weiss et al., "RNA Aptamers Specifically Interact with the Prion Protein PrP" Journal of Virology (1997) 71(11): 8790-8797.

White et al., "Single treatment with RNAi against prion protein rescues early neuronal dysfunction and prolongs survival in mice with prion diseases" PNAS (2008) 105(29):10238-10243.

Woolf et al., "Specificity of antisense oligonucleotides in vivo" PNAS (1992) 89: 7305-7309.

Extended European Search Report for 19888227.6 dated Jan. 5, 2023, 7 pages.

(56) References Cited

OTHER PUBLICATIONS

International Search Report for PCT/US23/063353 dated Jul. 31, 2023, 19 pages.

* cited by examiner

COMPOUNDS AND METHODS FOR REDUCING PRION EXPRESSION

SEQUENCE LISTING

The present application is being filed along with a Sequence Listing in electronic format. The Sequence Listing is provided as a file entitled BIOL0345USASEQ_ST25.txt, created on May 11, 2021, which is 601,804 bytes in size. The information in the electronic format of the sequence listing is incorporated herein by reference in its entirety.

FIELD

Provided are compounds, methods, and pharmaceutical compositions for reducing the amount of prion RNA (PRNP RNA) in a cell or animal, and in certain instances reducing the amount of prion protein (PrP protein) in a cell or animal. Such compounds, methods, and pharmaceutical compositions are useful to ameliorate at least one symptom or hallmark of a neurodegenerative disease. Such symptoms and hallmarks include spongiform changes in the brain, development of abnormal protein aggregates, neuronal loss, markers of neuronal loss, rapidly progressing dementia, and death. Such neurodegenerative diseases include prion diseases, Creutzfeldt-Jakob disease (CJD), variant Creutzfeldt-Jakob Disease (vCJD), familial Creutzfeldt-Jakob Disease (fCJD), Gerstmann-Straussler-Scheinker syndrome, fatal familial insomnia, kuru, Alzheimer's disease, or Parkinson's disease.

BACKGROUND

Prion diseases are a family of rare, progressive, neurodegenerative disorders that affect both humans and non-human animals. Such diseases are caused by the misfolding of the normal prion protein ("PrP$^C$") and are distinguished by long incubation periods and characteristic spongiform changes associated with neuronal loss (Senesi, et al., "In vivo prion models and the disconnection between transmissibility and neurotoxicity", *Ageing Research Reviews* 2017, 36: 156-164; Erana, et al., *Biochem. And Biophys. Res. Comm.*, "Prion-like disorders and Transmissible Spongiform Encephalopathies: An overview of the mechanistic features that are shared by the various disease-related misfolded proteins", 2017, 483: 1125-1136). Hallmarks of prion diseases include, but are not limited to, spongiform changes in the brain, development of abnormal protein aggregates, neuronal loss, and markers of neuronal loss. Symptoms of prion diseases include, but are not limited to, rapidly progressing dementia, personality changes, ataxia, hallucinations, myoclonus (muscle jerks), chorea, autonomic disturbances, impaired vision, insomnia, blindness, loss of speech, coma, and death.

Prion protein can occur in several distinct conformational states: a normal cellular form, PrP$^C$, and the protease-resistant scrapie, disease-causing form, hypothesized to represent an ensemble of misfolded conformers, collectively referred to as scrapie or disease-causing prion protein, "PrP$^{Sc}$" (Sensei, 2017). The scrapie form of the prion protein, PrP$^{Sc}$, is the causative agent of transmissible spongiform encephalopathies. Both forms of the protein have the same amino acid sequence, encoded by PRNP RNA, and differ only in how they are folded in three-dimensional space. However, certain mutations in PRNP RNA cause a predisposition of the expressed protein to adopt the folding state of the disease-causing PrP$^{Sc}$ (Mastrianni, "The genetics of prion diseases", *Genetic Med.*, 2010, 12(4):187-195). PrP$^{Sc}$ forms aggregates and is resistant to proteolytic degradation by proteinase K. The infectious PrP$^{Sc}$ can cause misfolding of normal cellular PrP$^C$, converting it to the proteinase K-resistant PrP$^{Sc}$. This causes an increase in cellular levels of PrP$^{Sc}$, leading to increased protein aggregation as well as spread of the misfolded form throughout the CNS. The patient rapidly develops the characteristic signs and symptoms of prion disease, which is always fatal.

In addition to prion disease, PrP$^C$ has also been implicated as a molecular target in synucleinopathies, such as Parkinson's disease and dementia with Lewy bodies (Ferreira, et. al., "α-synuclein interacts with PrP$^C$ to induce cognitive impairment through mGluR5 and NMDAR2B", *Nature Neuroscience*, 2017, 20:1569-157) and Alzheimer's disease (Purro, et al., "Alzheimer's", *Biological Psychiatry*, 2018, 83(4):358-368).

Both PrP$^C$ and PrP$^{Sc}$ can be detected in cerebrospinal fluid (CSF). PrP$^C$ can be detected in CSF by standard methods such as western blot. The infectious PrP$^{Sc}$ can be detected in the CSF of prion-infected patients via a RT-QuIC test (real-time quaking induced conversion), as described by Orru, et. al., *mBio*, "Rapid and sensitive RT-QuIC detection of human Creutzfeldt-Jakob disease using cerebrospinal fluid," 2015, 6(1): c02451-14. This test distinguishes PrP$^{Sc}$ from PrP$^C$ by the ability of CSF samples to induce the misfolding of a recombinant PrP substrate.

Currently there is a lack of acceptable options for treating neurodegenerative diseases. It is therefore an object herein to provide compounds, methods, and pharmaceutical compositions for the treatment of such diseases.

SUMMARY OF THE INVENTION

Provided herein are compounds, methods and pharmaceutical compositions for reducing the amount or activity of PRNP RNA, and in certain embodiments reducing the amount of PrP protein in a cell or animal. In certain embodiments, the animal has a neurodegenerative disease. In certain embodiments, the neurodegenerative disease is a prion disease, Creutzfeldt-Jakob disease (CJD), variant Creutzfeldt-Jakob Disease (vCJD), familial Creutzfeldt-Jakob Disease (fCJD), Gerstmann-Straussler-Scheinker syndrome (GSS), fatal familial insomnia (FFI), kuru, Alzheimer's disease, or Parkinson's disease. In certain embodiments, compounds useful for reducing expression of PRNP RNA are oligomeric compounds. In certain embodiments, compounds useful for reducing expression of PRNP RNA are modified oligonucleotides.

Also provided are methods useful for ameliorating at least one symptom or hallmark of a neurodegenerative disease. In certain embodiments, the neurodegenerative disease is a prion disease, Creutzfeldt-Jakob disease (CJD), variant Creutzfeldt-Jakob Disease (vCJD), familial Creutzfeldt-Jakob Disease (fCJD), Gerstmann-Straussler-Scheinker syndrome, fatal familial insomnia, kuru, Alzheimer's disease, or Parkinson's disease. In certain embodiments, the symptom or hallmark includes spongiform changes in the brain, development of abnormal protein aggregates, neuronal loss, markers of neuronal loss, rapidly progressing dementia, and death.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well-known and commonly used in the art. Where permitted, all patents, applications, published applications and other publications and other data referred to throughout in the disclosure are incorporated by reference herein in their entirety.

Unless otherwise indicated, the following terms have the following meanings:

Definitions

As used herein, "2'-deoxynucleoside" means a nucleoside comprising a 2'-H(H) deoxyribosyl sugar moiety, as found in naturally occurring deoxyribonucleic acids (DNA). In certain embodiments, a 2'-deoxynucleoside may comprise a modified nucleobase or may comprise an RNA nucleobase (uracil). Unless otherwise specified, a 2'-deoxynucleoside has the β-D configuration.

As used herein, "2'-substituted nucleoside" means a nucleoside comprising a 2'-substituted sugar moiety. As used herein, "2'-substituted" in reference to a sugar moiety means a sugar moiety comprising at least one 2-substituent group other than H or OH.

As used herein, "5-methyl cytosine" means a cytosine modified with a methyl group attached to the 5 position. A 5-methyl cytosine is a modified nucleobase.

As used herein, "administering" means providing a pharmaceutical agent to an animal.

As used herein, "animal" means a human or non-human animal.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means an oligomeric compound capable of achieving at least one antisense activity.

As used herein, "ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom. In certain embodiments, the symptom or hallmark is spongiform changes in the brain, development of abnormal protein aggregates, neuronal loss, markers of neuronal loss, rapidly progressing dementia, and death.

As used herein, "bicyclic nucleoside" or "BNA" means a nucleoside comprising a bicyclic sugar moiety.

As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "cleavable moiety" means a bond or group of atoms that is cleaved under physiological conditions, for example, inside a cell, an animal, or a human.

As used herein, "complementary" in reference to an oligonucleotide means that at least 70% of the nucleobases of the oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include adenine (A) and thymine (T), adenine (A) and uracil (U), cytosine (C) and guanine (G), 5-methyl cytosine (mC) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that oligonucleotides are complementary to another oligonucleotide or nucleic acid at each nucleoside of the oligonucleotide.

As used herein, "conjugate group" means a group of atoms that is directly attached to an oligonucleotide. Conjugate groups include a conjugate moiety and a conjugate linker that attaches the conjugate moiety to the oligonucleotide.

As used herein, "conjugate linker" means a single bond or a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "constrained ethyl" or "cEt" or "cEt modified sugar" means a β-D ribosyl bicyclic sugar moiety wherein the second ring of the bicyclic sugar is formed via a bridge connecting the 4'-carbon and the 2'-carbon of the β-D ribosyl sugar moiety, wherein the bridge has the formula 4'-CH(CH$_3$)—O-2', and wherein the methyl group of the bridge is in the S configuration.

As used herein, "cEt nucleoside" means a nucleoside comprising cEt modified sugar.

As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

As used herein, "gapmer" means a modified oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings." Unless otherwise indicated, "gapmer" refers to a sugar motif. Unless otherwise indicated, the sugar moieties of the nucleosides of the gap of a gapmer are unmodified 2'-β-D-deoxyribosyl. Thus, the term "MOE gapmer" indicates a gapmer having a sugar motif of 2'-MOE nucleosides in both wings and a gap of 2'-deoxynucleosides. Unless otherwise indicated, a MOE gapmer may comprise one or more modified internucleoside linkages and/or modified nucleobases and such modifications do not necessarily follow the gapmer pattern of the sugar modifications.

As used herein, "hotspot region" is a range of nucleobases on a target nucleic acid that is amenable to oligomeric compound-mediated reduction of the amount or activity of the target nucleic acid.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, the term "internucleoside linkage" is the covalent linkage between adjacent nucleosides in an oligonucleotide. As used herein "modified internucleoside linkage" means any internucleoside linkage other than a phosphodiester internucleoside linkage. "Phosphorothioate internucleoside linkage" is a modified internucleoside linkage in which one of the non-bridging oxygen atoms of a phosphodiester internucleoside linkage is replaced with a sulfur atom.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic modified sugar moiety" means a modified sugar moiety that comprises a modification, such as a substituent, that does not form a bridge between two atoms of the sugar to form a second ring.

As used herein, "mismatch" or "non-complementary" means a nucleobase of a first oligonucleotide that is not complementary with the corresponding nucleobase of a second oligonucleotide or target nucleic acid when the first and second oligonucleotide are aligned.

As used herein, "MOE" means methoxyethyl. "2'-MOE" or "2'-MOE modified sugar" means a 2'-OCH$_2$CH$_2$OCH$_3$ group in place of the 2'-OH group of a ribosyl sugar moiety.

As used herein, "2'-MOE nucleoside" means a nucleoside comprising a 2'-MOE modified sugar.

As used herein, "motif" means the pattern of unmodified and/or modified sugar moieties, nucleobases, and/or internucleoside linkages, in an oligonucleotide.

As used herein, "RNA" means an RNA transcript that encodes a protein and includes pre-mRNA and mature mRNA unless otherwise specified.

As used herein, "neurodegenerative disease" means a condition marked by progressive loss of function or structure, including loss of motor function and death of neurons. In certain embodiments, the neurodegenerative disease is a prion disease. In certain embodiments, the neurodegenerative disease is any of Creutzfeldt-Jakob disease (CJD), variant Creutzfeldt-Jakob Disease (vCJD), familial Creutzfeldt-Jakob Disease (fCJD), Gerstmann-Straussler-Scheinker syndrome, fatal familial insomnia, kuru, Alzheimer's disease, or Parkinson's disease.

As used herein, "nucleobase" means an unmodified nucleobase or a modified nucleobase. As used herein an "unmodified nucleobase" is adenine (A), thymine (T), cytosine (C), uracil (U), or guanine (G). As used herein, a "modified nucleobase" is a group of atoms other than unmodified A, T, C, U, or G capable of pairing with at least one unmodified nucleobase. A "5-methyl cytosine" is a modified nucleobase. A universal base is a modified nucleobase that can pair with any one of the five unmodified nucleobases. As used herein, "nucleobase sequence" means the order of contiguous nucleobases in a nucleic acid or oligonucleotide independent of any sugar or internucleoside linkage modification.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a contiguous sequence (i.e., no additional nucleosides are presented between those that are linked).

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to an animal. Certain such carriers enable pharmaceutical compositions to be formulated as, for example, tablets, pills, dragees, capsules, liquids, gels, syrups, slurries, suspension and lozenges for the oral ingestion by a subject.

In certain embodiments, a pharmaceutically acceptable carrier or diluent is sterile water, sterile saline, sterile buffer solution or sterile artificial cerebrospinal fluid.

As used herein "pharmaceutically acceptable salts" means physiologically and pharmaceutically parent compound and do not impart undesired toxicological effects thereto.

As used herein "pharmaceutical composition" means a mixture of substances suitable for administering to a subject. For example, a pharmaceutical composition may comprise an oligomeric compound and a sterile aqueous solution. In certain embodiments, a pharmaceutical composition shows activity in free uptake assay in certain cell lines.

As used herein "PrP$^C$" means the normal cellular form of PrP protein.

As used herein "PrP$^{Sc}$" means the protease-resistant, disease-causing form of PrP protein.

As used herein "prodrug" means a therapeutic agent in a form outside the body that is converted to a different form within an animal or cells thereof. Typically, conversion of a prodrug within the animal is facilitated by the action of an enzymes (e.g., endogenous or viral enzyme) or chemicals present in cells or tissues and/or by physiologic conditions.

As used herein, "reducing or inhibiting the amount or activity" refers to a reduction or blockade of the transcriptional expression or activity relative to the transcriptional expression or activity in an untreated or control sample and does not necessarily indicate a total elimination of transcriptional expression or activity.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense compounds that act through RNase H.

As used herein, "self-complementary" in reference to an oligonucleotide means an oligonucleotide that at least partially hybridizes to itself.

As used herein, "siRNA" refers to a ribonucleic acid molecule having a duplex structure including two antiparallel and substantially complementary nucleic acid strands. The two strands forming the duplex structure may be different portions of one larger RNA molecule, or they may be separate RNA molecules. Where the two strands are part of one larger molecule, and therefore are connected by consecutive nucleobases between the 3'-end of one strand and the 5' end of the respective other strand forming the duplex structure, the connecting RNA chain is referred to as a "hairpin loop". The RNA strands may have the same or a different number of nucleotides.

As used herein, "standard cell assay" means the assay described in Example 1 and reasonable variations thereof.

As used herein, "stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the results of a synthetic method that is not designed to control the stereochemical configuration. In certain embodiments, a stereorandom chiral center is a stereorandom phosphorothioate internucleoside linkage.

As used herein, "sugar moiety" means an unmodified sugar moiety or a modified sugar moiety. As used herein, "unmodified sugar moiety" means a 2'-OH(H) ribosyl moiety, as found in RNA (an "unmodified RNA sugar moiety"), or a 2'-H(H) deoxyribosyl moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate.

As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or target nucleic acids.

As used herein, "symptom or hallmark" means any physical feature or test result that indicates the existence or extent of a disease or disorder. In certain embodiments, a symptom is apparent to a subject or to a medical professional examining or testing said subject. In certain embodiments, a hallmark is apparent upon invasive diagnostic testing, including, but not limited to, post-mortem tests.

As used herein, "target nucleic acid" and "target RNA" mean a nucleic acid that an antisense compound is designed to affect.

As used herein, "target region" means a portion of a target nucleic acid to which an oligomeric compound is designed to hybridize.

As used herein, "terminal group" means a chemical group or group of atoms that is covalently linked to a terminus of an oligonucleotide.

As used herein, "therapeutically effective amount" means an amount of a pharmaceutical agent that provides a therapeutic benefit to an animal. For example, a therapeutically effective amount improves a symptom of a disease.

Certain Embodiments

The present disclosure provides the following non-limiting numbered embodiments:

Embodiment 1. An oligomeric compound comprising a modified oligonucleotide consisting of 12 to 30 linked nucleosides wherein the nucleobase sequence of the modified oligonucleotide is at least 90% complementary to an equal length portion of a PRNP nucleic acid, and wherein the modified oligonucleotide comprises at least one modification selected from a modified sugar, a sugar surrogate, and a modified internucleoside linkage.

Embodiment 2. An oligomeric compound comprising a modified oligonucleotide consisting of 12 to 30 linked nucleosides and having a nucleobase sequence comprising at least 12, 13, 14, 15, 16, 17, 18, 19, or 20 nucleobases of any of SEQ ID NOS: 27-2744.

Embodiment 3. An oligomeric compound comprising a modified oligonucleotide consisting of 12 to 30 linked nucleosides and having a nucleobase sequence comprising at least 12, 13, 14, 15, 16, 17, 18, or 19 nucleobases of any of SEQ ID NOS: 2745-2766.

Embodiment 4. An oligomeric compound comprising a modified oligonucleotide consisting of 12 to 30 linked nucleosides and having a nucleobase sequence comprising at least 12, 13, 14, 15, 16, 17, or 18 nucleobases of any of SEQ ID NOS: 2767-2780.

Embodiment 5. An oligomeric compound comprising a modified oligonucleotide consisting of 12 to 30 linked nucleosides and having a nucleobase sequence comprising at least 12, 13, 14, 15, 16, or 17 nucleobases of any of SEQ ID NOS: 2781-2802.

Embodiment 6. An oligomeric compound comprising a modified oligonucleotide consisting of 12 to 30 linked nucleosides and having a nucleobase sequence comprising at least 12, 13, 14, 15, or 16 nucleobases of any of SEQ ID NOS: 2803-2806.

Embodiment 7. An oligomeric compound comprising a modified oligonucleotide consisting of 12 to 30 linked nucleosides and having a nucleobase sequence comprising a portion of at least 8, at least 9, at least 10, at least 11, at least 12, at least 13, at least 14, at least 15, at least 16, at least 17, at least 18, at least 19, or at least 20 contiguous nucleobases, wherein the portion is complementary to:
an equal length portion of nucleobases 5,635-5,677 of SEQ ID NO: 2;
an equal length portion of nucleobases 5,791-5,826 of SEQ ID NO: 2; or
an equal length portion of nucleobases 14,366-14,410 of SEQ ID NO: 2.

Embodiment 8. An oligomeric compound comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, or at least 18 contiguous nucleobases of a nucleobase sequence selected from:
SEQ ID Nos: 530, 607, 684, 761, 838, 915, 1914, 1992, 2069, 2146, 2237, 2301, 2302, 2536, 2640, 2750, 2759, 2760, 2764, 2788-2793, 2803-2806;
SEQ ID Nos: 1225, 1302, 1379, 1456, 2240, 2307, 2308, 2383, 2471, 2537, 2568, 2647, 2736-2739, 2798-2801; or
SEQ ID Nos: 555, 632, 709, 786, 863, 940, 1017, 1862, 1939, 2017, 2094, 2171, 2257, 2334, 2407, 2408, 2488, 2508, 2543, 2612, 2659, 2677, 2757, 2766, 2794-2797.

Embodiment 9. An oligomeric compound comprising a modified oligonucleotide consisting of 12 to 30 linked nucleosides and having a nucleobase sequence comprising a portion of at least 8, at least 9, at least 10, at least 11, at least 12, at least 13, at least 14, at least 15, at least 16, at least 17, at least 18, at least 19, or at least 20 contiguous nucleobases, wherein the portion is complementary to:
an equal length portion of nucleobases 4,902-4,929 of SEQ ID NO: 2;
an equal length portion of nucleobases 5,000-5,026 of SEQ ID NO: 2;
an equal length portion of nucleobases 5,073-5,100 of SEQ ID NO: 2;
an equal length portion of nucleobases 5,515-5,559 of SEQ ID NO: 2;
an equal length portion of nucleobases 5,595-5,632 of SEQ ID NO: 2;
an equal length portion of nucleobases 5,666-5,690 of SEQ ID NO: 2;
an equal length portion of nucleobases 5,857-5,881 of SEQ ID NO: 2;
an equal length portion of nucleobases 9,352-9,377 of SEQ ID NO: 2;
an equal length portion of nucleobases 11,331-11,358 of SEQ ID NO: 2;
an equal length portion of nucleobases 16,292-16,328 of SEQ ID NO: 2;
an equal length portion of nucleobases 17,120-17,151 of SEQ ID NO: 2;
an equal length portion of nucleobases 17,211-17,241 of SEQ ID NO: 2;
an equal length portion of nucleobases 17,281-17,331 of SEQ ID NO: 2;
an equal length portion of nucleobases 17,410-17,445 of SEQ ID NO: 2;
an equal length portion of nucleobases 17,601-17,641 of SEQ ID NO: 2;
an equal length portion of nucleobases 17,635-17,670 of SEQ ID NO: 2;
an equal length portion of nucleobases 17,663-17,712 of SEQ ID NO: 2;
an equal length portion of nucleobases 17,753-17,781 of SEQ ID NO: 2; or
an equal length portion of nucleobases 17,985-18,016 of SEQ ID NO: 2.

Embodiment 10. The oligomeric compound of any of embodiments 1-9, wherein the modified oligonucleotide has a nucleobase sequence that is at least 80%, 85%, 90%, 95%, or 100% complementary to the nucleobase sequences of SEQ ID NO: 1, SEQ ID NO: 2, SEQ ID NO: 3, or SEQ ID NO: 4 when measured across the entire nucleobase sequence of the modified oligonucleotide.

Embodiment 11. The oligomeric compound of any of embodiments 1-10, wherein the modified oligonucleotide comprises at least one modified nucleoside.

Embodiment 12. The oligomeric compound of embodiment 11, wherein the modified oligonucleotide comprises at least one modified nucleoside comprising a modified sugar moiety.

Embodiment 13. The oligomeric compound of embodiment 12, wherein the modified oligonucleotide comprises at least one modified nucleoside comprising a bicyclic sugar moiety.

Embodiment 14. The oligomeric compound of embodiment 13, wherein the modified oligonucleotide comprises at least one modified nucleoside comprising a bicyclic sugar moiety having a 2'-4' bridge, wherein the 2'-4' bridge is selected from —O—CH$_2$—; and —O—CH(CH$_3$)—.

Embodiment 15. The oligomeric compound of any of embodiments 11-14, wherein the modified oligonucleotide comprises at least one modified nucleoside comprising a non-bicyclic modified sugar moiety.

Embodiment 16. The oligomeric compound of embodiment 17, wherein the modified oligonucleotide comprises at least one modified nucleoside comprising a non-bicyclic modified sugar moiety comprising a 2'-MOE modified sugar or 2'-OMe modified sugar.

Embodiment 17. The oligomeric compound of any of embodiments 11-16, wherein the modified oligonucleotide comprises at least one modified nucleoside comprising a sugar surrogate.

Embodiment 18. The oligomeric compound of embodiment 15, wherein the modified oligonucleotide comprises at least one modified nucleoside comprising a sugar surrogate selected from morpholino and PNA.

Embodiment 19. The oligomeric compound of any of embodiments 1-12 or 15-18, wherein the modified oligonucleotide does not comprise a bicyclic sugar moiety.

Embodiment 20. The oligomeric compound of any of embodiments 1-19, wherein the modified oligonucleotide has a sugar motif comprising:
- a 5'-region consisting of 1-7 linked 5'-region nucleosides;
- a central region consisting of 6-10 linked central region nucleosides; and
- a 3'-region consisting of 1-7 linked 3'-region nucleosides; wherein
- each of the 5'-region nucleosides and each of the 3'-region nucleosides comprises a modified sugar and each of the central region nucleosides comprises a 2'-deoxyribosyl sugar.

Embodiment 21. The oligomeric compound of embodiment 20, wherein the modified oligonucleotide has
- a 5'-region consisting of 4 linked 5'-region nucleosides;
- a central region consisting of 8 linked central region nucleosides; and
- a 3'-region consisting of 4 linked 3'-region nucleosides; wherein
- each of the 5'-region nucleosides comprises a 2'-MOE modified sugar, each of the 3'-region nucleosides comprises either a 2'-MOE modified sugar or a cEt modified sugar, and each of the central region nucleosides comprises a 2'-deoxyribosyl sugar.

Embodiment 22. The oligomeric compound of embodiment 20, wherein the modified oligonucleotide has
- a 5'-region consisting of 4 linked 5'-region nucleosides;
- a central region consisting of 8 linked central region nucleosides; and
- a 3'-region consisting of 5 linked 3'-region nucleosides; wherein
- each of the 5'-region nucleosides comprises a 2'-MOE modified sugar, each of the 3'-region nucleosides comprises either a 2'-MOE modified sugar or a cEt modified sugar, and each of the central region nucleosides comprises a 2'-deoxyribosyl sugar.

Embodiment 23. The oligomeric compound of embodiment 20, wherein the modified oligonucleotide has
- a 5'-region consisting of 5 linked 5'-region nucleosides;
- a central region consisting of 8 linked central region nucleosides; and
- a 3'-region consisting of 5 linked 3'-region nucleosides; wherein
- each of the 5'-region and each of the 3'-region nucleosides comprises a 2'-MOE modified sugar, and each of the central region nucleosides comprises a 2'-deoxyribosyl sugar.

Embodiment 24. The oligomeric compound of embodiment 20, wherein the modified oligonucleotide has
- a 5'-region consisting of 5 linked 5'-region nucleosides;
- a central region consisting of 9 linked central region nucleosides; and
- a 3'-region consisting of 5 linked 3'-region nucleosides; wherein
- each of the 3'-region nucleosides comprises either a 2'-MOE modified sugar or a cEt modified sugar, and each of the central region nucleosides comprises a 2'-deoxyribosyl sugar.

Embodiment 25. The oligomeric compound of embodiment 20, wherein the modified oligonucleotide has
- a 5'-region consisting of 5 linked 5'-region nucleosides;
- a central region consisting of 9 linked central region nucleosides; and
- a 3'-region consisting of 5 linked 3'-region nucleosides; wherein
- each of the 5'-region nucleosides and each of the 3'-region nucleosides comprises a 2'-MOE modified sugar, and each of the central region nucleosides comprises a 2'-deoxyribosyl sugar.

Embodiment 26. The oligomeric compound of embodiment 20, wherein the modified oligonucleotide has a sugar motif comprising:
- a 5'-region consisting of 6 linked 5'-region nucleosides;
- a central region consisting of 10 linked central region nucleosides; and
- a 3'-region consisting of 4 linked 3'-region nucleosides; wherein
- each of the 5'-region nucleosides and each of the 3'-region nucleosides comprises a 2'-MOE modified sugar, and each of the central region nucleosides comprises a 2'-deoxyribosyl sugar.

Embodiment 27. The oligomeric compound of embodiment 20, wherein the modified oligonucleotide has a sugar motif comprising:
- a 5'-region consisting of 6 linked 5'-region nucleosides;
- a central region consisting of 10 linked central region nucleosides; and
- a 3'-region consisting of 4 linked 3'-region nucleosides; wherein
- each of the 3'-region nucleosides comprises either a 2'-MOE modified sugar or a cEt modified sugar, and each of the central region nucleosides comprises a 2'-deoxyribosyl sugar.

Embodiment 28. The oligomeric compound of embodiment 20, wherein the modified oligonucleotide has a sugar motif comprising:
- a 5'-region consisting of 5 linked 5'-region nucleosides;
- a central region consisting of 10 linked central region nucleosides; and
- a 3'-region consisting of 5 linked 3'-region nucleosides; wherein
- each of the 5'-region nucleosides and each of the 3'-region nucleosides comprises a 2'-MOE modified sugar, and each of the central region nucleosides comprises a 2'-deoxyribosyl sugar.

Embodiment 29. The oligomeric compound of embodiment 20, wherein the modified oligonucleotide has a sugar motif comprising:
- a 5'-region consisting of 5 linked 5'-region nucleosides;
- a central region consisting of 10 linked central region nucleosides; and
- a 3'-region consisting of 5 linked 3'-region nucleosides; wherein
- each of the 3'-region nucleosides comprises either a 2'-MOE modified sugar or a cEt modified sugar, and each of the central region nucleosides comprises a 2'-deoxyribosyl sugar.

Embodiment 30. The oligomeric compound of embodiment 20, wherein the modified oligonucleotide has a sugar motif comprising:
- a 5'-region consisting of 4 linked 5'-region nucleosides;
- a central region consisting of 10 linked central region nucleosides; and
- a 3'-region consisting of 6 linked 3'-region nucleosides; wherein
- each of the 5'-region nucleosides and each of the 3'-region nucleosides comprises a 2'-MOE modified sugar, and each of the central region nucleosides comprises a 2'-deoxyribosyl sugar.

Embodiment 31. The oligomeric compound of embodiment 20, wherein the modified oligonucleotide has
a 5'-region consisting of 3 linked 5'-region nucleosides;
a central region consisting of 10 linked central region nucleosides; and
a 3'-region consisting of 7 linked 3'-region nucleosides; wherein
each of the 5'-region nucleosides and each of the 3'-region nucleosides comprises a 2'-MOE modified sugar, and each of the central region nucleosides comprises a 2'-deoxyribosyl sugar.

Embodiment 32. The oligomeric compound of embodiment 20, wherein the modified oligonucleotide has
a 5'-region consisting of 7 linked 5'-region nucleosides;
a central region consisting of 10 linked central region nucleosides; and
a 3'-region consisting of 3 linked 3'-region nucleosides; wherein
each of the 5'-region nucleosides and each of the 3'-region nucleosides comprises a 2'-MOE modified sugar, and each of the central region nucleosides comprises a 2'-deoxyribosyl sugar.

Embodiment 33. The oligomeric compound of any of embodiments 20-32, wherein the 2'-deoxyribosyl sugar is a 2'-β-D-deoxyribosyl sugar.

Embodiment 34. The oligomeric compound of any of embodiments 1-19, wherein the modified oligonucleotide has a sugar motif comprising:
a 5'-region consisting of 1-6 linked 5'-region nucleosides;
a central region consisting of 6-10 linked central region nucleosides; and
a 3'-region consisting of 1-6 linked 3'-region nucleosides; wherein
each of the 5'-region nucleosides and each of the 3'-region nucleosides comprises a modified sugar, and the central region has the following formula:

(Nd)(Nx)(Nd)n wherein Nx is a 2'-OMe nucleoside and each Nd is a 2'-Q-D-deoxynucleoside; and n is from 6 to 8.

Embodiment 35. The oligomeric compound of embodiment 34, wherein the modified oligonucleotide has a sugar motif comprising:
a 5'-region consisting of 5 linked 5'-region nucleosides;
a central region consisting of 8 linked central region nucleosides; and
a 3'-region consisting of 5 linked 3'-region nucleosides; wherein
each of the 5'-region nucleosides and each of the 3'-region nucleosides comprises a 2'-MOE modified sugar,
and the central region has the following formula:

(Nd)(Nx)(Nd)n wherein Nx is a nucleoside comprising a 2'-OMe sugar and each Nd is a nucleoside comprising s a 2'-deoxyribosyl sugar;
and n is 6.

Embodiment 36. The oligomeric compound of embodiment 34, wherein the modified oligonucleotide has a sugar motif comprising:
a 5'-region consisting of 5 linked 5'-region nucleosides;
a central region consisting of 8 linked central region nucleosides; and
a 3'-region consisting of 5 linked 3'-region nucleosides; wherein
each of the 5'-region nucleosides and each of the 3'-region nucleosides comprises a 2'-MOE modified sugar,
and the central region has the following formula:

(Nd)(Nx)(Nd)n wherein Nx is a nucleoside comprising a 2'-OMe sugar and each Nd is a nucleoside comprising s a 2'-deoxyribosyl sugar;
and n is 6.

Embodiment 37. The oligomeric compound of embodiment 34, wherein the modified oligonucleotide has a sugar motif comprising:
a 5'-region consisting of 5 linked 5'-region nucleosides;
a central region consisting of 10 linked central region nucleosides; and
a 3'-region consisting of 5 linked 3'-region nucleosides; wherein
each of the 5'-region nucleosides and each of the 3'-region nucleosides comprises a 2'-MOE modified sugar,
and the central region has the following formula:

(Nd)(Nx)(Nd)n wherein Nx is a nucleoside comprising a 2'-OMe sugar and each Nd is a nucleoside comprising s a 2'-deoxyribosyl sugar;
and n is 8.

Embodiment 38. The oligomeric compound of any of embodiments 34-37, wherein the 2'-deoxyribosyl sugar is a 2'-β-D-deoxyribosyl sugar.

Embodiment 39. The oligomeric compound of any of embodiments 1-38, wherein the modified oligonucleotide comprises at least one modified internucleoside linkage.

Embodiment 40. The oligomeric compound of embodiment 39, wherein each internucleoside linkage of the modified oligonucleotide is a modified internucleoside linkage.

Embodiment 41. The oligomeric compound of embodiment 39 or 40 wherein at least one internucleoside linkage is a phosphorothioate internucleoside linkage.

Embodiment 42. The oligomeric compound of embodiment 39 or 41 wherein the modified oligonucleotide comprises at least one phosphodiester internucleoside linkage.

Embodiment 43. The oligomeric compound of any of embodiments 39, 41, or 42, wherein each internucleoside linkage is independently selected from a phosphodiester internucleoside linkage or a phosphorothioate internucleoside linkage.

Embodiment 44. The oligomeric compound of any of embodiments 1-43, wherein the modified oligonucleotide comprises at least one modified nucleobase.

Embodiment 45. The oligomeric compound of embodiment 44, wherein the modified nucleobase is a 5-methyl cytosine.

Embodiment 46. The oligomeric compound of any of embodiments 1-45, wherein the modified oligonucleotide consists of 12-30, 12-22, 12-20, 14-20, 15-25, 16-20, 18-22 or 18-20 linked nucleosides.

Embodiment 47. The oligomeric compound of any of embodiments 1-21, 33, 34, or 38-46 wherein the modified oligonucleotide consists of 16 linked nucleosides.

Embodiment 48. The oligomeric compound of any of embodiments 1-20, 22, 33, 34, or 38-46 wherein the modified oligonucleotide consists of 17 linked nucleosides.

Embodiment 49. The oligomeric compound of any of embodiments 1-20, 23, 33, 34-36 or 38-46 wherein the modified oligonucleotide consists of 18 linked nucleosides.

Embodiment 50. The oligomeric compound of any of embodiments 1-20, 24, 25, 33, 34, or 38-46 wherein the modified oligonucleotide consists of 19 linked nucleosides.

Embodiment 51. The oligomeric compound of any of embodiments 1-20, 26-34, or 37-46, wherein the modified oligonucleotide consists of 20 linked nucleosides.

Embodiment 52. The oligomeric compound of embodiment 39, wherein the modified oligonucleotide has the internucleoside linkage motif soosssssssssooooss, sooooosssssssssooss, sooooosssssssssssooss, sooooosssssssssOss, ssoooosssssssssssOs, soooooosssssssssoos, soooossssssssssooss, sooossssssss-sooss, sooossssssssssoss, or soossssssssssoos wherein "s" represents a phosphoothioate internucleoside linkage and "o" represents a phosphodiester internucleoside linkage.

Embodiment 53. The oligomeric compound of any of embodiments 1-52, consisting of the modified oligonucleotide.

Embodiment 54. The oligomeric compound of any of embodiments 1-52, comprising a conjugate group comprising a conjugate moiety and a conjugate linker.

Embodiment 55. The oligomeric compound of embodiment 54, wherein the conjugate group comprises a GalNAc cluster comprising 1-3 GalNAc ligands.

Embodiment 56. The oligomeric compound of embodiments 54 or 55, wherein the conjugate linker consists of a single bond.

Embodiment 57. The oligomeric compound of embodiment 54, wherein the conjugate linker is cleavable.

Embodiment 58. The oligomeric compound of embodiment 54, wherein the conjugate linker comprises 1-3 linker-nucleosides.

Embodiment 59. The oligomeric compound of any of embodiments 54-58, wherein the conjugate group is attached to the modified oligonucleotide at the 5'-end of the modified oligonucleotide.

Embodiment 60. The oligomeric compound of any of embodiments 54-58, wherein the conjugate group is attached to the modified oligonucleotide at the 3'-end of the modified oligonucleotide.

Embodiment 61. The oligomeric compound of any of embodiments 1-60 comprising a terminal group.

Embodiment 62. The oligomeric compound of any of embodiments 1-61 wherein the oligomeric compound is a singled-stranded oligomeric compound.

Embodiment 63. The oligomeric compound of any of embodiments 1-57 or 59-62, wherein the oligomeric compound does not comprise linker-nucleosides.

Embodiment 64. An oligomeric duplex comprising an oligomeric compound of any of embodiments 1-61 or 63.

Embodiment 65. An antisense compound comprising or consisting of an oligomeric compound of any of embodiments 1-63 or an oligomeric duplex of embodiment 64.

Embodiment 66. A pharmaceutical composition comprising an oligomeric compound of any of embodiments 1-63 or an oligomeric duplex of embodiment 64 and a pharmaceutically acceptable carrier or diluent.

Embodiment 67. The pharmaceutical composition of embodiment 66, comprising a pharmaceutically acceptable diluent, wherein the pharmaceutically acceptable diluent is phosphate-buffered saline or artificial cerebrospinal fluid.

Embodiment 68. The pharmaceutical composition of embodiment 67, wherein the pharmaceutical composition consists essentially of the modified oligonucleotide and phosphate-buffered saline or artificial cerebrospinal fluid.

Embodiment 69. A method comprising administering to an animal a pharmaceutical composition of any of embodiments 66-68.

Embodiment 70. A method of treating a disease associated with PRNP comprising administering to an individual having or at risk for developing a disease associated with PRNP a therapeutically effective amount of a pharmaceutical composition according to any of embodiments 66-68; and thereby treating the disease associated with PRNP.

Embodiment 71. A method of reducing PrP protein in the CSF of an individual having or at risk for developing a disease associated with PRNP a therapeutically effective amount of a pharmaceutical composition according any of embodiments 66-68; and thereby reducing PrP protein in the CSF.

Embodiment 72. The method of embodiment 71, wherein the PrP protein is PrP$^C$.

Embodiment 73. The method of embodiment 71, wherein the PrP protein is PrP$^{Sc}$.

Embodiment 74. The method of embodiment 71, wherein the PrP protein is both PrP$^C$ and PrP$^{Sc}$.

Embodiment 75. The method of embodiment 70 or 71, wherein the administering is by intrathecal administration.

Embodiment 76. The method of embodiment 70 or embodiment 71, wherein the disease associated with PRNP is a neurodegenerative disease.

Embodiment 77. The method of embodiment 76, wherein the neurodegenerative disease is selected from among prion diseases, Creutzfeldt-Jakob disease (CJD), variant Creutzfeldt-Jakob Disease (vCJD), familial Creutzfeldt-Jakob Disease (fCJD), Gerstmann-Straussler-Scheinker syndrome, fatal familial insomnia, kuru, Alzheimer's disease, or Parkinson's disease.

Embodiment 78. The method of any of embodiments 70-77, wherein at least one symptom or hallmark of the neurodegenerative disease is ameliorated.

Embodiment 79. The method of embodiment 78, wherein the symptom or hallmark is any of spongiform changes in the brain, development of abnormal protein aggregates, neuronal loss, markers of neuronal loss, rapidly progressing dementia, or death.

Embodiment 80. A method of reducing PRNP RNA in a cell comprising contacting the cell with an oligomeric compound according to any of embodiments 1-63, an oligomeric duplex according to embodiment 64, or an antisense compound according to embodiment 65; and thereby reducing PRNP RNA in the cell.

Embodiment 81. A method of reducing PrP protein in a cell comprising contacting the cell with an oligomeric compound according to any of embodiments 1-63, an oligomeric duplex according to embodiment 64, or an antisense compound according to embodiment 65; and thereby reducing PrP in the cell.

Embodiment 82. The method of embodiment 81, wherein the PrP protein is PrP$^C$.

Embodiment 83. The method of embodiment 81, wherein the PrP protein is PrP$^{Sc}$ Embodiment 84. The method of embodiment 81, wherein the PrP protein is both PrP$^C$ and PrP$^{Sc}$ Embodiment 85. The method of any of embodiments 80-84, wherein the cell is in an animal.

Embodiment 86. A modified oligonucleotide according to the following chemical structure:
(SEQ ID NO: 1914)
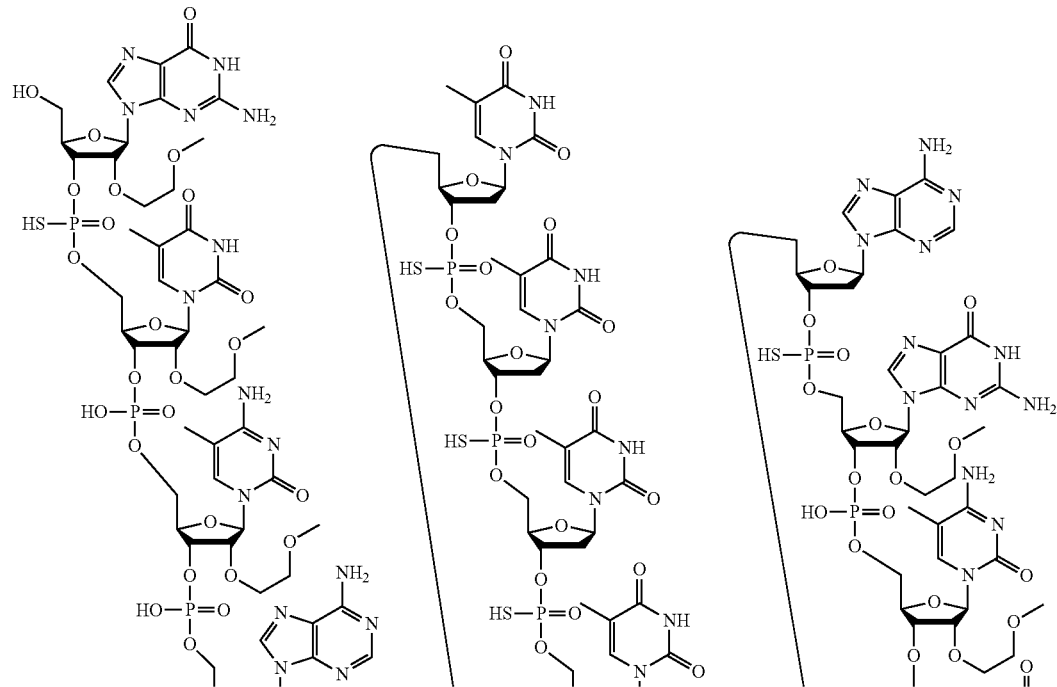
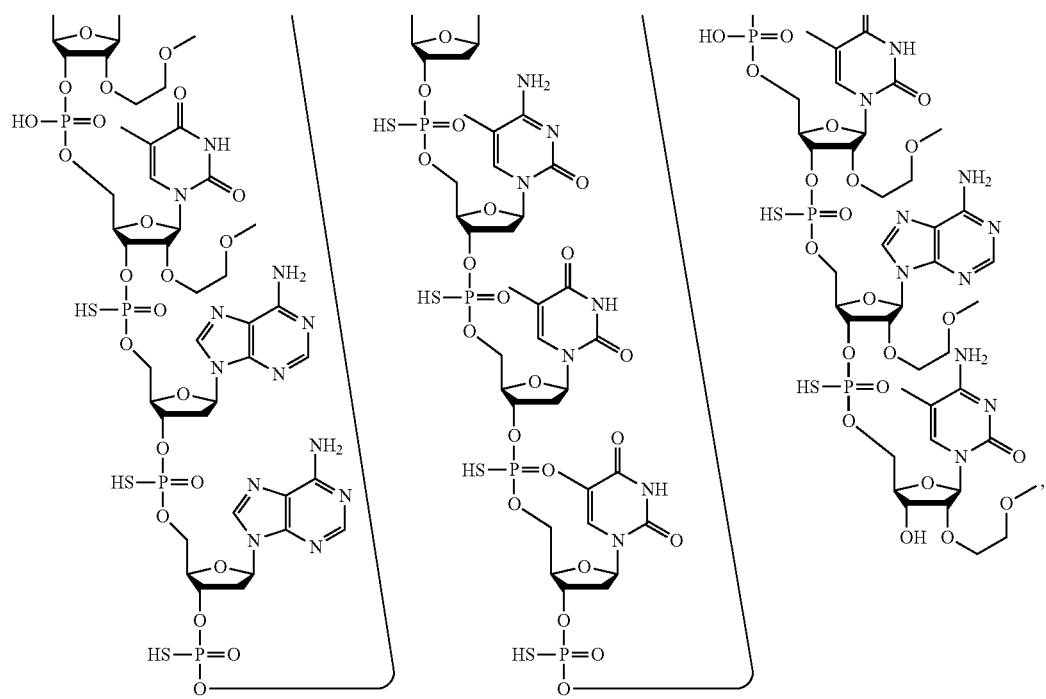
or a salt thereof.

Embodiment 87. A modified oligonucleotide according to the following chemical structure:
(SEQ ID NO: 1914)
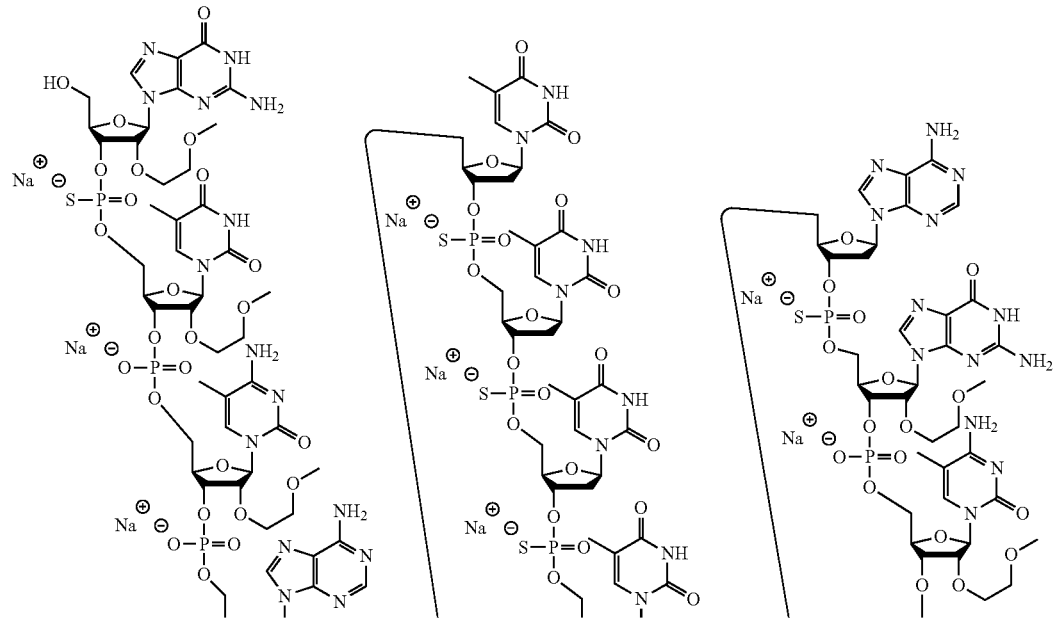
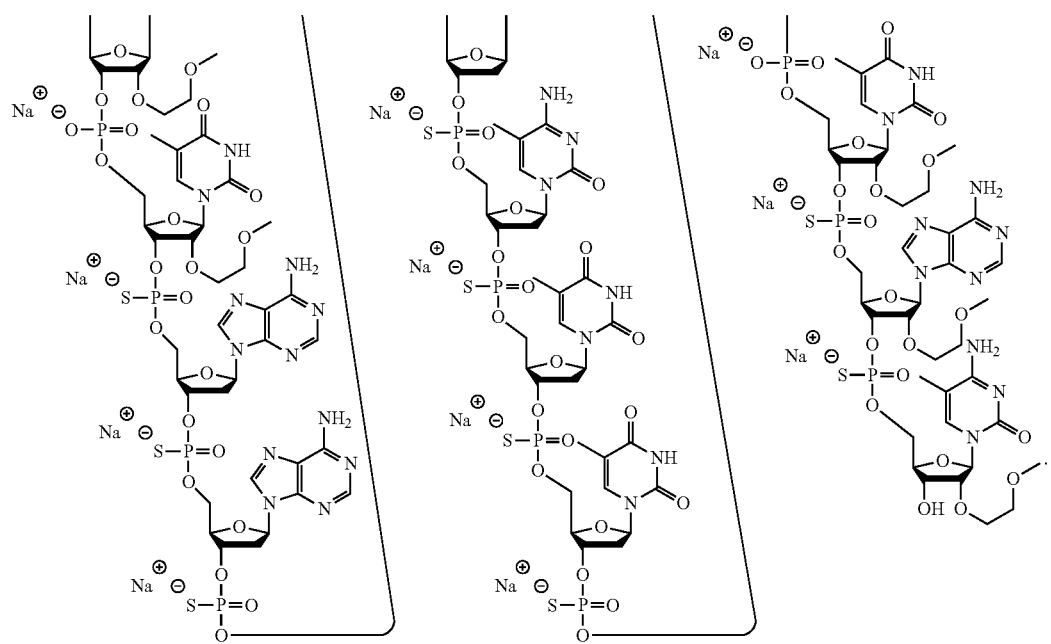

Embodiment 88. A modified oligonucleotide according to the following chemical structure:
(SEQ ID NO: 1914)
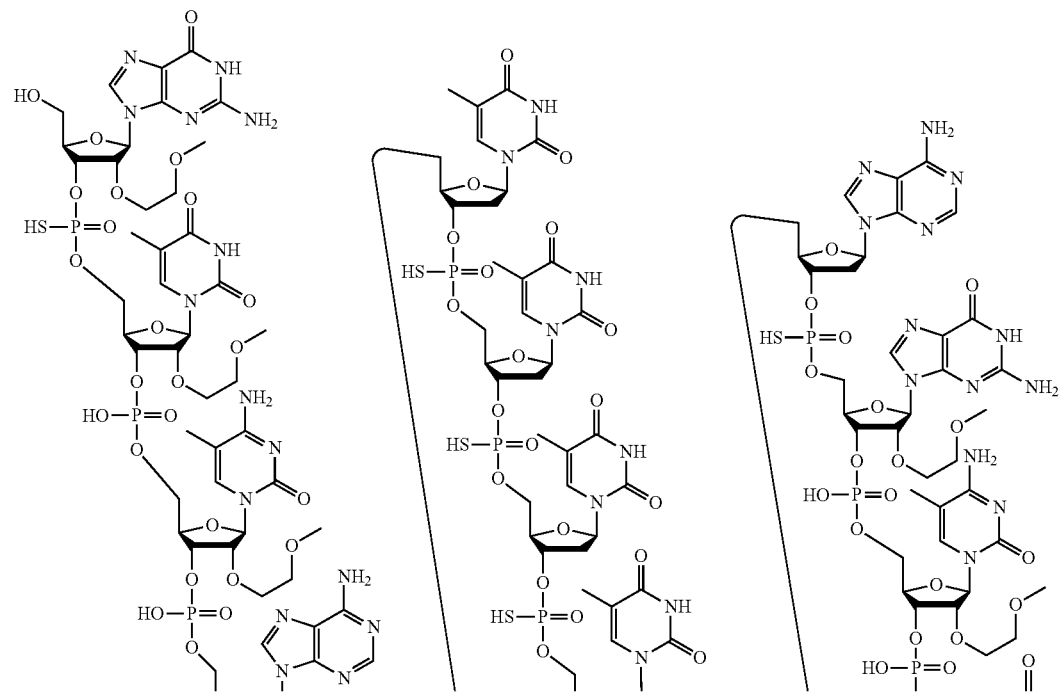
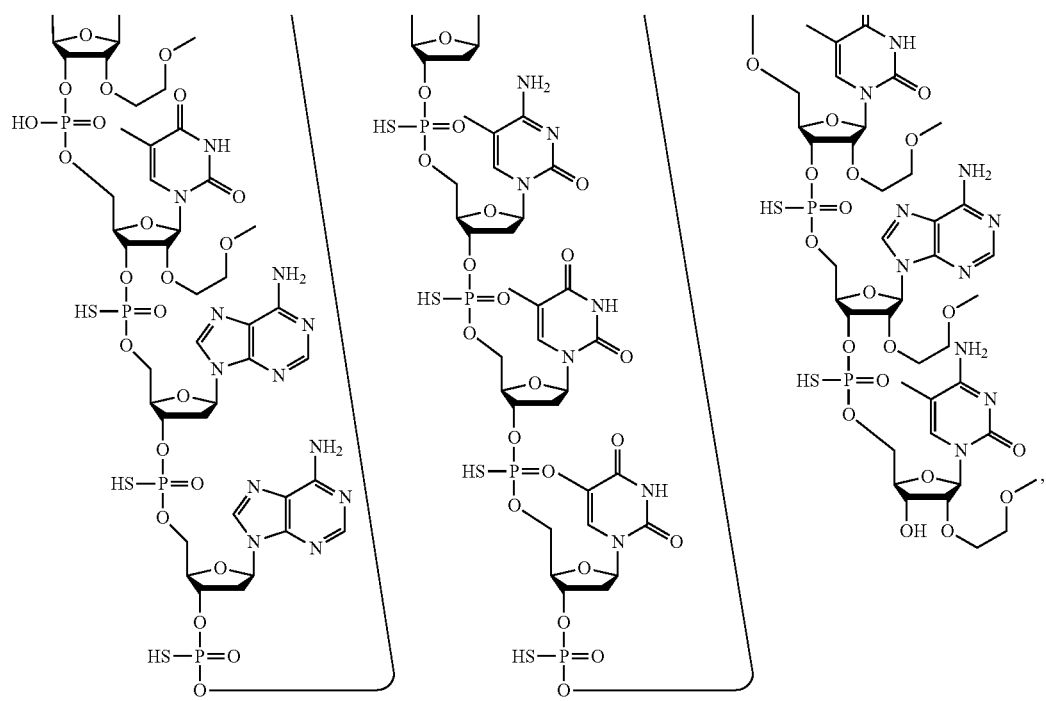
or a salt thereof.

Embodiment 89. A modified oligonucleotide according to the following chemical structure:
(SEQ ID NO: 1914)
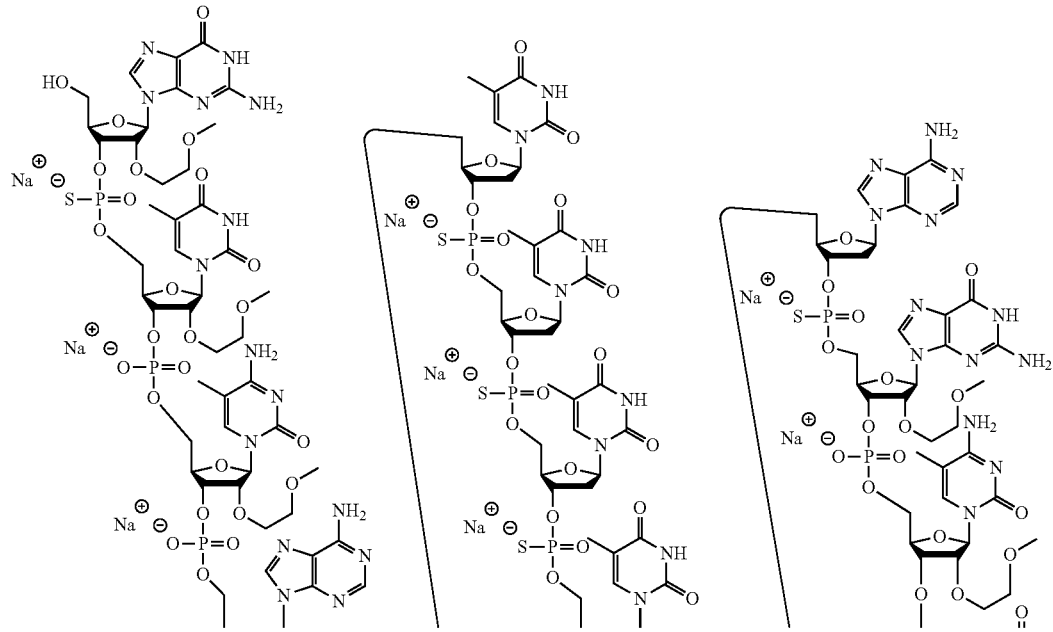
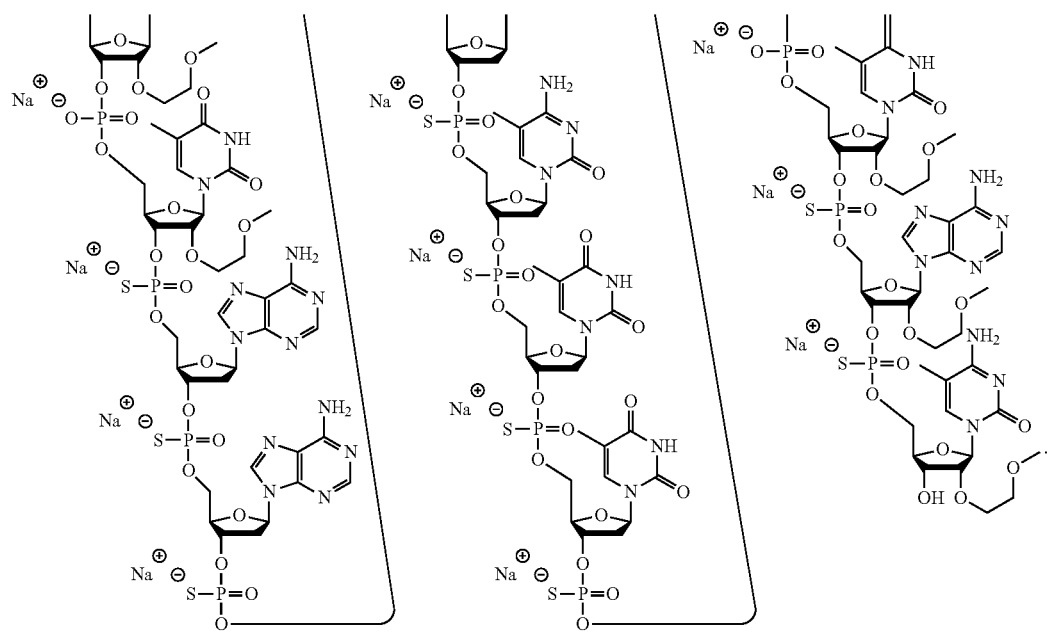

Embodiment 90. A modified oligonucleotide according to the following chemical structure:
(SEQ ID NO: 1939)
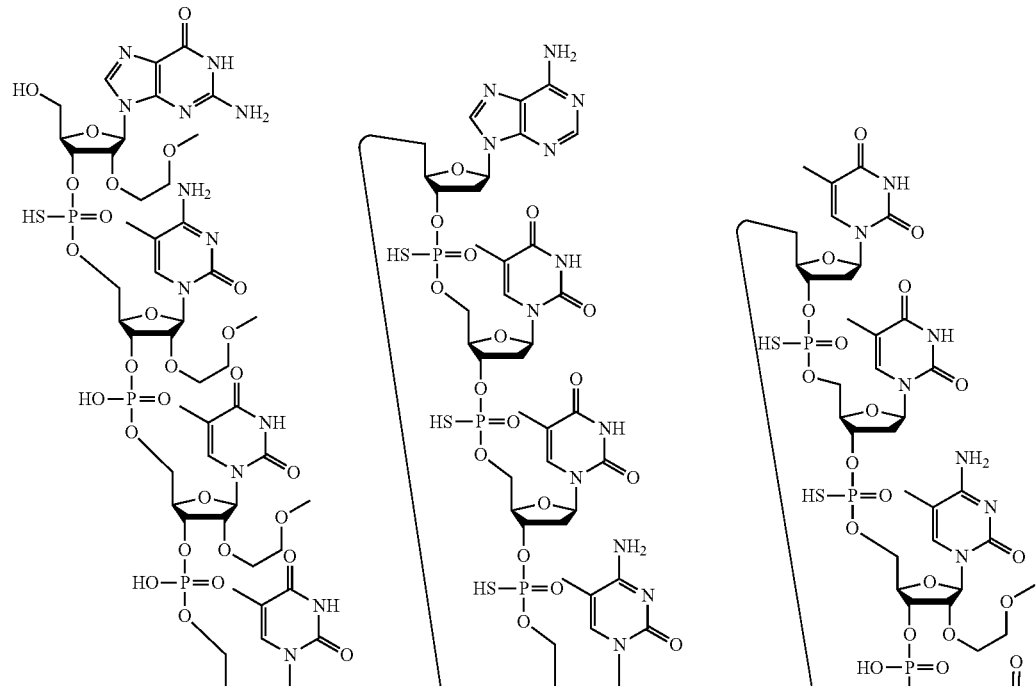
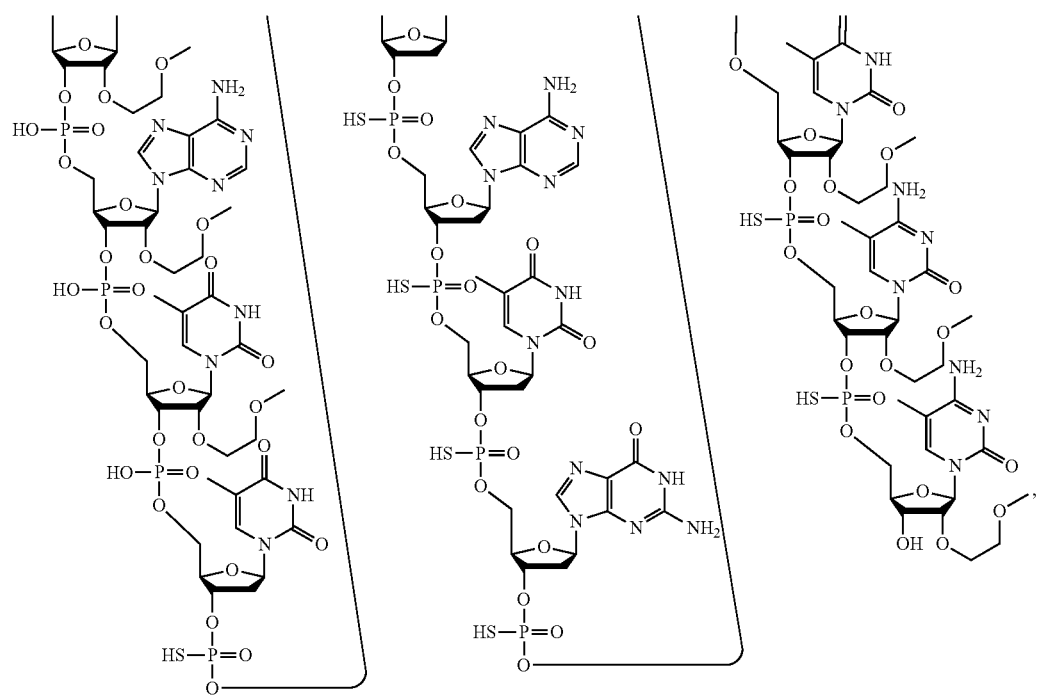
or a salt thereof.

Embodiment 91. A modified oligonucleotide according to the following chemical structure:
(SEQ ID NO: 1939)
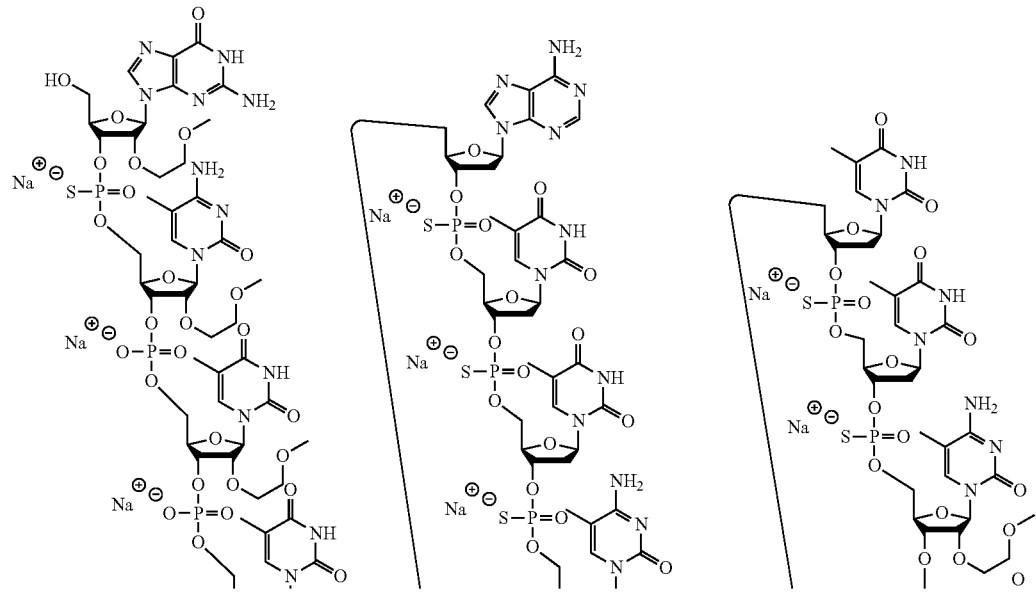
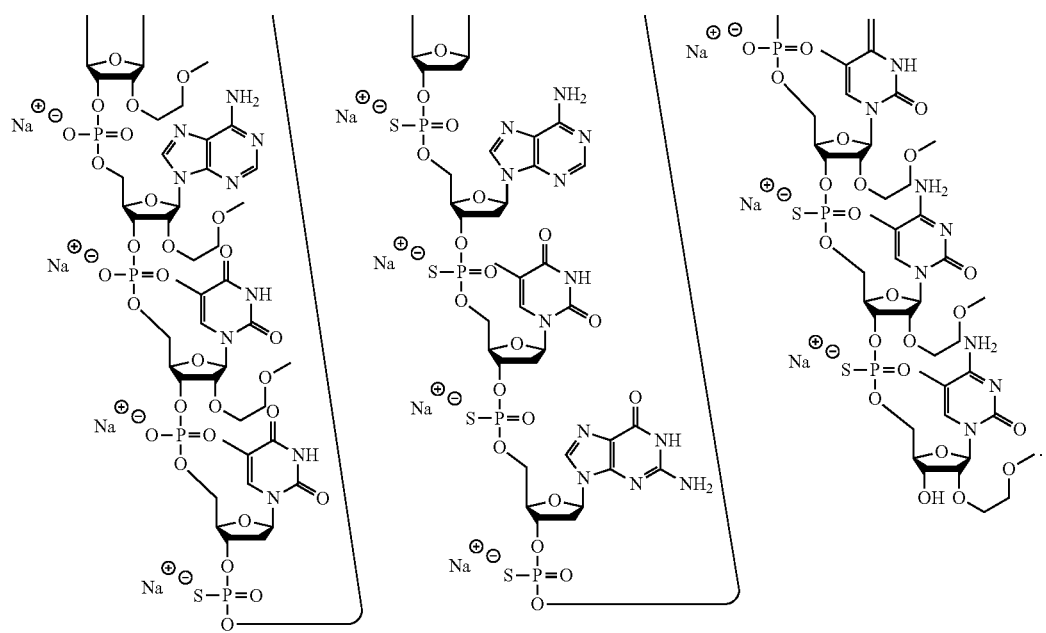

Embodiment 92. A modified oligonucleotide according to the following chemical structure:
(SEQ ID NO: 2302)
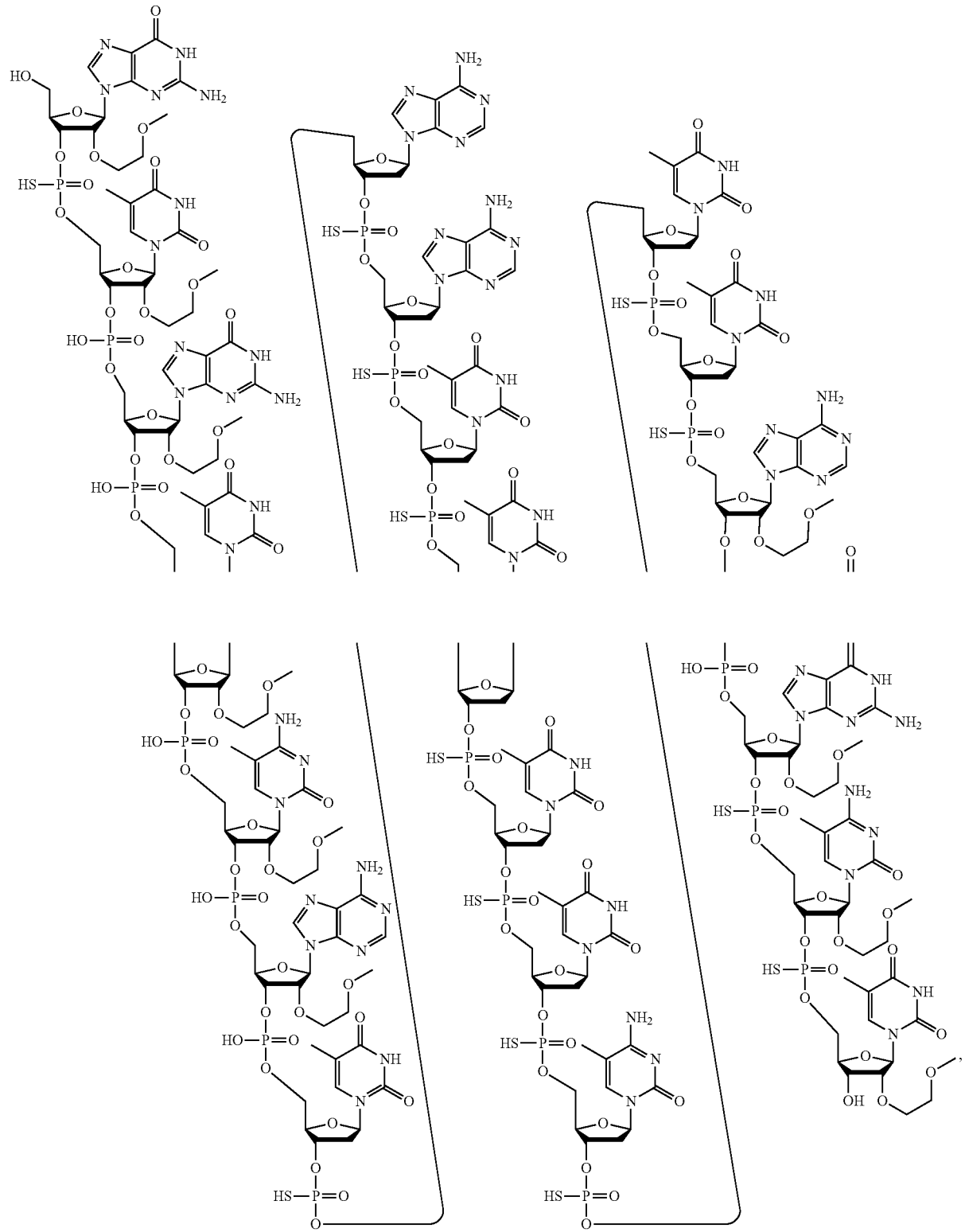
or a salt thereof.

Embodiment 93. A modified oligonucleotide according to the following chemical structure:
(SEQ ID NO: 2302)
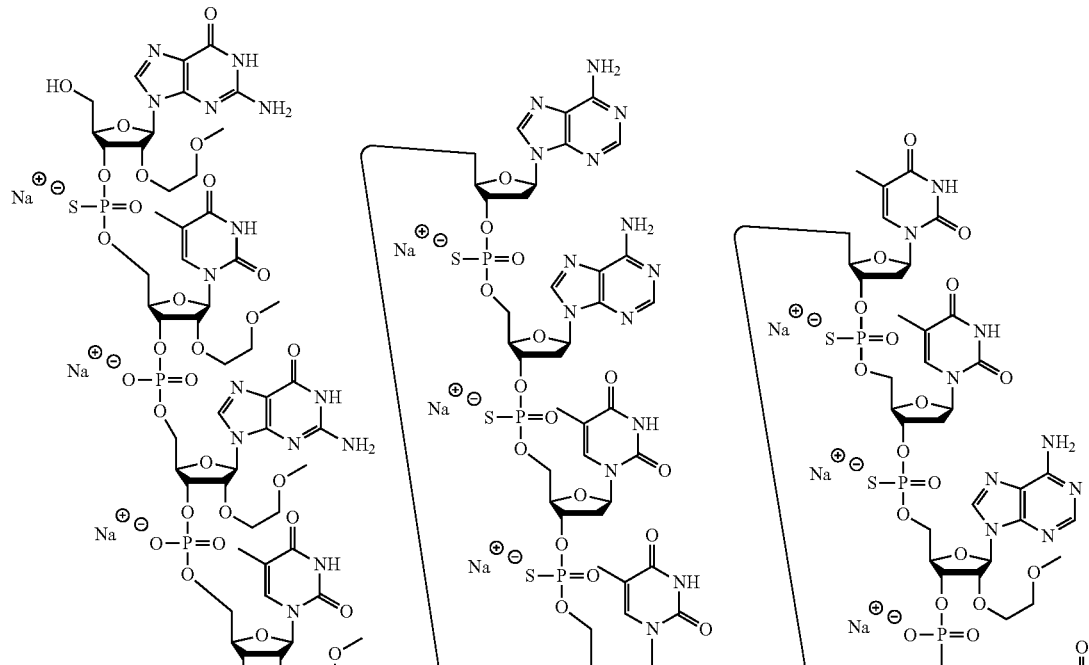
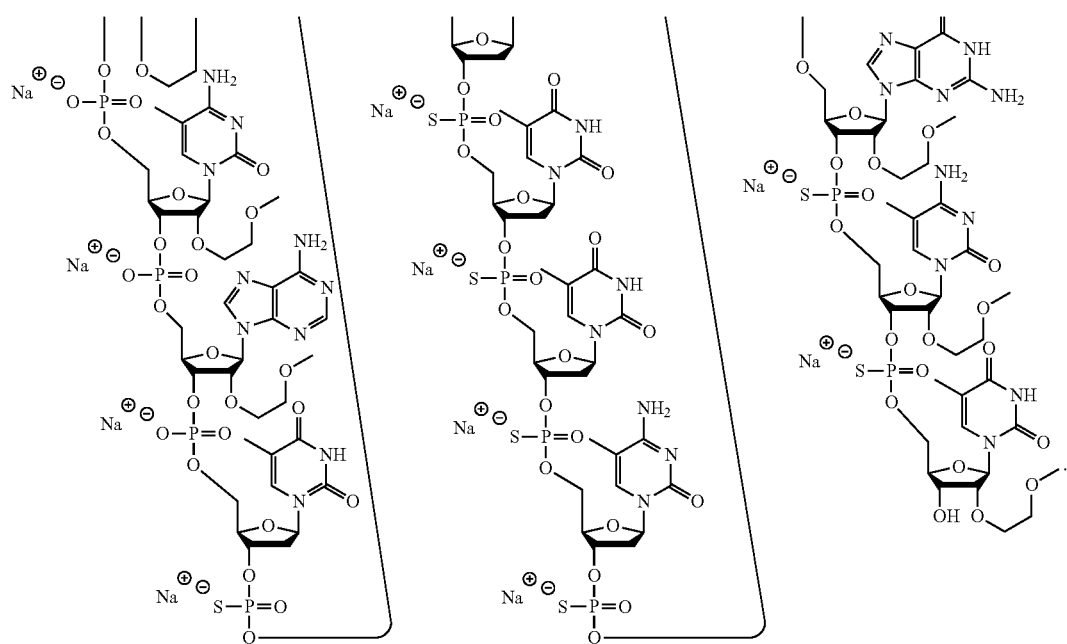

Embodiment 94. A modified oligonucleotide according to the following chemical structure:
(SEQ ID NO: 2750)
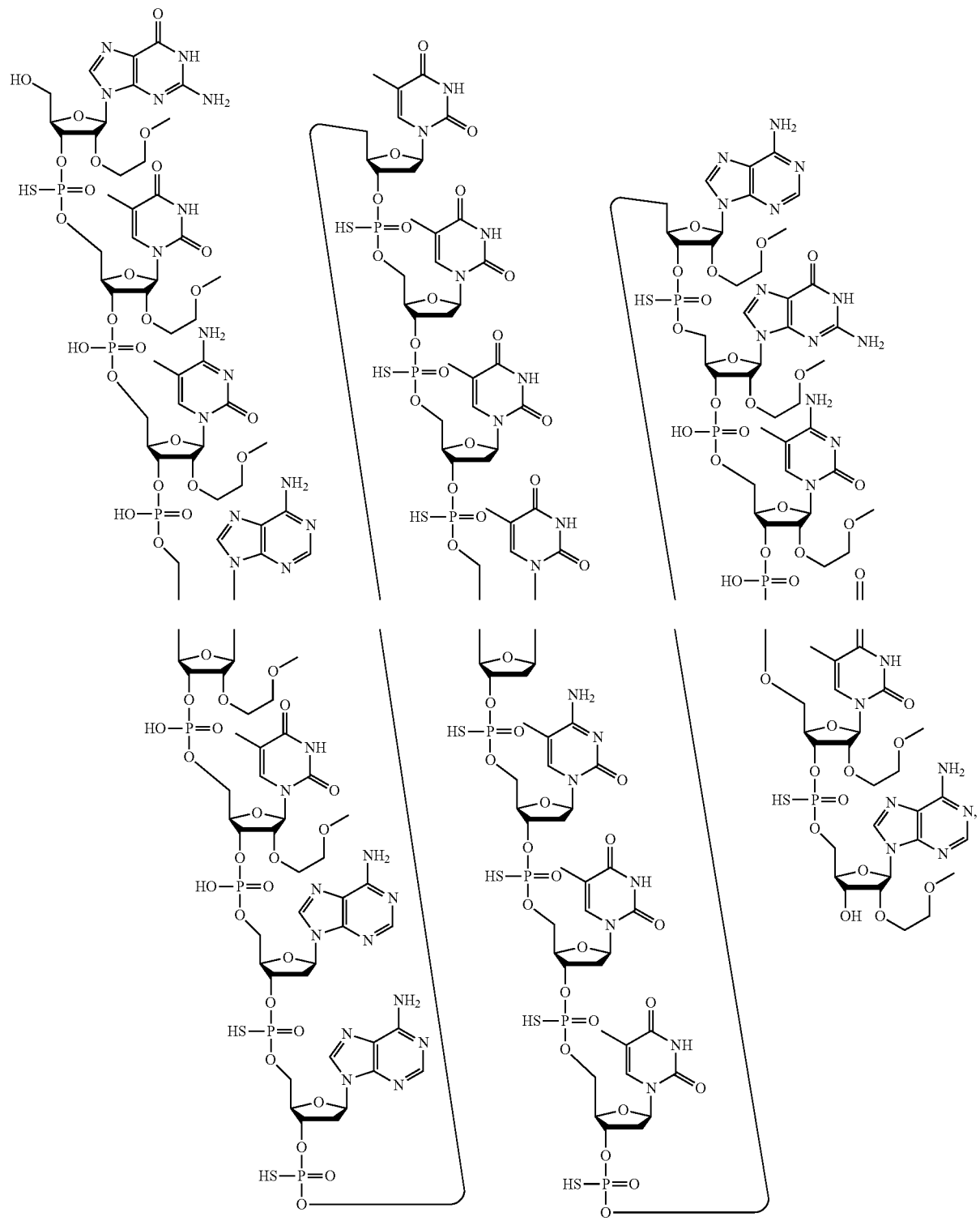
or a salt thereof.

Embodiment 95. A modified oligonucleotide according to the following chemical structure:
(SEQ ID NO: 2750)
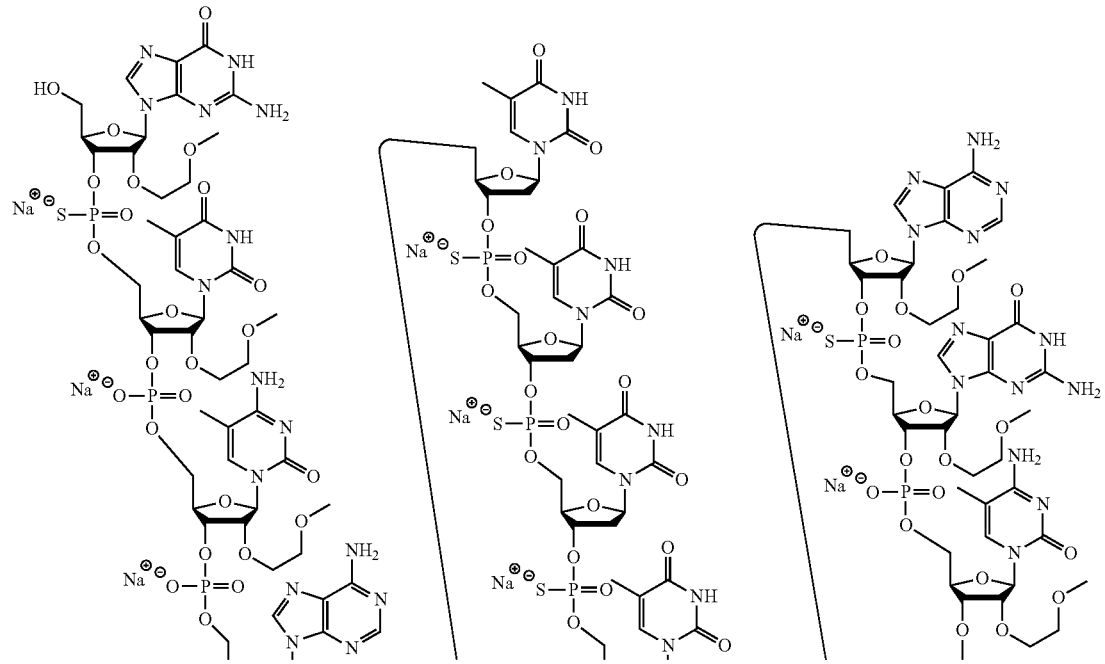
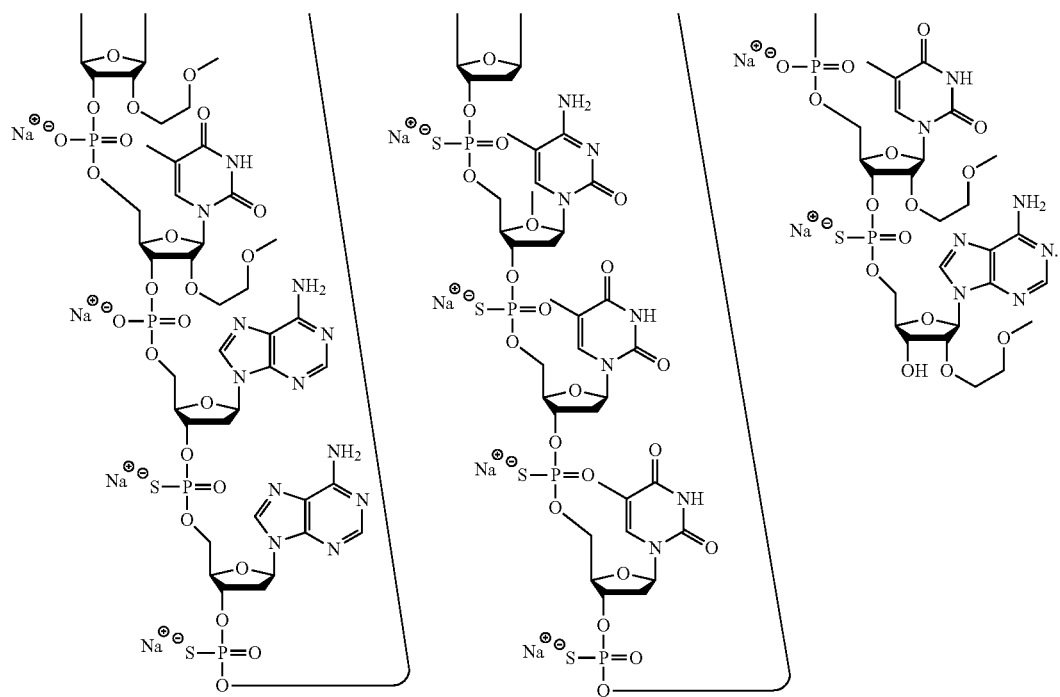

Embodiment 96. A modified oligonucleotide according to the following chemical structure:
(SEQ ID NO: 2739)
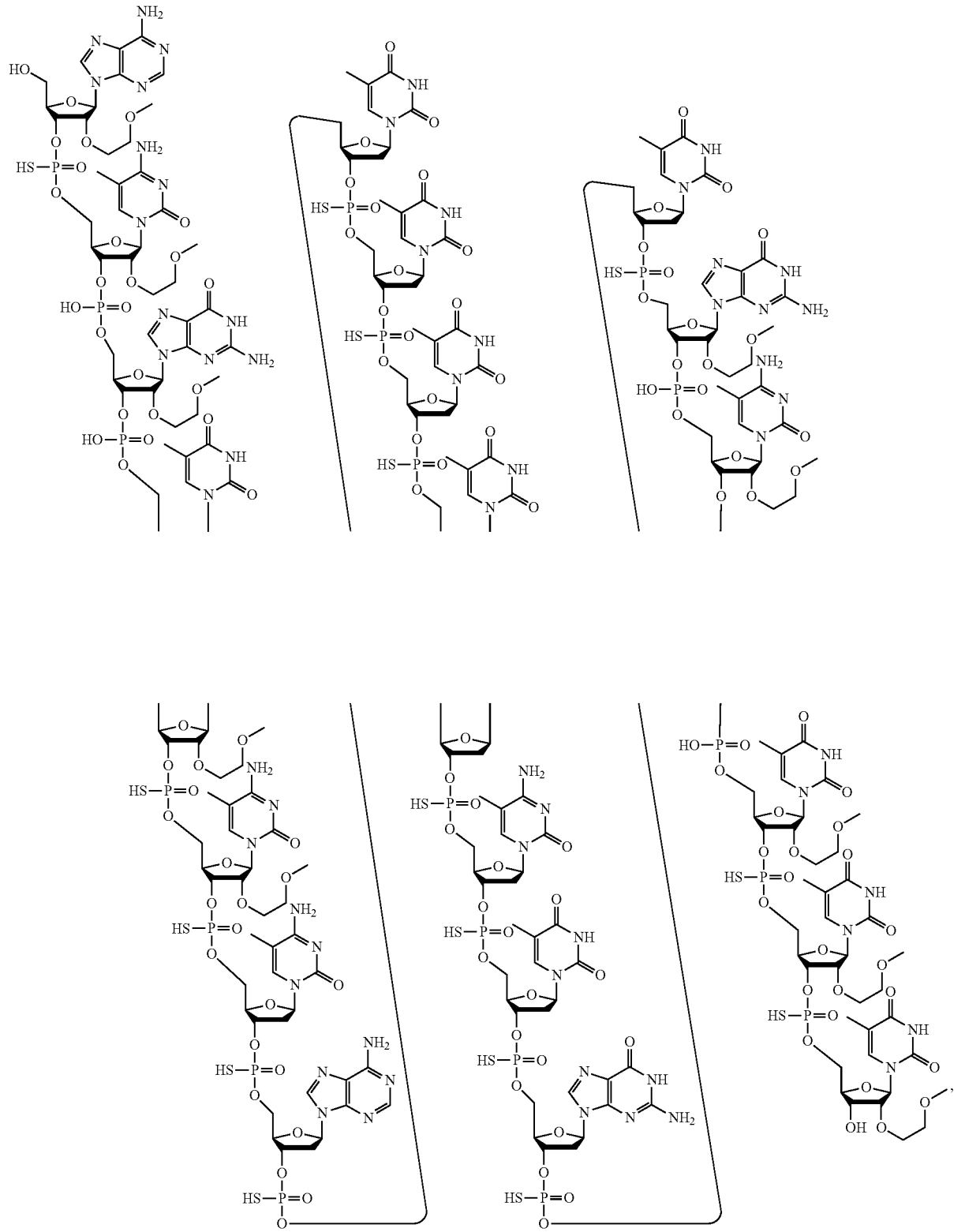
or a salt thereof.

Embodiment 97. A modified oligonucleotide according to the following chemical structure:
(SEQ ID NO: 2739)
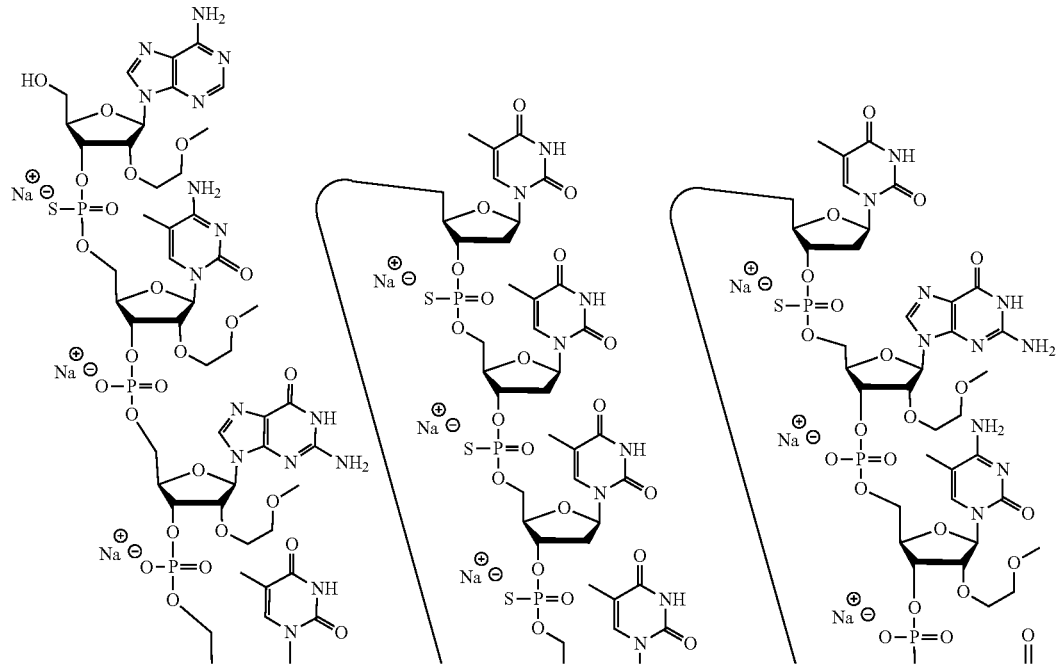
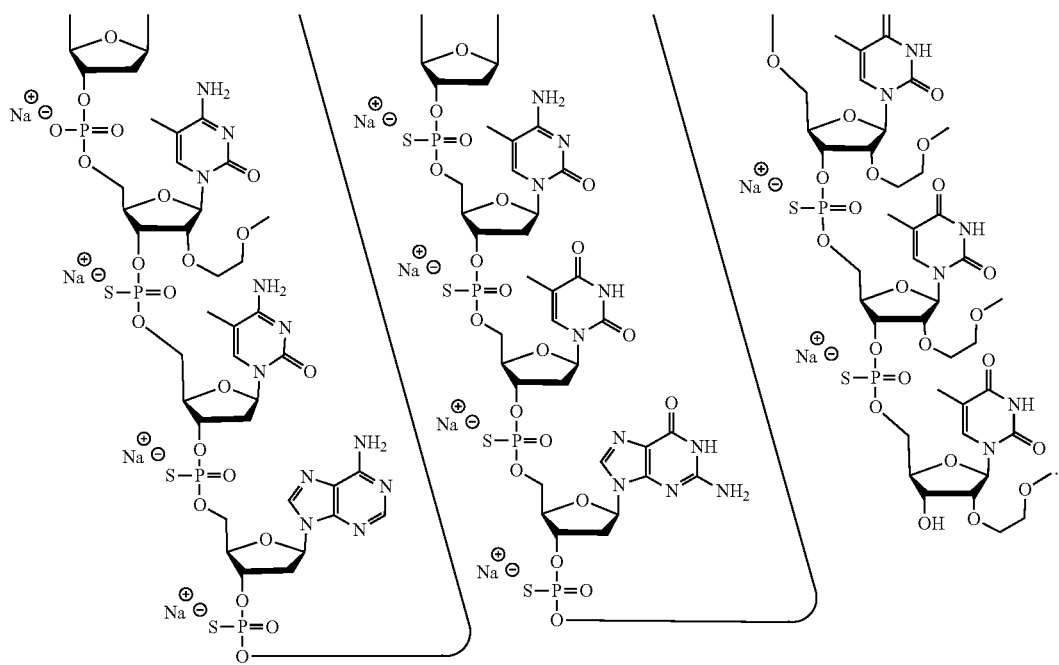

Embodiment 98. The modified oligonucleotide of embodiment 86, 88, 90, 92, 94, or 96 which is a sodium salt of the chemical structure.

Embodiment 99. A compound comprising a modified oligonucleotide according to the following chemical notation: Ges Teo $^m$Ceo Aeo Tes Ads Ads Tds Tds Tds Tds $^m$Cds Tds Tds Ads Geo $^m$Ceo Tes Aes $^m$Ce (SEQ ID NO: 1914), wherein,
A=an adenine nucleobase,
$^m$C=a 5-methyl cytosine nucleobase,
G=a guanine nucleobase,
T=a thymine nucleobase,
e=a 2'-MOE modified sugar,
d=a 2'-β-D deoxyribosyl sugar,
s=a phosphorothioate internucleoside linkage, and
o=a phosphodiester internucleoside linkage.

Embodiment 100. A compound comprising a modified oligonucleotide according to the following chemical notation: Ges Teo $^m$Ceo Aeo Teo Aeo Ads Tds Tds Tds Tds $^m$Cds Tds Tds Ads Gds $^m$Ceo Tes Aes $^m$Ce (SEQ ID NO: 1914), wherein,
A=an adenine nucleobase,
$^m$C=a 5-methyl cytosine nucleobase,
G=a guanine nucleobase,
T=a thymine nucleobase,
c=a 2'-MOE modified sugar,
d=a 2'-β-D deoxyribosyl sugar,
s=a phosphorothioate internucleoside linkage, and
o=a phosphodiester internucleoside linkage.

Embodiment 101. A compound comprising a modified oligonucleotide according to the following chemical notation: Ges $^m$Ceo Teo Teo Aeo Teo Tds Ads Tds Tds $^m$Cds Ads Tds Gds Tds Tds $^m$Ceo Tes $^m$Ces $^m$Ce (SEQ ID NO: 1939), wherein,
A=an adenine nucleobase,
$^m$C=a 5-methyl cytosine nucleobase,
G=a guanine nucleobase,
T=a thymine nucleobase,
e=a 2'-MOE modified sugar,
d=a 2'-β-D deoxyribosyl sugar,
s=a phosphorothioate internucleoside linkage, and
o=a phosphodiester internucleoside linkage.

Embodiment 102. A compound comprising a modified oligonucleotide according to the following chemical notation: Ges Teo Geo Teo $^m$Ceo Aeo Tds Ads Ads Tds Tds Tds Tds $^m$Cds Tds Tds Aeo Ges $^m$Ces Te (SEQ ID NO: 2302), wherein,
A=an adenine nucleobase,
mC=a 5-methyl cytosine nucleobase,
G=a guanine nucleobase,
T=a thymine nucleobase,
e=a 2'-MOE modified sugar,
d=a 2'-β-D deoxyribosyl sugar,
s=a phosphorothioate internucleoside linkage, and
o=a phosphodiester internucleoside linkage.

Embodiment 103. A compound comprising a modified oligonucleotide according to the following chemical notation: Ges Teo mCeo Aeo Teo Ads Ads Tds Tds Tds Tds mCds Tds Tds Aes Geo mCeo Tes Ae (SEQ ID NO: 2750), wherein,
A=an adenine nucleobase,
mC=a 5-methyl cytosine nucleobase,
G=a guanine nucleobase,
T=a thymine nucleobase,
e=a 2'-MOE modified sugar,
d=a 2'-β-D deoxyribosyl sugar,
s=a phosphorothioate internucleoside linkage, and
o=a phosphodiester internucleoside linkage.

Embodiment 104. A compound comprising a modified oligonucleotide according to the following chemical notation: Aes mCeo Geo Teo mCes mCds Ads Tds Tds Tds Tds mCds Tds Gds Tds Geo mCeo Tes Tes Te (SEQ ID NO: 2739), wherein,
A=an adenine nucleobase,
mC=a 5-methyl cytosine nucleobase,
G=a guanine nucleobase,
T=a thymine nucleobase,
c=a 2'-MOE modified sugar,
d=a 2'-β-D deoxyribosyl sugar,
s=a phosphorothioate internucleoside linkage, and
o=a phosphodiester internucleoside linkage.

Embodiment 105. The compound of any of embodiments 99-104, comprising the modified oligonucleotide covalently linked to a conjugate group.

Embodiment 106. A chirally enriched population of modified oligonucleotides of any of embodiments 86-105, wherein the population is enriched for modified oligonucleotides comprising at least one particular phosphorothioate internucleoside linkage having a particular stereochemical configuration.

Embodiment 107. The chirally enriched population of embodiment 106, wherein the population is enriched for modified oligonucleotides comprising at least one particular phosphorothioate internucleoside linkage having the (Sp) or (Rp) configuration.

Embodiment 108. The chirally enriched population of embodiment 106, wherein the population is enriched for modified oligonucleotides having a particular, independently selected stereochemical configuration at each phosphorothioate internucleoside linkage Embodiment 109. The chirally enriched population of embodiment 106, wherein the population is enriched for modified oligonucleotides having the (Sp) or (Rp) configuration at each phosphorothioate internucleoside linkage.

Embodiment 110. The chirally enriched population of embodiment 106, wherein the population is enriched for modified oligonucleotides having the (Rp) configuration at one particular phosphorothioate internucleoside linkage and the (Sp) configuration at each of the remaining phosphorothioate internucleoside linkages.

Embodiment 111. The chirally enriched population of embodiment 106 or embodiment 108 wherein the population is enriched for modified oligonucleotides having at least 3 contiguous phosphorothioate internucleoside linkages in the Sp, Sp, and Rp configurations, in the 5' to 3' direction.

Embodiment 112. A population of modified oligonucleotides of any of embodiments 86-105, wherein all of the phosphorothioate internucleoside linkages of the modified oligonucleotide are stereorandom. Embodiment 113. A pharmaceutical composition comprising the population of modified oligonucleotides of any of embodiments 106-112 and a pharmaceutically acceptable carrier or diluent.

Embodiment 114. A pharmaceutical composition of any of embodiments 86-105, and a pharmaceutically acceptable diluent or carrier.

Embodiment 115. The pharmaceutical composition of embodiment 114, comprising a pharmaceutically acceptable diluent, wherein the pharmaceutically acceptable diluent is phosphate-buffered saline or artificial cerebrospinal fluid.

Embodiment 116. The pharmaceutical composition of embodiment 115, wherein the pharmaceutical composition consists essentially of the modified oligonucleotide and phosphate-buffered saline or artificial cerebrospinal fluid.

I. Certain Oligonucleotides

In certain embodiments, provided herein are oligomeric compounds comprising oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 4', and/or 5' positions. In certain embodiments one or more non-bridging substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)- alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5-methyl (R or S), 5'-vinyl, and 5'-methoxy. In certain embodiments, non-bicyclic modified sugar moieties comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836).

In certain embodiments, a 2'-substituted non-bicyclic modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted non-bicyclic modified nucleoside comprises a sugar moiety comprising a non-bridging 2'-substituent group selected from: F, OCH$_3$, and OCH$_2$CH$_2$OCH$_3$.

Certain modified sugar moieties comprise a substituent that bridges two atoms of the furanosyl ring to form a second ring, resulting in a bicyclic sugar moiety. In certain such embodiments, the bicyclic sugar moiety comprises a bridge between the 4' and the 2 furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt"), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., J. Org. Chem., 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)—O- 2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., *Nucleic Acids Research*, 1997, 25(22), 4429-4443, Alback et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J Org. Chem.*, 1998, 63, 10035-10039; Srivastava et al., *J. Am. Chem. Soc.*, 20017, 129, 8362-8379; Wengel et a., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

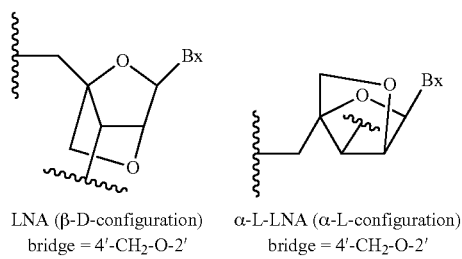

LNA (β-D-configuration)
bridge = 4'-CH$_2$-O-2'

α-L-LNA (α-L-configuration)
bridge = 4'-CH$_2$-O-2'

α-L-methyleneoxy (4'-CH$_2$—O-2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

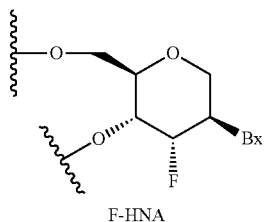

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

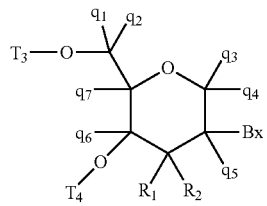

wherein, independently, for each of said modified THP nucleoside:
Bx is a nucleobase moiety;
T$_3$ and T$_4$ are each, independently, an internucleoside linking group linking the modified THP nucleoside to the remainder of an oligonucleotide or one of T$_3$ and T$_4$ is an internucleoside linking group linking the modified THP nucleoside to the remainder of an oligonucleotide and the other of T$_3$ and T$_4$ is H, a hydroxyl protecting group, a linked conjugate group, or a 5' or 3'-terminal group;
q$_1$, q$_2$, q$_3$, q$_4$, q$_5$, q$_6$ and q$_7$ are each, independently, H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, or substituted C$_2$-C$_6$ alkynyl; and
each of R$_1$ and R$_2$ is independently selected from among: hydrogen, halogen, substituted or unsubstituted alkoxy, NJ$_1$J$_2$, SJ$_1$, N$_3$, OC(=X)J$_1$, OC(=X)NJ$_1$J$_2$, NJ$_3$C(=X)NJ$_1$J$_2$, and CN, wherein X is O, S or NJ$_1$, and each J$_1$, J$_2$, and J$_3$ is, independently, H or C$_1$-C$_6$ alkyl.

In certain embodiments, modified THP nucleosides are provided wherein q$_1$, q$_2$, q$_3$, q$_4$, q$_5$, q$_6$ and q$_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

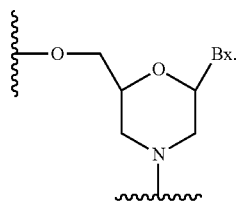

In certain embodiments, morpholinos may be modified, for example by adding or altering various substituent groups from the above morpholino structure. Such sugar surrogates are referred to herein as "modified morpholinos." In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Certain Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoyleytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P═O") (also referred to as unmodified or naturally occurring linkages), phosphotriesters, methylphosphonates, phosphoramidates, and phosphorothioates ("P═S"), and phosphorodithioates ("HS—P═S"). Representative non-phosphorus containing internucleoside linking groups include but are not limited to methylenemethylimino (—CH$_2$—N(CH$_3$)—O—CH$_2$—), thiodiester, thionocarbamate (—O—C(═O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., JACS 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

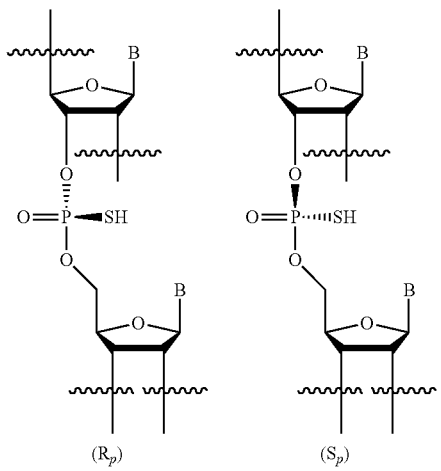

Unless otherwise indicated, chiral internucleoside linkages of modified oligonucleotides described herein can be stereorandom or in a particular stereochemical configuration.

Neutral internucleoside linkages include, without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), methoxypropyl, and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 6 or 7 nucleosides. In certain embodiments, each nucleoside of each wing of a gapmer is a modified nucleoside. In certain embodiments, at least one nucleoside of each wing of a gapmer is a modified nucleoside. In certain embodiments, at least two nucleosides of each wing of a gapmer are modified nucleosides. In certain embodiments, at least three nucleosides of each wing of a gapmer are modified nucleosides. In certain embodiments, at least four nucleosides of each wing of a gapmer are modified nucleosides.

In certain embodiments, the gap of a gapmer comprises 7-12 nucleosides. In certain embodiments, each nucleoside of the gap of a gapmer is an unmodified 2'-deoxynucleoside. In certain embodiments, at least one nucleoside of the gap of a gapmer is a modified nucleoside. In certain embodiments, at least one nucleoside of the gap of a gapmer comprises a 2'-deoxyfuranosyl sugar moiety that has an isomeric configuration other than the (i-D-ribosyl configuration.

In certain embodiments, the gapmer is a deoxy gapmer. In certain embodiments, the nucleosides on the gap side of each wing/gap junction are unmodified 2'-deoxynucleosides and the nucleosides on the wing sides of each wing/gap junction are modified nucleosides. In certain embodiments, each nucleoside of the gap is an unmodified 2'-deoxynucleoside. In certain embodiments, each nucleoside of each wing of a gapmer is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain embodiments, each nucleoside of the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

Herein, the lengths (number of nucleosides) of the three regions of a gapmer may be provided using the notation [# of nucleosides in the 5'-wing]-[# of nucleosides in the gap]-[# of nucleosides in the 3'-wing]. Thus, a 5-10-5 gapmer consists of 5 linked nucleosides in each wing and 10 linked nucleosides in the gap. Where such nomenclature is followed by a specific modification, that modification is the modification in each sugar of each wing and the gap nucleosides comprise unmodified deoxynucleosides. Thus, a 5-10-5 MOE gapmer consists of 5 linked 2'-MOE modified nucleosides in the 5'-wing, 10 linked deoxynucleosides in the gap, and 5 linked 2'-MOE nucleosides in the 3'-wing. In certain such embodiments, the deoxynucleosides in the gap comprise a 2'-β-D-deoxyribosyl sugar. A mixed wing gapmer has at least two different modified sugars in the 5' and/or 3' wing.

In certain embodiments, modified oligonucleotides are 5-10-5 MOE gapmers. In certain embodiments, modified oligonucleotides are 4-10-6 MOE gapmers. In certain embodiments, modified oligonucleotides are 6-10-4 MOE gapmers. In certain embodiments, modified oligonucleotides are 3-10-7 MOE gapmers. In certain embodiments, modified oligonucleotides are 7-10-3 MOE gapmers. In certain embodiments, modified oligonucleotides are 5-8-5 MOE gapmers. In certain embodiments, modified oligonucleotides are 5-9-5 MOE gapmers. In certain embodiments, modified oligonucleotides are X—Y—Z MOE gapmers, wherein X and Z are independently selected from 1, 2, 3, 4, 5, 6, or 7 linked 2'-MOE nucleosides and Y is selected from 7, 8, 9, 10, or 11 linked deoxynucleosides.

In certain embodiments, modified oligonucleotides have a sugar motif selected from the following (5' to 3'): eeeedddddddddddkkeee, eeeeedddddddddddkkee, eeeeeddddddddddkkeee, eeeedddddddddkkeee, eeeedddddddddkkee, eeeeedyddddddddeeeee, eeeeedydddddddeeeee, or eeeeeedyddddddddeeee, wherein 'd' represents a 2'-deoxyribosyl sugar moiety, 'e' represents a 2'-MOE sugar moiety, 'k' represents a cEt sugar moiety, and 'y' represents a 2'-OMe sugar moiety.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methyl cytosines. In certain embodiments, all of the cytosine nucleobases are 5-methyl cytosines and all of the other nucleobases of the modified oligonucleotide are unmodified nucleobases.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, each internucleoside linking group is a phosphodiester internucleoside linkage (P=O). In certain embodiments, each internucleoside linking group of a modified oligonucleotide is a phosphorothioate internucleoside linkage (P=S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate a (Sp) phosphorothioate, and a (Rp) phosphorothioate. In certain embodiments, the sugar motif of a modified oligonucleotide is a gapmer and the internucleoside linkages within the gap are all modified. In certain such embodiments, some or all of the internucleoside linkages in the wings are unmodified phosphodiester internucleoside linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

C. Certain Lengths

It is possible to increase or decrease the length of an oligonucleotide without eliminating activity. For example, in Woolf et al. (Proc. Natl. Acad. Sci. USA 89:7305-7309, 1992), a series of oligonucleotides 13-25 nucleobases in length were tested for their ability to induce cleavage of a target RNA in an oocyte injection model. Oligonucleotides 25 nucleobases in length with 8 or 11 mismatch bases near the ends of the oligonucleotides were able to direct specific cleavage of the target RNA, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

D. Certain Modified Oligonucleotides

In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

E. Certain Populations of Modified Oligonucleotides

Populations of modified oligonucleotides in which all of the modified oligonucleotides of the population have the same molecular formula can be stereorandom populations or chirally enriched populations. All of the chiral centers of all of the modified oligonucleotides are stereorandom in a stereorandom population. In a chirally enriched population, at least one particular chiral center is not stereorandom in the modified oligonucleotides of the population. In certain embodiments, the modified oligonucleotides of a chirally enriched population are enriched for β-D ribosyl sugar moieties, and all of the phosphorothioate internucleoside linkages are stereorandom. In certain embodiments, the modified oligonucleotides of a chirally enriched population are enriched for both β-D ribosyl sugar moieties and at least one, particular phosphorothioate internucleoside linkage in a particular stereochemical configuration.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid.

II. Certain Oligomeric Compounds

In certain embodiments, provided herein are oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., Bioorg. Med. Chem. Lett., 1994, 4, 1053-1060), a thioether, e.g., hexyl-S-tritylthiol (Manoharan et al., Ann. N. Y. Acad. Sci., 1992, 660, 306-309; Manoharan et al., Bioorg. Med. Chem. Lett., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid a palmityl moiety (Mishra et al., Biochim. Biophys. Acta, 1995, 1264, 229-237), an octadecylamine or hexylamino-carbonyl-oxycholesterol moiety (Crooke et al., J. Pharmacol. Exp. Ther., 1996, 277, 923-937), a tocopherol group (Nishina et al., Molecular Therapy Nucleic Acids, 2015, 4, e220; and Nishina et al., Molecular Therapy, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methyl cytosine, 4-N-benzoyl-5-methyl cytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxynucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

B. Certain Terminal Groups

In certain embodiments, oligomeric compounds comprise one or more terminal groups. In certain such embodiments, oligomeric compounds comprise a stabilized 5'-phosphate.

Stabilized 5'-phosphates include, but are not limited to 5'-phosphanates, including, but not limited to 5'-vinylphosphonates. In certain embodiments, terminal groups comprise one or more abasic nucleosides and/or inverted nucleosides. In certain embodiments, terminal groups comprise one or more 2'-linked nucleosides. In certain such embodiments, the 2'-linked nucleoside is an abasic nucleoside.

III. Oligomeric Duplexes

In certain embodiments, oligomeric compounds described herein comprise an oligonucleotide, having a nucleobase sequence complementary to that of a target nucleic acid. In certain embodiments, an oligomeric compound is paired with a second oligomeric compound to form an oligomeric duplex. Such oligomeric duplexes comprise a first oligomeric compound having a region complementary to a target nucleic acid and a second oligomeric compound having a region complementary to the first oligomeric compound. In certain embodiments, the first oligomeric compound of an oligomeric duplex comprises or consists of (1) a modified or unmodified oligonucleotide and optionally a conjugate group and (2) a second modified or unmodified oligonucleotide and optionally a conjugate group. Either or both oligomeric compounds of an oligomeric duplex may comprise a conjugate group. The oligonucleotides of each oligomeric compound of an oligomeric duplex may include non-complementary overhanging nucleosides.

IV. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they reduce or inhibit the amount or activity of a target nucleic acid by 25% or more in the standard cell assay. In certain embodiments, antisense compounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are antisense compounds that are sufficiently "DNA-like" to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein and/or a phenotypic change in a cell or animal.

V. Certain Target Nucleic Acids

In certain embodiments, oligomeric compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature mRNA and a pre-mRNA, including intronic, exonic and untranslated regions. In certain embodiments, the target RNA is a mature mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is the RNA transcriptional product of a retrogene. In certain embodiments, the target nucleic acid is a non-coding RNA. In certain such embodiments, the target non-coding RNA is selected from: a long non-coding RNA, a short non-coding RNA, an intronic RNA molecule.

A. Complementarity/Mismatches to the Target Nucleic Acid

It is possible to introduce mismatch bases without eliminating activity. For example, Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and a 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligonucleotides are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a region that is 100% or fully complementary to a target nucleic acid. In certain embodiments, the region of full complementarity is from 6 to 20, 10 to 18, or 18 to 20 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligonucleotide is improved. In certain embodiments, the mismatch is specifically positioned within an oligonucleotide having a gapmer motif. In certain embodiments, the mismatch is at position 1, 2, 3, 4, 5, 6, 7, or 8 from the 5'-end of the gap region. In certain embodiments, the mismatch is at position 9, 8, 7, 6, 5, 4, 3, 2, 1 from the 3'-end of the gap region. In certain embodiments, the mismatch is at position 1, 2, 3, or 4 from the 5'-end of the wing region. In certain embodiments, the mismatch is at position 4, 3, 2, or 1 from the 3'-end of the wing region.

B. PRNP

In certain embodiments, oligomeric compounds comprise or consist of an oligonucleotide comprising a region that is complementary to a target nucleic acid, wherein the target nucleic acid is PRNP. In certain embodiments, PRNP nucleic acid has the sequence set forth in SEQ ID NO: I (GENBANK Accession No: NM_000311.4) or SEQ ID NO: 2 (GENBANK Accession No: NC_000020.11 truncated from nucleotides 4683001 to 4705000). In certain embodiments, PRNP nucleic acid has the sequence set forth in SEQ ID NO: 3 (GENBANK Accession No.: NM_001080123.2), which is a splicing variant of SEQ ID NO: 1. In certain embodiments, PRNP nucleic acid has the sequence set forth in SEQ ID NO: 4 (ENSEMBL Accession No. ENST00000359125.6 from ENSEMBL version 98: September 2019, human reference assembly version GRCh38.p13 located on the reverse strand of chromosome 20 (CM000682.2) from positions 63,406, 137 to U.S. Pat. No. 63,472,590; Yates, et al., "Ensembl 2020", Nucleic Acids Research, gkz966, 2019), which is a splicing variant of SEQ ID NO: 1.

In certain embodiments, contacting a cell with an oligomeric compound complementary to SEQ ID NO: 1, SEQ ID NO: 2, SEQ ID NO: 3, or SEQ ID NO: 4 reduces the amount of PRNP RNA, and in certain embodiments reduces the amount of PrP protein. In certain embodiments, the oligomeric compound consists of a modified oligonucleotide. In certain embodiments, contacting a cell with an oligomeric compound complementary to SEQ ID NO: 1, SEQ ID NO: 2, SEQ ID NO: 3, or SEQ ID NO: 4 ameliorates one or more symptom or hallmark of a neurodegenerative disease. In certain embodiments, the oligomeric compound consists of a modified oligonucleotide. In certain embodiments, the symptom or hallmark is spongiform changes in the brain, development of abnormal protein aggregates, neuronal loss, markers of neuronal loss, rapidly progressing dementia, and death. In certain embodiments, the oligomeric compound consists of a modified oligonucleotide.

In certain embodiments, administration of an oligomeric compound complementary to SEQ ID NO: 1, SEQ ID NO: 2, SEQ ID NO: 3, or SEQ ID NO: 4 reduces the detectable amount of PrP protein in the CSF. In certain embodiments, the PrP protein is $PrP^C$. In certain embodiments, the PrP protein is $PrP^{Sc}$. In certain embodiments, the PrP protein is $PrP^C$ and $PrP^{Sc}$.

C. Certain Target Nucleic Acids in Certain Tissues

In certain embodiments, oligomeric compounds comprise or consist of an oligonucleotide comprising a region that is complementary to a target nucleic acid, wherein the target nucleic acid is expressed in a pharmacologically relevant tissue. In certain embodiments, the pharmacologically relevant tissues are the cells and tissues that comprise the central nervous system (CNS). Such tissues include brain tissues, such as, cortex, substantia nigra, striatum, midbrain, and brainstem and spinal cord.

VI. Certain Pharmaceutical Compositions

In certain embodiments, described herein are pharmaceutical compositions comprising one or more oligomeric compounds. In certain embodiments, the one or more oligomeric compounds each consists of a modified oligonucleotide. In certain embodiments, the pharmaceutical composition comprises a pharmaceutically acceptable diluent or carrier. In certain embodiments, a pharmaceutical composition comprises or consists of a sterile saline solution and one or more oligomeric compound. In certain embodiments, the sterile saline is pharmaceutical grade saline. In certain embodiments, a pharmaceutical composition comprises or consists of one or more oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, the sterile PBS is pharmaceutical grade PBS. In certain embodiments, a pharmaceutical composition comprises or consists of one or more oligomeric compound and artificial cerebrospinal fluid. In certain embodiments, the artificial cerebrospinal fluid is pharmaceutical grade.

In certain embodiments, a pharmaceutical composition comprises a modified oligonucleotide and artificial cerebrospinal fluid. In certain embodiments, a pharmaceutical composition consists of a modified oligonucleotide and artificial cerebrospinal fluid. In certain embodiments, a pharmaceutical composition consists essentially of a modified oligonucleotide and artificial cerebrospinal fluid. In certain embodiments, the artificial cerebrospinal fluid is pharmaceutical grade.

In certain embodiments, pharmaceutical compositions comprise one or more oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to an animal, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal (IT), intracerebroventricular (ICV), etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

VII. Certain Compositions

1. Compound No. 1238994

In certain embodiments, Compound No. 1238994 is characterized as a 5-10-5 MOE gapmer having a sequence of (from 5' to 3') GTCATAATTTTCTTAGCTAC (SEQ ID NO: 1914), wherein each of nucleosides 1-5 and 16-20 (from 5' to 3') are 2'-MOE nucleosides and each of nucleosides 6-15 are 2'-R-D-deoxynucleosides, wherein the internucleoside linkages between nucleosides 2 to 3, 3 to 4, 4 to 5, 16 to 17, and 17 to 18 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No. 1238994 is represented by the following chemical notation (5' to 3'): Ges Teo $^m$Ceo Aeo Tes Ads Ads Tds Tds Tds Tds $^m$Cds Tds Tds Ads Geo $^m$Ceo Tes Aes $^m$Ce (SEQ ID NO: 1914), wherein, A=an adenine nucleobase,
$^m$C=a 5-methyl cytosine nucleobase,
G=a guanine nucleobase,
T=a thymine nucleobase,
e=a 2'-MOE modified sugar,
d=a 2'-β-D-deoxyribosyl sugar,
s=a phosphorothioate internucleoside linkage, and
o=a phosphodiester internucleoside linkage.

In certain embodiments, Compound No. 1238994 is represented by the following chemical structure:
(SEQ ID NO: 1914)
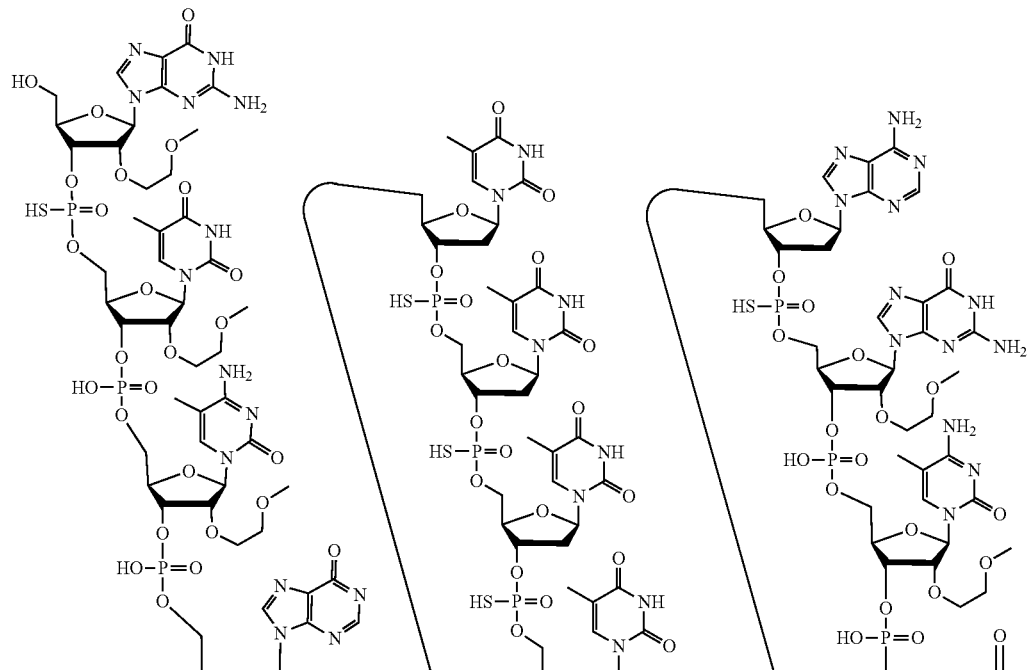
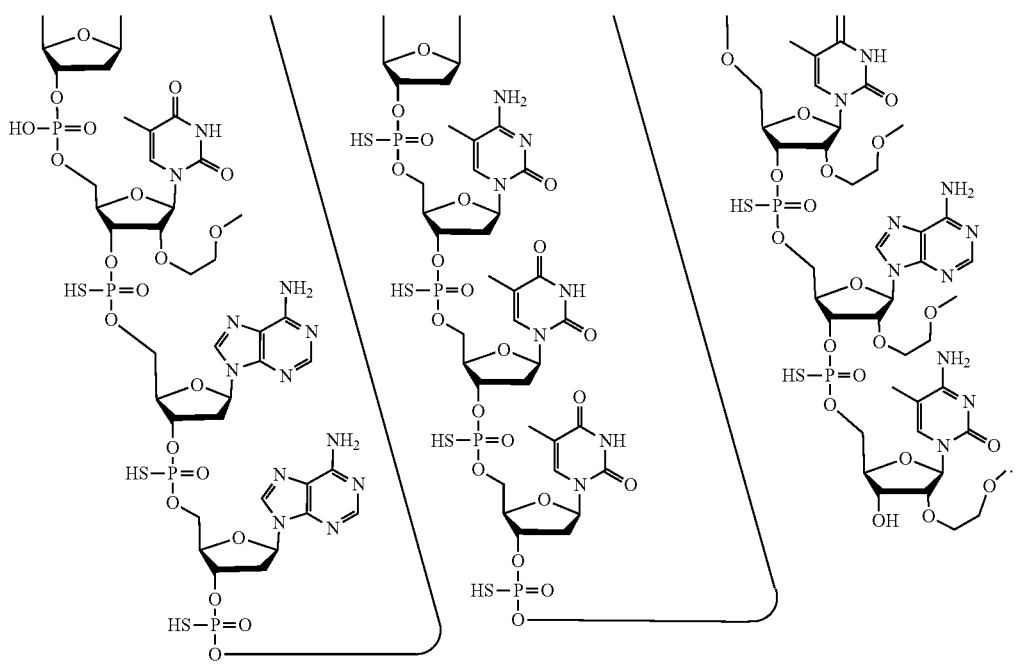

Structure 1. Compound No. 1238994

In certain embodiments, the sodium salt of Compound No. 1238994 is represented by the following chemical structure:

(SEQ ID NO: 1914)

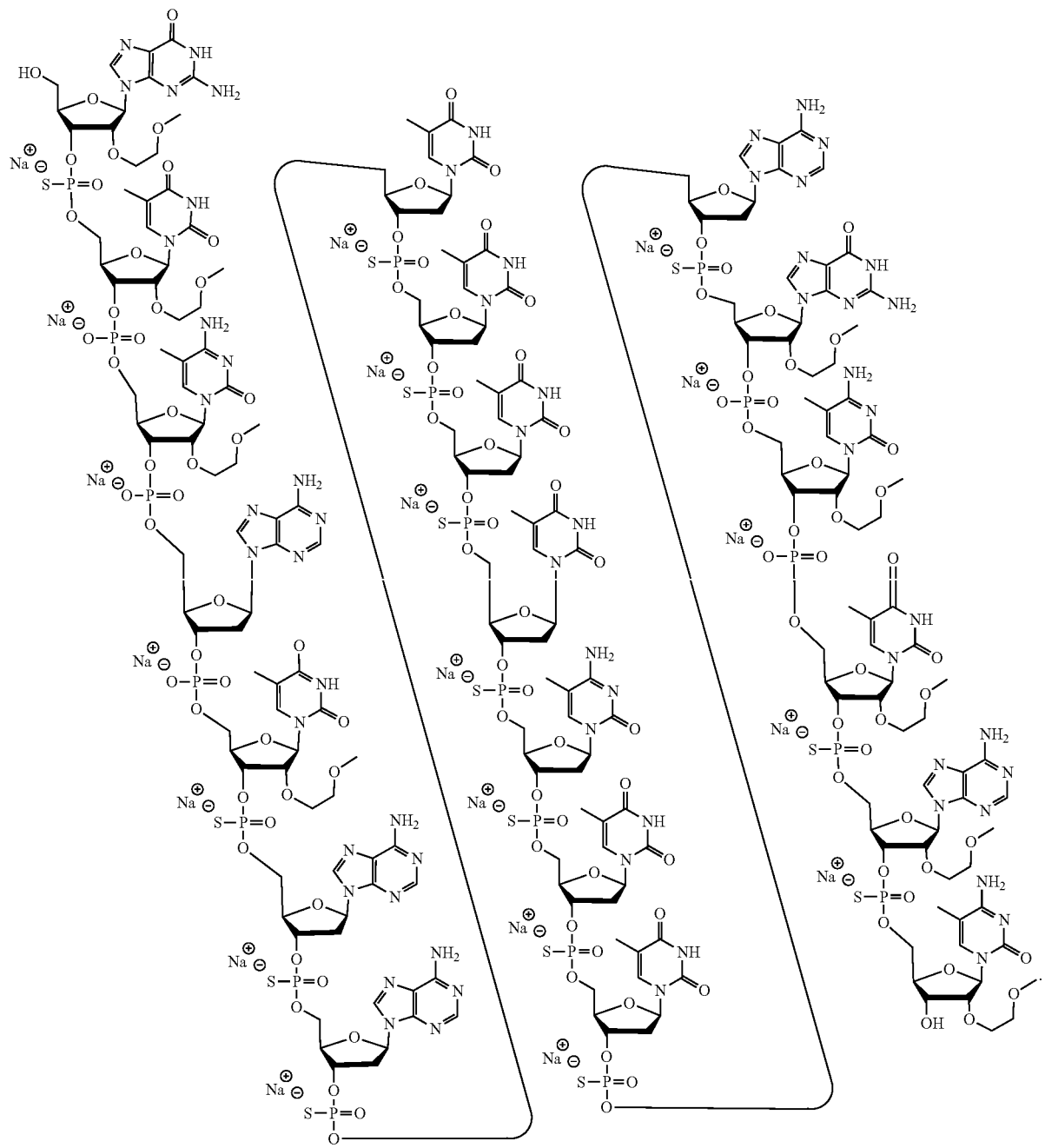

Structure 2. The Sodium Salt of Compound No. 1238994

2. Compound No. 1373021

In certain embodiments, Compound No. 1373021 is characterized as a 6-10-4 MOE gapmer having a sequence of (from 5' to 3') GTCATAATTTTCTTAGCTAC (SEQ ID NO: 1914), wherein each of nucleosides 1-6 and 17-20 (from 5' to 3') are 2'-MOE nucleosides and each of nucleosides 7-16 are 2'-β-D-deoxynucleosides, wherein the internucleoside linkages between nucleosides 2 to 3, 3 to 4, 4 to 5, 5 to 6, 6 to 7 and 17 to 18 are phosphodiester internucleoside linkages and the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methyl cytosine.

In certain embodiments, Compound No. 1373021 is represented by the following chemical notation (5' to 3'): Ges Teo $^m$Ceo Aeo Teo Aeo Ads Tds Tds Tds Tds $^m$Cds Tds Tds Ads Gds $^m$Ceo Tes Aes $^m$Ce (SEQ ID NO: 1914), wherein,
A=an adenine nucleobase,
$^m$C a 5-methyl cytosine nucleobase,
G=a guanine nucleobase,
T=a thymine nucleobase,
e=a 2'-MOE modified sugar,
d=a 2'-β-D deoxyribosyl sugar,
s=a phosphorothioate internucleoside linkage, and
o=a phosphodiester internucleoside linkage.

In certain embodiments, Compound No. 1373021 is represented by the following chemical structure:

(SEQ ID NO: 1914)

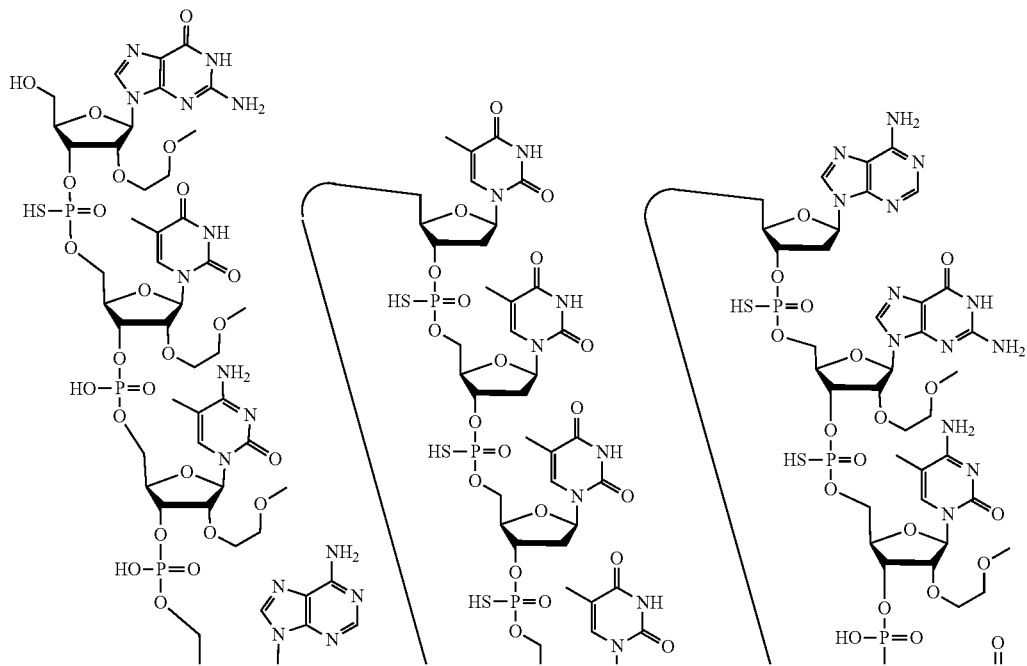

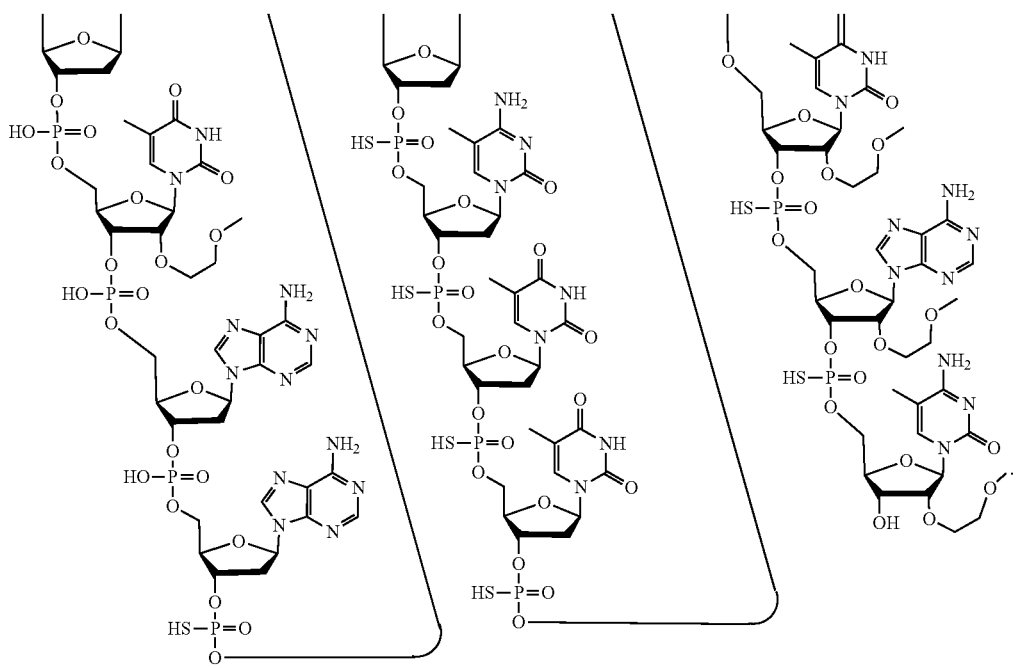

Structure 3. Compound No. 1373021

In certain embodiments, the sodium salt of Compound No. 1373021 is represented by the following chemical structure:

(SEQ ID NO: 1914)

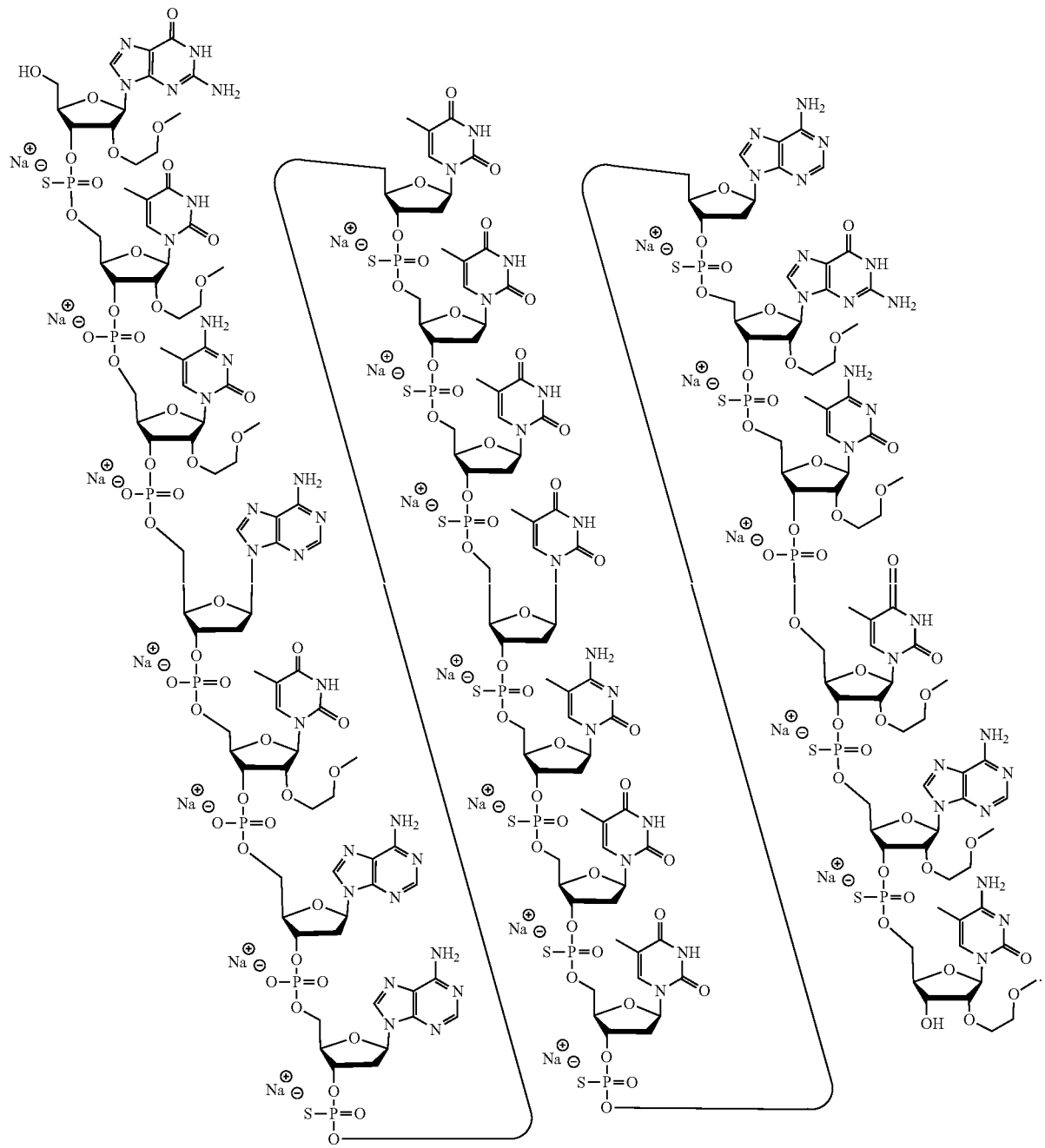

Structure 4. The Sodium Salt of Compound No. 1373021

3. Compound No. 1373022

In certain embodiments, Compound No. 1373022 is characterized as a 6-10-4 MOE gapmer having a sequence of (from 5' to 3') GCTTATTATTCATGTTCTCC (SEQ ID NO: 1939), wherein each of nucleosides 1-6 and 17-20 (from 5' to 3') are 2'-MOE nucleosides and each of nucleosides 7-16 are 2'-β-D-deoxynucleosides, wherein the internucleoside linkages between nucleosides 2 to 3, 3 to 4, 4 to 5, 5 to 6, 6 to 7 and 17 to 18 are phosphodiester internucleoside linkages and the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methyl cytosine.

In certain embodiments, Compound No. 1373022 is represented by the following chemical notation (5' to 3'): Ges $^m$Ceo Teo Teo Aeo Teo Tds Ads Tds Tds $^m$Cds Ads Tds Gds Tds Tds $^m$Ceo Tes $^m$Ces $^m$Ce (SEQ ID NO: 1939), wherein, A=an adenine nucleobase,
$^m$C=a 5-methyl cytosine nucleobase,
G=a guanine nucleobase,
T=a thymine nucleobase,
e=a 2'-MOE modified sugar,
d=a 2'-β-D deoxyribosyl sugar,
s=a phosphorothioate internucleoside linkage, and
o=a phosphodiester internucleoside linkage.

In certain embodiments, Compound No. 1373099 is represented by the following chemical structure:

(SEQ ID NO: 1939)

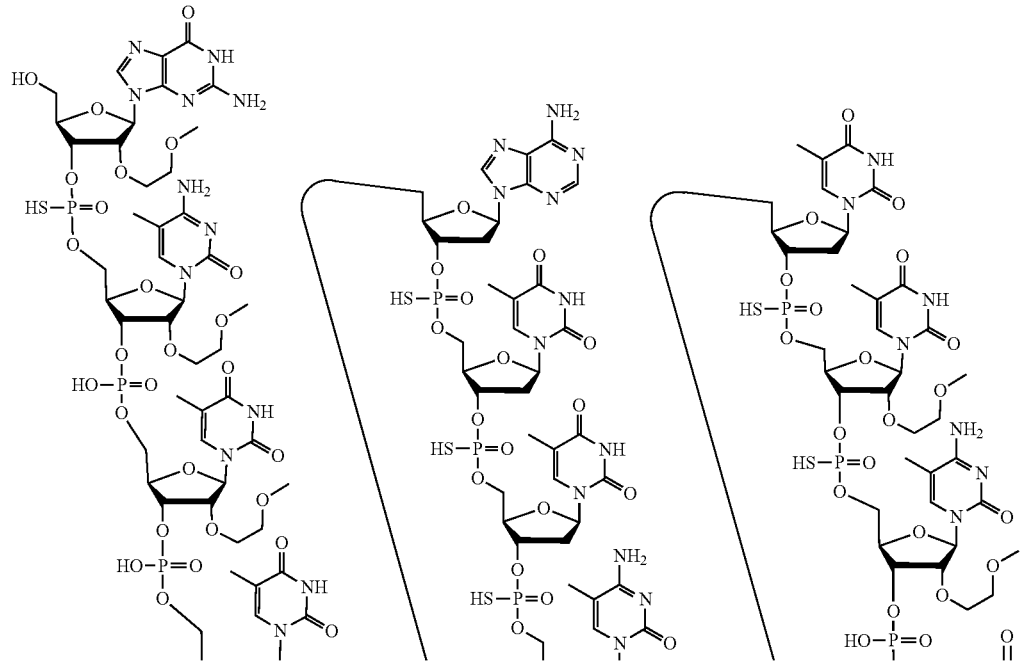

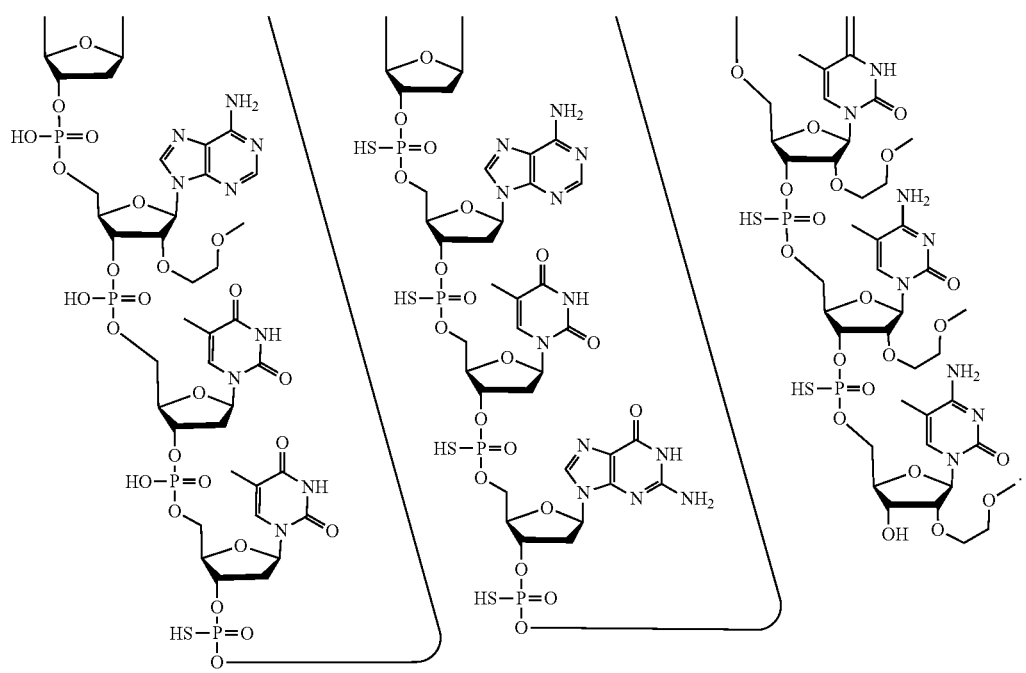

Structure 5. Compound No. 1373022

In certain embodiments, the sodium salt of Compound No. 1373022 is represented by the following chemical structure:

(SEQ ID NO: 1939)

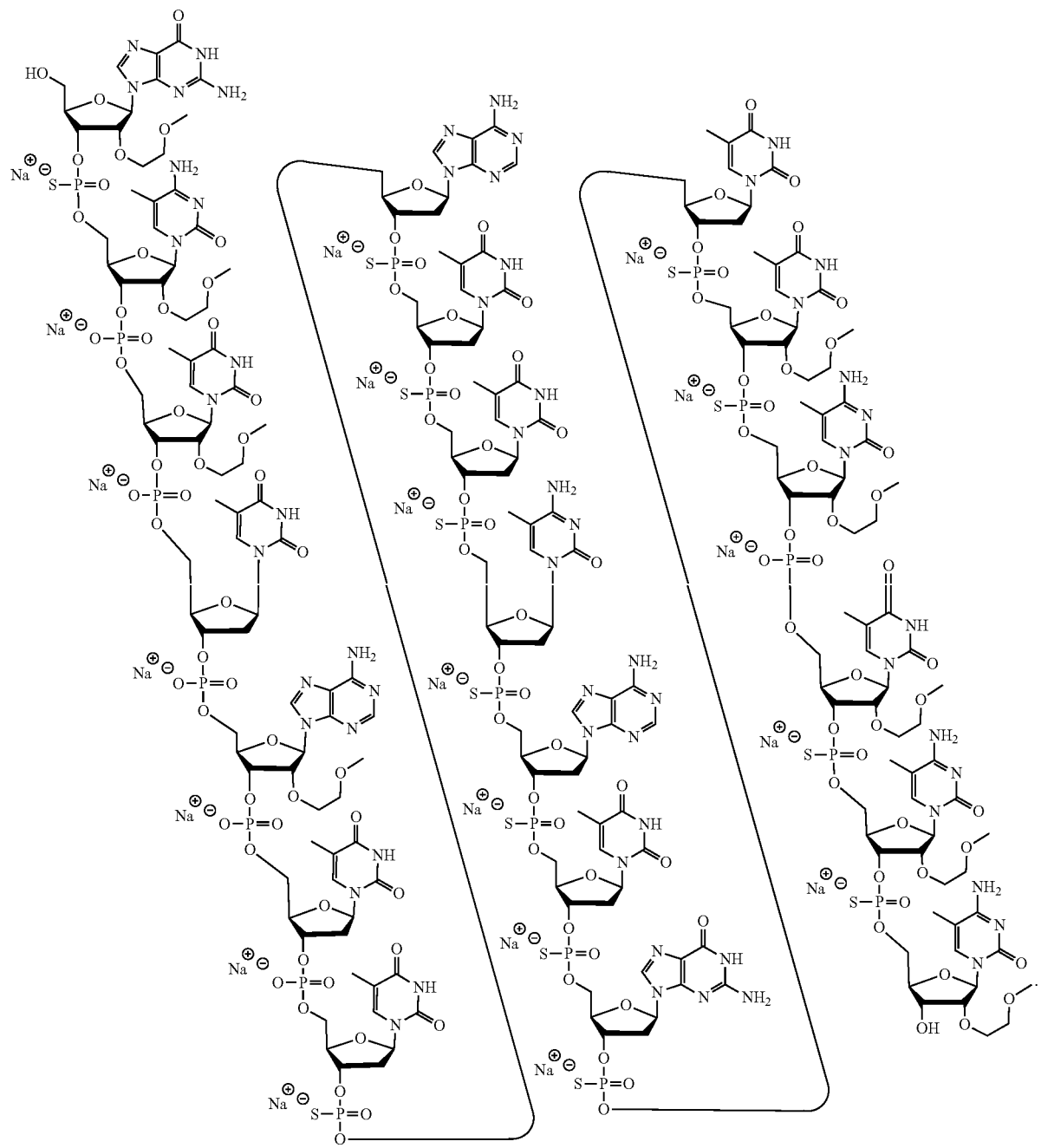

Structure 6. The Sodium Salt of Compound No. 1373022

4. Compound No. 1373023

In certain embodiments, Compound No. 1373023 is characterized as a 6-10-4 MOE gapmer having a sequence of (from 5' to 3') GTGTCATAATTTTCTTAGCT (SEQ ID NO: 2302), wherein each of nucleosides 1-6 and 17-20 (from 5' to 3') are 2'-MOE nucleosides and each of nucleosides 7-16 are 2'-β-D-deoxynucleosides, wherein the internucleoside linkages between nucleosides 2 to 3, 3 to 4, 4 to 5, 5 to 6, 6 to 7 and 17 to 18 are phosphodiester internucleoside linkages and the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methyl cytosine.

In certain embodiments, Compound No. 1373023 is represented by the following chemical notation (5' to 3'): Ges Teo Geo Teo $^m$Ceo Aeo Tds Ads Ads Tds Tds Tds Tds $^m$Cds Tds Tds Aeo Ges $^m$Ces Te (SEQ ID NO: 2302), wherein,
  A=an adenine nucleobase,
  $^m$C=a 5-methyl cytosine nucleobase,
  G=a guanine nucleobase,
  T=a thymine nucleobase,
  e=a 2'-MOE modified sugar,
  d=a 2'-Q-D deoxyribosyl sugar,
  s=a phosphorothioate internucleoside linkage, and
  o=a phosphodiester internucleoside linkage.

In certain embodiments, Compound No. 1373023 is represented by the following chemical structure:

(SEQ ID NO: 2302)

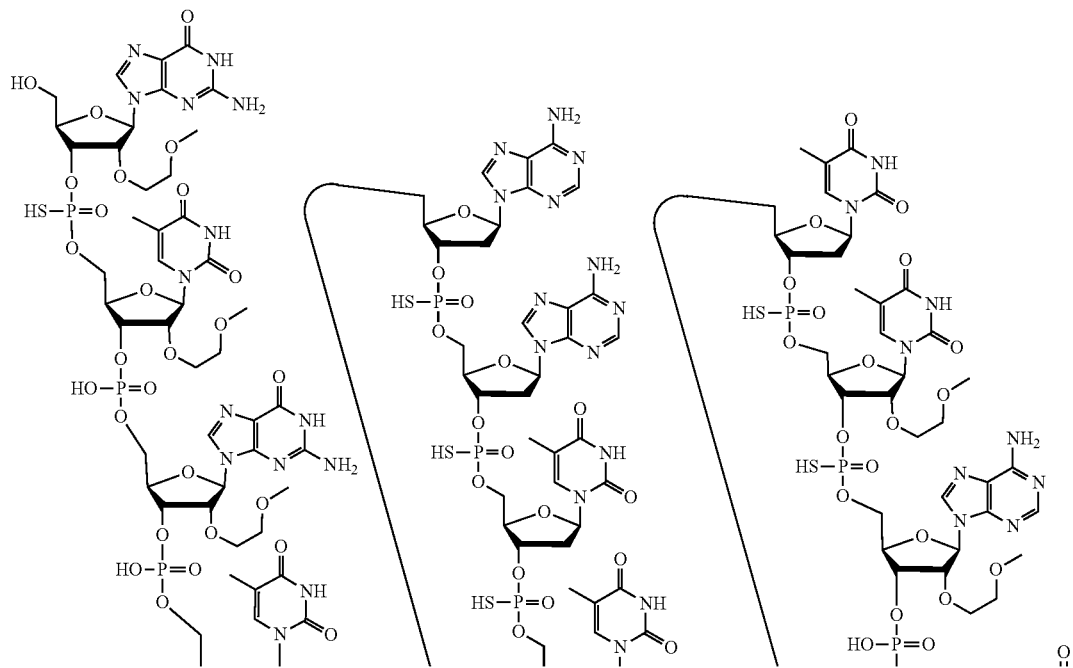

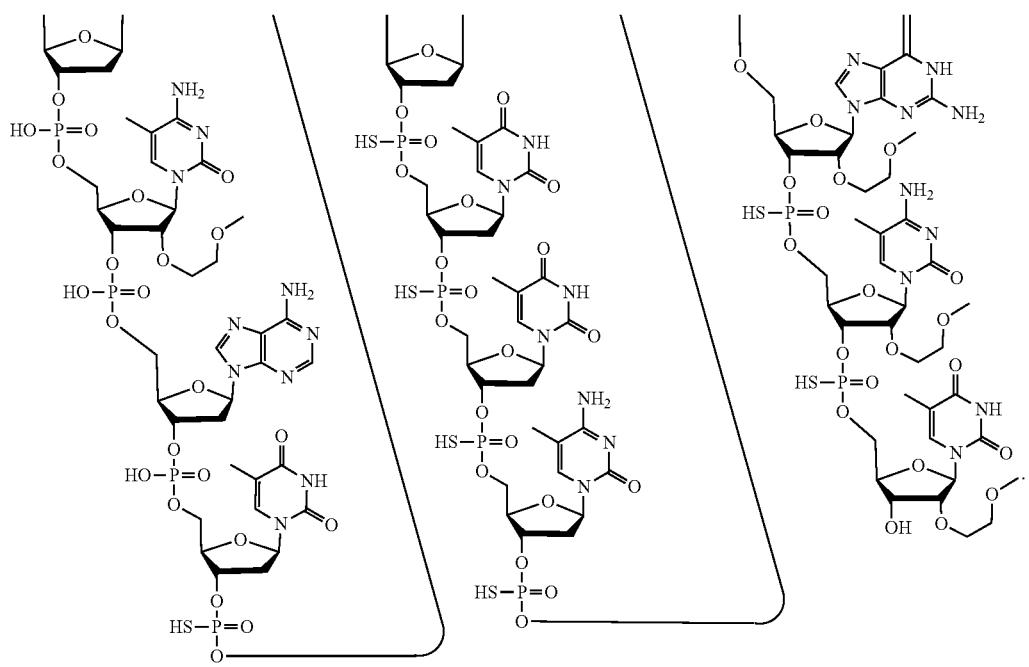

Structure 7. Compound No. 1332

In certain embodiments, the sodium salt of Compound No. 1373023 is represented by the following chemical structure:

(SEQ ID NO: 2302)

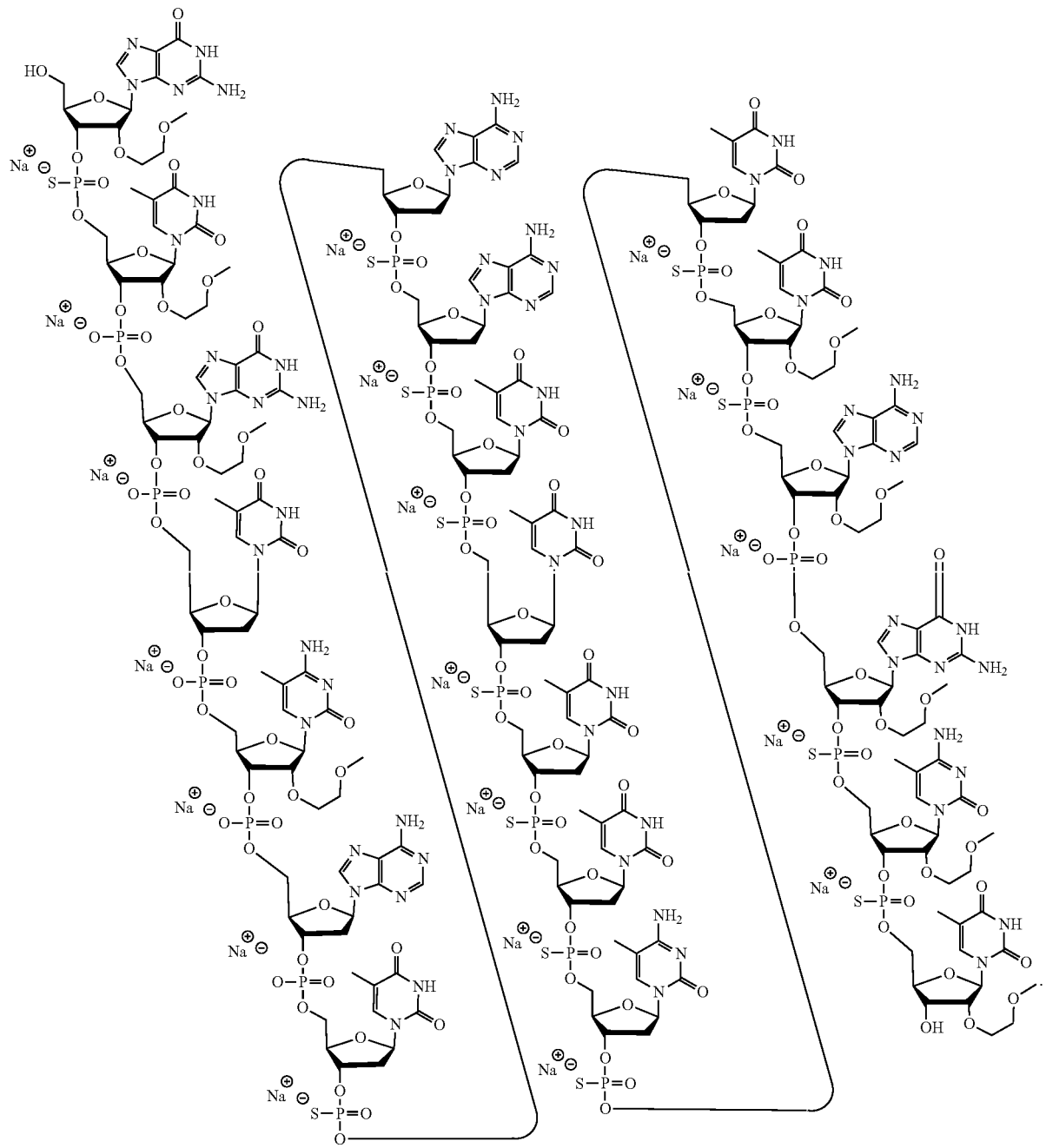

Structure 8. The Sodium Salt of Corn Pound No. 1373023

5. Compound No. 1373057

In certain embodiments, Compound No. 1373057 is characterized as a 5-9-5 MOE gapmer having a sequence of (from 5' to 3') GTCATAATTTTCTTAGCTA (SEQ ID NO: 2750), wherein each of nucleosides 1-5 and 15-19 (from 5' to 3') are 2'-MOE nucleosides and each of nucleosides 6-14 are 2'-β-D-deoxynucleosides, wherein the internucleoside linkages between nucleosides 2 to 3, 3 to 4, 4 to 5, 5 to 6, 16 to 17, and 17 to 18 are phosphodiester internucleoside linkages and the internucleoside linkages between nucleosides 1 to 2, 6 to 7, 7 to 8, 8 to 9, 9 to 10, 10 to 11, 11 to 12, 12 to 13, 13 to 14, 14 to 15, 15 to 16, and 18 to 19 are phosphorothioate internucleoside linkages, and wherein each cytosine is a 5-methyl cytosine.

In certain embodiments, Compound No. 1373057 is represented by the following chemical notation (5' to 3'): Ges Teo $^m$Ceo Aeo Teo Ads Ads Tds Tds Tds $^m$Cds Tds Tds Aes Geo $^m$Ceo Tes Ae (SEQ ID NO: 2750), wherein, A=an adenine nucleobase,
$^m$C a 5-methyl cytosine nucleobase,
G=a guanine nucleobase,
T=a thymine nucleobase,
e=a 2'-MOE modified sugar,
d=a 2'-R-D deoxyribosyl sugar,
s=a phosphorothioate internucleoside linkage, and
o=a phosphodiester internucleoside linkage.

In certain embodiments, Compound No. 1373057 is represented by the following chemical structure:

(SEQ ID NO: 2750)

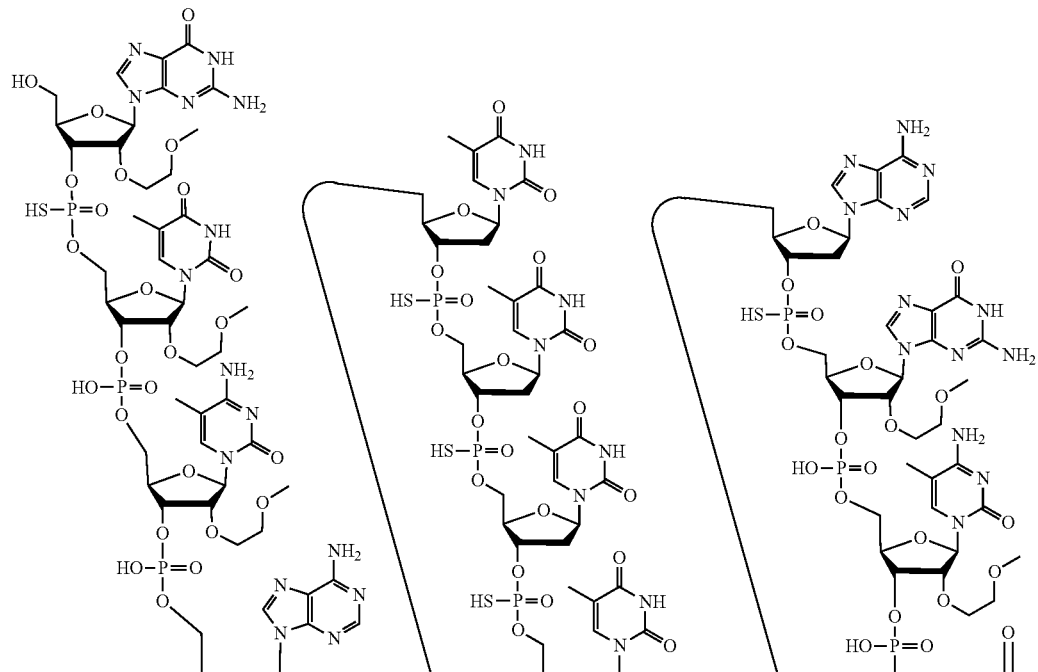

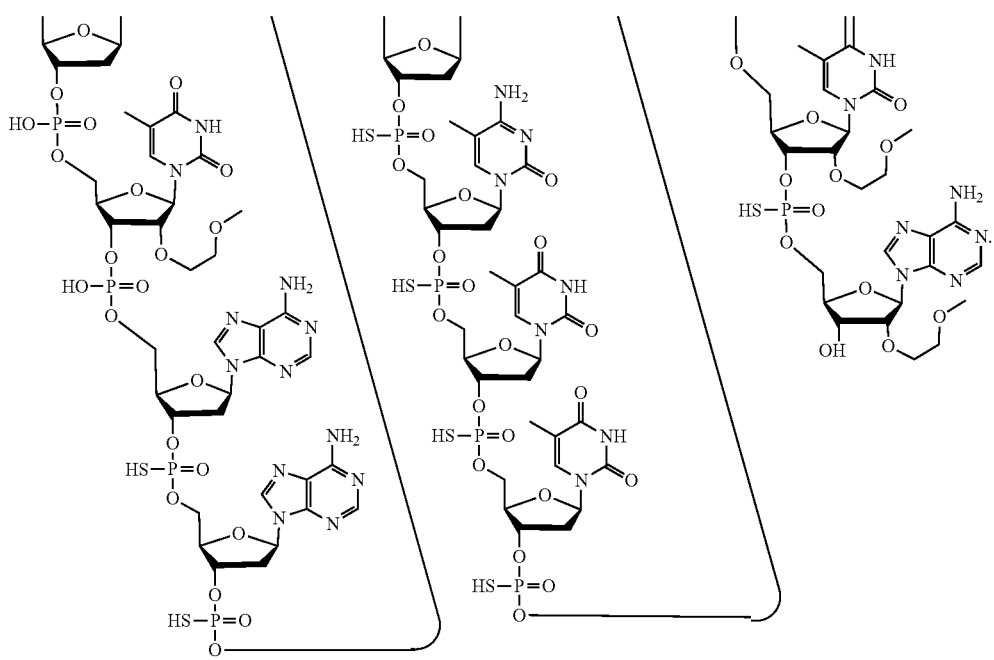

Structure 9. Compound No. 1373057

In certain embodiments, the sodium salt of Compound No. 1373057 is represented by the following chemical structure:

(SEQ ID NO: 2750)

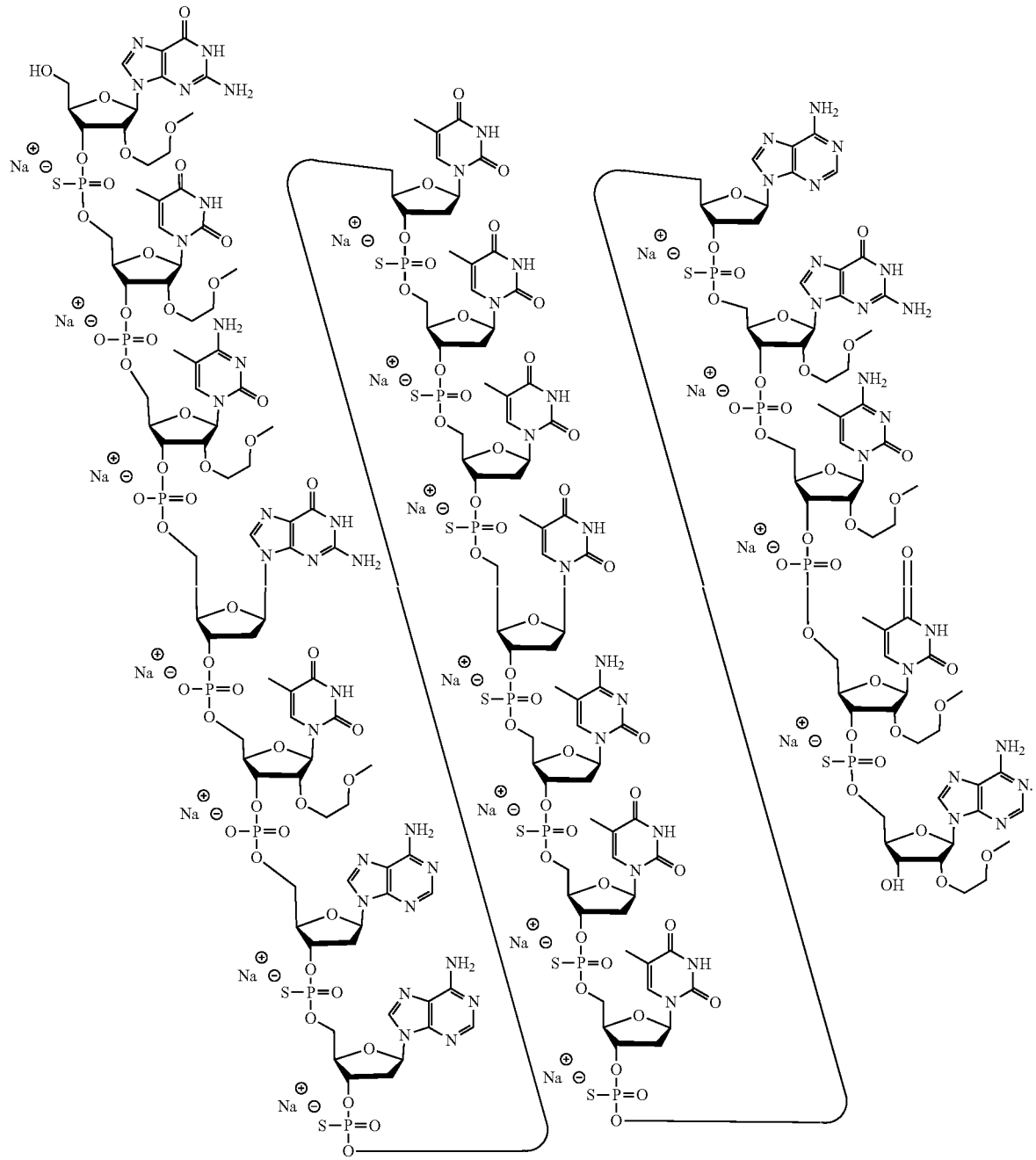

Structure 10. The Sodium Salt of Compound No. 1373057

6. Compound No. 1411016

In certain embodiments, Compound No. 1411016 is characterized as a 5-10-5 MOE gapmer having a sequence of (from 5' to 3') ACGTCCATTTTCTGTGCTTT (SEQ ID NO: 2739), wherein each of nucleosides 1-5 and 16-19 (from 5' to 3') are 2'-MOE nucleosides and each of nucleosides 6-15 are 2'-6l-D-deoxynucleosides, wherein the internucleoside linkages between nucleosides 2 to 3, 3 to 4, 4 to 5, 16 to 17, and 17 to 18 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No. 1411016 is represented by the following chemical notation (5' to 3'): Aes $^m$Ceo Geo Teo $^m$Ces $^m$Cds Ads Tds Tds Tds Tds $^m$Cds Tds Gds Tds Geo $^m$Ceo Tes Tes Te (SEQ ID NO: 2739), wherein, A=an adenine nucleobase,
$^m$C=a 5-methyl cytosine nucleobase,
G=a guanine nucleobase,
T=a thymine nucleobase,
e=a 2'-MOE modified sugar,
d=a 2'-Q-D deoxyribosyl sugar,
s=a phosphorothioate internucleoside linkage, and
o=a phosphodiester internucleoside linkage.

In certain embodiments, Compound No. 1411016 is represented by the following chemical structure:

(SEQ ID NO: 2739)

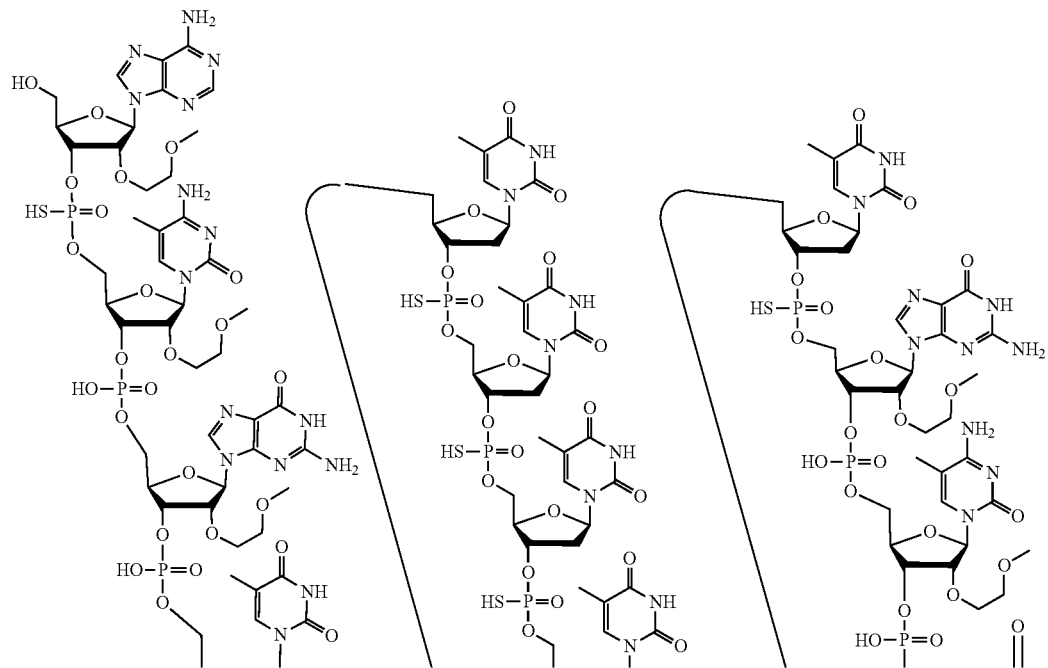

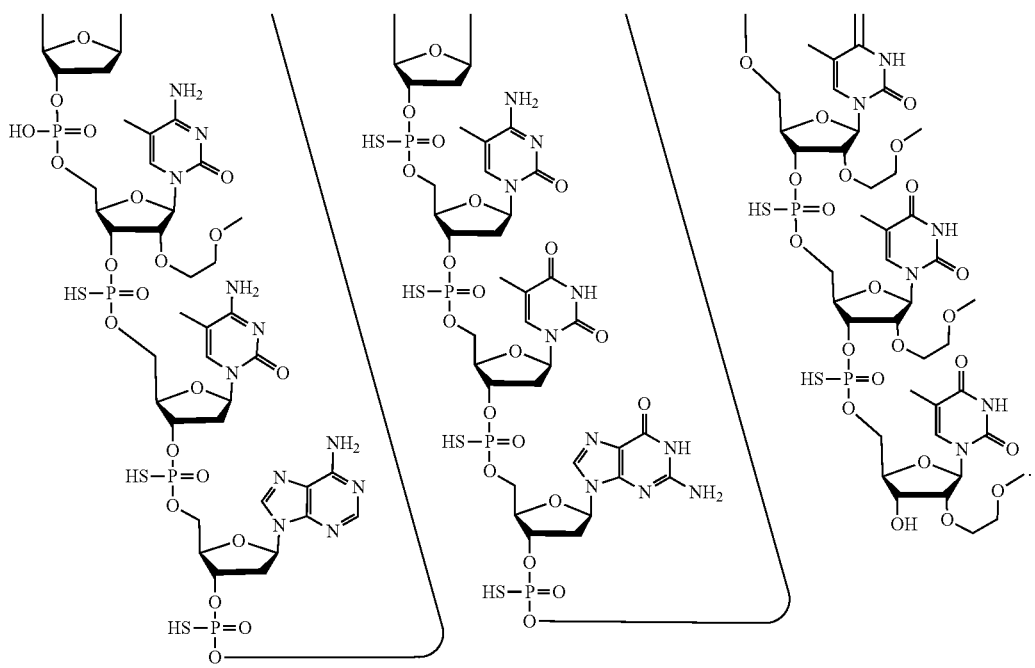

Structure 11. Compound No. 1411016

In certain embodiments, the sodium salt of Compound No. 1411016 is represented by the following chemical structure:

(SEQ ID NO: 2739)

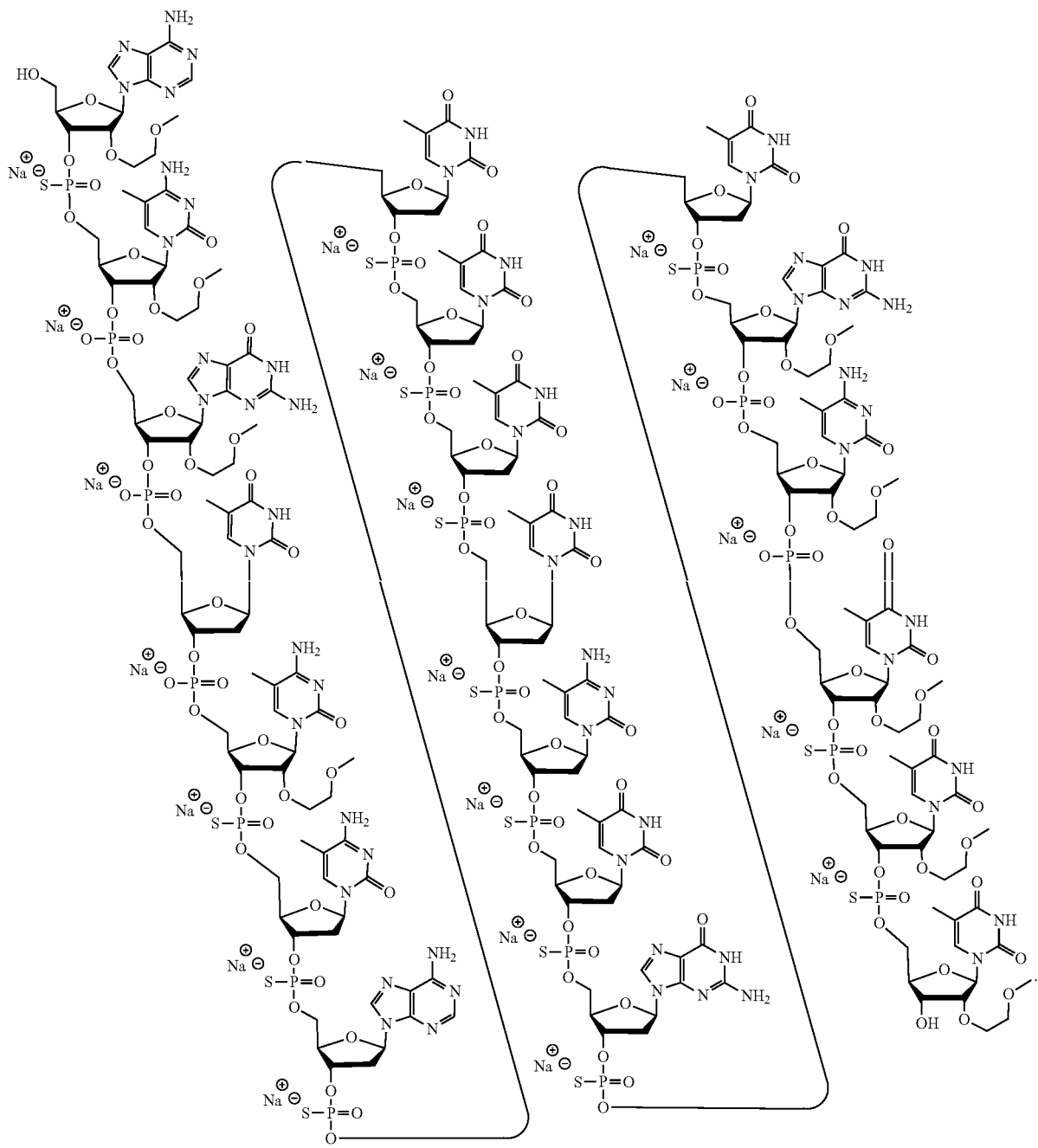

Structure 12. The Sodium Salt of Compound No. 1411016

VIII. Certain Comparator Compositions

In certain embodiments, Compound No. 169746, a 5-10-5 MOE gapmer having a sequence (from 5' to 3') of GTTATACTTTTACTGGCCTG (SEQ ID NO: 291), wherein each internucleoside linkage is a phosphorothioate internucleoside linkage, each cytosine is a 5-methyl cytosine, and wherein each of nucleosides 1-5 and 16-20 comprise a 2'-MOE modified sugar, which was previously described in WO2010/019270, incorporated herein by reference, is a comparator compound.

In certain embodiments, Compound No. 169750, a 5-10-5 MOE gapmer having a sequence (from 5' to 3') of TGCAT-ATTTCAAAGACCTGT (SEQ TD NO: 11), wherein each internucleoside linkage is a phosphorothioate internucleoside linkage, each cytosine is a 5-methyl cytosine, and wherein each of nucleosides 1-5 and 16-20 comprise a 2'-MOE modified sugar, which was previously described in WO2010/019270, incorporated herein by reference, is a comparator compound.

In certain embodiments, Compound No. 169753, a 5-10-5 MOE gapmer having a sequence (from 5' to 3') of GCCA-CATATAGGGTCCTTTA (SEQ ID NO: 66), wherein each internucleoside linkage is a phosphorothioate internucleoside linkage, each cytosine is a 5-methyl cytosine, and wherein each of nucleosides 1-5 and 16-20 comprise a 2'-MOE modified sugar, which was previously described in WO2010/019270, incorporated herein by reference, is a comparator compound.

In certain embodiments, Compound No. 169764, a 5-10-5 MOE gapmer having a sequence (from 5' to 3') of AGGGTCCTTTAAACATCTAA (SEQ ID NO: 450), wherein each internucleoside linkage is a phosphorothioate internucleoside linkage, each cytosine is a 5-methyl cytosine, and wherein each of nucleosides 1-5 and 16-20 comprise a 2'-MOE modified sugar, which was previously described in WO2010/019270, incorporated herein by reference, is a comparator compound.

Compound Nos. 169746, 169750, 169753, and 169764 were selected as comparator compounds because according to WO2010/019270, these compounds achieved >90% inhibition of PRNP RNA in a human cell line.

In certain embodiments, compounds described herein are superior relative to compounds described in WO2010/019270, because they demonstrate one or more improved properties, such as, in vivo efficacy and tolerability.

For example, as described herein, certain compounds Compound No. 1238994, Compound No. 1373021, Compound No. 1373022, Compound No. 1373023, Compound No. 1373057, and Compound No. 1411016 are more efficacious than comparator compounds in vivo. For example, as provided in Example 5, Compound No. 1238994, Compound No. 1373021, Compound No. 1373022, Compound No. 1373023, Compound No. 1373057, and Compound No. 1411016 achieve an average expression level (% control) of 27% (tables 65 and 75), 25% (tables 66 and 75), 30% (tables 66 and 75), 18% (tables 66 and 75), 25% (tables 66 and 75), and 24% (tables 71 and 72), respectively, in the spinal cord of transgenic mice, whereas comparator compounds Compound No. 169746, Compound No. 169750, and Compound No. 169764 achieve an average expression level (% control) of 52% (table 62), 61% (table 62), and 61% (table 62), respectively, in the spinal cord of transgenic mice. Therefore, certain compounds described herein are more efficacious than comparator compounds, Compound No. 169746, Compound No. 169750, and Compound No. 169764 in this assay.

For example, as provided in Example 5, Compound No. 1238994, Compound No. 1373021, Compound No. 1373022, Compound No. 1373023, Compound No. 1373057, and Compound No. 1411016 achieve an average expression level (% control) of 44% (tables 65 and 75), 33% (tables 66 and 75), 35% (tables 66 and 75), 28% (tables 66 and 75), 52% (tables 66 and 75), and 36% (tables 71 and 72), respectively, in the cortex of transgenic mice, whereas comparator compounds Compound No. 169746, Compound No. 169750, and Compound No. 169764 achieve an average expression level (% control) of 67% (table 62), 73% (table 62), and 77% (table 62), respectively, in the cortex of transgenic mice. Therefore, certain compounds described herein are more efficacious than comparator compounds, Compound No. 169746, Compound No. 169750, and Compound No. 169764 in this assay.

For example, as described herein, certain compounds Compound No. 1238994, Compound No. 1373021, Compound No. 1373022, Compound No. 1373023, Compound No. 1373057, and Compound No. 1411016 achieved average 3-hour FOB scores in mice of 0 (table 83), 2.5 (table 84), 1.8 (table 84), 0 (table 84), 0 (table 85), and 1.8 (table 94), respectively, at a dose of 700 μg. Compound No. 169753 achieved a 3-hour FOB scores in mouse of 4.2 (table 83). Therefore Compound No. 1238994, Compound No. 1373021, Compound No. 1373022, Compound No. 1373023, Compound No. 1373057, and Compound No. 1411016 described herein are more tolerable than comparator compound Compound No. 169753 in this assay.

For example, as described herein, certain compounds Compound No. 1238994, Compound No. 1373021, Compound No. 1373022, Compound No. 1373023, Compound No. 1373057, and Compound No. 1411016 achieved average 3-hour FOB scores in rat of 1.0 (table 107), 3.0 (table 97), 1.5 (table 97), 1.3 (table 97), 0.8 (table 98) and 3.3 (table 108), respectively, at a dose of 3 mg. Compound No. 169753 achieved a 3-hour FOB score in rat of 5.5 (table 106). Therefore Compound No. 1238994, Compound No. 1373021, Compound No. 1373022, Compound No. 1373023, Compound No. 1373057, and Compound No. 1411016 described herein are more tolerable than comparator compound Compound No. 169753 in this assay.

For example, as described herein, certain compounds Compound No. 1238994, Compound No. 1373021, Compound No. 1373022, Compound No. 1373023, Compound No. 1373057, and Compound No. 1411016, are more tolerable in a long-term study in rats than comparator Compound No. 169753. For example, as provided in Example 8, Compound No. 1238994, Compound No. 1373021, Compound No. 1373022, Compound No. 1373023, Compound No. 1373057, and Compound No. 1411016 had no onset of an adverse event during the course of the study. In contrast, each rat treated with Compound No. 169753 had adverse event onset by 5 weeks post-treatment. Therefore, certain compounds described herein are more tolerable than comparator compounds Compound No. 169753 in this assay.

IX. Certain Hotspot Regions

1. Nucleobases 5635-5677 of SEQ ID NO: 2

In certain embodiments, nucleobases 5635-5677 of SEQ ID NO: 2 comprise a hotspot region. In certain embodiments, modified oligonucleotides are complementary within nucleobases 5635-5677 of SEQ ID NO: 2. In certain embodiments, modified oligonucleotides are 16 nucleobases in length. In certain embodiments, modified oligonucleotides are 17 nucleobases in length. In certain embodiments, modified oligonucleotides are 19 nucleobases in length. In certain embodiments, modified oligonucleotides are 20 nucleobases in length. In certain embodiments, modified oligonucleotides are gapmers. In certain embodiments, modified oligonucleotides are 5-10-5, 6-10-4, 4-10-6, 5-9-5, 4-8-5, or 4-8-4 gapmers. In certain embodiments, the gapmers are MOE gapmers. In certain embodiments, the gapmers are mixed wing gapmers. In certain embodiments, the mixed wing gapmers have the sugar motif in order from 5' to 3': eeeeedddddddddkkeee, eeeeeedddddddddkkee, eeeeedddddddddkkeee, eeeedddddddkkeee, or eeeedddddddkkee; wherein 'd' represents a 2'-β-D-deoxyribosyl sugar moiety, 'k' represents a cEt sugar moiety, and 'e' represents a 2'-MOE sugar moiety. In certain embodiments, the nucleosides of the modified oligonucleotides are linked by phosphorothioate internucleoside linkages and phosphodiester internucleoside linkages. In certain embodiments, the phosphodiester ("o") and phosphorothioate ("s")

internucleoside linkages are arranged in order from 5' to 3': sooosssssssssssoooss, sooossssssssssssooss, sooooosssssssssssoss, sooooossssssssssssoos, soosssssssssssooss or soossssssssssoos.

The reduction of PRNP RNA in vitro in the standard cell assay. In certain embodiments, modified oligonucleotides complementary within nucleobases 14366-14410 of SEQ ID NO: 2 achieve an average of 39% reduction of PRNP RNA in the cortex in the standard in vivo assay.

4. Additional Hotspot Regions

In certain embodiments, the ranges described in the Table below comprise hotspot regions. Each hotspot region begins with the nucleobase of SEQ ID NO:1 identified in the "Start Site SEQ ID NO: 1" column and ends with the nucleobase of SEQ ID NO: 1 identified in the "Stop Site SEQ ID NO: 1" column, and/or begins with the nucleobase of SEQ ID NO: 2 identified in the "Start Site SEQ ID NO: 2" column and ends with the nucleobase of SEQ ID NO: 2 identified in the "Stop Site SEQ ID NO: 2" column. In certain embodiments, modified oligonucleotides are complementary within any of the hotspot regions 1-21, as defined in the table below. In certain embodiments, modified oligonucleotides are 16 nucleobases in length. In certain embodiments, modified oligonucleotides are 17 nucleobases in length. In certain embodiments, modified oligonucleotides are 18 nucleobases in length. In certain embodiments, modified oligonucleotides are 19 nucleobases in length. In certain embodiments, modified oligonucleotides are 20 nucleobases in length. In certain embodiments, modified oligonucleotides are gapmers. In certain embodiments, modified oligonucleotides are 5-10-5, 6-10-4, 4-10-6, 3-10-7, 7-10-3, 5-9-5, 5-8-5, 4-8-4, or 5-8-4 gapmers. In certain embodiments, the gapmers are MOE gapmers. In certain embodiments, the gapmers are mixed wing gapmers. In certain embodiments, the mixed wing gapmers have the sugar motif in order from 5' to 3': eeeeedddddddddkkeee, eeeeeedddddddddkkee, eeeeedddddddddkkeee, or eeeedddddddddkkee; wherein 'd' represents a 2'-β-D-deoxyribosyl sugar moiety, 'k' represents a cEt sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3'). In certain embodiments, the gapmers have the sugar motif in order from 5' to 3': eeeeedyddddddddeeeee or eeeedydddddddeeeee; wherein 'd' represents a 2'-β-D-deoxyribosyl sugar moiety, 'k' represents a cEt sugar moiety, 'e' represents a 2'-MOE sugar moiety, and 'y' represents a 2'-OMe sugar moiety. In certain embodiments, the nucleosides of the modified oligonucleotides are linked by phosphorothioate internucleoside linkages and phosphodiester internucleoside linkages. In certain embodiments, the phosphodiester ("o") and phosphorothioate ("s") internucleoside linkages are arranged in order from 5' to 3': sooosssssssss-sooooss, sooossssssssssoooss, sooosssssssssssooss, sooooosssssssssssoss, ssooooosssssssssssos, sooooosssssssss-soos, sooosssssssssssooss, soosssssssssooss, sooosssssssss-sooss, or sooossssssssssoos.

The nucleobase sequence of compounds listed in the "Compound No. in range" column in the table below are complementary to SEQ ID NO: 1 and/or SEQ ID NO: 2 within the specified hotspot region. The nucleobase sequence of the oligonucleotides listed in the "SEQ ID NO: in range" column in the table below are complementary to the target sequence, SEQ ID NO: 1 and/or SEQ ID NO: 2, within the specified hotspot region.

In certain embodiments, modified oligonucleotides complementary to nucleobases within the hotspot region achieve at least "Min. % Red. in vitro" (minimum % reduction, relative to untreated control cells) of PRNP RNA in vitro in the standard cell assay, as indicated in the table below. In certain embodiments, modified oligonucleotides complementary to nucleobases within the hotspot region achieve an average of "Avg. % Red. in vitro" (average % reduction, relative to untreated control cells) of PRNP RNA in vitro in the standard cell assay, as indicated in the table below. In certain embodiments, modified oligonucleotides complementary to nucleobases within the hotspot region achieve a maximum of "Max. % Red. in vitro" (maximum % reduction, relative to untreated control cells) of PRNP RNA in vitro in the standard cell assay, as indicated in the table below.

TABLE 1

Hotspot Regions of PRNP

| Hotspot ID | Start Site SEQ ID NO: 1 | Stop Site SEQ ID NO: 1 | Start Site SEQ ID NO: 2 | Stop Site SEQ ID NO: 2 | Min. % Reduction | Max. % Reduction | Avg. % Reduction | Compound ID in range | SEQ ID in range |
|---|---|---|---|---|---|---|---|---|---|
| 1 | n/a | n/a | 5633 | 5677 | 36 | 93 | 75 | 1238994-1239003, 1270398-1270400, 1270564, 1270668, 1373021, 1373023, 1373032, 1373034, 1373050, 1373057, 1373063, 1373065, 1418398-1418403, 1418409-1418411, 1418418-1418420, 1418423, 1418425 | 530, 607, 684, 761, 838, 915, 1914, 2069, 2146, 2237, 2301, 2302, 2536, 2640, 2750, 2759, 2760, 2764, 2788-2793, 2803-2806 |
| 2 | n/a | n/a | 5791 | 5826 | 55 | 92 | 77 | 1239051-1239054, 1270565, 1270415-1270419, 1270596, 1355720, 1411004-1411007, 1411013-1411016, 1418412-1418415, 1418426, 1423120-1423123, 1423126 | 1225, 1302, 1379, 1456, 2240, 2307, 2308, 2383, 2471, 2537, 2568, 2647, 2736-2739, 2744, 2798-2801 |
| 3 | n/a | n/a | 14366 | 14410 | 44 | 88 | 62 | 1239543-1239554, 1270516-1270521, 1270571, 1270640, 1355714, 1355734, | 555, 632, 709, 786, 863, 940, 1017, 1862, 1939, 2017, |

TABLE 1-continued

Hotspot Regions of PRNP

| Hotspot ID | Start Site SEQ ID NO: 1 | Stop Site SEQ ID NO: 1 | Start Site SEQ ID NO: 2 | Stop Site SEQ ID NO: 2 | Min. % Reduction | Max. % Reduction | Avg. % Reduction | Compound ID in range | SEQ ID in range |
|---|---|---|---|---|---|---|---|---|---|
| | | | | | | | | 1373022, 1373031, 1373051, 1373061, 1418404-1418407, 1418421, 1418426 | 2094, 2171, 2257, 2334, 2407, 2408, 2488, 2508, 2543, 2612, 2659, 2677, 2757, 2765, 2794-2797 |
| 4 | n/a | n/a | 4902 | 4929 | 72 | 98 | 90 | 1238802-1238805, 1270342-1270345 | 829, 906, 2060, 2137, 2228, 2283, 2446-2447 |
| 5 | n/a | n/a | 5000 | 5026 | 78 | 98 | 89 | 1238834-1238839 1270351-1270352 | 1446, 1523, 1600, 1676, 1753, 1830, 2285-2286 |
| 6 | n/a | n/a | 5073 | 5100 | 65 | 98 | 85 | 1201241, 1238863-1238864, 1270357-1270362 | 159, 524, 601, 2287-2288, 2231, 2373, 2452-2453 |
| 7 | n/a | n/a | 5515 | 5559 | 66 | 98 | 86 | 1238973-1238975, 1270373-1270387, 1270560-1270561, 1270593, 1270629, 1270666 | 529, 606, 683, 2233-2235, 2293-2297, 2376-2377, 2457-2461, 2532-2533, 2565, 2601, 2638 |
| 8 | n/a | n/a | 5595 | 5632 | 73 | 98 | 85 | 1201248, 1238987-1238992, 1270388-1270394 1270562-1270563, 1270594, 1270630 | 237, 1376, 1453, 1530, 1607, 1683, 1760, 2236, 2298-2300, 2378, 2462-2463, 2534-2535, 2566, 2602 |
| 9 | n/a | n/a | 5666 | 5690 | 74 | 97 | 87 | 1239008, 1239009, 1239010, 1239011, 1239012, 1270402, 1355708 | 1300, 1377, 1454, 1531, 1608, 2466 |
| 10 | n/a | n/a | 5857 | 5881 | 80 | 93 | 87 | 1239062-1239066 1270424 | 610, 687, 764, 1995, 2072, 2310 |
| 11 | n/a | n/a | 9352 | 9377 | 70 | 94 | 86 | 1239345-1239347, 1270486-1270488, 1270602 | 546, 1853, 1930, 2252, 2483, 2503, 2574 |
| 12 | n/a | n/a | 11331 | 11358 | 79 | 95 | 89 | 1239447-1239448, 1270510-1270515 | 1243, 1320, 2256, 2333, 2405, 2406, 2487, 2507 |
| 13 | 1329 | 1360 | 17120 | 17151 | 70 | 96 | 86 | 1238243-1238245, 1270227-1270233, 1270548, 1270579, 1335685, 1373020, 1373026-1373027, 1373029-1373030, 1373036-1373037, 1373042-1373046, 1373048, 1373053, 1373055, 1373058-1373060, 1373064, 1373067, 1373070, 1373072-1373075, 1418386, 1418388, 1418416, 1418390-1418393 | 1650, 1726, 1803, 2190-2191, 2264, 2342-2344, 2417, 2520, 2551, 2746, 2748, 2751, 2752, 2763, 2767-2768, 2778-2783 |
| 14 | 1420 | 1450 | 17211 | 17241 | 69 | 97 | 88 | 1201109, 1238254-1238255, 1270234-1270239, 1270580, 1270651 | 368, 804, 881, 2192-2193, 2265, 2345-2346, 2418, 2552, 2623 |
| 15 | 1490 | 1540 | 17281 | 17331 | 72 | 97 | 86 | 1238268-1238271, 1270246-1270253, 1270550, 1270582, 1270615, 1406261 | 497, 574, 651, 1881, 2196-2197, 2267, 2349-2351, |

TABLE 1-continued

Hotspot Regions of PRNP

| Hotspot ID | Start Site SEQ ID NO: 1 | Stop Site SEQ ID NO: 1 | Start Site SEQ ID NO: 2 | Stop Site SEQ ID NO: 2 | Min. % Reduction | Max. % Reduction | Avg. % Reduction | Compound ID in range | SEQ ID in range |
|---|---|---|---|---|---|---|---|---|---|
| 16 | 1619 | 1654 | 17410 | 17445 | 53 | 97 | 83 | 1201121, 1238284-1238286, 1270261-1270263, 1270583, 1270652 | 2420-2421, 2522, 2554, 2587, 2732 370, 1421, 1498, 1575, 2201, 2269, 2354, 2555, 2624 |
| 17 | 1810 | 1850 | 17601 | 17641 | 64 | 97 | 85 | 1238319-1238335, 1270264-1270266, 1270584, 1270653, 1355707 | 500, 807, 884, 961, 1038, 1115, 1192, 1269, 1346, 1423, 1500, 1577, 1654, 1730, 1807, 1884, 2115, 2202, 2355, 2423, 2556, 2625 |
| 18 | 1844 | 1879 | 17635 | 17670 | 69 | 96 | 82 | 1201138, 1238336-1238346, 1270269-1270272, 1270585 | 296, 577, 654, 731, 808, 885, 962, 1039, 1116, 1962, 2039, 2116, 2204, 2356-2357, 2424, 2557 |
| 19 | 1872 | 1921 | 17663 | 17712 | 66 | 97 | 81 | 1238356-1238374, 1270274-1270278, 1270586, 1270617-1270618 | 501, 578, 655, 732, 809, 886, 963, 1040, 1117, 1194, 1271, 1349, 1425, 1502, 1579, 1885, 1963, 2040, 2117, 2206, 2271, 2358-2359, 2425, 2558, 2589-2590 |
| 20 | 1962 | 1990 | 17753 | 17781 | 63 | 95 | 85 | 1201141-1201145, 1238398, 1270281-1270284, 1355706, 1373078, 1393330, 1393332, 1393334-1393335, 1393337-1393338, 1393342, 1418417, 1418422, 1418394-1418397 | 65-66, 143, 220, 297, 1733, 2208, 2360, 2426, 2427, 2754, 2755, 2771, 2772, 2776, 2784-2787 |
| 21 | 2194 | 2225 | 17985 | 18016 | 46 | 98 | 87 | 1238515-1238517, 1270306-1270311, 1270554, 1270622 | 1970, 2047, 2124, 2216-2217, 2277, 2365, 2434-2435, 2526, and 2594 |

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intenended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT^mCGAUCG," wherein ^mC indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as u or R such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms, unless specified otherwise. Likewise, tautomeric forms of the compounds herein are also included unless otherwise indicated. Unless otherwise indicated, compounds described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1H$ hydrogen atoms. Isotopic substitutions encompassed by the compounds herein include but are not limited to: $^2H$ or $^3H$ in place of $^1H$, $^{13}C$ or $^{14}C$ in place of $^{12}C$, $^{15}N$ in place of $^{14}N$, $^{17}O$ or $^{18}O$ in place of $^{16}O$, and $^{33}S$, $^{34}S$, $^{35}S$, or $^{36}S$ in place of $^{32}S$. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Examples

Example 1: Effect of Modified Oligonucleotides on Human PRNP RNA In Vitro, Single Dose Modified oligonucleotides complementary to human PRNP nucleic acid were synthesized and tested for their effect on PRNP RNA levels in vitro.

The modified oligonucleotides in the tables below are 5-10-5 MOE gapmers with mixed internucleoside linkages. The gapmers are 20 nucleosides in length, wherein the central gap segment consists of ten 2'-β-D-deoxynucleosides and the 3' and 5' wings each consist of five 2'-MOE modified nucleosides. The sugar motif of the gapmers is (from 5' to 3'): eeeeedddddddddddeeeee; wherein "d" represents a 2'-β-D-deoxyribosyl sugar, and 'e' represents a 2'-MOE modified ribosyl sugar. The internucleoside linkage motif for the gapmers is (from 5' to 3'): sooossssssssssssooss; wherein 'o' represents a phosphodiester internucleoside linkage and 's' represents a phosphorothioate internucleoside linkage. Each cytosine residue is a 5-methyl cytosine.

"Start site" indicates the 5'-most nucleoside to which the gapmer is complementary to in the human gene sequence. "Stop site" indicates the 3'-most nucleoside to which the gapmer is complementary to in the human gene sequence. Most of the modified oligonucleotides listed in the Tables below are complementary to the human PRNP mRNA sequence, designated herein as SEQ ID NO: 1 (GENBANK Accession NO: NM_000311.4) and/or the human PRNP genomic sequence, designated herein as SEQ ID NO: 2 (GENBANK Accession NO: NC_000020.11 truncated from nucleotides 4683001 to 4705000). In addition, certain modified oligonucleotides are complementary to the human PRNP mRNA designated herein as SEQ ID NO: 3 (GENBANK Accession NO: NM_001080123.2). 'N/A' indicates that the modified oligonucleotide is not complementary to that particular gene sequence with 100% complementarity.

Cultured A431 cells at a density of 20,000 cells per well were treated with 4,000 nM of modified oligonucleotide by free uptake. After a treatment period of approximately 48 hours, total RNA was isolated from the cells and PRNP RNA levels were measured by quantitative real-time RTPCR. Human PRNP primer probe set RTS42354 (forward sequence CCTCTCCTCACGACCGA, designated herein as SEQ ID NO: 21; reverse sequence CCCAGTGTTC-CATCCTCCA, designated herein as SEQ ID NO: 22; probe sequence CCACAAAGAGAACCAGCATCCAGCA, designated herein as SEQ ID NO: 23) was used to measure RNA levels. In addition, mRNA levels modulated by modified oligonucleotides described herein in tables 12 and 13 were measured using an additional human PRNP primer probe set, RTS42359 (forward sequence AGTG-GAACAAGCCGAGTAAG, designated herein as SEQ ID NO: 24; reverse sequence CCTCATAGT-CACTGCCGAAAT, designated herein as SEQ ID NO: 25; probe sequence AACCAACATGAAGCACATGGCTGG, designated herein as SEQ ID NO: 26). PRNP RNA levels were normalized using RIBOGREEN®. Results are presented in the tables below are normalized to PRNP RNA levels in untreated control cells (UTC). Values marked with an asterisk (*) result from oligonucleotides that are complementary to the amplicon region of the primer probe set. Additional assays may be used to measure the potency and efficacy of the modified oligonucleotides complementary to the amplicon region.

TABLE 2

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1200909 | 12 | 31 | 3105 | 3124 | CCCCGTTACATAATGGAGAA | 92 | 27 |
| 1200915 | 96 | 115 | 3189 | 3208 | GCCTGCGGGTGCCATCGCTC | 90 | 28 |
| 1200921 | 105 | 124 | 3198 | 3217 | GTTGATACCGCCTGCGGGTG | 99 | 29 |
| 1200927 | 112 | 131 | 3205 | 3224 | TGCATCAGTTGATACCGCCT | 90 | 30 |
| 1200933 | 161 | 180 | 3254 | 3273 | GCCGGGAATGAGTCACCGGA | 86 | 31 |
| 1200939 | 211 | 230 | 3304 | 3323 | CGGGCGGCCGGCCGAGGTTT | 91 | 32 |
| 1200945 | 236 | 255 | 3329 | 3348 | CCCGGCGCACACTCTGTGCC | 98 | 33 |
| 1200951 | 251 | 270 | 3344 | 3363 | CCAATTGCCGCGCGGCCCGG | 84 | 34 |
| 1200957 | 340 | 359 | 3433 | 3452 | GAGGACAGGCGACGCGCGGG | 95 | 35 |
| 1200965 | 353 | 372 | 3446 | 3465 | AGCGACTGGCTCGGAGGACA | 95 | 36 |
| 1200971 | 384 | 403 | 3477 | 3496 | GAGAGGAGAAGCTCGCGGCG | 84* | 37 |
| 1200977 | 422 | 441 | 16213 | 16232 | AAGGTTCGCCATAATGACTG | 23* | 38 |
| 1200983 | 524 | 543 | 16315 | 16334 | GTATCGGCTGCCCCCAGTGT | 53* | 39 |
| 1200989 | 531 | 550 | 16322 | 16341 | GCCCCGGGTATCGGCTGCCC | 131* | 40 |
| 1200995 | 560 | 579 | 16351 | 16370 | TGGGTAGCGGTTGCCTCCAG | 91 | 41 |
| 1201001 | 571 | 590 | 16362 | 16381 | CCGCCCTGAGGTGGGTAGCG | 89 | 42 |
| 1201007 | 725 | 744 | 16516 | 16535 | TGGCTTACTCGGCTTGTTCC | 41 | 43 |
| 1201013 | 798 | 817 | 16589 | 16608 | GCATGTAGCCGCCAAGGCCC | 86 | 44 |
| 1201019 | 826 | 845 | 16617 | 16636 | ATGATGGGCCTGCTCATGGC | 70 | 45 |
| 1201025 | 851 | 870 | 16642 | 16661 | GTCCTCATAGTCACTGCCGA | 68 | 46 |
| 1201031 | 869 | 888 | 16660 | 16679 | GTTTTCACGATAGTAACGGT | 39 | 47 |
| 1201037 | 904 | 923 | 16695 | 16714 | GGCCTGTAGTACACTTGGTT | 85 | 48 |
| 1201043 | 920 | 939 | 16711 | 16730 | GCTGTACTCATCCATGGGCC | 93 | 49 |
| 1201049 | 981 | 1000 | 16772 | 16791 | TGGTGACCGTGTGCTGCTTG | 51 | 50 |
| 1201055 | 1003 | 1022 | 16794 | 16813 | AAGTTCTCCCCCTTGGTGGT | 50 | 51 |
| 1201061 | 1016 | 1035 | 16807 | 16826 | GTCGGTCTCGGTGAAGTTCT | 52 | 52 |
| 1201067 | 1046 | 1065 | 16837 | 16856 | CTGCTCAACCACGCGCTCCA | 60 | 53 |
| 1201075 | 1095 | 1114 | 16886 | 16905 | CTCTCTGGTAATAGGCCTGA | 63 | 54 |
| 1201081 | 1228 | 1247 | 17019 | 17038 | CGCCTCCCTCAAGCTGGAAA | 93 | 55 |
| 1201087 | 1238 | 1257 | 17029 | 17048 | AGGTGGATACCGCCTCCCTC | 85 | 56 |
| 1201093 | 1307 | 1326 | 17098 | 17117 | AGGGTATTGATTAGCCTATC | 55 | 57 |
| 1201099 | 1393 | 1412 | 17184 | 17203 | AGCAACGGCTCATGATGAAC | 25 | 58 |
| 1201105 | 1404 | 1423 | 17195 | 17214 | GGCCTGGCATTAGCAACGGC | 80 | 59 |
| 1201111 | 1472 | 1491 | 17263 | 17282 | AACCTGTTGCACTAAGTCCA | 17 | 60 |
| 1201117 | 1561 | 1580 | 17352 | 17371 | GCATTAGTATACTGAGCTCT | 48 | 61 |
| 1201123 | 1651 | 1670 | 17442 | 17461 | GGCCTCCTAACAAACCTGGC | 77 | 62 |
| 1201129 | 1742 | 1761 | 17533 | 17552 | TCTCGGTACACACAGAGCTC | 98 | 63 |

TABLE 2-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201135 | 1788 | 1807 | 17579 | 17598 | AGCTGCTGTGTAGCCCATAC | 26 | 64 |
| 1201141 | 1962 | 1981 | 17753 | 17772 | CCACATATAGGGTCCTTTAA | 18 | 65 |
| 1201142 | 1963 | 1982 | 17754 | 17773 | GCCACATATAGGGTCCTTTA | 9 | 66 |
| 1201148 | 2585 | 2604 | 18376 | 18395 | CACGCAAAAGGGTTTCCCAC | 58 | 67 |
| 1201154 | 2607 | 2626 | 18398 | 18417 | TGCACATTGTAAGCCTAAGG | 6 | 68 |
| 1201160 | N/A | N/A | 3553 | 3572 | TCACTCGGCCCCCGCGGCTC | 99 | 69 |
| 1201166 | N/A | N/A | 3592 | 3611 | CCGGGCACCCTTGCGCCTGG | 93 | 70 |
| 1201172 | N/A | N/A | 3691 | 3710 | CCCGAGCGGAGACCAGCGCA | 74 | 71 |
| 1201178 | N/A | N/A | 3702 | 3721 | AAGCCGCCTCACCCGAGCGG | 84 | 72 |
| 1201184 | N/A | N/A | 3755 | 3774 | CCAGCCCCCAACGCGCAGT | 71 | 73 |
| 1201190 | N/A | N/A | 3848 | 3867 | CGATCGCCCGCTGGGCCGGA | 78 | 74 |
| 1201196 | N/A | N/A | 3872 | 3891 | CTCCCGGAGTTCCCTGGGCG | 88 | 75 |
| 1201204 | N/A | N/A | 3981 | 4000 | TGGGCCCCGATCTCGGCCTC | 85 | 76 |
| 1201210 | N/A | N/A | 4071 | 4090 | CCGGAACTCCCCCGGCGGGC | 73 | 77 |
| 1201216 | N/A | N/A | 4081 | 4100 | ACCGAGGCTCCCGGAACTCC | 84 | 78 |
| 1201222 | N/A | N/A | 4180 | 4199 | ACGGCCGCAAGGCTGCAGCC | 71 | 79 |
| 1201228 | N/A | N/A | 4227 | 4246 | CGCCCCGCCCGTCAGTCCG | 84 | 80 |
| 1201234 | N/A | N/A | 4604 | 4623 | TGACCGTGGTGGAATTGCGA | 49 | 81 |
| 1201240 | N/A | N/A | 4759 | 4778 | TGCTAATTAAACCGTGATGC | 32 | 82 |
| 1201246 | N/A | N/A | 5419 | 5438 | GCCCCCAATAACTCATACAT | 91 | 83 |
| 1201252 | N/A | N/A | 5744 | 5763 | GGTGCAGTTAATAACCCACT | 69 | 84 |
| 1201258 | N/A | N/A | 6539 | 6558 | TAGTTGGTTGACAGCCATGT | 68 | 85 |
| 1201264 | N/A | N/A | 6850 | 6869 | ACCTCCCTTAAAGTGATCAC | 81 | 86 |
| 1201270 | N/A | N/A | 6986 | 7005 | AGTCAGAGAGTGCCTAGCGA | 57 | 87 |
| 1201276 | N/A | N/A | 7283 | 7302 | GCTTAATTAGTTACATCGGG | 3 | 88 |
| 1201282 | N/A | N/A | 7390 | 7409 | AGCTAGTAAGAACTTATCCC | 46 | 89 |
| 1201288 | N/A | N/A | 9029 | 9048 | TCTTAGATTTTGGACGGGA | 12 | 90 |
| 1201294 | N/A | N/A | 9692 | 9711 | AGCTCTATTAATAGGTTAGG | 9 | 91 |
| 1201300 | N/A | N/A | 10098 | 10117 | GCGGTGATGCCATCTACTGA | 86 | 92 |
| 1201306 | N/A | N/A | 10591 | 10610 | GTGGACTGCTAAGACTAGGG | 22 | 93 |
| 1201312 | N/A | N/A | 10805 | 10824 | GCTATATATAGGTGACCCAC | 76 | 94 |
| 1201318 | N/A | N/A | 12095 | 12114 | GCACGATAAAGCTGACTCTG | 61 | 95 |
| 1201324 | N/A | N/A | 13539 | 13558 | TGCAATTAGTGTGATCATGC | 33 | 96 |
| 1201330 | N/A | N/A | 13750 | 13769 | AGTGGCCTAGTCCTCTGGCA | 83 | 97 |
| 1201336 | N/A | N/A | 13946 | 13965 | AGTTAAGGATCTATGAGCTC | 74 | 98 |
| 1201342 | N/A | N/A | 14282 | 14301 | CGCTTGACCCATAGACATGC | 66 | 99 |

TABLE 2-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201348 | N/A | N/A | 14624 | 14643 | TGGGCCCCATGTAACCTGGT | 97 | 100 |
| 1201354 | N/A | N/A | 14721 | 14740 | TCCTCTTAATATGCGGGTCA | 74 | 101 |
| 1201360 | N/A | N/A | 14819 | 14838 | GACCATCTTATTCGGTGCTT | 41 | 102 |
| 1201366 | N/A | N/A | 14939 | 14958 | CCAATGCTCTAGAGTGACTG | 79 | 103 |
| 1201372 | N/A | N/A | 15466 | 15485 | GCAACCGAAACTGTTGCCAA | 81 | 104 |

TABLE 3

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1200910 | 14 | 33 | 3107 | 3126 | CTCCCCGTTACATAATGGAG | 76 | 105 |
| 1200916 | 98 | 117 | 3191 | 3210 | CCGCCTGCGGGTGCCATCGC | 102 | 106 |
| 1200922 | 106 | 125 | 3199 | 3218 | AGTTGATACCGCCTGCGGGT | 70 | 107 |
| 1200928 | 114 | 133 | 3207 | 3226 | CTTGCATCAGTTGATACCGC | 89 | 108 |
| 1200934 | 162 | 181 | 3255 | 3274 | GGCCGGGAATGAGTCACCGG | 104 | 109 |
| 1200940 | 212 | 231 | 3305 | 3324 | GCGGGCGGCCGGCCGAGGTT | 78 | 110 |
| 1200946 | 241 | 260 | 3334 | 3353 | CGCGGCCCGGCGCACACTCT | 77 | 111 |
| 1200952 | 253 | 272 | 3346 | 3365 | GACCAATTGCCGCGCGGCCC | 80 | 112 |
| 1200958 | 341 | 360 | 3434 | 3453 | GGAGGACAGGCGACGCGCGG | 113 | 113 |
| 1200966 | 355 | 374 | 3448 | 3467 | TCAGCGACTGGCTCGGAGGA | 98 | 114 |
| 1200972 | 416 | 435 | 16207 | 16226 | CGCCATAATGACTGCTCTGC | 19* | 115 |
| 1200978 | 424 | 443 | 16215 | 16234 | CCAAGGTTCGCCATAATGAC | 25* | 116 |
| 1200984 | 525 | 544 | 16316 | 16335 | GGTATCGGCTGCCCCCAGTG | 20* | 117 |
| 1200990 | 532 | 551 | 16323 | 16342 | TGCCCCGGGTATCGGCTGCC | 108* | 118 |
| 1200996 | 561 | 580 | 16352 | 16371 | GTGGGTAGCGGTTGCCTCCA | 91 | 119 |
| 1201002 | 574 | 593 | 16365 | 16384 | CCACCGCCCTGAGGTGGGTA | 54 | 120 |
| 1201008 | 726 | 745 | 16517 | 16536 | TTGGCTTACTCGGCTTGTTC | 35 | 121 |
| 1201014 | 799 | 818 | 16590 | 16609 | AGCATGTAGCCGCCAAGGCC | 88 | 122 |
| 1201020 | 829 | 848 | 16620 | 16639 | TGTATGATGGGCCTGCTCAT | 69 | 123 |
| 1201026 | 852 | 871 | 16643 | 16662 | GGTCCTCATAGTCACTGCCG | 72 | 124 |
| 1201032 | 878 | 897 | 16669 | 16688 | ACGGTGCATGTTTTCACGAT | 69 | 125 |
| 1201038 | 905 | 924 | 16696 | 16715 | GGGCCTGTAGTACACTTGGT | 79 | 126 |
| 1201044 | 942 | 961 | 16733 | 16752 | CGTGCACAAAGTTGTTCTGG | 87 | 127 |
| 1201050 | 982 | 1001 | 16773 | 16792 | GTGGTGACCGTGTGCTGCTT | 55 | 128 |
| 1201056 | 1008 | 1027 | 16799 | 16818 | CGGTGAAGTTCTCCCCCTTG | 67 | 129 |
| 1201062 | 1017 | 1036 | 16808 | 16827 | CGTCGGTCTCGGTGAAGTTC | 58 | 130 |

TABLE 3-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201068 | 1047 | 1066 | 16838 | 16857 | TCTGCTCAACCACGCGCTCC | 90 | 131 |
| 1201076 | 1104 | 1123 | 16895 | 16914 | TGCTCGATCCTCTCTGGTAA | 77 | 132 |
| 1201082 | 1233 | 1252 | 17024 | 17043 | GATACCGCCTCCCTCAAGCT | 47 | 133 |
| 1201088 | 1239 | 1258 | 17030 | 17049 | CAGGTGGATACCGCCTCCCT | 99 | 134 |
| 1201094 | 1310 | 1329 | 17101 | 17120 | CCAAGGGTATTGATTAGCCT | 16 | 135 |
| 1201100 | 1398 | 1417 | 17189 | 17208 | GCATTAGCAACGGCTCATGA | 63 | 136 |
| 1201106 | 1406 | 1425 | 17197 | 17216 | CTGGCCTGGCATTAGCAACG | 66 | 137 |
| 1201112 | 1474 | 1493 | 17265 | 17284 | TCAACCTGTTGCACTAAGTC | 23 | 138 |
| 1201118 | 1562 | 1581 | 17353 | 17372 | GGCATTAGTATACTGAGCTC | 49 | 139 |
| 1201124 | 1660 | 1679 | 17451 | 17470 | GTATCATGTGGCCTCCTAAC | 14 | 140 |
| 1201130 | 1744 | 1763 | 17535 | 17554 | GTTCTCGGTACACACAGAGC | 83 | 141 |
| 1201136 | 1833 | 1852 | 17624 | 17643 | CTAGCCAGAGGTTCAGTGTT | 46 | 142 |
| 1201142 | 1963 | 1982 | 17754 | 17773 | GCCACATATAGGGTCCTTTA | 7 | 66 |
| 1201143 | 1965 | 1984 | 17756 | 17775 | ATGCCACATATAGGGTCCTT | 10 | 143 |
| 1201149 | 2586 | 2605 | 18377 | 18396 | CCACGCAAAAGGGTTTCCCA | 36 | 144 |
| 1201155 | 2609 | 2628 | 18400 | 18419 | AGTGCACATTGTAAGCCTAA | 47 | 145 |
| 1201161 | N/A | N/A | 3556 | 3575 | TCCTCACTCGGCCCCCGCGG | 74 | 146 |
| 1201167 | N/A | N/A | 3596 | 3615 | CCGGCCGGGCACCCTTGCGC | 104 | 147 |
| 1201173 | N/A | N/A | 3693 | 3712 | CACCCGAGCGGAGACCAGCG | 94 | 148 |
| 1201179 | N/A | N/A | 3704 | 3723 | CCAAGCCGCCTCACCCGAGC | 61 | 149 |
| 1201185 | N/A | N/A | 3790 | 3809 | CCACCGACCTCCCTAACGGG | 101 | 150 |
| 1201191 | N/A | N/A | 3849 | 3868 | GCGATCGCCCGCTGGGCCGG | 95 | 151 |
| 1201198 | N/A | N/A | 3877 | 3896 | CGGCCCTCCCGGAGTTCCCT | 81 | 152 |
| 1201205 | N/A | N/A | 3984 | 4003 | TTCTGGGCCCCGATCTCGGC | 105 | 153 |
| 1201211 | N/A | N/A | 4072 | 4091 | CCCGGAACTCCCCCGGCGGG | 92 | 154 |
| 1201217 | N/A | N/A | 4083 | 4102 | GCACCGAGGCTCCCGGAACT | 78 | 155 |
| 1201223 | N/A | N/A | 4187 | 4206 | GGTGGCAACGGCCGCAAGGC | 87 | 156 |
| 1201229 | N/A | N/A | 4418 | 4437 | TGGTTGTTCCTTGGAGCCCC | 81 | 157 |
| 1201235 | N/A | N/A | 4606 | 4625 | TGTGACCGTGGTGGAATTGC | 35 | 158 |
| 1201241 | N/A | N/A | 5080 | 5099 | GGTGTGGAAGACTTGTGTTA | 35 | 159 |
| 1201247 | N/A | N/A | 5464 | 5483 | GCATCACCAGATTGCTTAAC | 49 | 160 |
| 1201253 | N/A | N/A | 5745 | 5764 | AGGTGCAGTTAATAACCCAC | 62 | 161 |
| 1201259 | N/A | N/A | 6542 | 6561 | GGCTAGTTGGTTGACAGCCA | 90 | 162 |
| 1201265 | N/A | N/A | 6925 | 6944 | CCCGTGATCAGGCTTCAGTG | 66 | 163 |
| 1201271 | N/A | N/A | 6987 | 7006 | CAGTCAGAGAGTGCCTAGCG | 51 | 164 |
| 1201277 | N/A | N/A | 7284 | 7303 | AGCTTAATTAGTTACATCGG | 18 | 165 |

TABLE 3-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201283 | N/A | N/A | 7435 | 7454 | CCCCGTTCATCTTATTCCCA | 44 | 166 |
| 1201289 | N/A | N/A | 9031 | 9050 | TCTCTTAGATTTTTGGACGG | 32 | 167 |
| 1201295 | N/A | N/A | 9851 | 9870 | GTGGGCACACTTAGCCACCC | 85 | 168 |
| 1201301 | N/A | N/A | 10127 | 10146 | GGTCTGGGACTTCCATAACC | 93 | 169 |
| 1201307 | N/A | N/A | 10592 | 10611 | GGTGGACTGCTAAGACTAGG | 52 | 170 |
| 1201313 | N/A | N/A | 10806 | 10825 | AGCTATATATAGGTGACCCA | 61 | 171 |
| 1201319 | N/A | N/A | 12109 | 12128 | AAGATTCTTGTTCAGCACGA | 53 | 172 |
| 1201325 | N/A | N/A | 13633 | 13652 | CCATTGTCATGGGACTCAAG | 49 | 173 |
| 1201331 | N/A | N/A | 13751 | 13770 | TAGTGGCCTAGTCCTCTGGC | 65 | 174 |
| 1201337 | N/A | N/A | 13947 | 13966 | GAGTTAAGGATCTATGAGCT | 60 | 175 |
| 1201343 | N/A | N/A | 14346 | 14365 | CGGGAGTGCAGGCTCCTTTA | 84 | 176 |
| 1201349 | N/A | N/A | 14639 | 14658 | CGTGGCCATACTGGCTGGGC | 83 | 177 |
| 1201355 | N/A | N/A | 14722 | 14741 | CTCCTCTTAATATGCGGGTC | 75 | 178 |
| 1201361 | N/A | N/A | 14823 | 14842 | ACATGACCATCTTATTCGGT | 55 | 179 |
| 1201367 | N/A | N/A | 15033 | 15052 | AACTAGGGCACCATCCCCTC | 78 | 180 |
| 1201373 | N/A | N/A | 15736 | 15755 | ACAGTACCTGCTGTACCCTA | 49 | 181 |

TABLE 4

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1200911 | 18 | 37 | 3111 | 3130 | CCAGCTCCCCGTTACATAAT | 90 | 182 |
| 1200917 | 99 | 118 | 3192 | 3211 | ACCGCCTGCGGGTGCCATCG | 112 | 183 |
| 1200923 | 107 | 126 | 3200 | 3219 | CAGTTGATACCGCCTGCGGG | 104 | 184 |
| 1200929 | 115 | 134 | 3208 | 3227 | ACTTGCATCAGTTGATACCG | 89 | 185 |
| 1200935 | 199 | 218 | 3292 | 3311 | CGAGGTTTAAGTTAAAGGGT | 86 | 186 |
| 1200941 | 224 | 243 | 3317 | 3336 | TCTGTGCCCCCGGCGGCGG | 80 | 187 |
| 1200947 | 243 | 262 | 3336 | 3355 | CGCGCGGCCCGGCGCACACT | 80 | 188 |
| 1200953 | 254 | 273 | 3347 | 3366 | GGACCAATTGCCGCGCGGCC | 81 | 189 |
| 1200959 | 342 | 361 | 3435 | 3454 | CGGAGGACAGGCGACGCGCG | 98 | 190 |
| 1200967 | 359 | 378 | 3452 | 3471 | GCTGTCAGCGACTGGCTCGG | 95 | 191 |
| 1200973 | 417 | 436 | 16208 | 16227 | TCGCCATAATGACTGCTCTG | 15* | 192 |
| 1200979 | 428 | 447 | 16219 | 16238 | GCAGCCAAGGTTCGCCATAA | 20* | 193 |
| 1200985 | 526 | 545 | 16317 | 16336 | GGGTATCGGCTGCCCCCAGT | 87* | 194 |
| 1200991 | 535 | 554 | 16326 | 16345 | CCCTGCCCCGGGTATCGGCT | 85 | 195 |
| 1200997 | 562 | 581 | 16353 | 16372 | GGTGGGTAGCGGTTGCCTCC | 90 | 196 |

TABLE 4 -continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201003 | 720 | 739 | 16511 | 16530 | TACTCGGCTTGTTCCACTGA | 78 | 197 |
| 1201009 | 730 | 749 | 16521 | 16540 | GTTTTTGGCTTACTCGGCTT | 41 | 198 |
| 1201015 | 800 | 819 | 16591 | 16610 | CAGCATGTAGCCGCCAAGGC | 69 | 199 |
| 1201021 | 830 | 849 | 16621 | 16640 | ATGTATGATGGGCCTGCTCA | 59 | 200 |
| 1201027 | 863 | 882 | 16654 | 16673 | ACGATAGTAACGGTCCTCAT | 41 | 201 |
| 1201033 | 879 | 898 | 16670 | 16689 | AACGGTGCATGTTTTCACGA | 67 | 202 |
| 1201039 | 906 | 925 | 16697 | 16716 | TGGGCCTGTAGTACACTTGG | 82 | 203 |
| 1201045 | 974 | 993 | 16765 | 16784 | CGTGTGCTGCTTGATTGTGA | 41 | 204 |
| 1201051 | 983 | 1002 | 16774 | 16793 | TGTGGTGACCGTGTGCTGCT | 83 | 205 |
| 1201057 | 1009 | 1028 | 16800 | 16819 | TCGGTGAAGTTCTCCCCCTT | 52 | 206 |
| 1201063 | 1038 | 1057 | 16829 | 16848 | CCACGCGCTCCATCATCTTA | 62 | 207 |
| 1201069 | 1050 | 1069 | 16841 | 16860 | ACATCTGCTCAACCACGCGC | 59 | 208 |
| 1201077 | 1105 | 1124 | 16896 | 16915 | ATGCTCGATCCTCTCTGGTA | 77 | 209 |
| 1201083 | 1234 | 1253 | 17025 | 17044 | GGATACCGCCTCCCTCAAGC | 26 | 210 |
| 1201089 | 1243 | 1262 | 17034 | 17053 | GCTGCAGGTGGATACCGCCT | 94 | 211 |
| 1201095 | 1311 | 1330 | 17102 | 17121 | GCCAAGGGTATTGATTAGCC | 9 | 212 |
| 1201101 | 1399 | 1418 | 17190 | 17209 | GGCATTAGCAACGGCTCATG | 40 | 213 |
| 1201107 | 1410 | 1429 | 17201 | 17220 | TTTACTGGCCTGGCATTAGC | 44 | 214 |
| 1201113 | 1480 | 1499 | 17271 | 17290 | TTAGCCTCAACCTGTTGCAC | 33 | 215 |
| 1201119 | 1563 | 1582 | 17354 | 17373 | GGGCATTAGTATACTGAGCT | 15 | 216 |
| 1201125 | 1722 | 1741 | 17513 | 17532 | ATGCTCCAGCGGGCTGAGCC | 110 | 217 |
| 1201131 | 1748 | 1767 | 17539 | 17558 | CCCAGTTCTCGGTACACACA | 41 | 218 |
| 1201137 | 1839 | 1858 | 17630 | 17649 | TGTCCTCTAGCCAGAGGTTC | 93 | 219 |
| 1201142 | 1963 | 1982 | 17754 | 17773 | GCCACATATAGGGTCCTTTA | 9 | 66 |
| 1201144 | 1967 | 1986 | 17758 | 17777 | GAATGCCACATATAGGGTCC | 18 | 220 |
| 1201150 | 2587 | 2606 | 18378 | 18397 | ACCACGCAAAAGGGTTTCCC | 45 | 221 |
| 1201156 | 2617 | 2636 | 18408 | 18427 | AACGATTCAGTGCACATTGT | 23 | 222 |
| 1201162 | N/A | N/A | 3557 | 3576 | GTCCTCACTCGGCCCCCGCG | 61 | 223 |
| 1201168 | N/A | N/A | 3599 | 3618 | CGCCCGGCCGGGCACCCTTG | 86 | 224 |
| 1201174 | N/A | N/A | 3694 | 3713 | TCACCCGAGCGGAGACCAGC | 81 | 225 |
| 1201180 | N/A | N/A | 3707 | 3726 | AAGCCAAGCCGCCTCACCCG | 77 | 226 |
| 1201186 | N/A | N/A | 3809 | 3828 | GCGCTGAGACACCCCGGCGC | 108 | 227 |
| 1201192 | N/A | N/A | 3850 | 3869 | AGCGATCGCCCGCTGGGCCG | 94 | 228 |
| 1201200 | N/A | N/A | 3878 | 3897 | GCGGCCCTCCCGGAGTTCCC | 72 | 229 |
| 1201206 | N/A | N/A | 3986 | 4005 | CGTTCTGGGCCCCGATCTCG | 53 | 230 |
| 1201212 | N/A | N/A | 4073 | 4092 | TCCCGGAACTCCCCCGGCGG | 92 | 231 |

TABLE 4 -continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201218 | N/A | N/A | 4120 | 4139 | CCGCCTCCCGGGAGGAACGC | 81 | 232 |
| 1201224 | N/A | N/A | 4193 | 4212 | CCAGGCGGTGGCAACGGCCG | 93 | 233 |
| 1201230 | N/A | N/A | 4425 | 4444 | CCGAGGCTGGTTGTTCCTTG | 94 | 234 |
| 1201236 | N/A | N/A | 4618 | 4637 | GGCGAGGATGGATGTGACCG | 59 | 235 |
| 1201242 | N/A | N/A | 5082 | 5101 | TCGGTGTGGAAGACTTGTGT | 43 | 236 |
| 1201248 | N/A | N/A | 5612 | 5631 | GGTGTTATACATTTAGGCTC | 20 | 237 |
| 1201254 | N/A | N/A | 6201 | 6220 | GCTAAACTAGATTTGTGCCT | 73 | 238 |
| 1201260 | N/A | N/A | 6543 | 6562 | TGGCTAGTTGGTTGACAGCC | 101 | 239 |
| 1201266 | N/A | N/A | 6935 | 6954 | GGAATTGGCACCCGTGATCA | 73 | 240 |
| 1201272 | N/A | N/A | 6988 | 7007 | CCAGTCAGAGAGTGCCTAGC | 81 | 241 |
| 1201278 | N/A | N/A | 7324 | 7343 | CACTAAAGCCTTCTAGCCCA | 66 | 242 |
| 1201284 | N/A | N/A | 7557 | 7576 | GGTGCACTTGACCTGCCAGG | 114 | 243 |
| 1201290 | N/A | N/A | 9317 | 9336 | AGTCCCTAAATCAGCTGTAG | 63 | 244 |
| 1201296 | N/A | N/A | 9852 | 9871 | GGTGGGCACACTTAGCCACC | 94 | 245 |
| 1201302 | N/A | N/A | 10140 | 10159 | TGAGAGTTGCCCGGGTCTGG | 77 | 246 |
| 1201308 | N/A | N/A | 10626 | 10645 | GATCAAATCTGTGGAGCCCC | 94 | 247 |
| 1201314 | N/A | N/A | 10807 | 10826 | CAGCTATATATAGGTGACCC | 64 | 248 |
| 1201320 | N/A | N/A | 13260 | 13279 | TTCCATGGTCTTGATGGCGA | 56 | 249 |
| 1201326 | N/A | N/A | 13697 | 13716 | GGTCAATACCTGTTTATTAC | 24 | 250 |
| 1201332 | N/A | N/A | 13752 | 13771 | GTAGTGGCCTAGTCCTCTGG | 85 | 251 |
| 1201338 | N/A | N/A | 13980 | 13999 | CGGGCTTTGAATGTGCCTCA | 77 | 252 |
| 1201344 | N/A | N/A | 14500 | 14519 | GGCTAAAGTTTGCTCAGTGG | 24 | 253 |
| 1201350 | N/A | N/A | 14676 | 14695 | AGTGAGGCTCCTTTGTACTC | 61 | 254 |
| 1201356 | N/A | N/A | 14723 | 14742 | TCTCCTCTTAATATGCGGGT | 64 | 255 |
| 1201362 | N/A | N/A | 14824 | 14843 | AACATGACCATCTTATTCGG | 73 | 256 |
| 1201368 | N/A | N/A | 15058 | 15077 | GCTACTCATACACCCCAGGA | 45 | 257 |
| 1201374 | N/A | N/A | 15737 | 15756 | AACAGTACCTGCTGTACCCT | 58 | 258 |

TABLE 5

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1200912 | 19 | 38 | 3112 | 3131 | TCCAGCTCCCCGTTACATAA | 77 | 259 |
| 1200918 | 100 | 119 | 3193 | 3212 | TACCGCCTGCGGGTGCCATC | 77 | 260 |
| 1200924 | 108 | 127 | 3201 | 3220 | TCAGTTGATACCGCCTGCGG | 87 | 261 |
| 1200930 | 116 | 135 | 3209 | 3228 | CACTTGCATCAGTTGATACC | 87 | 262 |

TABLE 5-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1200936 | 206 | 225 | 3299 | 3318 | GGCCGGCCGAGGTTTAAGTT | 96 | 263 |
| 1200942 | 231 | 250 | 3324 | 3343 | CGCACACTCTGTGCCCCCGG | 98 | 264 |
| 1200948 | 246 | 265 | 3339 | 3358 | TGCCGCGCGGCCCGGCGCAC | 89 | 265 |
| 1200954 | 255 | 274 | 3348 | 3367 | GGGACCAATTGCCGCGCGGC | 80 | 266 |
| 1200960 | 343 | 362 | 3436 | 3455 | TCGGAGGACAGGCGACGCGC | 113 | 267 |
| 1200968 | 361 | 380 | 3454 | 3473 | CGGCTGTCAGCGACTGGCTC | 90 | 268 |
| 1200974 | 418 | 437 | 16209 | 16228 | TTCGCCATAATGACTGCTCT | 17* | 269 |
| 1200980 | 429 | 448 | 16220 | 16239 | AGCAGCCAAGGTTCGCCATA | 23* | 270 |
| 1200986 | 527 | 546 | 16318 | 16337 | CGGGTATCGGCTGCCCCCAG | 69* | 271 |
| 1200992 | 536 | 555 | 16327 | 16346 | GCCCTGCCCCGGGTATCGGC | 97 | 272 |
| 1200998 | 563 | 582 | 16354 | 16373 | AGGTGGGTAGCGGTTGCCTC | 73 | 273 |
| 1201004 | 721 | 740 | 16512 | 16531 | TTACTCGGCTTGTTCCACTG | 49 | 274 |
| 1201010 | 731 | 750 | 16522 | 16541 | GGTTTTTGGCTTACTCGGCT | 11 | 275 |
| 1201016 | 801 | 820 | 16592 | 16611 | CCAGCATGTAGCCGCCAAGG | 50 | 276 |
| 1201022 | 836 | 855 | 16627 | 16646 | GCCGAAATGTATGATGGGCC | 86 | 277 |
| 1201028 | 864 | 883 | 16655 | 16674 | CACGATAGTAACGGTCCTCA | 49 | 278 |
| 1201034 | 882 | 901 | 16673 | 16692 | GGTAACGGTGCATGTTTTCA | 34 | 279 |
| 1201040 | 909 | 928 | 16700 | 16719 | CCATGGGCCTGTAGTACACT | 79 | 280 |
| 1201046 | 975 | 994 | 16766 | 16785 | CCGTGTGCTGCTTGATTGTG | 38 | 281 |
| 1201052 | 984 | 1003 | 16775 | 16794 | TTGTGGTGACCGTGTGCTGC | 63 | 282 |
| 1201058 | 1010 | 1029 | 16801 | 16820 | CTCGGTGAAGTTCTCCCCCT | 66 | 283 |
| 1201064 | 1040 | 1059 | 16831 | 16850 | AACCACGCGCTCCATCATCT | 41 | 284 |
| 1201070 | 1053 | 1072 | 16844 | 16863 | TACACATCTGCTCAACCACG | 45 | 285 |
| 1201078 | 1112 | 1131 | 16903 | 16922 | GAGGACCATGCTCGATCCTC | 77 | 286 |
| 1201084 | 1235 | 1254 | 17026 | 17045 | TGGATACCGCCTCCCTCAAG | 47 | 287 |
| 1201090 | 1304 | 1323 | 17095 | 17114 | GTATTGATTAGCCTATCCGG | 52 | 288 |
| 1201096 | 1312 | 1331 | 17103 | 17122 | TGCCAAGGGTATTGATTAGC | 21 | 289 |
| 1201102 | 1400 | 1419 | 17191 | 17210 | TGGCATTAGCAACGGCTCAT | 28 | 290 |
| 1201108 | 1418 | 1437 | 17209 | 17228 | GTTATACTTTTACTGGCCTG | 28 | 291 |
| 1201114 | 1555 | 1574 | 17346 | 17365 | GTATACTGAGCTCTAGCTGC | 67 | 292 |
| 1201120 | 1564 | 1583 | 17355 | 17374 | AGGGCATTAGTATACTGAGC | 4 | 293 |
| 1201126 | 1723 | 1742 | 17514 | 17533 | CATGCTCCAGCGGGCTGAGC | 104 | 294 |
| 1201132 | 1755 | 1774 | 17546 | 17565 | ACATCACCCCAGTTCTCGGT | 23 | 295 |
| 1201138 | 1846 | 1865 | 17637 | 17656 | GTGAATATGTCCTCTAGCCA | 12 | 296 |
| 1201142 | 1963 | 1982 | 17754 | 17773 | GCCACATATAGGGTCCTTTA | 11 | 66 |
| 1201145 | 1968 | 1987 | 17759 | 17778 | GGAATGCCACATATAGGGTC | 13 | 297 |

TABLE 5-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201151 | 2599 | 2618 | 18390 | 18409 | GTAAGCCTAAGGACCACGCA | 21 | 298 |
| 1201157 | 2652 | 2671 | 18443 | 18462 | CCTGTTAATGGTGTCCACTT | 11 | 299 |
| 1201163 | N/A | N/A | 3584 | 3603 | CCTTGCGCCTGGGACCCGAG | 76 | 300 |
| 1201169 | N/A | N/A | 3670 | 3689 | CCGGGCAGGCCCGAGACGCG | 79 | 301 |
| 1201175 | N/A | N/A | 3695 | 3714 | CTCACCCGAGCGGAGACCAG | 97 | 302 |
| 1201181 | N/A | N/A | 3709 | 3728 | CGAAGCCAAGCCGCCTCACC | 89 | 303 |
| 1201187 | N/A | N/A | 3841 | 3860 | CCGCTGGGCCGGACCCGCGC | 92 | 304 |
| 1201193 | N/A | N/A | 3852 | 3871 | CCAGCGATCGCCCGCTGGGC | 84 | 305 |
| 1201201 | N/A | N/A | 3882 | 3901 | GCTGGCGGCCCTCCCGGAGT | 73 | 306 |
| 1201207 | N/A | N/A | 4029 | 4048 | GCACCCTCTGGGCATCGCGG | 85 | 307 |
| 1201213 | N/A | N/A | 4074 | 4093 | CTCCCGGAACTCCCCCGGCG | 85 | 308 |
| 1201219 | N/A | N/A | 4158 | 4177 | CCTCGGAGAAGCTCAGGCGG | 110 | 309 |
| 1201225 | N/A | N/A | 4196 | 4215 | TCTCCAGGCGGTGGCAACGG | 92 | 310 |
| 1201231 | N/A | N/A | 4426 | 4445 | TCCGAGGCTGGTTGTTCCTT | 60 | 311 |
| 1201237 | N/A | N/A | 4634 | 4653 | GCTGTGGCTCTGCGATGGCG | 92 | 312 |
| 1201243 | N/A | N/A | 5235 | 5254 | GCAACCTTCCAGCAAGGGTT | 85 | 313 |
| 1201249 | N/A | N/A | 5614 | 5633 | CTGGTGTTATACATTTAGGC | 40 | 314 |
| 1201255 | N/A | N/A | 6219 | 6238 | ACAATCTGTTGTGGTTCAGC | 7 | 315 |
| 1201261 | N/A | N/A | 6546 | 6565 | GTTTGGCTAGTTGGTTGACA | 32 | 316 |
| 1201267 | N/A | N/A | 6939 | 6958 | TCAGGGAATTGGCACCCGTG | 77 | 317 |
| 1201273 | N/A | N/A | 7051 | 7070 | GGTCCATGATCAGAATTACC | 80 | 318 |
| 1201279 | N/A | N/A | 7325 | 7344 | GCACTAAAGCCTTCTAGCCC | 74 | 319 |
| 1201285 | N/A | N/A | 7559 | 7578 | AGGGTGCACTTGACCTGCCA | 74 | 320 |
| 1201291 | N/A | N/A | 9318 | 9337 | GAGTCCCTAAATCAGCTGTA | 46 | 321 |
| 1201297 | N/A | N/A | 9863 | 9882 | GCTAGTACACAGGTGGGCAC | 75 | 322 |
| 1201303 | N/A | N/A | 10144 | 10163 | GGAGTGAGAGTTGCCCGGGT | 95 | 323 |
| 1201309 | N/A | N/A | 10650 | 10669 | GGTGGGCTTAAGGACCAAAA | 87 | 324 |
| 1201315 | N/A | N/A | 11775 | 11794 | GATTTGGAACCTGCATGGCT | 73 | 325 |
| 1201321 | N/A | N/A | 13443 | 13462 | AGCCTACGAAAACCAACGGC | 95 | 326 |
| 1201327 | N/A | N/A | 13703 | 13722 | GGTAATGGTCAATACCTGTT | 46 | 327 |
| 1201333 | N/A | N/A | 13754 | 13773 | AAGTAGTGGCCTAGTCCTCT | 61 | 328 |
| 1201339 | N/A | N/A | 13984 | 14003 | GAGTCGGGCTTTGAATGTGC | 37 | 329 |
| 1201345 | N/A | N/A | 14618 | 14637 | CCATGTAACCTGGTTCAGGC | 47 | 330 |
| 1201351 | N/A | N/A | 14708 | 14727 | CGGGTCACATCATGCCACTT | 64 | 331 |
| 1201357 | N/A | N/A | 14814 | 14833 | TCTTATTCGGTGCTTCCATC | 36 | 332 |
| 1201363 | N/A | N/A | 14882 | 14901 | ATCTCAGTAGCTCTACCTTG | 41 | 333 |

TABLE 5-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201369 | N/A | N/A | 15107 | 15126 | CCCTGATGTAGTCCCCACAA | 95 | 334 |
| 1201375 | N/A | N/A | 15789 | 15808 | GGGCACTTAGCTCCAAGAGC | 52 | 335 |

TABLE 6

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1200913 | 46 | 65 | 3139 | 3158 | TCTTTAATTGGAAATTCGGC | 97 | 336 |
| 1200919 | 101 | 120 | 3194 | 3213 | ATACCGCCTGCGGGTGCCAT | 80 | 337 |
| 1200925 | 110 | 129 | 3203 | 3222 | CATCAGTTGATACCGCCTGC | 90 | 338 |
| 1200931 | 128 | 147 | 3221 | 3240 | GATTCGCTTGAACACTTGCA | 103 | 339 |
| 1200937 | 208 | 227 | 3301 | 3320 | GCGGCCGGCCGAGGTTTAAG | 104 | 340 |
| 1200943 | 234 | 253 | 3327 | 3346 | CGGCGCACACTCTGTGCCCC | 101 | 341 |
| 1200949 | 248 | 267 | 3341 | 3360 | ATTGCCGCGCGGCCCGGCGC | 97 | 342 |
| 1200955 | 278 | 297 | 3371 | 3390 | GCTCGCGGGCGGAGGTCGGC | 80 | 343 |
| 1200963 | 345 | 364 | 3438 | 3457 | GCTCGGAGGACAGGCGACGC | 131 | 344 |
| 1200969 | 364 | 383 | 3457 | 3476 | CCGCGGCTGTCAGCGACTGG | 93 | 345 |
| 1200975 | 419 | 438 | 16210 | 16229 | GTTCGCCATAATGACTGCTC | 21* | 346 |
| 1200981 | 432 | 451 | 16223 | 16242 | TCCAGCAGCCAAGGTTCGCC | 22* | 347 |
| 1200987 | 528 | 547 | 16319 | 16338 | CCGGGTATCGGCTGCCCCCA | 100* | 348 |
| 1200993 | 537 | 556 | 16328 | 16347 | TGCCCTGCCCCGGGTATCGG | 67 | 349 |
| 1200999 | 564 | 583 | 16355 | 16374 | GAGGTGGGTAGCGGTTGCCT | 83 | 350 |
| 1201005 | 723 | 742 | 16514 | 16533 | GCTTACTCGGCTTGTTCCAC | 18 | 351 |
| 1201011 | 732 | 751 | 16523 | 16542 | TGGTTTTTGGCTTACTCGGC | 19 | 352 |
| 1201017 | 803 | 822 | 16594 | 16613 | TCCCAGCATGTAGCCGCCAA | 83 | 353 |
| 1201023 | 837 | 856 | 16628 | 16647 | TGCCGAAATGTATGATGGGC | 84 | 354 |
| 1201029 | 865 | 884 | 16656 | 16675 | TCACGATAGTAACGGTCCTC | 47 | 355 |
| 1201035 | 883 | 902 | 16674 | 16693 | GGGTAACGGTGCATGTTTTC | 42 | 356 |
| 1201041 | 911 | 930 | 16702 | 16721 | ATCCATGGGCCTGTAGTACA | 77 | 357 |
| 1201047 | 978 | 997 | 16769 | 16788 | TGACCGTGTGCTGCTTGATT | 46 | 358 |
| 1201053 | 987 | 1006 | 16778 | 16797 | TGGTTGTGGTGACCGTGTGC | 78 | 359 |
| 1201059 | 1011 | 1030 | 16802 | 16821 | TCTCGGTGAAGTTCTCCCCC | 58 | 360 |
| 1201065 | 1043 | 1062 | 16834 | 16853 | CTCAACCACGCGCTCCATCA | 36 | 361 |
| 1201071 | 1059 | 1078 | 16850 | 16869 | GGGTGATACACATCTGCTCA | 93 | 362 |
| 1201079 | 1114 | 1133 | 16905 | 16924 | AAGAGGACCATGCTCGATCC | 84 | 363 |
| 1201085 | 1236 | 1255 | 17027 | 17046 | GTGGATACCGCCTCCCTCAA | 61 | 364 |

TABLE 6 -continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201091 | 1305 | 1324 | 17096 | 17115 | GGTATTGATTAGCCTATCCG | 27 | 365 |
| 1201097 | 1316 | 1335 | 17107 | 17126 | TCAGTGCCAAGGGTATTGAT | 76 | 366 |
| 1201103 | 1401 | 1420 | 17192 | 17211 | CTGGCATTAGCAACGGCTCA | 52 | 367 |
| 1201109 | 1421 | 1440 | 17212 | 17231 | GCTGTTATACTTTTACTGGC | 19 | 368 |
| 1201115 | 1556 | 1575 | 17347 | 17366 | AGTATACTGAGCTCTAGCTG | 67 | 369 |
| 1201121 | 1635 | 1654 | 17426 | 17445 | TGGCAGAAATGTTGTCGGGT | 13 | 370 |
| 1201127 | 1729 | 1748 | 17520 | 17539 | AGAGCTCATGCTCCAGCGGG | 95 | 371 |
| 1201133 | 1756 | 1775 | 17547 | 17566 | AACATCACCCCAGTTCTCGG | 23 | 372 |
| 1201139 | 1938 | 1957 | 17729 | 17748 | CTAAAATGGGAGGTTGCCTC | 98 | 373 |
| 1201142 | 1963 | 1982 | 17754 | 17773 | GCCACATATAGGGTCCTTTA | 11 | 66 |
| 1201146 | 1998 | 2017 | 17789 | 17808 | GCTGCCTTAATTACCTATAG | 46 | 374 |
| 1201152 | 2600 | 2619 | 18391 | 18410 | TGTAAGCCTAAGGACCACGC | 27 | 375 |
| 1201158 | 2653 | 2672 | 18444 | 18463 | ACCTGTTAATGGTGTCCACT | 24 | 376 |
| 1201164 | N/A | N/A | 3585 | 3604 | CCCTTGCGCCTGGGACCCGA | 85 | 377 |
| 1201170 | N/A | N/A | 3686 | 3705 | GCGGAGACCAGCGCAGCCGG | 93 | 378 |
| 1201176 | N/A | N/A | 3698 | 3717 | CGCCTCACCCGAGCGGAGAC | 101 | 379 |
| 1201182 | N/A | N/A | 3710 | 3729 | GCGAAGCCAAGCCGCCTCAC | 82 | 380 |
| 1201188 | N/A | N/A | 3842 | 3861 | CCCGCTGGGCCGGACCCGCG | 100 | 381 |
| 1201194 | N/A | N/A | 3853 | 3872 | GCCAGCGATCGCCCGCTGGG | 110 | 382 |
| 1201202 | N/A | N/A | 3895 | 3914 | CCCTGCGGAGCCCGCTGGCG | 107 | 383 |
| 1201208 | N/A | N/A | 4031 | 4050 | AAGCACCCTCTGGGCATCGC | 70 | 384 |
| 1201214 | N/A | N/A | 4079 | 4098 | CGAGGCTCCCGGAACTCCCC | 79 | 385 |
| 1201220 | N/A | N/A | 4163 | 4182 | GCCCCCCTCGGAGAAGCTCA | 77 | 386 |
| 1201226 | N/A | N/A | 4203 | 4222 | GGCCGCTTCTCCAGGCGGTG | 106 | 387 |
| 1201232 | N/A | N/A | 4427 | 4446 | ATCCGAGGCTGGTTGTTCCT | 52 | 388 |
| 1201238 | N/A | N/A | 4640 | 4659 | CGGAGAGCTGTGGCTCTGCG | 93 | 389 |
| 1201244 | N/A | N/A | 5236 | 5255 | GGCAACCTTCCAGCAAGGGT | 58 | 390 |
| 1201250 | N/A | N/A | 5622 | 5641 | CTACTGCCCTGGTGTTATAC | 52 | 391 |
| 1201256 | N/A | N/A | 6339 | 6358 | ATGCACCCGAGTGGCCTCTG | 80 | 392 |
| 1201262 | N/A | N/A | 6547 | 6566 | GGTTTGGCTAGTTGGTTGAC | 26 | 393 |
| 1201268 | N/A | N/A | 6941 | 6960 | TCTCAGGGAATTGGCACCCG | 71 | 394 |
| 1201274 | N/A | N/A | 7231 | 7250 | ACCCCATAATGTCCCTTGTC | 82 | 395 |
| 1201280 | N/A | N/A | 7326 | 7345 | GGCACTAAAGCCTTCTAGCC | 102 | 396 |
| 1201286 | N/A | N/A | 7560 | 7579 | AAGGGTGCACTTGACCTGCC | 101 | 397 |
| 1201292 | N/A | N/A | 9490 | 9509 | GCATTCCCATTAATGTGGTG | 41 | 398 |
| 1201298 | N/A | N/A | 9919 | 9938 | GTCTTCACCTGAGATGTAGT | 45 | 399 |

TABLE 6 -continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201304 | N/A | N/A | 10147 | 10166 | GGAGGAGTGAGAGTTGCCCG | 87 | 400 |
| 1201310 | N/A | N/A | 10662 | 10681 | GATACTTAGCTTGGTGGGCT | 53 | 401 |
| 1201316 | N/A | N/A | 11827 | 11846 | GCTTATCAGGATAGCACAAA | 57 | 402 |
| 1201322 | N/A | N/A | 13457 | 13476 | TGGGACTGAAGGTCAGCCTA | 109 | 403 |
| 1201328 | N/A | N/A | 13746 | 13765 | GCCTAGTCCTCTGGCATATT | 105 | 404 |
| 1201334 | N/A | N/A | 13758 | 13777 | AGTCAAGTAGTGGCCTAGTC | 46 | 405 |
| 1201340 | N/A | N/A | 13995 | 14014 | GGAATGACACTGAGTCGGGC | 58 | 406 |
| 1201346 | N/A | N/A | 14619 | 14638 | CCCATGTAACCTGGTTCAGG | 78 | 407 |
| 1201352 | N/A | N/A | 14718 | 14737 | TCTTAATATGCGGGTCACAT | 61 | 408 |
| 1201358 | N/A | N/A | 14815 | 14834 | ATCTTATTCGGTGCTTCCAT | 44 | 409 |
| 1201364 | N/A | N/A | 14905 | 14924 | GCATACATTGGATCTATCAG | 22 | 410 |
| 1201370 | N/A | N/A | 15181 | 15200 | GGTCATGCCAGTTAGGGTTT | 22 | 411 |
| 1201376 | N/A | N/A | 15796 | 15815 | TTACCCTGGGCACTTAGCTC | 85 | 412 |

TABLE 7

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1200914 | 91 | 110 | 3184 | 3203 | CGGGTGCCATCGCTCCCTGA | 68 | 413 |
| 1200920 | 102 | 121 | 3195 | 3214 | GATACCGCCTGCGGGTGCCA | 77 | 414 |
| 1200926 | 111 | 130 | 3204 | 3223 | GCATCAGTTGATACCGCCTG | 103 | 415 |
| 1200932 | 138 | 157 | 3231 | 3250 | AACGAGTTGAGATTCGCTTG | 96 | 416 |
| 1200938 | 209 | 228 | 3302 | 3321 | GGCGGCCGGCCGAGGTTTAA | 89 | 417 |
| 1200944 | 235 | 254 | 3328 | 3347 | CCGGCGCACACTCTGTGCCC | 96 | 418 |
| 1200950 | 250 | 269 | 3343 | 3362 | CAATTGCCGCGCGGCCCGGC | 76 | 419 |
| 1200956 | 279 | 298 | 3372 | 3391 | CGCTCGCGGGCGGAGGTCGG | 116 | 420 |
| 1200964 | 352 | 371 | 3445 | 3464 | GCGACTGGCTCGGAGGACAG | 107 | 421 |
| 1200970 | 366 | 385 | 3459 | 3478 | CGCCGCGGCTGTCAGCGACT | 99 | 422 |
| 1200976 | 421 | 440 | 16212 | 16231 | AGGTTCGCCATAATGACTGC | 25* | 423 |
| 1200982 | 485 | 504 | 16276 | 16295 | GCGCTTCTTGCAGAGGCCCA | 42* | 424 |
| 1200988 | 529 | 548 | 16320 | 16339 | CCCGGGTATCGGCTGCCCCC | 82* | 425 |
| 1200994 | 559 | 578 | 16350 | 16369 | GGGTAGCGGTTGCCTCCAGG | 99 | 426 |
| 1201000 | 568 | 587 | 16359 | 16378 | CCCTGAGGTGGGTAGCGGTT | 95 | 427 |
| 1201006 | 724 | 743 | 16515 | 16534 | GGCTTACTCGGCTTGTTCCA | 30 | 428 |
| 1201012 | 796 | 815 | 16587 | 16606 | ATGTAGCCGCCAAGGCCCCC | 97 | 429 |
| 1201018 | 805 | 824 | 16596 | 16615 | CTTCCCAGCATGTAGCCGCC | 83 | 430 |

TABLE 7 -continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201024 | 850 | 869 | 16641 | 16660 | TCCTCATAGTCACTGCCGAA | 60 | 431 |
| 1201030 | 866 | 885 | 16657 | 16676 | TTCACGATAGTAACGGTCCT | 59 | 432 |
| 1201036 | 901 | 920 | 16692 | 16711 | CTGTAGTACACTTGGTTGGG | 35 | 433 |
| 1201042 | 916 | 935 | 16707 | 16726 | TACTCATCCATGGGCCTGTA | 75 | 434 |
| 1201048 | 980 | 999 | 16771 | 16790 | GGTGACCGTGTGCTGCTTGA | 46 | 435 |
| 1201054 | 998 | 1017 | 16789 | 16808 | CTCCCCCTTGGTGGTTGTGG | 73 | 436 |
| 1201060 | 1013 | 1032 | 16804 | 16823 | GGTCTCGGTGAAGTTCTCCC | 93 | 437 |
| 1201066 | 1045 | 1064 | 16836 | 16855 | TGCTCAACCACGCGCTCCAT | 72 | 438 |
| 1201072 | 1089 | 1108 | 16880 | 16899 | GGTAATAGGCCTGAGATTCC | 25 | 439 |
| 1201080 | 1118 | 1137 | 16909 | 16928 | GGAGAAGAGGACCATGCTCG | 88 | 440 |
| 1201086 | 1237 | 1256 | 17028 | 17047 | GGTGGATACCGCCTCCCTCA | 95 | 441 |
| 1201092 | 1306 | 1325 | 17097 | 17116 | GGGTATTGATTAGCCTATCC | 32 | 442 |
| 1201098 | 1392 | 1411 | 17183 | 17202 | GCAACGGCTCATGATGAACT | 18 | 443 |
| 1201104 | 1402 | 1421 | 17193 | 17212 | CCTGGCATTAGCAACGGCTC | 74 | 444 |
| 1201110 | 1446 | 1465 | 17237 | 17256 | AGTCCAGATTAACCAATGGT | 27 | 445 |
| 1201116 | 1557 | 1576 | 17348 | 17367 | TAGTATACTGAGCTCTAGCT | 35 | 446 |
| 1201122 | 1637 | 1656 | 17428 | 17447 | CCTGGCAGAAATGTTGTCGG | 57 | 447 |
| 1201128 | 1739 | 1758 | 17530 | 17549 | CGGTACACACAGAGCTCATG | 50 | 448 |
| 1201134 | 1781 | 1800 | 17572 | 17591 | GTGTAGCCCATACTGTGAAA | 22 | 449 |
| 1201140 | 1954 | 1973 | 17745 | 17764 | AGGGTCCTTTAAACATCTAA | 29 | 450 |
| 1201142 | 1963 | 1982 | 17754 | 17773 | GCCACATATAGGGTCCTTTA | 8 | 66 |
| 1201147 | 2120 | 2139 | 17911 | 17930 | ATCCTCTATGATGATGGTGC | 74 | 451 |
| 1201153 | 2601 | 2620 | 18392 | 18411 | TTGTAAGCCTAAGGACCACG | 34 | 452 |
| 1201159 | 2656 | 2675 | 18447 | 18466 | AAGACCTGTTAATGGTGTCC | 33 | 453 |
| 1201165 | N/A | N/A | 3589 | 3608 | GGCACCCTTGCGCCTGGGAC | 79 | 454 |
| 1201171 | N/A | N/A | 3687 | 3706 | AGCGGAGACCAGCGCAGCCG | 82 | 455 |
| 1201177 | N/A | N/A | 3699 | 3718 | CCGCCTCACCCGAGCGGAGA | 98 | 456 |
| 1201183 | N/A | N/A | 3712 | 3731 | AAGCGAAGCCAAGCCGCCTC | 92 | 457 |
| 1201189 | N/A | N/A | 3845 | 3864 | TCGCCCGCTGGGCCGGACCC | 67 | 458 |
| 1201195 | N/A | N/A | 3871 | 3890 | TCCCGGAGTTCCCTGGGCGC | 101 | 459 |
| 1201203 | N/A | N/A | 3898 | 3917 | GCGCCCTGCGGAGCCCGCTG | 93 | 460 |
| 1201209 | N/A | N/A | 4070 | 4089 | CGGAACTCCCCCGGCGGGCG | 66 | 461 |
| 1201215 | N/A | N/A | 4080 | 4099 | CCGAGGCTCCCGGAACTCCC | 119 | 462 |
| 1201221 | N/A | N/A | 4164 | 4183 | AGCCCCCCTCGGAGAAGCTC | 78 | 463 |
| 1201227 | N/A | N/A | 4205 | 4224 | TGGGCCGCTTCTCCAGGCGG | 71 | 464 |
| 1201233 | N/A | N/A | 4452 | 4471 | GGAGACCGGTGACCCAAGGG | 52 | 465 |

TABLE 7-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201239 | N/A | N/A | 4720 | 4739 | CGCGGCCATGAAGATCCTCA | 79 | 466 |
| 1201245 | N/A | N/A | 5242 | 5261 | GTTTTGGGCAACCTTCCAGC | 50 | 467 |
| 1201251 | N/A | N/A | 5743 | 5762 | GTGCAGTTAATAACCCACTT | 42 | 468 |
| 1201257 | N/A | N/A | 6343 | 6362 | ACAGATGCACCCGAGTGGCC | 67 | 469 |
| 1201263 | N/A | N/A | 6640 | 6659 | GTGGATATAGTTGCCTTGGA | 19 | 470 |
| 1201269 | N/A | N/A | 6942 | 6961 | TTCTCAGGGAATTGGCACCC | 69 | 471 |
| 1201275 | N/A | N/A | 7239 | 7258 | CGACCTTCACCCCATAATGT | 72 | 472 |
| 1201281 | N/A | N/A | 7327 | 7346 | AGGCACTAAAGCCTTCTAGC | 89 | 473 |
| 1201287 | N/A | N/A | 8977 | 8996 | GACTTACACTTCACTTAGAC | 68 | 474 |
| 1201293 | N/A | N/A | 9691 | 9710 | GCTCTATTAATAGGTTAGGA | 7 | 475 |
| 1201299 | N/A | N/A | 10074 | 10093 | GGACAAACTGGTGGAGGGTC | 75 | 476 |
| 1201305 | N/A | N/A | 10229 | 10248 | GGAGTCCATGCAGCTAGCAG | 62 | 477 |
| 1201311 | N/A | N/A | 10795 | 10814 | GGTGACCCACAACACATTAT | 84 | 478 |
| 1201317 | N/A | N/A | 11828 | 11847 | CGCTTATCAGGATAGCACAA | 63 | 479 |
| 1201323 | N/A | N/A | 13538 | 13557 | GCAATTAGTGTGATCATGCA | 58 | 480 |
| 1201329 | N/A | N/A | 13749 | 13768 | GTGGCCTAGTCCTCTGGCAT | 80 | 481 |
| 1201335 | N/A | N/A | 13764 | 13783 | GTCACCAGTCAAGTAGTGGC | 97 | 482 |
| 1201341 | N/A | N/A | 13997 | 14016 | AGGGAATGACACTGAGTCGG | 69 | 483 |
| 1201347 | N/A | N/A | 14623 | 14642 | GGGCCCCATGTAACCTGGTT | 86 | 484 |
| 1201353 | N/A | N/A | 14719 | 14738 | CTCTTAATATGCGGGTCACA | 47 | 485 |
| 1201359 | N/A | N/A | 14817 | 14836 | CCATCTTATTCGGTGCTTCC | 32 | 486 |
| 1201365 | N/A | N/A | 14908 | 14927 | CCAGCATACATTGGATCTAT | 30 | 487 |
| 1201371 | N/A | N/A | 15188 | 15207 | GTACTCAGGTCATGCCAGTT | 29 | 488 |
| 1201377 | N/A | N/A | 16166 | 16185 | GAGTCCCATATTTATGTTGA | 84 | 489 |

TABLE 8

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201142 | 1963 | 1982 | 17754 | 17773 | GCCACATATAGGGTCCTTTA | 11 | 66 |
| 1238115 | 38 | 57 | 3131 | 3150 | TGGAAATTCGGCCCAAAGCT | 97 | 490 |
| 1238137 | 70 | 89 | 3163 | 3182 | GTGGCTCATTGACTGTAAAA | 112 | 491 |
| 1238159 | 148 | 167 | 3241 | 3260 | CACCGGAAAAAACGAGTTGA | 101 | 492 |
| 1238181 | 607 | 626 | 16398 | 16417 | CCCCAGCCACCACCATGAGG | 58 | 493 |
|  | 631 | 650 | 16422 | 16441 |  |  |  |
|  | 679 | 698 | 16470 | 16489 |  |  |  |
| 1238203 | 742 | 761 | 16533 | 16552 | TGCTTCATGTTGGTTTTTGG | 18 | 494 |

TABLE 8 -continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1238225 | 1183 | 1202 | 16974 | 16993 | GAAGACCTTCCTCATCCCAC | 84 | 495 |
| 1238247 | 1358 | 1377 | 17149 | 17168 | TTGACCAGCATCTCAGGTCT | 107 | 496 |
| 1238269 | 1497 | 1516 | 17288 | 17307 | CTGTTCTGAGATTTGTTTTA | 25 | 497 |
| 1238291 | 1658 | 1677 | 17449 | 17468 | ATCATGTGGCCTCCTAACAA | 30 | 498 |
| 1238313 | 1801 | 1820 | 17592 | 17611 | ACTCTTGTTGAACAGCTGCT | 13 | 499 |
| 1238335 | 1830 | 1849 | 17621 | 17640 | GCCAGAGGTTCAGTGTTGTG | 19 | 500 |
| 1238357 | 1874 | 1893 | 17665 | 17684 | TTTCATATATGTTACAGTTA | 34 | 501 |
| 1238379 | 1910 | 1929 | 17701 | 17720 | CCATTCCCAAACATTTGATT | 87 | 502 |
| 1238401 | 1994 | 2013 | 17785 | 17804 | CCTTAATTACCTATAGTTTA | 34 | 503 |
| 1238423 | 2030 | 2049 | 17821 | 17840 | CCTTCAGTGTCTAGAAGGCA | 92 | 504 |
| 1238445 | 2080 | 2099 | 17871 | 17890 | TGTATGTCAAAATCATTCTG | 23 | 505 |
| 1238467 | 2115 | 2134 | 17906 | 17925 | CTATGATGATGGTGCTTTCA | 18 | 506 |
| 1238489 | 2145 | 2164 | 17936 | 17955 | ACACTGACCATTTTTAATT | 46 | 507 |
| 1238511 | 2173 | 2192 | 17964 | 17983 | AAGAAATGCAAGCAGTTCTT | 54 | 508 |
| 1238533 | 2234 | 2253 | 18025 | 18044 | CAATTACAGAAACTATGAAC | 86 | 509 |
| 1238555 | 2265 | 2284 | 18056 | 18075 | AGATTGTCTCCCTATTCTTT | 29 | 510 |
| 1238577 | 2298 | 2317 | 18089 | 18108 | TATTTCTGTCATCTCCAACC | 33 | 511 |
| 1238599 | 2322 | 2341 | 18113 | 18132 | TCTTTTTCCACTTCAAATCA | 55 | 512 |
| 1238621 | 2367 | 2386 | 18158 | 18177 | AACAATTCAGGGAATAATTT | 82 | 513 |
| 1238643 | 2405 | 2424 | 18196 | 18215 | GCAGAAAAGTAATACATATC | 25 | 514 |
| 1238665 | 2510 | 2529 | 18301 | 18320 | ACTGCTCTAAACAAAACTCC | 76 | 515 |
| 1238687 | 2566 | 2585 | 18357 | 18376 | CATATTAAGTATTCAGTACC | 61 | 516 |
| 1238709 | 2710 | 2729 | 18501 | 18520 | ACAAGAACATGCAAAGTTAC | 67 | 517 |
| 1238731 | N/A | N/A | 4714 | 4733 | CATGAAGATCCTCATCATTA | 72 | 518 |
| 1238753 | N/A | N/A | 4813 | 4832 | CTACCAGGAGTTTTCCCTAA | 66 | 519 |
| 1238775 | N/A | N/A | 4851 | 4870 | TTTTGATAATTATATTTGTA | 78 | 520 |
| 1238797 | N/A | N/A | 4892 | 4911 | CCAGAAGTTAACATATTTA | 17 | 521 |
| 1238819 | N/A | N/A | 4959 | 4978 | AAAATTGCTCCTTTCCACTG | 54 | 522 |
| 1238841 | N/A | N/A | 5009 | 5028 | TACTGGTTAGCTTTTTTCA | 41 | 523 |
| 1238863 | N/A | N/A | 5076 | 5095 | TGGAAGACTTGTGTTAGATA | 2 | 524 |
| 1238885 | N/A | N/A | 5119 | 5138 | TTTGCCATTTATCTATTATA | 37 | 525 |
| 1238907 | N/A | N/A | 5164 | 5183 | CAAACATGCTCTAATTTGCA | 49 | 526 |
| 1238929 | N/A | N/A | 5303 | 5322 | TGCAGAACCATCTTTGTGAC | 73 | 527 |
| 1238951 | N/A | N/A | 5414 | 5433 | CAATAACTCATACATACAGA | 57 | 528 |
| 1238973 | N/A | N/A | 5518 | 5537 | GCAGGTAAGTTCTCAGGAGT | 19 | 529 |
| 1238995 | N/A | N/A | 5639 | 5658 | TGTCATAATTTTCTTAGCTA | 16 | 530 |

TABLE 8 -continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1239017 | N/A | N/A | 5691 | 5710 | GGCTCCAAAATCATGATTTT | 81 | 531 |
| 1239039 | N/A | N/A | 5736 | 5755 | TAATAACCCACTTTTTTACT | 93 | 532 |
| 1239061 | N/A | N/A | 5846 | 5865 | ACCAAAGGAAAATTAAGATC | 66 | 533 |
| 1239083 | N/A | N/A | 5982 | 6001 | GCTAAAAATCTTTTATTCTA | 85 | 534 |
| 1239105 | N/A | N/A | 6290 | 6309 | TGACCCTCATTTTCTGTGAC | 57 | 535 |
| 1239127 | N/A | N/A | 6425 | 6444 | TAATTCTAAAAATCTGTGGC | 58 | 536 |
| 1239149 | N/A | N/A | 6502 | 6521 | CAGAAACTTCTGTTATGTTA | 26 | 537 |
| 1239171 | N/A | N/A | 6689 | 6708 | TGGGTTAGATACAGACATGT | 40 | 538 |
| 1239193 | N/A | N/A | 6856 | 6875 | AGGATTACCTCCCTTAAAGT | 80 | 539 |
| 1239215 | N/A | N/A | 7199 | 7218 | AGTAAATTCCCTTGTTATAT | 65 | 540 |
| 1239237 | N/A | N/A | 7621 | 7640 | CATTATGAAATTATACTCAA | 95 | 541 |
| 1239259 | N/A | N/A | 8160 | 8179 | CTATCTTTCTATTTGTGTCT | 28 | 542 |
| 1239281 | N/A | N/A | 8330 | 8349 | TTAGATCTGAAACGAGACAA | 81 | 543 |
| 1239303 | N/A | N/A | 8642 | 8661 | GAAGCAAATTCAACAGCTCA | 87 | 544 |
| 1239325 | N/A | N/A | 8982 | 9001 | CATCAGACTTACACTTCACT | 60 | 545 |
| 1239347 | N/A | N/A | 9355 | 9374 | GGTGGTAGTTTTTCAAATCA | 18 | 546 |
| 1239369 | N/A | N/A | 9565 | 9584 | GGATAGTCTCTTTCCATCAT | 37 | 547 |
| 1239391 | N/A | N/A | 9879 | 9898 | AGGGTCAAAATTCAATGCTA | 42 | 548 |
| 1239413 | N/A | N/A | 10678 | 10697 | ACACAGTTTTGAATAAGATA | 76 | 549 |
| 1239435 | N/A | N/A | 10781 | 10800 | CATTATTGTGCCACCAAGCC | 86 | 550 |
| 1239457 | N/A | N/A | 12411 | 12430 | TTCTTTGCAGGGATATGCAA | 91 | 551 |
| 1239479 | N/A | N/A | 13523 | 13542 | ATGCACATAGAAAATCCAAC | 66 | 552 |
| 1239501 | N/A | N/A | 13736 | 13755 | CTGGCATATTTCAAGATATC | 63 | 553 |
| 1239523 | N/A | N/A | 14136 | 14155 | TAGTATTTTGACAATGGCC | 29 | 554 |
| 1239545 | N/A | N/A | 14368 | 14387 | TGCTTATTATTCATGTTCTC | 36 | 555 |
| 1239567 | N/A | N/A | 14697 | 14716 | ATGCCACTTCCCTTGTCCCT | 67 | 556 |
| 1239589 | N/A | N/A | 14920 | 14939 | GAATTTCTCTCCCAGCATA | 73 | 557 |
| 1239611 | N/A | N/A | 15212 | 15231 | TTGAAAGTTACAAGCAGAGT | 52 | 558 |
| 1239633 | N/A | N/A | 15334 | 15353 | AACTGGATAATATTCATAAA | 84 | 559 |
| 1239655 | N/A | N/A | 15411 | 15430 | CCTTTATCACCCAATTAGCT | 71 | 560 |
| 1239677 | N/A | N/A | 15489 | 15508 | TTTTAGTACATTTAATGAAA | 92 | 561 |
| 1239699 | N/A | N/A | 15672 | 15691 | TATAATGGCATATACTGGAA | 58 | 562 |
| 1239721 | N/A | N/A | 15738 | 15757 | AAACAGTACCTGCTGTACCC | 76 | 563 |
| 1239743 | N/A | N/A | 15823 | 15842 | AATCTCTTTTCAAATTAAAG | 83 | 564 |
| 1239765 | N/A | N/A | 15854 | 15873 | CCTTTGGAGAATGTACATTC | 41 | 565 |
| 1239787 | N/A | N/A | 15913 | 15932 | TTCTAATTTTGTACCAAAA | 63 | 566 |

TABLE 9

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201142 | 1963 | 1982 | 17754 | 17773 | GCCACATATAGGGTCCTTTA | 6 | 66 |
| 1238116 | 39 | 58 | 3132 | 3151 | TTGGAAATTCGGCCCAAAGC | 79 | 567 |
| 1238138 | 71 | 90 | 3164 | 3183 | CGTGGCTCATTGACTGTAAA | 77 | 568 |
| 1238160 | 150 | 169 | 3243 | 3262 | GTCACCGGAAAAAACGAGTT | 109 | 569 |
| 1238182 | 608 632 | 627 651 | 16399 16423 | 16418 16442 | CCCCCAGCCACCACCATGAG | 75 | 570 |
| 1238204 | 747 | 766 | 16538 | 16557 | CCATGTGCTTCATGTTGGTT | 61 | 571 |
| 1238226 | 1184 | 1203 | 16975 | 16994 | GGAAGACCTTCCTCATCCCA | 85 | 572 |
| 1238248 | 1359 | 1378 | 17150 | 17169 | CTTGACCAGCATCTCAGGTC | 84 | 573 |
| 1238270 | 1514 | 1533 | 17305 | 17324 | GGCAAAGGTATTTCAGACTG | 8 | 574 |
| 1238292 | 1659 | 1678 | 17450 | 17469 | TATCATGTGGCCTCCTAACA | 40 | 575 |
| 1238314 | 1802 | 1821 | 17593 | 17612 | TACTCTTGTTGAACAGCTGC | 17 | 576 |
| 1238336 | 1845 | 1864 | 17636 | 17655 | TGAATATGTCCTCTAGCCAG | 31 | 577 |
| 1238358 | 1875 | 1894 | 17666 | 17685 | CTTTCATATATGTTACAGTT | 11 | 578 |
| 1238380 | 1911 | 1930 | 17702 | 17721 | ACCATTCCCAAACATTTGAT | 83 | 579 |
| 1238402 | 1995 | 2014 | 17786 | 17805 | GCCTTAATTACCTATAGTTT | 13 | 580 |
| 1238424 | 2031 | 2050 | 17822 | 17841 | GCCTTCAGTGTCTAGAAGGC | 93 | 581 |
| 1238446 | 2081 | 2100 | 17872 | 17891 | CTGTATGTCAAAATCATTCT | 23 | 582 |
| 1238468 | 2117 | 2136 | 17908 | 17927 | CTCTATGATGATGGTGCTTT | 18 | 583 |
| 1238490 | 2147 | 2166 | 17938 | 17957 | GCACACTGACCATTTTTTAA | 9 | 584 |
| 1238512 | 2176 | 2195 | 17967 | 17986 | ATAAAGAAATGCAAGCAGTT | 42 | 585 |
| 1238534 | 2235 | 2254 | 18026 | 18045 | CCAATTACAGAAACTATGAA | 59 | 586 |
| 1238556 | 2266 | 2285 | 18057 | 18076 | TAGATTGTCTCCCTATTCTT | 59 | 587 |
| 1238578 | 2299 | 2318 | 18090 | 18109 | ATATTTCTGTCATCTCCAAC | 36 | 588 |
| 1238600 | 2326 | 2345 | 18117 | 18136 | AATTTCTTTTTCCACTTCAA | 14 | 589 |
| 1238622 | 2372 | 2391 | 18163 | 18182 | TATCAAACAATTCAGGGAAT | 34 | 590 |
| 1238644 | 2409 | 2428 | 18200 | 18219 | CATTGCAGAAAAGTAATACA | 66 | 591 |
| 1238666 | 2512 | 2531 | 18303 | 18322 | TAACTGCTCTAAACAAAACT | 85 | 592 |
| 1238688 | 2574 | 2593 | 18365 | 18384 | GTTTCCCACATATTAAGTAT | 22 | 593 |
| 1238710 | 2716 | 2735 | 18507 | 18526 | AACAAAACAAGAACATGCAA | 74 | 594 |
| 1238732 | N/A | N/A | 4715 | 4734 | CCATGAAGATCCTCATCATT | 84 | 595 |
| 1238754 | N/A | N/A | 4814 | 4833 | TCTACCAGGAGTTTTCCCTA | 86 | 596 |
| 1238776 | N/A | N/A | 4858 | 4877 | CCTATGTTTTTGATAATTAT | 65 | 597 |
| 1238798 | N/A | N/A | 4893 | 4912 | TCCAGAAGTTTAACATATTT | 58 | 598 |
| 1238820 | N/A | N/A | 4960 | 4979 | TAAAATTGCTCCTTTCCACT | 58 | 599 |
| 1238842 | N/A | N/A | 5020 | 5039 | GCTTTTCCCCTTACTGGTTA | 34 | 600 |
| 1238864 | N/A | N/A | 5077 | 5096 | GTGGAAGACTTGTGTTAGAT | 3 | 601 |

TABLE 9 -continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1238886 | N/A | N/A | 5121 | 5140 | ATTTTGCCATTTATCTATTA | 42 | 602 |
| 1238908 | N/A | N/A | 5172 | 5191 | TGATAACCCAAACATGCTCT | 47 | 603 |
| 1238930 | N/A | N/A | 5304 | 5323 | CTGCAGAACCATCTTTGTGA | 77 | 604 |
| 1238952 | N/A | N/A | 5416 | 5435 | CCCAATAACTCATACATACA | 72 | 605 |
| 1238974 | N/A | N/A | 5520 | 5539 | TTGCAGGTAAGTTCTCAGGA | 4 | 606 |
| 1238996 | N/A | N/A | 5641 | 5660 | TGTGTCATAATTTTCTTAGC | 9 | 607 |
| 1239018 | N/A | N/A | 5693 | 5712 | CAGGCTCCAAAATCATGATT | 54 | 608 |
| 1239040 | N/A | N/A | 5738 | 5757 | GTTAATAACCCACTTTTTTA | 96 | 609 |
| 1239062 | N/A | N/A | 5857 | 5876 | GCAATATATTCACCAAAGGA | 10 | 610 |
| 1239084 | N/A | N/A | 5983 | 6002 | GGCTAAAAATCTTTTATTCT | 49 | 611 |
| 1239106 | N/A | N/A | 6292 | 6311 | CCTGACCCTCATTTTCTGTG | 69 | 612 |
| 1239128 | N/A | N/A | 6427 | 6446 | CATAATTCTAAAAATCTGTG | 76 | 613 |
| 1239150 | N/A | N/A | 6503 | 6522 | GCAGAAACTTCTGTTATGTT | 37 | 614 |
| 1239172 | N/A | N/A | 6699 | 6718 | TAGCCATCACTGGGTTAGAT | 37 | 615 |
| 1239194 | N/A | N/A | 6858 | 6877 | GAAGGATTACCTCCCTTAAA | 81 | 616 |
| 1239216 | N/A | N/A | 7203 | 7222 | GCTAAGTAAATTCCCTTGTT | 45 | 617 |
| 1239238 | N/A | N/A | 7622 | 7641 | ACATTATGAAATTATACTCA | 74 | 618 |
| 1239260 | N/A | N/A | 8161 | 8180 | GCTATCTTTCTATTTGTGTC | 22 | 619 |
| 1239282 | N/A | N/A | 8344 | 8363 | GAGAGCTTTTCCTCTTAGAT | 78 | 620 |
| 1239304 | N/A | N/A | 8643 | 8662 | CGAAGCAAATTCAACAGCTC | 63 | 621 |
| 1239326 | N/A | N/A | 8983 | 9002 | GCATCAGACTTACACTTCAC | 19 | 622 |
| 1239348 | N/A | N/A | 9368 | 9387 | ATGAGCTCAACAGGGTGGTA | 69 | 623 |
| 1239370 | N/A | N/A | 9566 | 9585 | AGGATAGTCTCTTTCCATCA | 28 | 624 |
| 1239392 | N/A | N/A | 9939 | 9958 | GTAGAGATAAACATTTGGGC | 17 | 625 |
| 1239414 | N/A | N/A | 10679 | 10698 | GACACAGTTTTGAATAAGAT | 44 | 626 |
| 1239436 | N/A | N/A | 10787 | 10806 | ACAACACATTATTGTGCCAC | 74 | 627 |
| 1239458 | N/A | N/A | 12454 | 12473 | TGCTATCGAATACTATGCAG | 93 | 628 |
| 1239480 | N/A | N/A | 13531 | 13550 | GTGTGATCATGCACATAGAA | 67 | 629 |
| 1239502 | N/A | N/A | 13738 | 13757 | CTCTGGCATATTTCAAGATA | 72 | 630 |
| 1239524 | N/A | N/A | 14158 | 14177 | CCATATTTATAAATTTACAA | 75 | 631 |
| 1239546 | N/A | N/A | 14369 | 14388 | GTGCTTATTATTCATGTTCT | 27 | 632 |
| 1239568 | N/A | N/A | 14779 | 14798 | TCTTCAACAGCCTCCCAACC | 74 | 633 |
| 1239590 | N/A | N/A | 14921 | 14940 | TGAATTTTCTCTCCCAGCAT | 75 | 634 |
| 1239612 | N/A | N/A | 15218 | 15237 | ATATATTTGAAAGTTACAAG | 77 | 635 |
| 1239634 | N/A | N/A | 15345 | 15364 | GCTAATGATTAAACTGGATA | 45 | 636 |
| 1239656 | N/A | N/A | 15414 | 15433 | TTACCTTTATCACCCAATTA | 97 | 637 |
| 1239678 | N/A | N/A | 15491 | 15510 | GTTTTTAGTACATTTAATGA | 72 | 638 |

TABLE 9-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1239700 | N/A | N/A | 15673 | 15692 | CTATAATGGCATATACTGGA | 31 | 639 |
| 1239722 | N/A | N/A | 15739 | 15758 | TAAACAGTACCTGCTGTACC | 89 | 640 |
| 1239744 | N/A | N/A | 15825 | 15844 | AAAATCTCTTTTCAAATTAA | 74 | 641 |
| 1239766 | N/A | N/A | 15863 | 15882 | ATTTATGACCCTTTGGAGAA | 85 | 642 |
| 1239788 | N/A | N/A | 15914 | 15933 | CTTCTAATTTTTGTACCAAA | 27 | 643 |

TABLE 10

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201142 | 1963 | 1982 | 17754 | 17773 | GCCACATATAGGGTCCTTTA | 11 | 66 |
| 1238117 | 42 | 61 | 3135 | 3154 | TAATTGGAAATTCGGCCCAA | 92 | 644 |
| 1238139 | 103 | 122 | 3196 | 3215 | TGATACCGCCTGCGGGTGCC | 99 | 645 |
| 1238161 | 151 | 170 | 3244 | 3263 | AGTCACCGGAAAAAACGAGT | 105 | 646 |
| 1238183 | 609 633 | 628 652 | 16400 16424 | 16419 16443 | GCCCCCAGCCACCACCATGA | 55 | 647 |
| 1238205 | 786 | 805 | 16577 | 16596 | CAAGGCCCCCCACCACTGCC | 95 | 648 |
| 1238227 | 1185 | 1204 | 16976 | 16995 | AGGAAGACCTTCCTCATCCC | 82 | 649 |
| 1238249 | 1383 | 1402 | 17174 | 17193 | CATGATGAACTCAATCAAAG | 45 | 650 |
| 1238271 | 1521 | 1540 | 17312 | 17331 | GTATCCAGGCAAAGGTATTT | 19 | 651 |
| 1238293 | 1661 | 1680 | 17452 | 17471 | AGTATCATGTGGCCTCCTAA | 12 | 652 |
| 1238315 | 1804 | 1823 | 17595 | 17614 | TTTACTCTTGTTGAACAGCT | 15 | 653 |
| 1238337 | 1847 | 1866 | 17638 | 17657 | TGTGAATATGTCCTCTAGCC | 21 | 654 |
| 1238359 | 1876 | 1895 | 17667 | 17686 | CCTTTCATATATGTTACAGT | 7 | 655 |
| 1238381 | 1912 | 1931 | 17703 | 17722 | CACCATTCCCAAACATTTGA | 87 | 656 |
| 1238403 | 1996 | 2015 | 17787 | 17806 | TGCCTTAATTACCTATAGTT | 45 | 657 |
| 1238425 | 2037 | 2056 | 17828 | 17847 | AGATTTGCCTTCAGTGTCTA | 110 | 658 |
| 1238447 | 2082 | 2101 | 17873 | 17892 | CCTGTATGTCAAAATCATTC | 37 | 659 |
| 1238469 | 2118 | 2137 | 17909 | 17928 | CCTCTATGATGATGGTGCTT | 22 | 660 |
| 1238491 | 2148 | 2167 | 17939 | 17958 | TGCACACTGACCATTTTTTA | 18 | 661 |
| 1238513 | 2188 | 2207 | 17979 | 17998 | TATGAGACAGAAATAAAGAA | 71 | 662 |
| 1238535 | 2240 | 2259 | 18031 | 18050 | AAAAGCCAATTACAGAAACT | 81 | 663 |
| 1238557 | 2267 | 2286 | 18058 | 18077 | TTAGATTGTCTCCCTATTCT | 54 | 664 |
| 1238579 | 2300 | 2319 | 18091 | 18110 | CATATTTCTGTCATCTCCAA | 37 | 665 |
| 1238601 | 2327 | 2346 | 18118 | 18137 | GAATTTCTTTTTCCACTTCA | 25 | 666 |
| 1238623 | 2373 | 2392 | 18164 | 18183 | ATATCAAACAATTCAGGGAA | 58 | 667 |

TABLE 10 -continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1238645 | 2420 | 2439 | 18211 | 18230 | GCCAATAATAACATTGCAGA | 21 | 668 |
| 1238667 | 2513 | 2532 | 18304 | 18323 | TTAACTGCTCTAAACAAAAC | 105 | 669 |
| 1238689 | 2575 | 2594 | 18366 | 18385 | GGTTTCCCACATATTAAGTA | 25 | 670 |
| 1238711 | 2720 | 2739 | 18511 | 18530 | ATATAACAAAACAAGAACAT | 74 | 671 |
| 1238733 | N/A | N/A | 4716 | 4735 | GCCATGAAGATCCTCATCAT | 63 | 672 |
| 1238755 | N/A | N/A | 4820 | 4839 | TCCTATTCTACCAGGAGTTT | 88 | 673 |
| 1238777 | N/A | N/A | 4859 | 4878 | TCCTATGTTTTTGATAATTA | 81 | 674 |
| 1238799 | N/A | N/A | 4895 | 4914 | TTTCCAGAAGTTTAACATAT | 62 | 675 |
| 1238821 | N/A | N/A | 4961 | 4980 | GTAAAATTGCTCCTTTCCAC | 53 | 676 |
| 1238843 | N/A | N/A | 5021 | 5040 | TGCTTTTCCCCTTACTGGTT | 53 | 677 |
| 1238865 | N/A | N/A | 5094 | 5113 | AATATTTTCCTTTCGGTGTG | 46 | 678 |
| 1238887 | N/A | N/A | 5122 | 5141 | CATTTTGCCATTTATCTATT | 54 | 679 |
| 1238909 | N/A | N/A | 5173 | 5192 | ATGATAACCCAAACATGCTC | 65 | 680 |
| 1238931 | N/A | N/A | 5306 | 5325 | GACTGCAGAACCATCTTTGT | 64 | 681 |
| 1238953 | N/A | N/A | 5417 | 5436 | CCCCAATAACTCATACATAC | 66 | 682 |
| 1238975 | N/A | N/A | 5535 | 5554 | TGTTTGTTTCTTCCATTGCA | 12 | 683 |
| 1238997 | N/A | N/A | 5642 | 5661 | ATGTGTCATAATTTTCTTAG | 18 | 684 |
| 1239019 | N/A | N/A | 5694 | 5713 | ACAGGCTCCAAAATCATGAT | 41 | 685 |
| 1239041 | N/A | N/A | 5739 | 5758 | AGTTAATAACCCACTTTTTT | 78 | 686 |
| 1239063 | N/A | N/A | 5859 | 5878 | GAGCAATATATTCACCAAAG | 7 | 687 |
| 1239085 | N/A | N/A | 5986 | 6005 | GTTGGCTAAAAATCTTTTAT | 33 | 688 |
| 1239107 | N/A | N/A | 6301 | 6320 | ACAGCCTTTCCTGACCCTCA | 50 | 689 |
| 1239129 | N/A | N/A | 6428 | 6447 | GCATAATTCTAAAAATCTGT | 70 | 690 |
| 1239151 | N/A | N/A | 6504 | 6523 | TGCAGAAACTTCTGTTATGT | 62 | 691 |
| 1239173 | N/A | N/A | 6703 | 6722 | GCTGTAGCCATCACTGGGTT | 46 | 692 |
| 1239195 | N/A | N/A | 6859 | 6878 | TGAAGGATTACCTCCCTTAA | 82 | 693 |
| 1239217 | N/A | N/A | 7219 | 7238 | CCCTTGTCTCTTCTGAGCTA | 73 | 694 |
| 1239239 | N/A | N/A | 7623 | 7642 | GACATTATGAAATTATACTC | 43 | 695 |
| 1239261 | N/A | N/A | 8162 | 8181 | GGCTATCTTTCTATTTGTGT | 47 | 696 |
| 1239283 | N/A | N/A | 8345 | 8364 | TGAGAGCTTTTCCTCTTAGA | 106 | 697 |
| 1239305 | N/A | N/A | 8644 | 8663 | GCGAAGCAAATTCAACAGCT | 62 | 698 |
| 1239327 | N/A | N/A | 8987 | 9006 | GGAGGCATCAGACTTACACT | 63 | 699 |
| 1239349 | N/A | N/A | 9371 | 9390 | TACATGAGCTCAACAGGGTG | 52 | 700 |
| 1239371 | N/A | N/A | 9567 | 9586 | AAGGATAGTCTCTTTCCATC | 44 | 701 |
| 1239393 | N/A | N/A | 9982 | 10001 | GGGAGTATCAATTTAAGCAA | 26 | 702 |
| 1239415 | N/A | N/A | 10719 | 10738 | GTCAGAATTCTAAGGGTCAA | 27 | 703 |

TABLE 10 -continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1239437 | N/A | N/A | 10790 | 10809 | CCCACAACACATTATTGTGC | 118 | 704 |
| 1239459 | N/A | N/A | 12463 | 12482 | GTACATATATGCTATCGAAT | 26 | 705 |
| 1239481 | N/A | N/A | 13536 | 13555 | AATTAGTGTGATCATGCACA | 61 | 706 |
| 1239503 | N/A | N/A | 13775 | 13794 | AGATACTCTCTGTCACCAGT | 71 | 707 |
| 1239525 | N/A | N/A | 14159 | 14178 | ACCATATTTATAAATTTACA | 92 | 708 |
| 1239547 | N/A | N/A | 14370 | 14389 | TGTGCTTATTATTCATGTTC | 39 | 709 |
| 1239569 | N/A | N/A | 14785 | 14804 | CTGATTTCTTCAACAGCCTC | 83 | 710 |
| 1239591 | N/A | N/A | 14922 | 14941 | CTGAATTTTCTCTCCCAGCA | 60 | 711 |
| 1239613 | N/A | N/A | 15236 | 15255 | GGTCATAAGCAAATCAAAAT | 26 | 712 |
| 1239635 | N/A | N/A | 15350 | 15369 | TCAGAGCTAATGATTAAACT | 54 | 713 |
| 1239657 | N/A | N/A | 15415 | 15434 | CTTACCTTTATCACCCAATT | 65 | 714 |
| 1239679 | N/A | N/A | 15493 | 15512 | TGGTTTTTAGTACATTTAAT | 39 | 715 |
| 1239701 | N/A | N/A | 15681 | 15700 | CGTAAAACCTATAATGGCAT | 53 | 716 |
| 1239723 | N/A | N/A | 15742 | 15761 | TGCTAAACAGTACCTGCTGT | 91 | 717 |
| 1239745 | N/A | N/A | 15828 | 15847 | TCAAAATCTCTTTTCAAAT | 114 | 718 |
| 1239767 | N/A | N/A | 15872 | 15891 | AGAATGACAATTTATGACCC | 45 | 719 |
| 1239789 | N/A | N/A | 15916 | 15935 | TTCTTCTAATTTTGTACCA | 47 | 720 |

TABLE 11

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201142 | 1963 | 1982 | 17754 | 17773 | GCCACATATAGGGTCCTTTA | 9 | 66 |
| 1238118 | 45 | 64 | 3138 | 3157 | CTTTAATTGGAAATTCGGCC | 96 | 721 |
| 1238140 | 104 | 123 | 3197 | 3216 | TTGATACCGCCTGCGGGTGC | 78 | 722 |
| 1238162 | 451 | 470 | 16242 | 16261 | GCCACAAAGAGAACCAGCAT | 71 | 723 |
| 1238184 | 610 634 | 629 653 | 16401 16425 | 16420 16444 | TGCCCCCAGCCACCACCATG | 56 | 724 |
| 1238206 | 787 | 806 | 16578 | 16597 | CCAAGGCCCCCCACCACTGC | 102 | 725 |
| 1238228 | 1186 | 1205 | 16977 | 16996 | CAGGAAGACCTTCCTCATCC | 99 | 726 |
| 1238250 | 1384 | 1403 | 17175 | 17194 | TCATGATGAACTCAATCAAA | 40 | 727 |
| 1238272 | 1583 | 1602 | 17374 | 17393 | ATGAAATCTCTACTAAGATA | 57 | 728 |
| 1238294 | 1662 | 1681 | 17453 | 17472 | AAGTATCATGTGGCCTCCTA | 22 | 729 |
| 1238316 | 1805 | 1824 | 17596 | 17615 | ATTTACTCTTGTTGAACAGC | 10 | 730 |
| 1238338 | 1848 | 1867 | 17639 | 17658 | CTGTGAATATGTCCTCTAGC | 13 | 731 |
| 1238360 | 1877 | 1896 | 17668 | 17687 | GCCTTTCATATATGTTACAG | 12 | 732 |

TABLE 11 -continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1238382 | 1914 | 1933 | 17705 | 17724 | GGCACCATTCCCAAACATTT | 92 | 733 |
| 1238404 | 1997 | 2016 | 17788 | 17807 | CTGCCTTAATTACCTATAGT | 23 | 734 |
| 1238426 | 2038 | 2057 | 17829 | 17848 | GAGATTTGCCTTCAGTGTCT | 53 | 735 |
| 1238448 | 2087 | 2106 | 17878 | 17897 | GCTCTCCTGTATGTCAAAAT | 48 | 736 |
| 1238470 | 2122 | 2141 | 17913 | 17932 | TCATCCTCTATGATGATGGT | 67 | 737 |
| 1238492 | 2149 | 2168 | 17940 | 17959 | TTGCACACTGACCATTTTTT | 19 | 738 |
| 1238514 | 2189 | 2208 | 17980 | 17999 | TTATGAGACAGAAATAAAGA | 99 | 739 |
| 1238536 | 2241 | 2260 | 18032 | 18051 | CAAAAGCCAATTACAGAAAC | 80 | 740 |
| 1238558 | 2268 | 2287 | 18059 | 18078 | TTTAGATTGTCTCCCTATTC | 55 | 741 |
| 1238580 | 2301 | 2320 | 18092 | 18111 | TCATATTTCTGTCATCTCCA | 19 | 742 |
| 1238602 | 2328 | 2347 | 18119 | 18138 | AGAATTTCTTTTTCCACTTC | 25 | 743 |
| 1238624 | 2374 | 2393 | 18165 | 18184 | AATATCAAACAATTCAGGGA | 62 | 744 |
| 1238646 | 2422 | 2441 | 18213 | 18232 | AAGCCAATAATAACATTGCA | 47 | 745 |
| 1238668 | 2520 | 2539 | 18311 | 18330 | TCAGATGTTAACTGCTCTAA | 27 | 746 |
| 1238690 | 2576 | 2595 | 18367 | 18386 | GGGTTTCCCACATATTAAGT | 56 | 747 |
| 1238712 | 2721 | 2740 | 18512 | 18531 | TATATAACAAAACAAGAACA | 105 | 748 |
| 1238734 | N/A | N/A | 4741 | 4760 | GCTCTCAGAACAAGAAAATA | 73 | 749 |
| 1238756 | N/A | N/A | 4822 | 4841 | AATCCTATTCTACCAGGAGT | 79 | 750 |
| 1238778 | N/A | N/A | 4863 | 4882 | CTGTTCCTATGTTTTTGATA | 65 | 751 |
| 1238800 | N/A | N/A | 4899 | 4918 | GATTTTTCCAGAAGTTTAAC | 47 | 752 |
| 1238822 | N/A | N/A | 4962 | 4981 | AGTAAAATTGCTCCTTTCCA | 47 | 753 |
| 1238844 | N/A | N/A | 5038 | 5057 | CATCCTACCCCTCTGCCTGC | 82 | 754 |
| 1238866 | N/A | N/A | 5095 | 5114 | TAATATTTTCCTTTCGGTGT | 37 | 755 |
| 1238888 | N/A | N/A | 5123 | 5142 | TCATTTTGCCATTTATCTAT | 41 | 756 |
| 1238910 | N/A | N/A | 5175 | 5194 | AAATGATAACCCAAACATGC | 45 | 757 |
| 1238932 | N/A | N/A | 5322 | 5341 | CCAAGGTCACAAAATTGACT | 102 | 758 |
| 1238954 | N/A | N/A | 5423 | 5442 | AAATGCCCCCAATAACTCAT | 54 | 759 |
| 1238976 | N/A | N/A | 5554 | 5573 | ATACATGCCTGTTTTTGTTT | 60 | 760 |
| 1238998 | N/A | N/A | 5643 | 5662 | AATGTGTCATAATTTTCTTA | 24 | 761 |
| 1239020 | N/A | N/A | 5697 | 5716 | ATCACAGGCTCCAAAATCAT | 78 | 762 |
| 1239042 | N/A | N/A | 5741 | 5760 | GCAGTTAATAACCCACTTTT | 22 | 763 |
| 1239064 | N/A | N/A | 5860 | 5879 | AGAGCAATATATTCACCAAA | 10 | 764 |
| 1239086 | N/A | N/A | 5987 | 6006 | CGTTGGCTAAAAATCTTTTA | 29 | 765 |
| 1239108 | N/A | N/A | 6305 | 6324 | GATCACAGCCTTTCCTGACC | 50 | 766 |
| 1239130 | N/A | N/A | 6430 | 6449 | CAGCATAATTCTAAAAATCT | 99 | 767 |
| 1239152 | N/A | N/A | 6506 | 6525 | GGTGCAGAAACTTCTGTTAT | 58 | 768 |
| 1239174 | N/A | N/A | 6704 | 6723 | TGCTGTAGCCATCACTGGGT | 49 | 769 |

TABLE 11-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1239196 | N/A | N/A | 6860 | 6879 | CTGAAGGATTACCTCCCTTA | 78 | 770 |
| 1239218 | N/A | N/A | 7226 | 7245 | ATAATGTCCCTTGTCTCTTC | 44 | 771 |
| 1239240 | N/A | N/A | 7698 | 7717 | ACACAATACATATAATCTTA | 50 | 772 |
| 1239262 | N/A | N/A | 8163 | 8182 | AGGCTATCTTTCTATTTGTG | 38 | 773 |
| 1239284 | N/A | N/A | 8346 | 8365 | TTGAGAGCTTTTCCTCTTAG | 92 | 774 |
| 1239306 | N/A | N/A | 8646 | 8665 | TAGCGAAGCAAATTCAACAG | 78 | 775 |
| 1239328 | N/A | N/A | 9033 | 9052 | GATCTCTTAGATTTTTGGAC | 25 | 776 |
| 1239350 | N/A | N/A | 9380 | 9399 | TAGAATAAATACATGAGCTC | 92 | 777 |
| 1239372 | N/A | N/A | 9635 | 9654 | TGAAAATCAATATCATTCCT | 58 | 778 |
| 1239394 | N/A | N/A | 9983 | 10002 | TGGGAGTATCAATTTAAGCA | 15 | 779 |
| 1239416 | N/A | N/A | 10721 | 10740 | GTGTCAGAATTCTAAGGGTC | 29 | 780 |
| 1239438 | N/A | N/A | 10791 | 10810 | ACCCACAACACATTATTGTG | 83 | 781 |
| 1239460 | N/A | N/A | 12468 | 12487 | GTGTGGTACATATATGCTAT | 29 | 782 |
| 1239482 | N/A | N/A | 13542 | 13561 | ATTTGCAATTAGTGTGATCA | 83 | 783 |
| 1239504 | N/A | N/A | 13777 | 13796 | TAAGATACTCTCTGTCACCA | 57 | 784 |
| 1239526 | N/A | N/A | 14190 | 14209 | ACTAAATATTTATAATGGAT | 85 | 785 |
| 1239548 | N/A | N/A | 14371 | 14390 | CTGTGCTTATTATTCATGTT | 34 | 786 |
| 1239570 | N/A | N/A | 14792 | 14811 | TTCTCACCTGATTTCTTCAA | 88 | 787 |
| 1239592 | N/A | N/A | 14925 | 14944 | TGACTGAATTTTCTCTCCCA | 74 | 788 |
| 1239614 | N/A | N/A | 15237 | 15256 | TGGTCATAAGCAAATCAAAA | 30 | 789 |
| 1239636 | N/A | N/A | 15351 | 15370 | TTCAGAGCTAATGATTAAAC | 70 | 790 |
| 1239658 | N/A | N/A | 15416 | 15435 | CCTTACCTTTATCACCCAAT | 53 | 791 |
| 1239680 | N/A | N/A | 15507 | 15526 | CATGTACAGTTCAATGGTTT | 49 | 792 |
| 1239702 | N/A | N/A | 15682 | 15701 | CCGTAAAACCTATAATGGCA | 28 | 793 |
| 1239724 | N/A | N/A | 15745 | 15764 | GATTGCTAAACAGTACCTGC | 22 | 794 |
| 1239746 | N/A | N/A | 15829 | 15848 | ATCAAAAATCTCTTTTCAAA | 93 | 795 |
| 1239768 | N/A | N/A | 15873 | 15892 | CAGAATGACAATTTATGACC | 39 | 796 |
| 1239790 | N/A | N/A | 15917 | 15936 | TTTCTTCTAATTTTTGTACC | 74 | 797 |

TABLE 12

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201142 | 1963 | 1982 | 17754 | 17773 | GCCACATATAGGGTCCTTTA | 7 | 66 |
| 1238122 | 51 | 70 | 3144 | 3163 | AATCATCTTTAATTGGAAAT | 108 | 798 |

TABLE 12 -continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1238144 | 120 | 139 | 3213 | 3232 | TGAACACTTGCATCAGTTGA | 87 | 799 |
| 1238166 | 468 | 487 | 16259 | 16278 | CCAGGTCACTCCATGTGGCC | 59* | 800 |
| 1238188 | 593 617 | 612 636 | 16384 16408 | 16403 16427 | ATGAGGCTGCCCCCAGCCAC | 75 | 801 |
| 1238210 | 858 | 877 | 16649 | 16668 | AGTAACGGTCCTCATAGTCA | 56 | 802 |
| 1238232 | 1199 | 1218 | 16990 | 17009 | AAGATGGTGAAAACAGGAAG | 67 | 803 |
| 1238254 | 1420 | 1439 | 17211 | 17230 | CTGTTATACTTTTACTGGCC | 21 | 804 |
| 1238276 | 1589 | 1608 | 17380 | 17399 | ATAGCTATGAAATCTCTACT | 32 | 805 |
| 1238298 | 1678 | 1697 | 17469 | 17488 | TAGGATTTTTTGAATAAGT | 33 | 806 |
| 1238320 | 1811 | 1830 | 17602 | 17621 | GACAATATTTACTCTTGTTG | 14 | 807 |
| 1238342 | 1854 | 1873 | 17645 | 17664 | TGTTCACTGTGAATATGTCC | 12 | 808 |
| 1238364 | 1884 | 1903 | 17675 | 17694 | CCCAGAAGCCTTTCATATAT | 31 | 809 |
| 1238386 | 1920 | 1939 | 17711 | 17730 | TCCAAGGGCACCATTCCCAA | 97 | 810 |
| 1238408 | 2003 | 2022 | 17794 | 17813 | TTTCAGCTGCCTTAATTACC | 37 | 811 |
| 1238430 | 2042 | 2061 | 17833 | 17852 | AAAGGAGATTTGCCTTCAGT | 82 | 812 |
| 1238452 | 2092 | 2111 | 17883 | 17902 | CTGCAGCTCTCCTGTATGTC | 71 | 813 |
| 1238474 | 2126 | 2145 | 17917 | 17936 | TACATCATCCTCTATGATGA | 96 | 814 |
| 1238496 | 2155 | 2174 | 17946 | 17965 | TTTTCTTTGCACACTGACCA | 15 | 815 |
| 1238518 | 2209 | 2228 | 18000 | 18019 | CTAATTCTGGTTTTGACAA | 61 | 816 |
| 1238540 | 2250 | 2269 | 18041 | 18060 | TCTTTGATTCAAAAGCCAAT | 51 | 817 |
| 1238562 | 2275 | 2294 | 18066 | 18085 | GATATTTTTTAGATTGTCTC | 42 | 818 |
| 1238584 | 2305 | 2324 | 18096 | 18115 | TCAATCATATTTCTGTCATC | 31 | 819 |
| 1238606 | 2334 | 2353 | 18125 | 18144 | ATTAACAGAATTTCTTTTTC | 86 | 820 |
| 1238628 | 2380 | 2399 | 18171 | 18190 | GGTGACAATATCAAACAATT | 18 | 821 |
| 1238650 | 2439 | 2458 | 18230 | 18249 | GAATACTCACAAAGTGCAAG | 37 | 822 |
| 1238672 | 2531 | 2550 | 18322 | 18341 | CATTAGACACTTCAGATGTT | 59 | 823 |
| 1238694 | 2621 | 2640 | 18412 | 18431 | ATGAAACGATTCAGTGCACA | 52 | 824 |
| 1238716 | 2730 | 2749 | 18521 | 18540 | CAATTTTTTATATAACAAA | 85 | 825 |
| 1238738 | N/A | N/A | 4747 | 4766 | CGTGATGCTCTCAGAACAAG | 27 | 826 |
| 1238760 | N/A | N/A | 4828 | 4847 | ATCCTTAATCCTATTCTACC | 86 | 827 |
| 1238782 | N/A | N/A | 4876 | 4895 | TTTATCCAATTCCCTGTTCC | 67 | 828 |
| 1238804 | N/A | N/A | 4904 | 4923 | TTGTTGATTTTCCAGAAGT | 28 | 829 |
| 1238826 | N/A | N/A | 4968 | 4987 | TGTGTAAGTAAAATTGCTCC | 41 | 830 |
| 1238848 | N/A | N/A | 5045 | 5064 | CAAATCACATCCTACCCCTC | 80 | 831 |
| 1238870 | N/A | N/A | 5100 | 5119 | AATCTTAATATTTTCCTTTC | 82 | 832 |
| 1238892 | N/A | N/A | 5132 | 5151 | AATGACTCATCATTTTGCCA | 28 | 833 |
| 1238914 | N/A | N/A | 5195 | 5214 | TGGTTATTTTAATAGATGTA | 18 | 834 |

TABLE 12 -continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1238936 | N/A | N/A | 5380 | 5399 | ATCATTTCCTCCATTCTATG | 69 | 835 |
| 1238958 | N/A | N/A | 5451 | 5470 | GCTTAACAAAATGTTTGTCA | 13 | 836 |
| 1238980 | N/A | N/A | 5581 | 5600 | TTCTAATTTTAGATCATTCT | 66 | 837 |
| 1239002 | N/A | N/A | 5655 | 5674 | TTCATTTCAGTTAATGTGTC | 23 | 838 |
| 1239024 | N/A | N/A | 5712 | 5731 | AGTTTTTCCCCACATATCAC | 50 | 839 |
| 1239046 | N/A | N/A | 5783 | 5802 | TTCAGATTTTTCACATATGC | 19 | 840 |
| 1239068 | N/A | N/A | 5865 | 5884 | TAGTGAGAGCAATATATTCA | 47 | 841 |
| 1239090 | N/A | N/A | 6141 | 6160 | GTTTTGAAAAATATTCAGGA | 53 | 842 |
| 1239112 | N/A | N/A | 6319 | 6338 | GATCAAGAGCTTGTGATCAC | 95 | 843 |
| 1239134 | N/A | N/A | 6443 | 6462 | CCCTTACATAATTCAGCATA | 68 | 844 |
| 1239156 | N/A | N/A | 6531 | 6550 | TGACAGCCATGTTCAGTGTC | 100 | 845 |
| 1239178 | N/A | N/A | 6725 | 6744 | CACTTAGGAGTTATTTTATA | 61 | 846 |
| 1239200 | N/A | N/A | 6878 | 6897 | CATTTATAATGCTTTTCACT | 70 | 847 |
| 1239222 | N/A | N/A | 7282 | 7301 | CTTAATTAGTTACATCGGGA | 9 | 848 |
| 1239244 | N/A | N/A | 7758 | 7777 | CGTGTGAGCATTCTTGTCTT | 81 | 849 |
| 1239266 | N/A | N/A | 8189 | 8208 | AACATTAATTATCCCCCCAT | 82 | 850 |
| 1239288 | N/A | N/A | 8417 | 8436 | CATTGTACCTCAACACAATA | 94 | 851 |
| 1239310 | N/A | N/A | 8751 | 8770 | ACCAGCATTATCCTGATGTC | 55 | 852 |
| 1239332 | N/A | N/A | 9067 | 9086 | TCAAAGGTAATTTTATAACC | 93 | 853 |
| 1239354 | N/A | N/A | 9422 | 9441 | CTAGGTATAATTTTTTTACC | 97 | 854 |
| 1239376 | N/A | N/A | 9652 | 9671 | TGTTGAAAAGTTTTCAATGA | 79 | 855 |
| 1239398 | N/A | N/A | 10096 | 10115 | GGTGATGCCATCTACTGAAA | 89 | 856 |
| 1239420 | N/A | N/A | 10736 | 10755 | TAACACACATTTCAAGTGTC | 92 | 857 |
| 1239442 | N/A | N/A | 11089 | 11108 | AGTACCATAACCTTTTTTTT | 53 | 858 |
| 1239464 | N/A | N/A | 12639 | 12658 | ACGGAAATATCATTCGACTC | 47 | 859 |
| 1239486 | N/A | N/A | 13554 | 13573 | CTAGCTGACACTATTTGCAA | 89 | 860 |
| 1239508 | N/A | N/A | 13879 | 13898 | AGAGGAGAAGAACCAGGCAC | 88 | 861 |
| 1239530 | N/A | N/A | 14214 | 14233 | GCATAAGGAATAATCAAACT | 57 | 862 |
| 1239552 | N/A | N/A | 14385 | 14404 | TTATGTTATTTCCTCTGTGC | 35 | 863 |
| 1239574 | N/A | N/A | 14812 | 14831 | TTATTCGGTGCTTCCATCAC | 68 | 864 |
| 1239596 | N/A | N/A | 14983 | 15002 | ATGTCAGCACCTTCTCCATT | 57 | 865 |
| 1239618 | N/A | N/A | 15270 | 15289 | CTAACATTATTGAAATGGGA | 42 | 866 |
| 1239640 | N/A | N/A | 15367 | 15386 | ATTATTTTTCATCTCCTTCA | 64 | 867 |
| 1239662 | N/A | N/A | 15420 | 15439 | AACCCCTTACCTTTATCACC | 52 | 868 |
| 1239684 | N/A | N/A | 15520 | 15539 | ATTCACCATATACCATGTAC | 51 | 869 |
| 1239706 | N/A | N/A | 15698 | 15717 | AAATCATCACTGTGTGCCGT | 42 | 870 |
| 1239728 | N/A | N/A | 15769 | 15788 | AGAGACCTATGACAATAGTA | 64 | 871 |

TABLE 12 -continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1239750 | N/A | N/A | 15834 | 15853 | ATCAAATCAAAAATCTCTTT | 91 | 872 |
| 1239772 | N/A | N/A | 15883 | 15902 | ATCAAACATCCAGAATGACA | 70 | 873 |
| 1239794 | N/A | N/A | 15949 | 15968 | GTTCATTATTTAACATTTTA | 74 | 874 |

TABLE 13

Reduction of PRNP RNA

| Compound ID | SEQ ID NO: 1 Site | SEQ ID NO: 1 Site | SEQ ID NO: 2 Site | SEQ ID NO: 2 Site | Sequence (5' to 3') | PRNP (% UTC) RTS 42354 | PRNP (% UTC) RTS 42359 | SEQ ID NO |
|---|---|---|---|---|---|---|---|---|
| 1201142 | 1963 | 1982 | 17754 | 17773 | GCCACATATAGGGTCCTTTA | 8 | 12 | 66 |
| 1238123 | 54 | 73 | 3147 | 3166 | AAAAATCATCTTTAATTGGA | 92 | 88 | 875 |
| 1238145 | 121 | 140 | 3214 | 3233 | TTGAACACTTGCATCAGTTG | 81 | 86 | 876 |
| 1238167 | 508 | 527 | 16299 | 16318 | GTGTTCCATCCTCCAGGCTT | 5* | 71 | 877 |
| 1238189 | 594 618 | 613 637 | 16385 16409 | 16404 16428 | CATGAGGCTGCCCCCAGCCA | 84 | 233 | 878 |
| 1238211 | 874 | 893 | 16665 | 16684 | TGCATGTTTTCACGATAGTA | 55 | 50 | 879 |
| 1238233 | 1264 | 1283 | 17055 | 17074 | TGAGACACCACCACTAAAAG | 68 | 72 | 880 |
| 1238255 | 1424 | 1443 | 17215 | 17234 | TTTGCTGTTATACTTTTACT | 13 | 14 | 881 |
| 1238277 | 1591 | 1610 | 17382 | 17401 | AAATAGCTATGAAATCTCTA | 31 | 40 | 882 |
| 1238299 | 1680 | 1699 | 17471 | 17490 | TCTAGGATTTTTTGAATAA | 60 | 70 | 883 |
| 1238321 | 1812 | 1831 | 17603 | 17622 | TGACAATATTTACTCTTGTT | 13 | 13 | 884 |
| 1238343 | 1855 | 1874 | 17646 | 17665 | ATGTTCACTGTGAATATGTC | 27 | 26 | 885 |
| 1238365 | 1885 | 1904 | 17676 | 17695 | TCCCAGAAGCCTTTCATATA | 32 | 25 | 886 |
| 1238387 | 1921 | 1940 | 17712 | 17731 | CTCCAAGGGCACCATTCCCA | 85 | 79 | 887 |
| 1238409 | 2009 | 2028 | 17800 | 17819 | TTTACTTTTCAGCTGCCTTA | 9 | 10 | 888 |
| 1238431 | 2043 | 2062 | 17834 | 17853 | CAAAGGAGATTTGCCTTCAG | 71 | 68 | 889 |
| 1238453 | 2093 | 2112 | 17884 | 17903 | ACTGCAGCTCTCCTGTATGT | 84 | 94 | 890 |
| 1238475 | 2127 | 2146 | 17918 | 17937 | TTACATCATCCTCTATGATG | 89 | 94 | 891 |
| 1238497 | 2156 | 2175 | 17947 | 17966 | CTTTTCTTTGCACACTGACC | 8 | 10 | 892 |
| 1238519 | 2210 | 2229 | 18001 | 18020 | CCTAATTCTGGTTTTTGACA | 27 | 36 | 893 |
| 1238541 | 2251 | 2270 | 18042 | 18061 | TTCTTTGATTCAAAAGCCAA | 72 | 78 | 894 |
| 1238563 | 2276 | 2295 | 18067 | 18086 | AGATATTTTTAGATTGTCT | 53 | 57 | 895 |
| 1238585 | 2306 | 2325 | 18097 | 18116 | ATCAATCATATTTCTGTCAT | 37 | 40 | 896 |
| 1238607 | 2339 | 2358 | 18130 | 18149 | TTAACATTAACAGAATTTCT | 66 | 56 | 897 |
| 1238629 | 2381 | 2400 | 18172 | 18191 | AGGTGACAATATCAAACAAT | 26 | 25 | 898 |
| 1238651 | 2440 | 2459 | 18231 | 18250 | AGAATACTCACAAAGTGCAA | 41 | 37 | 899 |
| 1238673 | 2532 | 2551 | 18323 | 18342 | GCATTAGACACTTCAGATGT | 35 | 43 | 900 |

TABLE 13 -continued

Reduction of PRNP RNA

| Compound ID | SEQ ID NO: 1 Site | SEQ ID NO: 1 Site | SEQ ID NO: 2 Site | SEQ ID NO: 2 Site | Sequence (5' to 3') | PRNP (% UTC) RTS 42354 | PRNP (% UTC) RTS 42359 | SEQ ID NO |
|---|---|---|---|---|---|---|---|---|
| 1238695 | 2629 | 2648 | 18420 | 18439 | ATTCTTACATGAAACGATTC | 69 | 54 | 901 |
| 1238717 | 2732 | 2751 | 18523 | 18542 | TACAATTTTTTTATATAACA | 117 | 118 | 902 |
| 1238739 | N/A | N/A | 4748 | 4767 | CCGTGATGCTCTCAGAACAA | 31 | 31 | 903 |
| 1238761 | N/A | N/A | 4829 | 4848 | AATCCTTAATCCTATTCTAC | 91 | 74 | 904 |
| 1238783 | N/A | N/A | 4877 | 4896 | ATTTATCCAATTCCCTGTTC | 89 | 80 | 905 |
| 1238805 | N/A | N/A | 4905 | 4924 | GTTGTTGATTTTTCCAGAAG | 7 | 8 | 906 |
| 1238827 | N/A | N/A | 4969 | 4988 | TTGTGTAAGTAAAATTGCTC | 47 | 49 | 907 |
| 1238849 | N/A | N/A | 5046 | 5065 | ACAAATCACATCCTACCCCT | 96 | 89 | 908 |
| 1238871 | N/A | N/A | 5101 | 5120 | TAATCTTAATATTTTCCTTT | 113 | 115 | 909 |
| 1238893 | N/A | N/A | 5133 | 5152 | AAATGACTCATCATTTTGCC | 26 | 24 | 910 |
| 1238915 | N/A | N/A | 5196 | 5215 | TTGGTTATTTTAATAGATGT | 33 | 28 | 911 |
| 1238937 | N/A | N/A | 5382 | 5401 | CTATCATTTCCTCCATTCTA | 68 | 91 | 912 |
| 1238959 | N/A | N/A | 5452 | 5471 | TGCTTAACAAAATGTTTGTC | 67 | 58 | 913 |
| 1238981 | N/A | N/A | 5582 | 5601 | GTTCTAATTTTAGATCATTC | 19 | 22 | 914 |
| 1239003 | N/A | N/A | 5658 | 5677 | ATGTTCATTTCAGTTAATGT | 20 | 19 | 915 |
| 1239025 | N/A | N/A | 5713 | 5732 | CAGTTTTTCCCCACATATCA | 38 | 37 | 916 |
| 1239047 | N/A | N/A | 5784 | 5803 | TTTCAGATTTTTCACATATG | 34 | 40 | 917 |
| 1239069 | N/A | N/A | 5888 | 5907 | GTGAACTATTTTTAAACGC | 35 | 31 | 918 |
| 1239091 | N/A | N/A | 6158 | 6177 | ATGGCTGAAATTGTTCAGTT | 75 | 53 | 919 |
| 1239113 | N/A | N/A | 6333 | 6352 | CCGAGTGGCCTCTGGATCAA | 58 | 69 | 920 |
| 1239135 | N/A | N/A | 6444 | 6463 | TCCCTTACATAATTCAGCAT | 59 | 63 | 921 |
| 1239157 | N/A | N/A | 6533 | 6552 | GTTGACAGCCATGTTCAGTG | 23 | 24 | 922 |
| 1239179 | N/A | N/A | 6736 | 6755 | CACACACTATTCACTTAGGA | 20 | 19 | 923 |
| 1239201 | N/A | N/A | 6879 | 6898 | ACATTTATAATGCTTTTCAC | 61 | 64 | 924 |
| 1239223 | N/A | N/A | 7286 | 7305 | GAAGCTTAATTAGTTACATC | 15 | 15 | 925 |
| 1239245 | N/A | N/A | 7788 | 7807 | TGCAGTACCATATGTTGAAT | 27 | 28 | 926 |
| 1239267 | N/A | N/A | 8190 | 8209 | CAACATTAATTATCCCCCA | 67 | 77 | 927 |
| 1239289 | N/A | N/A | 8418 | 8437 | GCATTGTACCTCAACACAAT | 48 | 56 | 928 |
| 1239311 | N/A | N/A | 8805 | 8824 | CAAGTTTTTTTCTAAGCAT | 48 | 37 | 929 |
| 1239333 | N/A | N/A | 9078 | 9097 | TCAGTCAGAATTCAAAGGTA | 41 | 32 | 930 |
| 1239355 | N/A | N/A | 9423 | 9442 | TCTAGGTATAATTTTTTTAC | 83 | 86 | 931 |
| 1239377 | N/A | N/A | 9668 | 9687 | AAAGATTTTCTTCAGATGTT | 58 | 61 | 932 |
| 1239399 | N/A | N/A | 10126 | 10145 | GTCTGGGACTTCCATAACCA | 84 | 56 | 933 |
| 1239421 | N/A | N/A | 10737 | 10756 | TTAACACACATTTCAAGTGT | 94 | 61 | 934 |
| 1239443 | N/A | N/A | 11090 | 11109 | CAGTACCATAACCTTTTTTT | 58 | 49 | 935 |
| 1239465 | N/A | N/A | 12640 | 12659 | GACGGAAATATCATTCGACT | 43 | 50 | 936 |

TABLE 13-continued

Reduction of PRNP RNA

| Compound ID | SEQ ID NO: 1 Site | SEQ ID NO: 1 Site | SEQ ID NO: 2 Site | SEQ ID NO: 2 Site | Sequence (5' to 3') | PRNP (% UTC) RTS 42354 | PRNP (% UTC) RTS 42359 | SEQ ID NO |
|---|---|---|---|---|---|---|---|---|
| 1239487 | N/A | N/A | 13667 | 13686 | GCTAAGAATACACTCAGAAA | 51 | 47 | 937 |
| 1239509 | N/A | N/A | 13924 | 13943 | AGAGACACCTGAACAGGCGA | 100 | 95 | 938 |
| 1239531 | N/A | N/A | 14215 | 14234 | AGCATAAGGAATAATCAAAC | 62 | 64 | 939 |
| 1239553 | N/A | N/A | 14386 | 14405 | ATTATGTTATTTCCTCTGTG | 40 | 46 | 940 |
| 1239575 | N/A | N/A | 14822 | 14841 | CATGACCATCTTATTCGGTG | 58 | 56 | 941 |
| 1239597 | N/A | N/A | 14985 | 15004 | TTATGTCAGCACCTTCTCCA | 62 | 50 | 942 |
| 1239619 | N/A | N/A | 15275 | 15294 | TTCTACTAACATTATTGAAA | 94 | 64 | 943 |
| 1239641 | N/A | N/A | 15368 | 15387 | AATTATTTTTCATCTCCTTC | 56 | 57 | 944 |
| 1239663 | N/A | N/A | 15421 | 15440 | AAACCCCTTACCTTTATCAC | 74 | 100 | 945 |
| 1239685 | N/A | N/A | 15522 | 15541 | TAATTCACCATATACCATGT | 74 | 53 | 946 |
| 1239707 | N/A | N/A | 15700 | 15719 | CCAAATCATCACTGTGTGCC | 48 | 35 | 947 |
| 1239729 | N/A | N/A | 15773 | 15792 | GAGCAGAGACCTATGACAAT | 75 | 70 | 948 |
| 1239751 | N/A | N/A | 15835 | 15854 | CATCAAATCAAAAATCTCTT | 90 | 82 | 949 |
| 1239773 | N/A | N/A | 15884 | 15903 | GATCAAACATCCAGAATGAC | 57 | 64 | 950 |
| 1239795 | N/A | N/A | 15951 | 15970 | TAGTTCATTATTTAACATTT | 67 | 55 | 951 |

TABLE 14

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | PRNP (% UTC) RTS 42359 | SEQ ID NO |
|---|---|---|---|---|---|---|---|---|
| 1201142 | 1963 | 1982 | 17754 | 17773 | GCCACATATAGGGTCCTTTA | 8 | 17 | 66 |
| 1238124 | 55 | 74 | 3148 | 3167 | TAAAAATCATCTTTAATTGG | 91 | 92 | 952 |
| 1238146 | 122 | 141 | 3215 | 3234 | CTTGAACACTTGCATCAGTT | 89 | 74 | 953 |
| 1238168 | 510 | 529 | 16301 | 16320 | CAGTGTTCCATCCTCCAGGC | 6* | 58 | 954 |
| 1238190 | 595 619 | 614 638 | 16386 16410 | 16405 16429 | CCATGAGGCTGCCCCCAGCC | 75 | 226 | 955 |
| 1238212 | 931 | 950 | 16722 | 16741 | TTGTTCTGGTTGCTGTACTC | 54 | 44 | 956 |
| 1238234 | 1267 | 1286 | 17058 | 17077 | GAGTGAGACACCACCACTAA | 86 | 70 | 957 |
| 1238256 | 1442 | 1461 | 17233 | 17252 | CAGATTAACCAATGGTTATT | 37 | 60 | 958 |
| 1238278 | 1602 | 1621 | 17393 | 17412 | AAAATATCTCTAAATAGCTA | 88 | 66 | 959 |
| 1238300 | 1681 | 1700 | 17472 | 17491 | CTCTAGGATTTTTTTGAATA | 38 | 54 | 960 |
| 1238322 | 1813 | 1832 | 17604 | 17623 | GTGACAATATTTACTCTTGT | 3 | 8 | 961 |
| 1238344 | 1858 | 1877 | 17649 | 17668 | GTTATGTTCACTGTGAATAT | 14 | 16 | 962 |
| 1238366 | 1886 | 1905 | 17677 | 17696 | GTCCCAGAAGCCTTTCATAT | 28 | 31 | 963 |
| 1238388 | 1928 | 1947 | 17719 | 17738 | AGGTTGCCTCCAAGGGCACC | 92 | 83 | 964 |
| 1238410 | 2010 | 2029 | 17801 | 17820 | ATTTACTTTTCAGCTGCCTT | 10 | 21 | 965 |

TABLE 14 -continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | PRNP (% UTC) RTS 42359 | SEQ ID NO |
|---|---|---|---|---|---|---|---|---|
| 1238432 | 2059 | 2078 | 17850 | 17869 | TTTCCAGGTAAATGGACAAA | 43 | 44 | 966 |
| 1238454 | 2098 | 2117 | 17889 | 17908 | TCACAACTGCAGCTCTCCTG | 24 | 32 | 967 |
| 1238476 | 2129 | 2148 | 17920 | 17939 | AATTACATCATCCTCTATGA | 87 | 83 | 968 |
| 1238498 | 2157 | 2176 | 17948 | 17967 | TCTTTTCTTTGCACACTGAC | 9 | 23 | 969 |
| 1238520 | 2211 | 2230 | 18002 | 18021 | ACCTAATTCTGGTTTTTGAC | 41 | 41 | 970 |
| 1238542 | 2252 | 2271 | 18043 | 18062 | ATTCTTTGATTCAAAAGCCA | 26 | 44 | 971 |
| 1238564 | 2277 | 2296 | 18068 | 18087 | AAGATATTTTTTAGATTGTC | 56 | 44 | 972 |
| 1238586 | 2307 | 2326 | 18098 | 18117 | AATCAATCATATTTCTGTCA | 39 | 36 | 973 |
| 1238608 | 2340 | 2359 | 18131 | 18150 | ATTAACATTAACAGAATTTC | 93 | 77 | 974 |
| 1238630 | 2382 | 2401 | 18173 | 18192 | TAGGTGACAATATCAAACAA | 34 | 48 | 975 |
| 1238652 | 2441 | 2460 | 18232 | 18251 | TAGAATACTCACAAAGTGCA | 51 | 43 | 976 |
| 1238674 | 2538 | 2557 | 18329 | 18348 | GTTAATGCATTAGACACTTC | 25 | 32 | 977 |
| 1238696 | 2635 | 2654 | 18426 | 18445 | CTTTGGATTCTTACATGAAA | 50 | 57 | 978 |
| 1238718 | 2744 | 2763 | 18535 | 18554 | ATATTAAACATTTACAATTT | 104 | 84 | 979 |
| 1238740 | N/A | N/A | 4749 | 4768 | ACCGTGATGCTCTCAGAACA | 37 | 42 | 980 |
| 1238762 | N/A | N/A | 4830 | 4849 | AAATCCTTAATCCTATTCTA | 86 | 85 | 981 |
| 1238784 | N/A | N/A | 4878 | 4897 | TATTTATCCAATTCCCTGTT | 63 | 59 | 982 |
| 1238806 | N/A | N/A | 4925 | 4944 | TCTTCTACAAATCTAAGAGC | 85 | 73 | 983 |
| 1238828 | N/A | N/A | 4977 | 4996 | CTCTGTGTTTGTGTAAGTAA | 50 | 59 | 984 |
| 1238850 | N/A | N/A | 5047 | 5066 | TACAAATCACATCCTACCCC | 93 | 62 | 985 |
| 1238872 | N/A | N/A | 5102 | 5121 | ATAATCTTAATATTTTCCTT | 73 | 100 | 986 |
| 1238894 | N/A | N/A | 5134 | 5153 | TAAATGACTCATCATTTTGC | 63 | 56 | 987 |
| 1238916 | N/A | N/A | 5198 | 5217 | TTTTGGTTATTTTAATAGAT | 74 | 95 | 988 |
| 1238938 | N/A | N/A | 5383 | 5402 | GCTATCATTTCCTCCATTCT | 32 | 34 | 989 |
| 1238960 | N/A | N/A | 5455 | 5474 | GATTGCTTAACAAAATGTTT | 68 | 81 | 990 |
| 1238982 | N/A | N/A | 5584 | 5603 | GTGTTCTAATTTTAGATCAT | 46 | 48 | 991 |
| 1239004 | N/A | N/A | 5661 | 5680 | ATAATGTTCATTTCAGTTAA | 72 | 57 | 992 |
| 1239026 | N/A | N/A | 5714 | 5733 | TCAGTTTTTCCCCACATATC | 23 | 26 | 993 |
| 1239048 | N/A | N/A | 5785 | 5804 | CTTTCAGATTTTTCACATAT | 51 | 44 | 994 |
| 1239070 | N/A | N/A | 5890 | 5909 | CTGTGAACTATTTTTTAAAC | 29 | 64 | 995 |
| 1239092 | N/A | N/A | 6194 | 6213 | TAGATTTGTGCCTCCAGGAA | 33 | 33 | 996 |
| 1239114 | N/A | N/A | 6347 | 6366 | TCACACAGATGCACCCGAGT | 61 | 73 | 997 |
| 1239136 | N/A | N/A | 6445 | 6464 | CTCCCTTACATAATTCAGCA | 56 | 68 | 998 |
| 1239158 | N/A | N/A | 6562 | 6581 | AGAATCTTTCACCTTGGTTT | 33 | 41 | 999 |
| 1239180 | N/A | N/A | 6745 | 6764 | GAATTGCTGCACACACTATT | 72 | 106 | 1000 |
| 1239202 | N/A | N/A | 6884 | 6903 | CTTCAACATTTATAATGCTT | 38 | 36 | 1001 |

TABLE 14 -continued
Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | PRNP (% UTC) RTS 42359 | SEQ ID NO |
|---|---|---|---|---|---|---|---|---|
| 1239224 | N/A | N/A | 7290 | 7309 | ACTTGAAGCTTAATTAGTTA | 63 | 88 | 1002 |
| 1239246 | N/A | N/A | 7865 | 7884 | GGAACAATTTAACTTTTTCC | 50 | 62 | 1003 |
| 1239268 | N/A | N/A | 8191 | 8210 | ACAACATTAATTATCCCCCC | 66 | 67 | 1004 |
| 1239290 | N/A | N/A | 8419 | 8438 | AGCATTGTACCTCAACACAA | 50 | 43 | 1005 |
| 1239312 | N/A | N/A | 8806 | 8825 | TCAAGTTTTTTTCTAAGCA | 66 | 63 | 1006 |
| 1239334 | N/A | N/A | 9091 | 9110 | AGTAAACACAATTTCAGTCA | 30 | 57 | 1007 |
| 1239356 | N/A | N/A | 9425 | 9444 | CATCTAGGTATAATTTTTTT | 87 | 140 | 1008 |
| 1239378 | N/A | N/A | 9671 | 9690 | AGAAAAGATTTTCTTCAGAT | 73 | 60 | 1009 |
| 1239400 | N/A | N/A | 10197 | 10216 | TGAGACATATTTTACAGAAA | 55 | 43 | 1010 |
| 1239422 | N/A | N/A | 10738 | 10757 | CTTAACACACATTTCAAGTG | 56 | 80 | 1011 |
| 1239444 | N/A | N/A | 11106 | 11125 | TGTAATATAATATTTACAGT | 82 | 85 | 1012 |
| 1239466 | N/A | N/A | 12669 | 12688 | GAATTTGATTACATCCTCAA | 66 | 78 | 1013 |
| 1239488 | N/A | N/A | 13693 | 13712 | AATACCTGTTTATTACTAAG | 83 | 61 | 1014 |
| 1239510 | N/A | N/A | 13929 | 13948 | CTCTTAGAGACACCTGAACA | 89 | 73 | 1015 |
| 1239532 | N/A | N/A | 14228 | 14247 | ACACATGTTATAAAGCATAA | 58 | 70 | 1016 |
| 1239554 | N/A | N/A | 14391 | 14410 | GAGATATTATGTTATTTCCT | 27 | 26 | 1017 |
| 1239576 | N/A | N/A | 14834 | 14853 | CAATTTTTCCAACATGACCA | 56 | 47 | 1018 |
| 1239598 | N/A | N/A | 14993 | 15012 | AAGGGCTTTTATGTCAGCAC | 44 | 52 | 1019 |
| 1239620 | N/A | N/A | 15276 | 15295 | TTTCTACTAACATTATTGAA | 93 | 84 | 1020 |
| 1239642 | N/A | N/A | 15369 | 15388 | AAATTATTTTTCATCTCCTT | 50 | 70 | 1021 |
| 1239664 | N/A | N/A | 15424 | 15443 | CAGAAACCCCTTACCTTTAT | 63 | 69 | 1022 |
| 1239686 | N/A | N/A | 15524 | 15543 | TATAATTCACCATATACCAT | 62 | 84 | 1023 |
| 1239708 | N/A | N/A | 15701 | 15720 | TCCAAATCATCACTGTGTGC | 53 | 53 | 1024 |
| 1239730 | N/A | N/A | 15774 | 15793 | AGAGCAGAGACCTATGACAA | 87 | 77 | 1025 |
| 1239752 | N/A | N/A | 15836 | 15855 | TCATCAAATCAAAAATCTCT | 76 | 35 | 1026 |
| 1239774 | N/A | N/A | 15887 | 15906 | ACAGATCAAACATCCAGAAT | 59 | 49 | 1027 |
| 1239796 | N/A | N/A | 15955 | 15974 | CTTTTAGTTCATTATTTAAC | 73 | 64 | 1028 |

TABLE 15
Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201142 | 1963 | 1982 | 17754 | 17773 | GCCACATATAGGGTCCTTTA | 13 | 66 |
| 1238125 | 57 | 76 | 3150 | 3169 | TGTAAAAATCATCTTTAATT | 104 | 1029 |
| 1238147 | 123 | 142 | 3216 | 3235 | GCTTGAACACTTGCATCAGT | 59 | 1030 |

TABLE 15-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1238169 | 512 | 531 | 16303 | 16322 | CCCAGTGTTCCATCCTCCAG | 9* | 1031 |
| 1238191 | 596 620 | 615 639 | 16387 16411 | 16406 16430 | ACCATGAGGCTGCCCCCAGC | 48 | 1032 |
| 1238213 | 966 | 985 | 16757 | 16776 | GCTTGATTGTGATATTGACG | 52 | 1033 |
| 1238235 | 1269 | 1288 | 17060 | 17079 | AAGAGTGAGACACCACCACT | 62 | 1034 |
| 1238257 | 1444 | 1463 | 17235 | 17254 | TCCAGATTAACCAATGGTTA | 41 | 1035 |
| 1238279 | 1605 | 1624 | 17396 | 17415 | TGGAAAATATCTCTAAATAG | 78 | 1036 |
| 1238301 | 1691 | 1710 | 17482 | 17501 | AGCTAAGAATCTCTAGGATT | 31 | 1037 |
| 1238323 | 1814 | 1833 | 17605 | 17624 | TGTGACAATATTTACTCTTG | 10 | 1038 |
| 1238345 | 1859 | 1878 | 17650 | 17669 | AGTTATGTTCACTGTGAATA | 17 | 1039 |
| 1238367 | 1893 | 1912 | 17684 | 17703 | ATTTCAAGTCCCAGAAGCCT | 34 | 1040 |
| 1238389 | 1929 | 1948 | 17720 | 17739 | GAGGTTGCCTCCAAGGGCAC | 83 | 1041 |
| 1238411 | 2012 | 2031 | 17803 | 17822 | CAATTTACTTTTCAGCTGCC | 32 | 1042 |
| 1238433 | 2060 | 2079 | 17851 | 17870 | GTTTCCAGGTAAATGGACAA | 77 | 1043 |
| 1238455 | 2101 | 2120 | 17892 | 17911 | CTTTCACAACTGCAGCTCTC | 30 | 1044 |
| 1238477 | 2131 | 2150 | 17922 | 17941 | TTAATTACATCATCCTCTAT | 93 | 1045 |
| 1238499 | 2158 | 2177 | 17949 | 17968 | TTCTTTTCTTTGCACACTGA | 15 | 1046 |
| 1238521 | 2212 | 2231 | 18003 | 18022 | GACCTAATTCTGGTTTTTGA | 56 | 1047 |
| 1238543 | 2253 | 2272 | 18044 | 18063 | TATTCTTTGATTCAAAAGCC | 50 | 1048 |
| 1238565 | 2279 | 2298 | 18070 | 18089 | CTAAGATATTTTTTAGATTG | 78 | 1049 |
| 1238587 | 2308 | 2327 | 18099 | 18118 | AAATCAATCATATTTCTGTC | 51 | 1050 |
| 1238609 | 2342 | 2361 | 18133 | 18152 | TAATTAACATTAACAGAATT | 92 | 1051 |
| 1238631 | 2383 | 2402 | 18174 | 18193 | CTAGGTGACAATATCAAACA | 29 | 1052 |
| 1238653 | 2442 | 2461 | 18233 | 18252 | ATAGAATACTCACAAAGTGC | 41 | 1053 |
| 1238675 | 2539 | 2558 | 18330 | 18349 | AGTTAATGCATTAGACACTT | 24 | 1054 |
| 1238697 | 2636 | 2655 | 18427 | 18446 | ACTTTGGATTCTTACATGAA | 54 | 1055 |
| 1238719 | 2745 | 2764 | 18536 | 18555 | GATATTAAACATTTACAATT | 92 | 1056 |
| 1238741 | N/A | N/A | 4751 | 4770 | AAACCGTGATGCTCTCAGAA | 30 | 1057 |
| 1238763 | N/A | N/A | 4831 | 4850 | AAAATCCTTAATCCTATTCT | 102 | 1058 |
| 1238785 | N/A | N/A | 4879 | 4898 | ATATTTATCCAATTCCCTGT | 46 | 1059 |
| 1238807 | N/A | N/A | 4929 | 4948 | CCTTTCTTCTACAAATCTAA | 71 | 1060 |
| 1238829 | N/A | N/A | 4988 | 5007 | TGTAAGACCTTCTCTGTGTT | 66 | 1061 |
| 1238851 | N/A | N/A | 5049 | 5068 | CATACAAATCACATCCTACC | 80 | 1062 |
| 1238873 | N/A | N/A | 5103 | 5122 | TATAATCTTAATATTTTCCT | 110 | 1063 |
| 1238895 | N/A | N/A | 5136 | 5155 | TGTAAATGACTCATCATTTT | 58 | 1064 |
| 1238917 | N/A | N/A | 5209 | 5228 | ACTATTAATTATTTTGGTTA | 76 | 1065 |
| 1238939 | N/A | N/A | 5384 | 5403 | AGCTATCATTTCCTCCATTC | 31 | 1066 |

TABLE 15-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1238961 | N/A | N/A | 5456 | 5475 | AGATTGCTTAACAAAATGTT | 86 | 1067 |
| 1238983 | N/A | N/A | 5585 | 5604 | GGTGTTCTAATTTTAGATCA | 33 | 1068 |
| 1239005 | N/A | N/A | 5662 | 5681 | CATAATGTTCATTTCAGTTA | 45 | 1069 |
| 1239027 | N/A | N/A | 5716 | 5735 | TGTCAGTTTTTCCCCACATA | 16 | 1070 |
| 1239049 | N/A | N/A | 5786 | 5805 | CCTTTCAGATTTTTCACATA | 41 | 1071 |
| 1239071 | N/A | N/A | 5919 | 5938 | TGGGTCCATTTCATCTAAAA | 60 | 1072 |
| 1239093 | N/A | N/A | 6207 | 6226 | GGTTCAGCTAAACTAGATTT | 28 | 1073 |
| 1239115 | N/A | N/A | 6355 | 6374 | GGTGTCAGTCACACAGATGC | 81 | 1074 |
| 1239137 | N/A | N/A | 6447 | 6466 | TGCTCCCTTACATAATTCAG | 81 | 1075 |
| 1239159 | N/A | N/A | 6563 | 6582 | GAGAATCTTTCACCTTGGTT | 45 | 1076 |
| 1239181 | N/A | N/A | 6752 | 6771 | GCTGTGAGAATTGCTGCACA | 78 | 1077 |
| 1239203 | N/A | N/A | 6886 | 6905 | ATCTTCAACATTTATAATGC | 64 | 1078 |
| 1239225 | N/A | N/A | 7302 | 7321 | AAACACATTACAACTTGAAG | 58 | 1079 |
| 1239247 | N/A | N/A | 8024 | 8043 | TATTTCTTTCCTGATAGTTC | 32 | 1080 |
| 1239269 | N/A | N/A | 8192 | 8211 | AACAACATTAATTATCCCCC | 67 | 1081 |
| 1239291 | N/A | N/A | 8420 | 8439 | AAGCATTGTACCTCAACACA | 67 | 1082 |
| 1239313 | N/A | N/A | 8807 | 8826 | ATCAAGTTTTTTTCTAAGC | 39 | 1083 |
| 1239335 | N/A | N/A | 9106 | 9125 | GCAAATAATCTACAAAGTAA | 93 | 1084 |
| 1239357 | N/A | N/A | 9434 | 9453 | CTATAAATTCATCTAGGTAT | 59 | 1085 |
| 1239379 | N/A | N/A | 9695 | 9714 | AGGAGCTCTATTAATAGGTT | 47 | 1086 |
| 1239401 | N/A | N/A | 10198 | 10217 | ATGAGACATATTTTACAGAA | 47 | 1087 |
| 1239423 | N/A | N/A | 10739 | 10758 | GCTTAACACACATTTCAAGT | 38 | 1088 |
| 1239445 | N/A | N/A | 11125 | 11144 | GCTGTCAAAAATTATACACT | 48 | 1089 |
| 1239467 | N/A | N/A | 12670 | 12689 | TGAATTTGATTACATCCTCA | 70 | 1090 |
| 1239489 | N/A | N/A | 13694 | 13713 | CAATACCTGTTTATTACTAA | 56 | 1091 |
| 1239511 | N/A | N/A | 13936 | 13955 | CTATGAGCTCTTAGAGACAC | 79 | 1092 |
| 1239533 | N/A | N/A | 14235 | 14254 | TGGGAAAACACATGTTATAA | 70 | 1093 |
| 1239555 | N/A | N/A | 14393 | 14412 | TTGAGATATTATGTTATTTC | 76 | 1094 |
| 1239577 | N/A | N/A | 14835 | 14854 | TCAATTTTTCCAACATGACC | 71 | 1095 |
| 1239599 | N/A | N/A | 14994 | 15013 | AAAGGGCTTTTATGTCAGCA | 25 | 1096 |
| 1239621 | N/A | N/A | 15283 | 15302 | GTTTATGTTTCTACTAACAT | 72 | 1097 |
| 1239643 | N/A | N/A | 15370 | 15389 | AAAATTATTTTTCATCTCCT | 79 | 1098 |
| 1239665 | N/A | N/A | 15425 | 15444 | TCAGAAACCCCTTACCTTTA | 87 | 1099 |
| 1239687 | N/A | N/A | 15525 | 15544 | ATATAATTCACCATATACCA | 69 | 1100 |
| 1239709 | N/A | N/A | 15703 | 15722 | GCTCCAAATCATCACTGTGT | 47 | 1101 |
| 1239731 | N/A | N/A | 15775 | 15794 | AAGAGCAGAGACCTATGACA | 98 | 1102 |

TABLE 15-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1239753 | N/A | N/A | 15837 | 15856 | TTCATCAAATCAAAAATCTC | 106 | 1103 |
| 1239775 | N/A | N/A | 15888 | 15907 | AACAGATCAAACATCCAGAA | 67 | 1104 |
| 1239797 | N/A | N/A | 15960 | 15979 | AATGACTTTTAGTTCATTAT | 91 | 1105 |

TABLE 16

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RT542354 | SEQ ID NO |
|---|---|---|---|---|---|---|---|
| 1201142 | 1963 | 1982 | 17754 | 17773 | GCCACATATAGGGTCCTTTA | 11 | 66 |
| 1238126 | 58 | 77 | 3151 | 3170 | CTGTAAAAATCATCTTTAAT | 119 | 1106 |
| 1238148 | 124 | 143 | 3217 | 3236 | CGCTTGAACACTTGCATCAG | 113 | 1107 |
| 1238170 | 513 | 532 | 16304 | 16323 | CCCCAGTGTTCCATCCTCCA | 7* | 1108 |
| 1238192 | 603 627 | 622 646 | 16394 16418 | 16413 16437 | AGCCACCACCATGAGGCTGC | 77 | 1109 |
| 1238214 | 1002 | 1021 | 16793 | 16812 | AGTTCTCCCCCTTGGTGGTT | 63 | 1110 |
| 1238236 | 1270 | 1289 | 17061 | 17080 | AAAGAGTGAGACACCACCAC | 67 | 1111 |
| 1238258 | 1451 | 1470 | 17242 | 17261 | AAATAAGTCCAGATTAACCA | 62 | 1112 |
| 1238280 | 1607 | 1626 | 17398 | 17417 | AATGGAAAATATCTCTAAAT | 95 | 1113 |
| 1238302 | 1692 | 1711 | 17483 | 17502 | GAGCTAAGAATCTCTAGGAT | 22 | 1114 |
| 1238324 | 1815 | 1834 | 17606 | 17625 | TTGTGACAATATTTACTCTT | 10 | 1115 |
| 1238346 | 1860 | 1879 | 17651 | 17670 | CAGTTATGTTCACTGTGAAT | 26 | 1116 |
| 1238368 | 1896 | 1915 | 17687 | 17706 | TTGATTTCAAGTCCCAGAAG | 26 | 1117 |
| 1238390 | 1933 | 1952 | 17724 | 17743 | ATGGGAGGTTGCCTCCAAGG | 108 | 1118 |
| 1238412 | 2013 | 2032 | 17804 | 17823 | GCAATTTACTTTTCAGCTGC | 40 | 1119 |
| 1238434 | 2062 | 2081 | 17853 | 17872 | TGGTTTCCAGGTAAATGGAC | 47 | 1120 |
| 1238456 | 2102 | 2121 | 17893 | 17912 | GCTTTCACAACTGCAGCTCT | 48 | 1121 |
| 1238478 | 2132 | 2151 | 17923 | 17942 | TTTAATTACATCATCCTCTA | 85 | 1122 |
| 1238500 | 2159 | 2178 | 17950 | 17969 | GTTCTTTTCTTTGCACACTG | 5 | 1123 |
| 1238522 | 2215 | 2234 | 18006 | 18025 | CTTGACCTAATTCTGGTTTT | 79 | 1124 |
| 1238544 | 2254 | 2273 | 18045 | 18064 | CTATTCTTTGATTCAAAAGC | 94 | 1125 |
| 1238566 | 2280 | 2299 | 18071 | 18090 | CCTAAGATATTTTTTAGATT | 87 | 1126 |
| 1238588 | 2310 | 2329 | 18101 | 18120 | TCAAATCAATCATATTTCTG | 88 | 1127 |
| 1238610 | 2346 | 2365 | 18137 | 18156 | ACTTTAATTAACATTAACAG | 105 | 1128 |
| 1238632 | 2384 | 2403 | 18175 | 18194 | GCTAGGTGACAATATCAAAC | 10 | 1129 |
| 1238654 | 2444 | 2463 | 18235 | 18254 | ACATGAATACTCACAAAGT | 85 | 1130 |
| 1238676 | 2542 | 2561 | 18333 | 18352 | AAAAGTTAATGCATTAGACA | 90 | 1131 |

TABLE 16-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RT542354 | SEQ ID NO |
|---|---|---|---|---|---|---|---|
| 1238698 | 2647 | 2666 | 18438 | 18457 | TAATGGTGTCCACTTTGGAT | 40 | 1132 |
| 1238720 | 2746 | 2765 | 18537 | 18556 | AGATATTAAACATTTACAAT | 104 | 1133 |
| 1238742 | N/A | N/A | 4762 | 4781 | AACTGCTAATTAAACCGTGA | 35 | 1134 |
| 1238764 | N/A | N/A | 4832 | 4851 | AAAAATCCTTAATCCTATTC | 99 | 1135 |
| 1238786 | N/A | N/A | 4880 | 4899 | CATATTTATCCAATTCCCTG | 86 | 1136 |
| 1238808 | N/A | N/A | 4931 | 4950 | TTCCTTTCTTCTACAAATCT | 84 | 1137 |
| 1238830 | N/A | N/A | 4989 | 5008 | CTGTAAGACCTTCTCTGTGT | 52 | 1138 |
| 1238852 | N/A | N/A | 5050 | 5069 | ACATACAAATCACATCCTAC | 87 | 1139 |
| 1238874 | N/A | N/A | 5104 | 5123 | TTATAATCTTAATATTTTCC | 91 | 1140 |
| 1238896 | N/A | N/A | 5137 | 5156 | GTGTAAATGACTCATCATTT | 11 | 1141 |
| 1238918 | N/A | N/A | 5210 | 5229 | TACTATTAATTATTTTGGTT | 119 | 1142 |
| 1238940 | N/A | N/A | 5385 | 5404 | TAGCTATCATTTCCTCCATT | 43 | 1143 |
| 1238962 | N/A | N/A | 5457 | 5476 | CAGATTGCTTAACAAAATGT | 78 | 1144 |
| 1238984 | N/A | N/A | 5586 | 5605 | AGGTGTTCTAATTTTAGATC | 22 | 1145 |
| 1239006 | N/A | N/A | 5663 | 5682 | ACATAATGTTCATTTCAGTT | 20 | 1146 |
| 1239028 | N/A | N/A | 5717 | 5736 | TTGTCAGTTTTTCCCCACAT | 15 | 1147 |
| 1239050 | N/A | N/A | 5788 | 5807 | TTCCTTTCAGATTTTTCACA | 62 | 1148 |
| 1239072 | N/A | N/A | 5922 | 5941 | CTGTGGGTCCATTTCATCTA | 29 | 1149 |
| 1239094 | N/A | N/A | 6227 | 6246 | GGATATGTACAATCTGTTGT | 33 | 1150 |
| 1239116 | N/A | N/A | 6372 | 6391 | AAATGATGATGCAATGAGGT | 35 | 1151 |
| 1239138 | N/A | N/A | 6453 | 6472 | AATGGCTGCTCCCTTACATA | 36 | 1152 |
| 1239160 | N/A | N/A | 6564 | 6583 | AGAGAATCTTTCACCTTGGT | 55 | 1153 |
| 1239182 | N/A | N/A | 6773 | 6792 | TCGACAAAAAAAATTCTCCT | 101 | 1154 |
| 1239204 | N/A | N/A | 6889 | 6908 | CTAATCTTCAACATTTATAA | 101 | 1155 |
| 1239226 | N/A | N/A | 7307 | 7326 | CCATAAAACACATTACAACT | 82 | 1156 |
| 1239248 | N/A | N/A | 8026 | 8045 | TTTATTTCTTTCCTGATAGT | 81 | 1157 |
| 1239270 | N/A | N/A | 8193 | 8212 | TAACAACATTAATTATCCCC | 61 | 1158 |
| 1239292 | N/A | N/A | 8422 | 8441 | AGAAGCATTGTACCTCAACA | 42 | 1159 |
| 1239314 | N/A | N/A | 8808 | 8827 | TATCAAGTTTTTTTTCTAAG | 86 | 1160 |
| 1239336 | N/A | N/A | 9108 | 9127 | CAGCAAATAATCTACAAAGT | 83 | 1161 |
| 1239358 | N/A | N/A | 9435 | 9454 | TCTATAAATTCATCTAGGTA | 59 | 1162 |
| 1239380 | N/A | N/A | 9707 | 9726 | TGGTTGAAAATCAGGAGCTC | 42 | 1163 |
| 1239402 | N/A | N/A | 10338 | 10357 | GTCTACAAAACATTTTTTCT | 71 | 1164 |
| 1239424 | N/A | N/A | 10741 | 10760 | TAGCTTAACACACATTTCAA | 52 | 1165 |
| 1239446 | N/A | N/A | 11204 | 11223 | CAGCCAGTATGTGTCAGCTT | 67 | 1166 |
| 1239468 | N/A | N/A | 12672 | 12691 | GATGAATTTGATTACATCCT | 61 | 1167 |
| 1239490 | N/A | N/A | 13696 | 13715 | GTCAATACCTGTTTATTACT | 63 | 1168 |

TABLE 16-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1239512 | N/A | N/A | 13938 | 13957 | ATCTATGAGCTCTTAGAGAC | 76 | 1169 |
| 1239534 | N/A | N/A | 14238 | 14257 | GAATGGGAAAACACATGTTA | 63 | 1170 |
| 1239556 | N/A | N/A | 14394 | 14413 | CTTGAGATATTATGTTATTT | 79 | 1171 |
| 1239578 | N/A | N/A | 14836 | 14855 | CTCAATTTTTCCAACATGAC | 64 | 1172 |
| 1239600 | N/A | N/A | 14997 | 15016 | TCTAAAGGGCTTTTATGTCA | 80 | 1173 |
| 1239622 | N/A | N/A | 15284 | 15303 | TGTTTATGTTTCTACTAACA | 83 | 1174 |
| 1239644 | N/A | N/A | 15371 | 15390 | GAAAATTATTTTTCATCTCC | 104 | 1175 |
| 1239666 | N/A | N/A | 15426 | 15445 | CTCAGAAACCCCTTACCTTT | 68 | 1176 |
| 1239688 | N/A | N/A | 15526 | 15545 | CATATAATTCACCATATACC | 66 | 1177 |
| 1239710 | N/A | N/A | 15704 | 15723 | GGCTCCAAATCATCACTGTG | 71 | 1178 |
| 1239732 | N/A | N/A | 15786 | 15805 | CACTTAGCTCCAAGAGCAGA | 94 | 1179 |
| 1239754 | N/A | N/A | 15839 | 15858 | CATTCATCAAATCAAAAATC | 89 | 1180 |
| 1239776 | N/A | N/A | 15889 | 15908 | AAACAGATCAAACATCCAGA | 52 | 1181 |
| 1239798 | N/A | N/A | 15961 | 15980 | GAATGACTTTTAGTTCATTA | 89 | 1182 |

TABLE 17

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201142 | 1963 | 1982 | 17754 | 17773 | GCCACATATAGGGTCCTTTA | 8 | 66 |
| 1238127 | 59 | 78 | 3152 | 3171 | ACTGTAAAAATCATCTTTAA | 92 | 1183 |
| 1238149 | 125 | 144 | 3218 | 3237 | TCGCTTGAACACTTGCATCA | 82 | 1184 |
| 1238171 | 521 | 540 | 16312 | 16331 | TCGGCTGCCCCCAGTGTTCC | 43* | 1185 |
| 1238193 | 604 | 623 | 16395 | 16414 | CAGCCACCACCATGAGGCTG | 82 | 1186 |
|  | 628 | 647 | 16419 | 16438 |  |  |  |
|  | 676 | 695 | 16467 | 16486 |  |  |  |
| 1238215 | 1005 | 1024 | 16796 | 16815 | TGAAGTTCTCCCCCTTGGTG | 78 | 1187 |
| 1238237 | 1300 | 1319 | 17091 | 17110 | TGATTAGCCTATCCGGGACA | 55 | 1188 |
| 1238259 | 1457 | 1476 | 17248 | 17267 | GTCCAAAAATAAGTCCAGAT | 4 | 1189 |
| 1238281 | 1611 | 1630 | 17402 | 17421 | TTAAAATGGAAAATATCTCT | 96 | 1190 |
| 1238303 | 1693 | 1712 | 17484 | 17503 | AGAGCTAAGAATCTCTAGGA | 40 | 1191 |
| 1238325 | 1816 | 1835 | 17607 | 17626 | GTTGTGACAATATTTACTCT | 5 | 1192 |
| 1238347 | 1862 | 1881 | 17653 | 17672 | TACAGTTATGTTCACTGTGA | 80 | 1193 |
| 1238369 | 1897 | 1916 | 17688 | 17707 | TTTGATTTCAAGTCCCAGAA | 10 | 1194 |
| 1238391 | 1947 | 1966 | 17738 | 17757 | TTTAAACATCTAAAATGGGA | 87 | 1195 |
| 1238413 | 2014 | 2033 | 17805 | 17824 | GGCAATTTACTTTTCAGCTG | 42 | 1196 |

TABLE 17-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1238435 | 2068 | 2087 | 17859 | 17878 | TCATTCTGGTTTCCAGGTAA | 16 | 1197 |
| 1238457 | 2103 | 2122 | 17894 | 17913 | TGCTTTCACAACTGCAGCTC | 75 | 1198 |
| 1238479 | 2133 | 2152 | 17924 | 17943 | TTTTAATTACATCATCCTCT | 100 | 1199 |
| 1238501 | 2160 | 2179 | 17951 | 17970 | AGTTCTTTTCTTTGCACACT | 6 | 1200 |
| 1238523 | 2216 | 2235 | 18007 | 18026 | ACTTGACCTAATTCTGGTTT | 30 | 1201 |
| 1238545 | 2255 | 2274 | 18046 | 18065 | CCTATTCTTTGATTCAAAAG | 71 | 1202 |
| 1238567 | 2281 | 2300 | 18072 | 18091 | ACCTAAGATATTTTTAGAT | 127 | 1203 |
| 1238589 | 2311 | 2330 | 18102 | 18121 | TTCAAATCAATCATATTTCT | 79 | 1204 |
| 1238611 | 2347 | 2366 | 18138 | 18157 | TACTTTAATTAACATTAACA | 94 | 1205 |
| 1238633 | 2385 | 2404 | 18176 | 18195 | TGCTAGGTGACAATATCAAA | 22 | 1206 |
| 1238655 | 2446 | 2465 | 18237 | 18256 | TTACATAGAATACTCACAAA | 67 | 1207 |
| 1238677 | 2547 | 2566 | 18338 | 18357 | CTTACAAAAGTTAATGCATT | 73 | 1208 |
| 1238699 | 2669 | 2688 | 18460 | 18479 | CATGCATATTTCAAAGACCT | 41 | 1209 |
| 1238721 | 2747 | 2766 | 18538 | 18557 | CAGATATTAAACATTTACAA | 98 | 1210 |
| 1238743 | N/A | N/A | 4763 | 4782 | GAACTGCTAATTAAACCGTG | 62 | 1211 |
| 1238765 | N/A | N/A | 4834 | 4853 | GTAAAAATCCTTAATCCTAT | 110 | 1212 |
| 1238787 | N/A | N/A | 4881 | 4900 | ACATATTTATCCAATTCCCT | 87 | 1213 |
| 1238809 | N/A | N/A | 4934 | 4953 | TTTTTCCTTTCTTCTACAAA | 88 | 1214 |
| 1238831 | N/A | N/A | 4990 | 5009 | ACTGTAAGACCTTCTCTGTG | 68 | 1215 |
| 1238853 | N/A | N/A | 5051 | 5070 | AACATACAAATCACATCCTA | 63 | 1216 |
| 1238875 | N/A | N/A | 5107 | 5126 | CTATTATAATCTTAATATTT | 102 | 1217 |
| 1238897 | N/A | N/A | 5139 | 5158 | TTGTGTAAATGACTCATCAT | 59 | 1218 |
| 1238919 | N/A | N/A | 5211 | 5230 | TTACTATTAATTATTTTGGT | 67 | 1219 |
| 1238941 | N/A | N/A | 5387 | 5406 | AGTAGCTATCATTTCCTCCA | 27 | 1220 |
| 1238963 | N/A | N/A | 5461 | 5480 | TCACCAGATTGCTTAACAAA | 73 | 1221 |
| 1238985 | N/A | N/A | 5587 | 5606 | CAGGTGTTCTAATTTTAGAT | 38 | 1222 |
| 1239007 | N/A | N/A | 5664 | 5683 | TACATAATGTTCATTTCAGT | 44 | 1223 |
| 1239029 | N/A | N/A | 5718 | 5737 | CTTGTCAGTTTTCCCCACA | 18 | 1224 |
| 1239051 | N/A | N/A | 5792 | 5811 | GCTTTTCCTTTCAGATTTTT | 15 | 1225 |
| 1239073 | N/A | N/A | 5923 | 5942 | ACTGTGGGTCCATTTCATCT | 22 | 1226 |
| 1239095 | N/A | N/A | 6229 | 6248 | CAGGATATGTACAATCTGTT | 37 | 1227 |
| 1239117 | N/A | N/A | 6386 | 6405 | GCTGATTTTACAAGAAATGA | 46 | 1228 |
| 1239139 | N/A | N/A | 6472 | 6491 | TTGATTACATTATTTTTAAA | 94 | 1229 |
| 1239161 | N/A | N/A | 6567 | 6586 | TTCAGAGAATCTTTCACCTT | 53 | 1230 |
| 1239183 | N/A | N/A | 6785 | 6804 | ATGGTTAACACATCGACAAA | 80 | 1231 |
| 1239205 | N/A | N/A | 6892 | 6911 | GGTCTAATCTTCAACATTTA | 75 | 1232 |
| 1239227 | N/A | N/A | 7309 | 7328 | GCCCATAAAACACATTACAA | 61 | 1233 |

TABLE 17-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1239249 | N/A | N/A | 8029 | 8048 | CTTTTTATTTCTTTCCTGAT | 62 | 1234 |
| 1239271 | N/A | N/A | 8194 | 8213 | TTAACAACATTAATTATCCC | 112 | 1235 |
| 1239293 | N/A | N/A | 8425 | 8444 | TGTAGAAGCATTGTACCTCA | 16 | 1236 |
| 1239315 | N/A | N/A | 8809 | 8828 | GTATCAAGTTTTTTTCTAA | 39 | 1237 |
| 1239337 | N/A | N/A | 9109 | 9128 | CCAGCAAATAATCTACAAAG | 86 | 1238 |
| 1239359 | N/A | N/A | 9438 | 9457 | TGTTCTATAAATTCATCTAG | 41 | 1239 |
| 1239381 | N/A | N/A | 9711 | 9730 | AGAATGGTTGAAAATCAGGA | 37 | 1240 |
| 1239403 | N/A | N/A | 10464 | 10483 | ATCATAGAATGTTTTTTCAA | 86 | 1241 |
| 1239425 | N/A | N/A | 10742 | 10761 | TTAGCTTAACACACATTTCA | 47 | 1242 |
| 1239447 | N/A | N/A | 11335 | 11354 | TTGTTGTTTCTTTTCTGGTA | 21 | 1243 |
| 1239469 | N/A | N/A | 12718 | 12737 | GGAAGAACTTTTTAAACAAA | 81 | 1244 |
| 1239491 | N/A | N/A | 13698 | 13717 | TGGTCAATACCTGTTTATTA | 43 | 1245 |
| 1239513 | N/A | N/A | 13974 | 13993 | TTGAATGTGCCTCATTTAAA | 98 | 1246 |
| 1239535 | N/A | N/A | 14239 | 14258 | TGAATGGGAAAACACATGTT | 82 | 1247 |
| 1239557 | N/A | N/A | 14395 | 14414 | ACTTGAGATATTATGTTATT | 71 | 1248 |
| 1239579 | N/A | N/A | 14839 | 14858 | CTTCTCAATTTTTCCAACAT | 84 | 1249 |
| 1239601 | N/A | N/A | 15011 | 15030 | TCAGTAGCTTTCAGTCTAAA | 67 | 1250 |
| 1239623 | N/A | N/A | 15285 | 15304 | CTGTTTATGTTTCTACTAAC | 55 | 1251 |
| 1239645 | N/A | N/A | 15373 | 15392 | TAGAAAATTATTTTTCATCT | 111 | 1252 |
| 1239667 | N/A | N/A | 15427 | 15446 | ACTCAGAAACCCCTTACCTT | 84 | 1253 |
| 1239689 | N/A | N/A | 15527 | 15546 | CCATATAATTCACCATATAC | 71 | 1254 |
| 1239711 | N/A | N/A | 15706 | 15725 | TAGGCTCCAAATCATCACTG | 40 | 1255 |
| 1239733 | N/A | N/A | 15791 | 15810 | CTGGGCACTTAGCTCCAAGA | 117 | 1256 |
| 1239755 | N/A | N/A | 15840 | 15859 | ACATTCATCAAATCAAAAAT | 116 | 1257 |
| 1239777 | N/A | N/A | 15890 | 15909 | CAAACAGATCAAACATCCAG | 96 | 1258 |
| 1239799 | N/A | N/A | 15962 | 15981 | TGAATGACTTTTAGTTCATT | 85 | 1259 |

TABLE 18

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RT542354 | SEQ ID NO |
|---|---|---|---|---|---|---|---|
| 1201142 | 1963 | 1982 | 17754 | 17773 | GCCACATATAGGGTCCTTTA | 9 | 66 |
| 1238128 | 60 | 79 | 3153 | 3172 | GACTGTAAAAATCATCTTTA | 79 | 1260 |
| 1238150 | 127 | 146 | 3220 | 3239 | ATTCGCTTGAACACTTGCAT | 84 | 1261 |
| 1238172 | 584 | 603 | 16375 | 16394 | CCCCCAGCCACCACCGCCCT | 79 | 1262 |

TABLE 18-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RT542354 | SEQ ID NO |
|---|---|---|---|---|---|---|---|
| 1238194 | 659 | 678 | 16450 | 16469 | CTGTCCCCAGCCACCACCAT | 51 | 1263 |
| 1238216 | 1036 | 1055 | 16827 | 16846 | ACGCGCTCCATCATCTTAAC | 67 | 1264 |
| 1238238 | 1301 | 1320 | 17092 | 17111 | TTGATTAGCCTATCCGGGAC | 77 | 1265 |
| 1238260 | 1460 | 1479 | 17251 | 17270 | TAAGTCCAAAAATAAGTCCA | 57 | 1266 |
| 1238282 | 1612 | 1631 | 17403 | 17422 | CTTAAAATGGAAAATATCTC | 99 | 1267 |
| 1238304 | 1753 | 1772 | 17544 | 17563 | ATCACCCCAGTTCTCGGTAC | 88 | 1268 |
| 1238326 | 1817 | 1836 | 17608 | 17627 | TGTTGTGACAATATTTACTC | 36 | 1269 |
| 1238348 | 1863 | 1882 | 17654 | 17673 | TTACAGTTATGTTCACTGTG | 70 | 1270 |
| 1238370 | 1898 | 1917 | 17689 | 17708 | ATTTGATTTCAAGTCCCAGA | 3 | 1271 |
| 1238392 | 1951 | 1970 | 17742 | 17761 | GTCCTTTAAACATCTAAAAT | 76 | 1272 |
| 1238414 | 2015 | 2034 | 17806 | 17825 | AGGCAATTTACTTTTCAGCT | 35 | 1273 |
| 1238436 | 2069 | 2088 | 17860 | 17879 | ATCATTCTGGTTTCCAGGTA | 15 | 1274 |
| 1238458 | 2104 | 2123 | 17895 | 17914 | GTGCTTTCACAACTGCAGCT | 40 | 1275 |
| 1238480 | 2134 | 2153 | 17925 | 17944 | TTTTTAATTACATCATCCTC | 93 | 1276 |
| 1238502 | 2161 | 2180 | 17952 | 17971 | CAGTTCTTTTCTTTGCACAC | 13 | 1277 |
| 1238524 | 2217 | 2236 | 18008 | 18027 | AACTTGACCTAATTCTGGTT | 80 | 1278 |
| 1238546 | 2256 | 2275 | 18047 | 18066 | CCCTATTCTTTGATTCAAAA | 45 | 1279 |
| 1238568 | 2287 | 2306 | 18078 | 18097 | TCTCCAACCTAAGATATTTT | 62 | 1280 |
| 1238590 | 2312 | 2331 | 18103 | 18122 | CTTCAAATCAATCATATTTC | 68 | 1281 |
| 1238612 | 2348 | 2367 | 18139 | 18158 | TTACTTTAATTAACATTAAC | 76 | 1282 |
| 1238634 | 2386 | 2405 | 18177 | 18196 | CTGCTAGGTGACAATATCAA | 30 | 1283 |
| 1238656 | 2448 | 2467 | 18239 | 18258 | TTTTACATAGAATACTCACA | 51 | 1284 |
| 1238678 | 2550 | 2569 | 18341 | 18360 | TACCTTACAAAAGTTAATGC | 59 | 1285 |
| 1238700 | 2670 | 2689 | 18461 | 18480 | ACATGCATATTTCAAAGACC | 37 | 1286 |
| 1238722 | 2748 | 2767 | 18539 | 18558 | TCAGATATTAAACATTTACA | 76 | 1287 |
| 1238744 | N/A | N/A | 4784 | 4803 | AAACACTTCAAATCATATGG | 84 | 1288 |
| 1238766 | N/A | N/A | 4835 | 4854 | TGTAAAAATCCTTAATCCTA | 77 | 1289 |
| 1238788 | N/A | N/A | 4882 | 4901 | AACATATTTATCCAATTCCC | 73 | 1290 |
| 1238810 | N/A | N/A | 4937 | 4956 | GATTTTTTCCTTTCTTCTAC | 52 | 1291 |
| 1238832 | N/A | N/A | 4993 | 5012 | TTCACTGTAAGACCTTCTCT | 40 | 1292 |
| 1238854 | N/A | N/A | 5052 | 5071 | TAACATACAAATCACATCCT | 85 | 1293 |
| 1238876 | N/A | N/A | 5108 | 5127 | TCTATTATAATCTTAATATT | 104 | 1294 |
| 1238898 | N/A | N/A | 5144 | 5163 | TTTTATTGTGTAAATGACTC | 66 | 1295 |
| 1238920 | N/A | N/A | 5215 | 5234 | GCTGTTACTATTAATTATTT | 54 | 1296 |
| 1238942 | N/A | N/A | 5388 | 5407 | AAGTAGCTATCATTTCCTCC | 44 | 1297 |
| 1238964 | N/A | N/A | 5462 | 5481 | ATCACCAGATTGCTTAACAA | 69 | 1298 |
| 1238986 | N/A | N/A | 5591 | 5610 | TTTCCAGGTGTTCTAATTTT | 57 | 1299 |

TABLE 18-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RT542354 | SEQ ID NO |
|---|---|---|---|---|---|---|---|
| 1239008 | N/A | N/A | 5666 | 5685 | GTTACATAATGTTCATTTCA | 19 | 1300 |
| 1239030 | N/A | N/A | 5719 | 5738 | ACTTGTCAGTTTTTCCCCAC | 20 | 1301 |
| 1239052 | N/A | N/A | 5795 | 5814 | TGTGCTTTTCCTTTCAGATT | 8 | 1302 |
| 1239074 | N/A | N/A | 5940 | 5959 | CCTTTCTCTTACAGAAAACT | 88 | 1303 |
| 1239096 | N/A | N/A | 6261 | 6280 | CTTTCAACCTTCCTAAGACC | 98 | 1304 |
| 1239118 | N/A | N/A | 6388 | 6407 | AAGCTGATTTTACAAGAAAT | 61 | 1305 |
| 1239140 | N/A | N/A | 6474 | 6493 | ATTTGATTACATTATTTTTA | 96 | 1306 |
| 1239162 | N/A | N/A | 6568 | 6587 | GTTCAGAGAATCTTTCACCT | 14 | 1307 |
| 1239184 | N/A | N/A | 6786 | 6805 | AATGGTTAACACATCGACAA | 49 | 1308 |
| 1239206 | N/A | N/A | 6917 | 6936 | CAGGCTTCAGTGCTAGGTCC | 85 | 1309 |
| 1239228 | N/A | N/A | 7340 | 7359 | GAGATCCAAATATAGGCACT | 19 | 1310 |
| 1239250 | N/A | N/A | 8038 | 8057 | TGGCACTTTCTTTTTATTTC | 12 | 1311 |
| 1239272 | N/A | N/A | 8235 | 8254 | TTCTATGGAATCTGTAGGTC | 14 | 1312 |
| 1239294 | N/A | N/A | 8519 | 8538 | GAGACAATAACCATACGATC | 38 | 1313 |
| 1239316 | N/A | N/A | 8884 | 8903 | CATGGAGCATGCTCCAAGAC | 86 | 1314 |
| 1239338 | N/A | N/A | 9113 | 9132 | GTCACCAGCAAATAATCTAC | 56 | 1315 |
| 1239360 | N/A | N/A | 9439 | 9458 | TTGTTCTATAAATTCATCTA | 58 | 1316 |
| 1239382 | N/A | N/A | 9755 | 9774 | AAGAAGAATACATTATGACC | 77 | 1317 |
| 1239404 | N/A | N/A | 10466 | 10485 | ACATCATAGAATGTTTTTTC | 49 | 1318 |
| 1239426 | N/A | N/A | 10743 | 10762 | ATTAGCTTAACACACATTTC | 56 | 1319 |
| 1239448 | N/A | N/A | 11336 | 11355 | GTTGTTGTTTCTTTTCTGGT | 5 | 1320 |
| 1239470 | N/A | N/A | 13314 | 13333 | GGTGACACATTATACAGAGA | 43 | 1321 |
| 1239492 | N/A | N/A | 13699 | 13718 | ATGGTCAATACCTGTTTATT | 53 | 1322 |
| 1239514 | N/A | N/A | 14090 | 14109 | AAACATTTATTTCATGTGCC | 51 | 1323 |
| 1239536 | N/A | N/A | 14240 | 14259 | ATGAATGGGAAAACACATGT | 118 | 1324 |
| 1239558 | N/A | N/A | 14397 | 14416 | CTACTTGAGATATTATGTTA | 80 | 1325 |
| 1239580 | N/A | N/A | 14841 | 14860 | AGCTTCTCAATTTTTCCAAC | 48 | 1326 |
| 1239602 | N/A | N/A | 15013 | 15032 | AGTCAGTAGCTTTCAGTCTA | 39 | 1327 |
| 1239624 | N/A | N/A | 15287 | 15306 | TCCTGTTTATGTTTCTACTA | 62 | 1328 |
| 1239646 | N/A | N/A | 15392 | 15411 | TGCAAATTTTTCTAAAAATT | 100 | 1329 |
| 1239668 | N/A | N/A | 15429 | 15448 | GAACTCAGAAACCCCTTACC | 58 | 1330 |
| 1239690 | N/A | N/A | 15528 | 15547 | ACCATATAATTCACCATATA | 48 | 1331 |
| 1239712 | N/A | N/A | 15708 | 15727 | CATAGGCTCCAAATCATCAC | 77 | 1332 |
| 1239734 | N/A | N/A | 15802 | 15821 | TCTCATTTACCCTGGGCACT | 53 | 1333 |
| 1239756 | N/A | N/A | 15842 | 15861 | GTACATTCATCAAATCAAAA | 51 | 1334 |

TABLE 18-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1239778 | N/A | N/A | 15891 | 15910 | ACAAACAGATCAAACATCCA | 86 | 1335 |
| 1239800 | N/A | N/A | 15964 | 15983 | GATGAATGACTTTTAGTTCA | 65 | 1336 |

TABLE 19

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201142 | 1963 | 1982 | 17754 | 17773 | GCCACATATAGGGTCCTTTA | 10 | 66 |
| 1238129 | 61 | 80 | 3154 | 3173 | TGACTGTAAAAATCATCTTT | 89 | 1337 |
| 1238151 | 129 | 148 | 3222 | 3241 | AGATTCGCTTGAACACTTGC | 87 | 1338 |
| 1238173 | 585 | 604 | 16376 | 16395 | GCCCCCAGCCACCACCGCCC | 83 | 1339 |
| 1238195 | 605 | 624 | 16396 | 16415 | CCAGCCACCACCATGAGGCT | 82 | 1340 |
|  | 629 | 648 | 16420 | 16439 |  |  |  |
|  | 677 | 696 | 16468 | 16487 |  |  |  |
| 1238217 | 1037 | 1056 | 16828 | 16847 | CACGCGCTCCATCATCTTAA | 50 | 1341 |
| 1238239 | 1302 | 1321 | 17093 | 17112 | ATTGATTAGCCTATCCGGGA | 52 | 1342 |
| 1238261 | 1462 | 1481 | 17253 | 17272 | ACTAAGTCCAAAAATAAGTC | 72 | 1343 |
| 1238283 | 1617 | 1636 | 17408 | 17427 | GTTTTCTTAAAATGGAAAAT | 83 | 1344 |
| 1238305 | 1761 | 1780 | 17552 | 17571 | AGTAAAACATCACCCCAGTT | 42 | 1345 |
| 1238327 | 1818 | 1837 | 17609 | 17628 | GTGTTGTGACAATATTTACT | 6 | 1346 |
| 1238349 | 1864 | 1883 | 17655 | 17674 | GTTACAGTTATGTTCACTGT | 60 | 1347 |
| 1238371 | 1899 | 1918 | 17690 | 17709 | CATTTGATTTCAAGTCCCAG | 9 | 1348 |
| 1238393 | 1952 | 1971 | 17743 | 17762 | GGTCCTTTAAACATCTAAAA | 52 | 1349 |
| 1238415 | 2016 | 2035 | 17807 | 17826 | AAGGCAATTTACTTTTCAGC | 62 | 1350 |
| 1238437 | 2070 | 2089 | 17861 | 17880 | AATCATTCTGGTTTCCAGGT | 8 | 1351 |
| 1238459 | 2106 | 2125 | 17897 | 17916 | TGGTGCTTTCACAACTGCAG | 33 | 1352 |
| 1238481 | 2135 | 2154 | 17926 | 17945 | TTTTTTAATTACATCATCCT | 94 | 1353 |
| 1238503 | 2162 | 2181 | 17953 | 17972 | GCAGTTCTTTTCTTTGCACA | 46 | 1354 |
| 1238525 | 2218 | 2237 | 18009 | 18028 | GAACTTGACCTAATTCTGGT | 22 | 1355 |
| 1238547 | 2257 | 2276 | 18048 | 18067 | TCCCTATTCTTTGATTCAAA | 52 | 1356 |
| 1238569 | 2289 | 2308 | 18080 | 18099 | CATCTCCAACCTAAGATATT | 84 | 1357 |
| 1238591 | 2313 | 2332 | 18104 | 18123 | ACTTCAAATCAATCATATTT | 93 | 1358 |
| 1238613 | 2350 | 2369 | 18141 | 18160 | TTTTACTTTAATTAACATTA | 72 | 1359 |
| 1238635 | 2392 | 2411 | 18183 | 18202 | ACATATCTGCTAGGTGACAA | 21 | 1360 |
| 1238657 | 2480 | 2499 | 18271 | 18290 | CTATGCAATATATATTTTAT | 114 | 1361 |
| 1238679 | 2553 | 2572 | 18344 | 18363 | CAGTACCTTACAAAAGTTAA | 36 | 1362 |
| 1238701 | 2671 | 2690 | 18462 | 18481 | TACATGCATATTTCAAAGAC | 58 | 1363 |

TABLE 19-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1238723 | 2749 | 2768 | 18540 | 18559 | GTCAGATATTAAACATTTAC | 56 | 1364 |
| 1238745 | N/A | N/A | 4787 | 4806 | GGGAAACACTTCAAATCATA | 51 | 1365 |
| 1238767 | N/A | N/A | 4836 | 4855 | TTGTAAAAATCCTTAATCCT | 70 | 1366 |
| 1238789 | N/A | N/A | 4883 | 4902 | TAACATATTTATCCAATTCC | 64 | 1367 |
| 1238811 | N/A | N/A | 4939 | 4958 | GTGATTTTTTCCTTTCTTCT | 22 | 1368 |
| 1238833 | N/A | N/A | 4999 | 5018 | CTTTTTTTCACTGTAAGACC | 40 | 1369 |
| 1238855 | N/A | N/A | 5053 | 5072 | ATAACATACAAATCACATCC | 83 | 1370 |
| 1238877 | N/A | N/A | 5109 | 5128 | ATCTATTATAATCTTAATAT | 100 | 1371 |
| 1238899 | N/A | N/A | 5151 | 5170 | ATTTGCATTTTATTGTGTAA | 66 | 1372 |
| 1238921 | N/A | N/A | 5216 | 5235 | TGCTGTTACTATTAATTATT | 72 | 1373 |
| 1238943 | N/A | N/A | 5389 | 5408 | AAAGTAGCTATCATTTCCTC | 61 | 1374 |
| 1238965 | N/A | N/A | 5471 | 5490 | TCTTAATGCATCACCAGATT | 53 | 1375 |
| 1238987 | N/A | N/A | 5599 | 5618 | TAGGCTCTTTTCCAGGTGTT | 9 | 1376 |
| 1239009 | N/A | N/A | 5667 | 5686 | GGTTACATAATGTTCATTTC | 4 | 1377 |
| 1239031 | N/A | N/A | 5720 | 5739 | TACTTGTCAGTTTTTCCCCA | 17 | 1378 |
| 1239053 | N/A | N/A | 5797 | 5816 | TCTGTGCTTTTCCTTTCAGA | 45 | 1379 |
| 1239075 | N/A | N/A | 5950 | 5969 | AACAATCTCTCCTTTCTCTT | 56 | 1380 |
| 1239097 | N/A | N/A | 6262 | 6281 | ACTTTCAACCTTCCTAAGAC | 94 | 1381 |
| 1239119 | N/A | N/A | 6389 | 6408 | TAAGCTGATTTTACAAGAAA | 70 | 1382 |
| 1239141 | N/A | N/A | 6477 | 6496 | GTTATTTGATTACATTATTT | 50 | 1383 |
| 1239163 | N/A | N/A | 6569 | 6588 | AGTTCAGAGAATCTTTCACC | 35 | 1384 |
| 1239185 | N/A | N/A | 6787 | 6806 | GAATGGTTAACACATCGACA | 27 | 1385 |
| 1239207 | N/A | N/A | 6924 | 6943 | CCGTGATCAGGCTTCAGTGC | 36 | 1386 |
| 1239229 | N/A | N/A | 7341 | 7360 | TGAGATCCAAATATAGGCAC | 59 | 1387 |
| 1239251 | N/A | N/A | 8040 | 8059 | AATGGCACTTTCTTTTTATT | 27 | 1388 |
| 1239273 | N/A | N/A | 8242 | 8261 | ATAGGGATTCTATGGAATCT | 57 | 1389 |
| 1239295 | N/A | N/A | 8526 | 8545 | ACAGAGTGAGACAATAACCA | 42 | 1390 |
| 1239317 | N/A | N/A | 8937 | 8956 | AATACAGGACATTCCATCCA | 78 | 1391 |
| 1239339 | N/A | N/A | 9211 | 9230 | GCAAGCTACAAAATTTTACT | 34 | 1392 |
| 1239361 | N/A | N/A | 9458 | 9477 | TTGCTTTTATGCTATTAGGT | 23 | 1393 |
| 1239383 | N/A | N/A | 9779 | 9798 | CAACTTATTTTAACAGTTTA | 77 | 1394 |
| 1239405 | N/A | N/A | 10474 | 10493 | GGACAGTAACATCATAGAAT | 20 | 1395 |
| 1239427 | N/A | N/A | 10744 | 10763 | GATTAGCTTAACACACATTT | 36 | 1396 |
| 1239449 | N/A | N/A | 11437 | 11456 | GGATTGTCTTTCTATTAAGA | 16 | 1397 |
| 1239471 | N/A | N/A | 13385 | 13404 | CAGATATTCAAAGTAACAAC | 50 | 1398 |
| 1239493 | N/A | N/A | 13701 | 13720 | TAATGGTCAATACCTGTTTA | 66 | 1399 |

TABLE 19-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1239515 | N/A | N/A | 14112 | 14131 | AACATTTTCAATTCAGTTAA | 77 | 1400 |
| 1239537 | N/A | N/A | 14281 | 14300 | GCTTGACCCATAGACATGCA | 67 | 1401 |
| 1239559 | N/A | N/A | 14424 | 14443 | CTTCATTATTCTCTGGAGCA | 26 | 1402 |
| 1239581 | N/A | N/A | 14851 | 14870 | TAAGCACCTCAGCTTCTCAA | 92 | 1403 |
| 1239603 | N/A | N/A | 15014 | 15033 | CAGTCAGTAGCTTTCAGTCT | 32 | 1404 |
| 1239625 | N/A | N/A | 15288 | 15307 | ATCCTGTTTATGTTTCTACT | 36 | 1405 |
| 1239647 | N/A | N/A | 15393 | 15412 | CTGCAAATTTTTCTAAAAAT | 116 | 1406 |
| 1239669 | N/A | N/A | 15430 | 15449 | TGAACTCAGAAACCCCTTAC | 74 | 1407 |
| 1239691 | N/A | N/A | 15559 | 15578 | AATACCCAGCTTGTTGAGAT | 56 | 1408 |
| 1239713 | N/A | N/A | 15709 | 15728 | TCATAGGCTCCAAATCATCA | 61 | 1409 |
| 1239735 | N/A | N/A | 15803 | 15822 | ATCTCATTTACCCTGGGCAC | 60 | 1410 |
| 1239757 | N/A | N/A | 15843 | 15862 | TGTACATTCATCAAATCAAA | 82 | 1411 |
| 1239779 | N/A | N/A | 15892 | 15911 | AACAAACAGATCAAACATCC | 69 | 1412 |
| 1239801 | N/A | N/A | 16014 | 16033 | CAACTCTTTCTCCTGCTCCA | 45 | 1413 |

TABLE 20

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RT542354 | SEQ ID NO |
|---|---|---|---|---|---|---|---|
| 1201142 | 1963 | 1982 | 17754 | 17773 | GCCACATATAGGGTCCTTTA | 10 | 66 |
| 1238130 | 62 | 81 | 3155 | 3174 | TTGACTGTAAAAATCATCTT | 110 | 1414 |
| 1238152 | 131 | 150 | 3224 | 3243 | TGAGATTCGCTTGAACACTT | 101 | 1415 |
| 1238174 | 587 | 606 | 16378 | 16397 | CTGCCCCCAGCCACCACCGC | 64 | 1416 |
| 1238196 | 606 630 678 | 625 649 697 | 16397 16421 16469 | 16416 16440 16488 | CCCAGCCACCACCATGAGGC | 80 | 1417 |
| 1238218 | 1039 | 1058 | 16830 | 16849 | ACCACGCGCTCCATCATCTT | 54 | 1418 |
| 1238240 | 1326 | 1345 | 17117 | 17136 | CCAGTGCCCATCAGTGCCAA | 31 | 1419 |
| 1238262 | 1463 | 1482 | 17254 | 17273 | CACTAAGTCCAAAAATAAGT | 69 | 1420 |
| 1238284 | 1619 | 1638 | 17410 | 17429 | GGGTTTTCTTAAAATGGAAA | 18 | 1421 |
| 1238306 | 1763 | 1782 | 17554 | 17573 | AAAGTAAAACATCACCCCAG | 60 | 1422 |
| 1238328 | 1819 | 1838 | 17610 | 17629 | AGTGTTGTGACAATATTTAC | 17 | 1423 |
| 1238350 | 1865 | 1884 | 17656 | 17675 | TGTTACAGTTATGTTCACTG | 18 | 1424 |
| 1238372 | 1900 | 1919 | 17691 | 17710 | ACATTTGATTTCAAGTCCCA | 11 | 1425 |
| 1238394 | 1953 | 1972 | 17744 | 17763 | GGGTCCTTTAAACATCTAAA | 49 | 1426 |
| 1238416 | 2017 | 2036 | 17808 | 17827 | GAAGGCAATTTACTTTTCAG | 100 | 1427 |
| 1238438 | 2071 | 2090 | 17862 | 17881 | AAATCATTCTGGTTTCCAGG | 23 | 1428 |

TABLE 20-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RT542354 | SEQ ID NO |
|---|---|---|---|---|---|---|---|
| 1238460 | 2107 | 2126 | 17898 | 17917 | ATGGTGCTTTCACAACTGCA | 18 | 1429 |
| 1238482 | 2136 | 2155 | 17927 | 17946 | ATTTTTTAATTACATCATCC | 106 | 1430 |
| 1238504 | 2163 | 2182 | 17954 | 17973 | AGCAGTTCTTTTCTTTGCAC | 57 | 1431 |
| 1238526 | 2219 | 2238 | 18010 | 18029 | TGAACTTGACCTAATTCTGG | 48 | 1432 |
| 1238548 | 2258 | 2277 | 18049 | 18068 | CTCCCTATTCTTTGATTCAA | 57 | 1433 |
| 1238570 | 2291 | 2310 | 18082 | 18101 | GTCATCTCCAACCTAAGATA | 48 | 1434 |
| 1238592 | 2314 | 2333 | 18105 | 18124 | CACTTCAAATCAATCATATT | 99 | 1435 |
| 1238614 | 2351 | 2370 | 18142 | 18161 | ATTTTACTTTAATTAACATT | 117 | 1436 |
| 1238636 | 2393 | 2412 | 18184 | 18203 | TACATATCTGCTAGGTGACA | 20 | 1437 |
| 1238658 | 2482 | 2501 | 18273 | 18292 | TCCTATGCAATATATATTTT | 100 | 1438 |
| 1238680 | 2554 | 2573 | 18345 | 18364 | TCAGTACCTTACAAAAGTTA | 71 | 1439 |
| 1238702 | 2673 | 2692 | 18464 | 18483 | AGTACATGCATATTTCAAAG | 24 | 1440 |
| 1238724 | 2754 | 2773 | 18545 | 18564 | TTTCAGTCAGATATTAAACA | 95 | 1441 |
| 1238746 | N/A | N/A | 4788 | 4807 | CGGGAAACACTTCAAATCAT | 54 | 1442 |
| 1238768 | N/A | N/A | 4837 | 4856 | TTTGTAAAAATCCTTAATCC | 117 | 1443 |
| 1238790 | N/A | N/A | 4885 | 4904 | TTTAACATATTTATCCAATT | 124 | 1444 |
| 1238812 | N/A | N/A | 4940 | 4959 | GGTGATTTTTCCTTTCTTC | 8 | 1445 |
| 1238834 | N/A | N/A | 5002 | 5021 | TAGCTTTTTTTCACTGTAAG | 22 | 1446 |
| 1238856 | N/A | N/A | 5054 | 5073 | AATAACATACAAATCACATC | 108 | 1447 |
| 1238878 | N/A | N/A | 5112 | 5131 | TTTATCTATTATAATCTTAA | 92 | 1448 |
| 1238900 | N/A | N/A | 5152 | 5171 | AATTTGCATTTTATTGTGTA | 70 | 1449 |
| 1238922 | N/A | N/A | 5218 | 5237 | GTTGCTGTTACTATTAATTA | 79 | 1450 |
| 1238944 | N/A | N/A | 5390 | 5409 | GAAAGTAGCTATCATTTCCT | 73 | 1451 |
| 1238966 | N/A | N/A | 5472 | 5491 | TTCTTAATGCATCACCAGAT | 52 | 1452 |
| 1238988 | N/A | N/A | 5600 | 5619 | TTAGGCTCTTTTCCAGGTGT | 17 | 1453 |
| 1239010 | N/A | N/A | 5668 | 5687 | TGGTTACATAATGTTCATTT | 3 | 1454 |
| 1239032 | N/A | N/A | 5721 | 5740 | TTACTTGTCAGTTTTTCCCC | 34 | 1455 |
| 1239054 | N/A | N/A | 5801 | 5820 | ATTTTCTGTGCTTTTCCTTT | 33 | 1456 |
| 1239076 | N/A | N/A | 5951 | 5970 | TAACAATCTCTCCTTTCTCT | 68 | 1457 |
| 1239098 | N/A | N/A | 6263 | 6282 | GACTTTCAACCTTCCTAAGA | 62 | 1458 |
| 1239120 | N/A | N/A | 6390 | 6409 | TTAAGCTGATTTTACAAGAA | 89 | 1459 |
| 1239142 | N/A | N/A | 6478 | 6497 | TGTTATTTGATTACATTATT | 71 | 1460 |
| 1239164 | N/A | N/A | 6570 | 6589 | AAGTTCAGAGAATCTTTCAC | 79 | 1461 |
| 1239186 | N/A | N/A | 6788 | 6807 | GGAATGGTTAACACATCGAC | 58 | 1462 |
| 1239208 | N/A | N/A | 6952 | 6971 | CTATAAAAGCTTCTCAGGGA | 69 | 1463 |
| 1239230 | N/A | N/A | 7385 | 7404 | GTAAGAACTTATCCCAAGGT | 35 | 1464 |

TABLE 20-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RT542354 | SEQ ID NO |
|---|---|---|---|---|---|---|---|
| 1239252 | N/A | N/A | 8042 | 8061 | TAAATGGCACTTTCTTTTTA | 58 | 1465 |
| 1239274 | N/A | N/A | 8245 | 8264 | TTGATAGGGATTCTATGGAA | 59 | 1466 |
| 1239296 | N/A | N/A | 8544 | 8563 | GTGTGATACATCACAGTAAC | 77 | 1467 |
| 1239318 | N/A | N/A | 8938 | 8957 | AAATACAGGACATTCCATCC | 87 | 1468 |
| 1239340 | N/A | N/A | 9242 | 9261 | ATCTAGGATTTAACCTGAAA | 100 | 1469 |
| 1239362 | N/A | N/A | 9462 | 9481 | TCTATTGCTTTTATGCTATT | 65 | 1470 |
| 1239384 | N/A | N/A | 9780 | 9799 | CCAACTTATTTTAACAGTTT | 70 | 1471 |
| 1239406 | N/A | N/A | 10475 | 10494 | AGGACAGTAACATCATAGAA | 59 | 1472 |
| 1239428 | N/A | N/A | 10745 | 10764 | TGATTAGCTTAACACACATT | 88 | 1473 |
| 1239450 | N/A | N/A | 11438 | 11457 | TGGATTGTCTTTCTATTAAG | 36 | 1474 |
| 1239472 | N/A | N/A | 13386 | 13405 | ACAGATATTCAAAGTAACAA | 109 | 1475 |
| 1239494 | N/A | N/A | 13702 | 13721 | GTAATGGTCAATACCTGTTT | 55 | 1476 |
| 1239516 | N/A | N/A | 14113 | 14132 | TAACATTTTCAATTCAGTTA | 113 | 1477 |
| 1239538 | N/A | N/A | 14305 | 14324 | CACAGCAGTGTTCCTAGACA | 57 | 1478 |
| 1239560 | N/A | N/A | 14425 | 14444 | GCTTCATTATTCTCTGGAGC | 92 | 1479 |
| 1239582 | N/A | N/A | 14878 | 14897 | CAGTAGCTCTACCTTGAAAA | 72 | 1480 |
| 1239604 | N/A | N/A | 15043 | 15062 | CAGGAAATCAAACTAGGGCA | 65 | 1481 |
| 1239626 | N/A | N/A | 15289 | 15308 | CATCCTGTTTATGTTTCTAC | 58 | 1482 |
| 1239648 | N/A | N/A | 15394 | 15413 | GCTGCAAATTTTCTAAAAA | 84 | 1483 |
| 1239670 | N/A | N/A | 15431 | 15450 | GTGAACTCAGAAACCCCTTA | 39 | 1484 |
| 1239692 | N/A | N/A | 15620 | 15639 | TGATCTGCAATTGTTTTTCT | 49 | 1485 |
| 1239714 | N/A | N/A | 15710 | 15729 | ATCATAGGCTCCAAATCATC | 66 | 1486 |
| 1239736 | N/A | N/A | 15804 | 15823 | GATCTCATTTACCCTGGGCA | 94 | 1487 |
| 1239758 | N/A | N/A | 15844 | 15863 | ATGTACATTCATCAAATCAA | 67 | 1488 |
| 1239780 | N/A | N/A | 15893 | 15912 | CAACAAACAGATCAAACATC | 92 | 1489 |
| 1239802 | N/A | N/A | 16017 | 16036 | ACACAACTCTTTCTCCTGCT | 44 | 1490 |

TABLE 21

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201142 | 1963 | 1982 | 17754 | 17773 | GCCACATATAGGGTCCTTTA | 13 | 66 |
| 1238131 | 63 | 82 | 3156 | 3175 | ATTGACTGTAAAAATCATCT | 91 | 1491 |
| 1238153 | 132 | 151 | 3225 | 3244 | TTGAGATTCGCTTGAACACT | 117 | 1492 |
| 1238175 | 597 621 | 616 640 | 16388 16412 | 16407 16431 | CACCATGAGGCTGCCCCCAG | 72 | 1493 |

TABLE 21-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1238197 | 683 | 702 | 16474 | 16493 | TTGACCCCAGCCACCACCAT | 64 | 1494 |
| 1238219 | 1048 | 1067 | 16839 | 16858 | ATCTGCTCAACCACGCGCTC | 84 | 1495 |
| 1238241 | 1327 | 1346 | 17118 | 17137 | TCCAGTGCCCATCAGTGCCA | 38 | 1496 |
| 1238263 | 1464 | 1483 | 17255 | 17274 | GCACTAAGTCCAAAAATAAG | 82 | 1497 |
| 1238285 | 1620 | 1639 | 17411 | 17430 | CGGGTTTTCTTAAAATGGAA | 13 | 1498 |
| 1238307 | 1764 | 1783 | 17555 | 17574 | AAAAGTAAAACATCACCCCA | 87 | 1499 |
| 1238329 | 1821 | 1840 | 17612 | 17631 | TCAGTGTTGTGACAATATTT | 9 | 1500 |
| 1238351 | 1866 | 1885 | 17657 | 17676 | ATGTTACAGTTATGTTCACT | 16 | 1501 |
| 1238373 | 1901 | 1920 | 17692 | 17711 | AACATTTGATTTCAAGTCCC | 8 | 1502 |
| 1238395 | 1955 | 1974 | 17746 | 17765 | TAGGGTCCTTTAAACATCTA | 68 | 1503 |
| 1238417 | 2019 | 2038 | 17810 | 17829 | TAGAAGGCAATTTACTTTTC | 72 | 1504 |
| 1238439 | 2074 | 2093 | 17865 | 17884 | TCAAAATCATTCTGGTTTCC | 50 | 1505 |
| 1238461 | 2108 | 2127 | 17899 | 17918 | GATGGTGCTTTCACAACTGC | 25 | 1506 |
| 1238483 | 2137 | 2156 | 17928 | 17947 | CATTTTTTAATTACATCATC | 118 | 1507 |
| 1238505 | 2164 | 2183 | 17955 | 17974 | AAGCAGTTCTTTTCTTTGCA | 35 | 1508 |
| 1238527 | 2220 | 2239 | 18011 | 18030 | ATGAACTTGACCTAATTCTG | 46 | 1509 |
| 1238549 | 2259 | 2278 | 18050 | 18069 | TCTCCCTATTCTTTGATTCA | 47 | 1510 |
| 1238571 | 2292 | 2311 | 18083 | 18102 | TGTCATCTCCAACCTAAGAT | 31 | 1511 |
| 1238593 | 2315 | 2334 | 18106 | 18125 | CCACTTCAAATCAATCATAT | 49 | 1512 |
| 1238615 | 2357 | 2376 | 18148 | 18167 | GGAATAATTTTACTTTAATT | 123 | 1513 |
| 1238637 | 2395 | 2414 | 18186 | 18205 | AATACATATCTGCTAGGTGA | 25 | 1514 |
| 1238659 | 2484 | 2503 | 18275 | 18294 | TGTCCTATGCAATATATATT | 69 | 1515 |
| 1238681 | 2555 | 2574 | 18346 | 18365 | TTCAGTACCTTACAAAAGTT | 89 | 1516 |
| 1238703 | 2676 | 2695 | 18467 | 18486 | TAAAGTACATGCATATTTCA | 74 | 1517 |
| 1238725 | 2780 | 2799 | 18571 | 18590 | GGTGGTGCTCATCTTCGCTC | 62 | 1518 |
| 1238747 | N/A | N/A | 4793 | 4812 | GGAAACGGGAAACACTTCAA | 69 | 1519 |
| 1238769 | N/A | N/A | 4840 | 4859 | ATATTTGTAAAAATCCTTAA | 108 | 1520 |
| 1238791 | N/A | N/A | 4886 | 4905 | GTTTAACATATTTATCCAAT | 25 | 1521 |
| 1238813 | N/A | N/A | 4941 | 4960 | TGGTGATTTTTCCTTTCTT | 16 | 1522 |
| 1238835 | N/A | N/A | 5003 | 5022 | TTAGCTTTTTTCACTGTAA | 11 | 1523 |
| 1238857 | N/A | N/A | 5059 | 5078 | ATATAAATAACATACAAATC | 105 | 1524 |
| 1238879 | N/A | N/A | 5113 | 5132 | ATTTATCTATTATAATCTTA | 104 | 1525 |
| 1238901 | N/A | N/A | 5154 | 5173 | CTAATTTGCATTTATTGTG | 48 | 1526 |
| 1238923 | N/A | N/A | 5244 | 5263 | AAGTTTTGGGCAACCTTCCA | 78 | 1527 |
| 1238945 | N/A | N/A | 5391 | 5410 | AGAAAGTAGCTATCATTTCC | 57 | 1528 |
| 1238967 | N/A | N/A | 5474 | 5493 | GCTTCTTAATGCATCACCAG | 30 | 1529 |
| 1238989 | N/A | N/A | 5601 | 5620 | TTTAGGCTCTTTTCCAGGTG | 18 | 1530 |

TABLE 21-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1239011 | N/A | N/A | 5669 | 5688 | GTGGTTACATAATGTTCATT | 11 | 1531 |
| 1239033 | N/A | N/A | 5726 | 5745 | CTTTTTTACTTGTCAGTTTT | 48 | 1532 |
| 1239055 | N/A | N/A | 5825 | 5844 | CCGACAATTTCAATGAAAAC | 61 | 1533 |
| 1239077 | N/A | N/A | 5954 | 5973 | ATATAACAATCTCTCCTTTC | 72 | 1534 |
| 1239099 | N/A | N/A | 6264 | 6283 | TGACTTTCAACCTTCCTAAG | 80 | 1535 |
| 1239121 | N/A | N/A | 6407 | 6426 | GCCATTTCTCTGCAAAATTA | 41 | 1536 |
| 1239143 | N/A | N/A | 6479 | 6498 | TTGTTATTTGATTACATTAT | 66 | 1537 |
| 1239165 | N/A | N/A | 6586 | 6605 | AAGTAAGTTAAAACTGAAGT | 94 | 1538 |
| 1239187 | N/A | N/A | 6836 | 6855 | GATCACACAATACTGTAACA | 30 | 1539 |
| 1239209 | N/A | N/A | 6981 | 7000 | GAGAGTGCCTAGCGATGGGA | 98 | 1540 |
| 1239231 | N/A | N/A | 7388 | 7407 | CTAGTAAGAACTTATCCCAA | 36 | 1541 |
| 1239253 | N/A | N/A | 8043 | 8062 | GTAAATGGCACTTTCTTTTT | 22 | 1542 |
| 1239275 | N/A | N/A | 8302 | 8321 | CCTTCACCCAATTTTAGGAT | 66 | 1543 |
| 1239297 | N/A | N/A | 8545 | 8564 | AGTGTGATACATCACAGTAA | 92 | 1544 |
| 1239319 | N/A | N/A | 8947 | 8966 | CAAACAGACAAATACAGGAC | 77 | 1545 |
| 1239341 | N/A | N/A | 9277 | 9296 | AACATTCATTCATAATGGCA | 60 | 1546 |
| 1239363 | N/A | N/A | 9464 | 9483 | AATCTATTGCTTTTATGCTA | 81 | 1547 |
| 1239385 | N/A | N/A | 9781 | 9800 | CCCAACTTATTTTAACAGTT | 57 | 1548 |
| 1239407 | N/A | N/A | 10529 | 10548 | GAGAAATTTCTATTTTCCTC | 60 | 1549 |
| 1239429 | N/A | N/A | 10746 | 10765 | TTGATTAGCTTAACACACAT | 53 | 1550 |
| 1239451 | N/A | N/A | 11439 | 11458 | ATGGATTGTCTTTCTATTAA | 24 | 1551 |
| 1239473 | N/A | N/A | 13415 | 13434 | ACAGTAGCAATAACTGACCA | 86 | 1552 |
| 1239495 | N/A | N/A | 13718 | 13737 | TCCTATTAAGTATATGGTAA | 119 | 1553 |
| 1239517 | N/A | N/A | 14114 | 14133 | CTAACATTTTCAATTCAGTT | 45 | 1554 |
| 1239539 | N/A | N/A | 14318 | 14337 | GTTTGGTTTTGTTCACAGCA | 25 | 1555 |
| 1239561 | N/A | N/A | 14427 | 14446 | TGGCTTCATTATTCTCTGGA | 33 | 1556 |
| 1239583 | N/A | N/A | 14879 | 14898 | TCAGTAGCTCTACCTTGAAA | 83 | 1557 |
| 1239605 | N/A | N/A | 15103 | 15122 | GATGTAGTCCCCACAATCTC | 120 | 1558 |
| 1239627 | N/A | N/A | 15290 | 15309 | ACATCCTGTTTATGTTTCTA | 42 | 1559 |
| 1239649 | N/A | N/A | 15395 | 15414 | AGCTGCAAATTTTTCTAAAA | 99 | 1560 |
| 1239671 | N/A | N/A | 15432 | 15451 | TGTGAACTCAGAAACCCCTT | 60 | 1561 |
| 1239693 | N/A | N/A | 15622 | 15641 | GATGATCTGCAATTGTTTTT | 59 | 1562 |
| 1239715 | N/A | N/A | 15718 | 15737 | TAGGTCAAATCATAGGCTCC | 72 | 1563 |
| 1239737 | N/A | N/A | 15805 | 15824 | AGATCTCATTTACCCTGGGC | 80 | 1564 |
| 1239759 | N/A | N/A | 15845 | 15864 | AATGTACATTCATCAAATCA | 98 | 1565 |

TABLE 21-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1239781 | N/A | N/A | 15899 | 15918 | CCAAAACAACAAACAGATCA | 90 | 1566 |
| 1239803 | N/A | N/A | 16018 | 16037 | AACACAACTCTTTCTCCTGC | 57 | 1567 |

TABLE 22

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1201142 | 1963 | 1982 | 17754 | 17773 | GCCACATATAGGGTCCTTTA | 11 | 66 |
| 1238132 | 65 | 84 | 3158 | 3177 | TCATTGACTGTAAAAATCAT | 93 | 1568 |
| 1238154 | 134 | 153 | 3227 | 3246 | AGTTGAGATTCGCTTGAACA | 107 | 1569 |
| 1238176 | 598 622 | 617 641 | 16389 16413 | 16408 16432 | CCACCATGAGGCTGCCCCCA | 64 | 1570 |
| 1238198 | 687 | 706 | 16478 | 16497 | CTCCTTGACCCCAGCCACCA | 64 | 1571 |
| 1238220 | 1055 | 1074 | 16846 | 16865 | GATACACATCTGCTCAACCA | 34 | 1572 |
| 1238242 | 1328 | 1347 | 17119 | 17138 | TTCCAGTGCCCATCAGTGCC | 41 | 1573 |
| 1238264 | 1469 | 1488 | 17260 | 17279 | CTGTTGCACTAAGTCCAAAA | 15 | 1574 |
| 1238286 | 1621 | 1640 | 17412 | 17431 | TCGGGTTTTCTTAAAATGGA | 17 | 1575 |
| 1238308 | 1765 | 1784 | 17556 | 17575 | GAAAAGTAAAACATCACCCC | 54 | 1576 |
| 1238330 | 1823 | 1842 | 17614 | 17633 | GTTCAGTGTTGTGACAATAT | 10 | 1577 |
| 1238352 | 1867 | 1886 | 17658 | 17677 | TATGTTACAGTTATGTTCAC | 45 | 1578 |
| 1238374 | 1902 | 1921 | 17693 | 17712 | AAACATTTGATTTCAAGTCC | 17 | 1579 |
| 1238396 | 1957 | 1976 | 17748 | 17767 | TATAGGGTCCTTTAAACATC | 23 | 1580 |
| 1238418 | 2020 | 2039 | 17811 | 17830 | CTAGAAGGCAATTTACTTTT | 86 | 1581 |
| 1238440 | 2075 | 2094 | 17866 | 17885 | GTCAAAATCATTCTGGTTTC | 8 | 1582 |
| 1238462 | 2109 | 2128 | 17900 | 17919 | TGATGGTGCTTTCACAACTG | 26 | 1583 |
| 1238484 | 2139 | 2158 | 17930 | 17949 | ACCATTTTTTAATTACATCA | 60 | 1584 |
| 1238506 | 2165 | 2184 | 17956 | 17975 | CAAGCAGTTCTTTTCTTTGC | 10 | 1585 |
| 1238528 | 2222 | 2241 | 18013 | 18032 | CTATGAACTTGACCTAATTC | 67 | 1586 |
| 1238550 | 2260 | 2279 | 18051 | 18070 | GTCTCCCTATTCTTTGATTC | 37 | 1587 |
| 1238572 | 2293 | 2312 | 18084 | 18103 | CTGTCATCTCCAACCTAAGA | 25 | 1588 |
| 1238594 | 2316 | 2335 | 18107 | 18126 | TCCACTTCAAATCAATCATA | 35 | 1589 |
| 1238616 | 2360 | 2379 | 18151 | 18170 | CAGGGAATAATTTTACTTTA | 27 | 1590 |
| 1238638 | 2397 | 2416 | 18188 | 18207 | GTAATACATATCTGCTAGGT | 19 | 1591 |
| 1238660 | 2486 | 2505 | 18277 | 18296 | TCTGTCCTATGCAATATATA | 62 | 1592 |
| 1238682 | 2556 | 2575 | 18347 | 18366 | ATTCAGTACCTTACAAAAGT | 54 | 1593 |
| 1238704 | 2699 | 2718 | 18490 | 18509 | CAAAGTTACAAATATAGAAA | 97 | 1594 |

TABLE 22-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1238726 | N/A | N/A | 3543 | 3562 | CCCGCGGCTCCCCTGCCCCC | 93 | 1595 |
| 1238748 | N/A | N/A | 4807 | 4826 | GGAGTTTTCCCTAAGGAAAC | 79 | 1596 |
| 1238770 | N/A | N/A | 4841 | 4860 | TATATTTGTAAAAATCCTTA | 93 | 1597 |
| 1238792 | N/A | N/A | 4887 | 4906 | AGTTTAACATATTTATCCAA | 69 | 1598 |
| 1238814 | N/A | N/A | 4942 | 4961 | CTGGTGATTTTTCCTTTCT | 10 | 1599 |
| 1238836 | N/A | N/A | 5004 | 5023 | GTTAGCTTTTTTTCACTGTA | 9 | 1600 |
| 1238858 | N/A | N/A | 5062 | 5081 | TAGATATAAATAACATACAA | 92 | 1601 |
| 1238880 | N/A | N/A | 5114 | 5133 | CATTTATCTATTATAATCTT | 86 | 1602 |
| 1238902 | N/A | N/A | 5155 | 5174 | TCTAATTTGCATTTTATTGT | 86 | 1603 |
| 1238924 | N/A | N/A | 5246 | 5265 | CCAAGTTTTGGGCAACCTTC | 43 | 1604 |
| 1238946 | N/A | N/A | 5392 | 5411 | CAGAAAGTAGCTATCATTTC | 57 | 1605 |
| 1238968 | N/A | N/A | 5476 | 5495 | CAGCTTCTTAATGCATCACC | 24 | 1606 |
| 1238990 | N/A | N/A | 5602 | 5621 | ATTTAGGCTCTTTTCCAGGT | 6 | 1607 |
| 1239012 | N/A | N/A | 5670 | 5689 | AGTGGTTACATAATGTTCAT | 26 | 1608 |
| 1239034 | N/A | N/A | 5727 | 5746 | ACTTTTTTACTTGTCAGTTT | 49 | 1609 |
| 1239056 | N/A | N/A | 5826 | 5845 | ACCGACAATTTCAATGAAAA | 42 | 1610 |
| 1239078 | N/A | N/A | 5958 | 5977 | GCAAATATAACAATCTCTCC | 55 | 1611 |
| 1239100 | N/A | N/A | 6266 | 6285 | GGTGACTTTCAACCTTCCTA | 52 | 1612 |
| 1239122 | N/A | N/A | 6411 | 6430 | TGTGGCCATTTCTCTGCAAA | 94 | 1613 |
| 1239144 | N/A | N/A | 6481 | 6500 | TATTGTTATTTGATTACATT | 97 | 1614 |
| 1239166 | N/A | N/A | 6670 | 6689 | TTTTGAATGTTTAATATGCA | 91 | 1615 |
| 1239188 | N/A | N/A | 6838 | 6857 | GTGATCACACAATACTGTAA | 76 | 1616 |
| 1239210 | N/A | N/A | 7011 | 7030 | ACATTGCTGGAACCCATCAC | 86 | 1617 |
| 1239232 | N/A | N/A | 7389 | 7408 | GCTAGTAAGAACTTATCCCA | 43 | 1618 |
| 1239254 | N/A | N/A | 8044 | 8063 | TGTAAATGGCACTTTCTTTT | 26 | 1619 |
| 1239276 | N/A | N/A | 8303 | 8322 | ACCTTCACCCAATTTTAGGA | 61 | 1620 |
| 1239298 | N/A | N/A | 8546 | 8565 | AAGTGTGATACATCACAGTA | 91 | 1621 |
| 1239320 | N/A | N/A | 8948 | 8967 | CCAAACAGACAAATACAGGA | 68 | 1622 |
| 1239342 | N/A | N/A | 9304 | 9323 | GCTGTAGTTAAACATTTCAT | 21 | 1623 |
| 1239364 | N/A | N/A | 9472 | 9491 | TGAACAATAATCTATTGCTT | 57 | 1624 |
| 1239386 | N/A | N/A | 9782 | 9801 | ACCCAACTTATTTAACAGT | 64 | 1625 |
| 1239408 | N/A | N/A | 10531 | 10550 | GAGAGAAATTTCTATTTTCC | 56 | 1626 |
| 1239430 | N/A | N/A | 10747 | 10766 | ATTGATTAGCTTAACACACA | 48 | 1627 |
| 1239452 | N/A | N/A | 11475 | 11494 | ATGCAACTTTCCTTAATGAA | 23 | 1628 |
| 1239474 | N/A | N/A | 13417 | 13436 | CTACAGTAGCAATAACTGAC | 91 | 1629 |
| 1239496 | N/A | N/A | 13726 | 13745 | TCAAGATATCCTATTAAGTA | 83 | 1630 |
| 1239518 | N/A | N/A | 14115 | 14134 | GCTAACATTTTCAATTCAGT | 23 | 1631 |

TABLE 22-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS42354 | SEQ ID NO |
|---|---|---|---|---|---|---|---|
| 1239540 | N/A | N/A | 14321 | 14340 | GGAGTTTGGTTTTGTTCACA | 21 | 1632 |
| 1239562 | N/A | N/A | 14472 | 14491 | CCATCACTCTACCTAAAACA | 97 | 1633 |
| 1239584 | N/A | N/A | 14892 | 14911 | CTATCAGCAAATCTCAGTAG | 59 | 1634 |
| 1239606 | N/A | N/A | 15161 | 15180 | TTGGAGGCTCTTTTAGGTGG | 40 | 1635 |
| 1239628 | N/A | N/A | 15293 | 15312 | TTAACATCCTGTTTATGTTT | 94 | 1636 |
| 1239650 | N/A | N/A | 15396 | 15415 | TAGCTGCAAATTTTTCTAAA | 74 | 1637 |
| 1239672 | N/A | N/A | 15433 | 15452 | TTGTGAACTCAGAAACCCCT | 60 | 1638 |
| 1239694 | N/A | N/A | 15624 | 15643 | GGGATGATCTGCAATTGTTT | 29 | 1639 |
| 1239716 | N/A | N/A | 15719 | 15738 | CTAGGTCAAATCATAGGCTC | 75 | 1640 |
| 1239738 | N/A | N/A | 15808 | 15827 | TAAAGATCTCATTTACCCTG | 85 | 1641 |
| 1239760 | N/A | N/A | 15846 | 15865 | GAATGTACATTCATCAAATC | 92 | 1642 |
| 1239782 | N/A | N/A | 15900 | 15919 | ACCAAAACAACAAACAGATC | 93 | 1643 |
| 1239804 | N/A | N/A | 16020 | 16039 | TGAACACAACTCTTTCTCCT | 71 | 1644 |

TABLE 23

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1201142 | 1963 | 1982 | 17754 | 17773 | GCCACATATAGGGTCCTTTA | 11 | 66 |
| 1238133 | 66 | 85 | 3159 | 3178 | CTCATTGACTGTAAAAATCA | 131 | 1645 |
| 1238155 | 135 | 154 | 3228 | 3247 | GAGTTGAGATTCGCTTGAAC | 102 | 1646 |
| 1238177 | 599<br>623 | 618<br>642 | 16390<br>16414 | 16409<br>16433 | ACCACCATGAGGCTGCCCCC | 69 | 1647 |
| 1238199 | 695 | 714 | 16486 | 16505 | GGTGCCACCTCCTTGACCCC | 90 | 1648 |
| 1238221 | 1060 | 1079 | 16851 | 16870 | TGGGTGATACACATCTGCTC | 65 | 1649 |
| 1238243 | 1329 | 1348 | 17120 | 17139 | TTTCCAGTGCCCATCAGTGC | 30 | 1650 |
| 1238265 | 1479 | 1498 | 17270 | 17289 | TAGCCTCAACCTGTTGCACT | 49 | 1651 |
| 1238287 | 1650 | 1669 | 17441 | 17460 | GCCTCCTAACAAACCTGGCA | 100 | 1652 |
| 1238309 | 1766 | 1785 | 17557 | 17576 | TGAAAAGTAAAACATCACCC | 41 | 1653 |
| 1238331 | 1824 | 1843 | 17615 | 17634 | GGTTCAGTGTTGTGACAATA | 9 | 1654 |
| 1238353 | 1868 | 1887 | 17659 | 17678 | ATATGTTACAGTTATGTTCA | 21 | 1655 |
| 1238375 | 1903 | 1922 | 17694 | 17713 | CAAACATTTGATTTCAAGTC | 69 | 1656 |
| 1238397 | 1958 | 1977 | 17749 | 17768 | ATATAGGGTCCTTTAAACAT | 42 | 1657 |
| 1238419 | 2021 | 2040 | 17812 | 17831 | TCTAGAAGGCAATTTACTTT | 123 | 1658 |
| 1238441 | 2076 | 2095 | 17867 | 17886 | TGTCAAAATCATTCTGGTTT | 18 | 1659 |

TABLE 23-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1238463 | 2110 | 2129 | 17901 | 17920 | ATGATGGTGCTTTCACAACT | 29 | 1660 |
| 1238485 | 2140 | 2159 | 17931 | 17950 | GACCATTTTTAATTACATC | 49 | 1661 |
| 1238507 | 2166 | 2185 | 17957 | 17976 | GCAAGCAGTTCTTTTCTTTG | 7 | 1662 |
| 1238529 | 2226 | 2245 | 18017 | 18036 | GAAACTATGAACTTGACCTA | 51 | 1663 |
| 1238551 | 2261 | 2280 | 18052 | 18071 | TGTCTCCCTATTCTTTGATT | 32 | 1664 |
| 1238573 | 2294 | 2313 | 18085 | 18104 | TCTGTCATCTCCAACCTAAG | 27 | 1665 |
| 1238595 | 2317 | 2336 | 18108 | 18127 | TTCCACTTCAAATCAATCAT | 37 | 1666 |
| 1238617 | 2361 | 2380 | 18152 | 18171 | TCAGGGAATAATTTTACTTT | 29 | 1667 |
| 1238639 | 2398 | 2417 | 18189 | 18208 | AGTAATACATATCTGCTAGG | 31 | 1668 |
| 1238661 | 2487 | 2506 | 18278 | 18297 | GTCTGTCCTATGCAATATAT | 53 | 1669 |
| 1238683 | 2557 | 2576 | 18348 | 18367 | TATTCAGTACCTTACAAAAG | 82 | 1670 |
| 1238705 | 2700 | 2719 | 18491 | 18510 | GCAAAGTTACAAATATAGAA | 59 | 1671 |
| 1238749 | N/A | N/A | 4808 | 4827 | AGGAGTTTTCCCTAAGGAAA | 60 | 1672 |
| 1238771 | N/A | N/A | 4842 | 4861 | TTATATTTGTAAAAATCCTT | 94 | 1673 |
| 1238793 | N/A | N/A | 4888 | 4907 | AAGTTTAACATATTTATCCA | 87 | 1674 |
| 1238815 | N/A | N/A | 4943 | 4962 | ACTGGTGATTTTTTCCTTTC | 33 | 1675 |
| 1238837 | N/A | N/A | 5005 | 5024 | GGTTAGCTTTTTTTCACTGT | 8 | 1676 |
| 1238859 | N/A | N/A | 5063 | 5082 | TTAGATATAAATAACATACA | 108 | 1677 |
| 1238881 | N/A | N/A | 5115 | 5134 | CCATTTATCTATTATAATCT | 48 | 1678 |
| 1238903 | N/A | N/A | 5157 | 5176 | GCTCTAATTTGCATTTTATT | 27 | 1679 |
| 1238925 | N/A | N/A | 5262 | 5281 | CAGACACTTGAAAATGCCAA | 68 | 1680 |
| 1238947 | N/A | N/A | 5393 | 5412 | GCAGAAAGTAGCTATCATTT | 11 | 1681 |
| 1238969 | N/A | N/A | 5477 | 5496 | CCAGCTTCTTAATGCATCAC | 29 | 1682 |
| 1238991 | N/A | N/A | 5611 | 5630 | GTGTTATACATTTAGGCTCT | 11 | 1683 |
| 1239013 | N/A | N/A | 5672 | 5691 | TTAGTGGTTACATAATGTTC | 31 | 1684 |
| 1239035 | N/A | N/A | 5730 | 5749 | CCCACTTTTTTACTTGTCAG | 36 | 1685 |
| 1239057 | N/A | N/A | 5828 | 5847 | TCACCGACAATTTCAATGAA | 77 | 1686 |
| 1239079 | N/A | N/A | 5959 | 5978 | AGCAAATATAACAATCTCTC | 27 | 1687 |
| 1239101 | N/A | N/A | 6267 | 6286 | TGGTGACTTTCAACCTTCCT | 98 | 1688 |
| 1239123 | N/A | N/A | 6413 | 6432 | TCTGTGGCCATTTCTCTGCA | 46 | 1689 |
| 1239145 | N/A | N/A | 6486 | 6505 | GTTATTATTGTTATTTGATT | 54 | 1690 |
| 1239167 | N/A | N/A | 6674 | 6693 | CATGTTTTGAATGTTTAATA | 93 | 1691 |
| 1239189 | N/A | N/A | 6845 | 6864 | CCTTAAAGTGATCACACAAT | 89 | 1692 |
| 1239211 | N/A | N/A | 7142 | 7161 | CTGAAAAAAATTTTGCACAA | 90 | 1693 |
| 1239233 | N/A | N/A | 7431 | 7450 | GTTCATCTTATTCCCATTTA | 31 | 1694 |
| 1239255 | N/A | N/A | 8080 | 8099 | GCTAAATTTATTCTGAAATA | 94 | 1695 |

TABLE 23-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1239277 | N/A | N/A | 8311 | 8330 | AAGATGCCACCTTCACCCAA | 74 | 1696 |
| 1239299 | N/A | N/A | 8603 | 8622 | TGATACAGTGGGATTCATCC | 108 | 1697 |
| 1239321 | N/A | N/A | 8965 | 8984 | ACTTAGACCAAATGGATCCA | 85 | 1698 |
| 1239343 | N/A | N/A | 9349 | 9368 | AGTTTTTCAAATCAACAAAT | 71 | 1699 |
| 1239365 | N/A | N/A | 9519 | 9538 | CCCAAGATATCATAATTTTA | 59 | 1700 |
| 1239387 | N/A | N/A | 9785 | 9804 | AGCACCCAACTTATTTTAAC | 69 | 1701 |
| 1239409 | N/A | N/A | 10629 | 10648 | GGAGATCAAATCTGTGGAGC | 47 | 1702 |
| 1239431 | N/A | N/A | 10759 | 10778 | GCACAATAATTTATTGATTA | 105 | 1703 |
| 1239453 | N/A | N/A | 12112 | 12131 | GTAAAGATTCTTGTTCAGCA | 23 | 1704 |
| 1239475 | N/A | N/A | 13429 | 13448 | AACGGCATTCCTCTACAGTA | 86 | 1705 |
| 1239497 | N/A | N/A | 13727 | 13746 | TTCAAGATATCCTATTAAGT | 90 | 1706 |
| 1239519 | N/A | N/A | 14117 | 14136 | CAGCTAACATTTTCAATTCA | 65 | 1707 |
| 1239541 | N/A | N/A | 14342 | 14361 | AGTGCAGGCTCCTTTAGGGC | 33 | 1708 |
| 1239563 | N/A | N/A | 14526 | 14545 | AAGGCTTTTCTTCCAGCTAC | 76 | 1709 |
| 1239585 | N/A | N/A | 14893 | 14912 | TCTATCAGCAAATCTCAGTA | 90 | 1710 |
| 1239607 | N/A | N/A | 15162 | 15181 | TTTGGAGGCTCTTTTAGGTG | 19 | 1711 |
| 1239629 | N/A | N/A | 15299 | 15318 | AATAAATTAACATCCTGTTT | 83 | 1712 |
| 1239651 | N/A | N/A | 15397 | 15416 | TTAGCTGCAAATTTTTCTAA | 72 | 1713 |
| 1239673 | N/A | N/A | 15443 | 15462 | TAGAACATTTTGTGAACTC | 30 | 1714 |
| 1239695 | N/A | N/A | 15625 | 15644 | TGGGATGATCTGCAATTGTT | 34 | 1715 |
| 1239717 | N/A | N/A | 15720 | 15739 | CCTAGGTCAAATCATAGGCT | 80 | 1716 |
| 1239739 | N/A | N/A | 15809 | 15828 | TTAAAGATCTCATTTACCCT | 118 | 1717 |
| 1239761 | N/A | N/A | 15847 | 15866 | AGAATGTACATTCATCAAAT | 74 | 1718 |
| 1239783 | N/A | N/A | 15901 | 15920 | TACCAAAACAACAAACAGAT | 77 | 1719 |
| 1239805 | N/A | N/A | 16021 | 16040 | GTGAACACAACTCTTTCTCC | 64 | 1720 |

TABLE 24

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1201142 | 1963 | 1982 | 17754 | 17773 | GCCACATATAGGGTCCTTTA | 12 | 66 |
| 1238134 | 67 | 86 | 3160 | 3179 | GCTCATTGACTGTAAAAATC | 96 | 1721 |
| 1238156 | 139 | 158 | 3232 | 3251 | AAACGAGTTGAGATTCGCTT | 101 | 1722 |
| 1238178 | 600 624 | 619 643 | 16391 16415 | 16410 16434 | CACCACCATGAGGCTGCCCC | 75 | 1723 |
| 1238200 | 697 | 716 | 16488 | 16507 | TGGGTGCCACCTCCTTGACC | 97 | 1724 |

TABLE 24-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1238222 | 1179 | 1198 | 16970 | 16989 | ACCTTCCTCATCCCACTATC | 105 | 1725 |
| 1238244 | 1336 | 1355 | 17127 | 17146 | TCTATGTTTTCCAGTGCCCA | 15 | 1726 |
| 1238266 | 1482 | 1501 | 17273 | 17292 | TTTTAGCCTCAACCTGTTGC | 48 | 1727 |
| 1238288 | 1655 | 1674 | 17446 | 17465 | ATGTGGCCTCCTAACAAACC | 86 | 1728 |
| 1238310 | 1767 | 1786 | 17558 | 17577 | GTGAAAAGTAAAACATCACC | 66 | 1729 |
| 1238332 | 1825 | 1844 | 17616 | 17635 | AGGTTCAGTGTTGTGACAAT | 31 | 1730 |
| 1238354 | 1869 | 1888 | 17660 | 17679 | TATATGTTACAGTTATGTTC | 40 | 1731 |
| 1238376 | 1904 | 1923 | 17695 | 17714 | CCAAACATTTGATTTCAAGT | 75 | 1732 |
| 1238398 | 1969 | 1988 | 17760 | 17779 | AGGAATGCCACATATAGGGT | 37 | 1733 |
| 1238420 | 2022 | 2041 | 17813 | 17832 | GTCTAGAAGGCAATTTACTT | 72 | 1734 |
| 1238442 | 2077 | 2096 | 17868 | 17887 | ATGTCAAAATCATTCTGGTT | 29 | 1735 |
| 1238464 | 2111 | 2130 | 17902 | 17921 | GATGATGGTGCTTTCACAAC | 33 | 1736 |
| 1238486 | 2141 | 2160 | 17932 | 17951 | TGACCATTTTTAATTACAT | 83 | 1737 |
| 1238508 | 2167 | 2186 | 17958 | 17977 | TGCAAGCAGTTCTTTTCTTT | 15 | 1738 |
| 1238530 | 2227 | 2246 | 18018 | 18037 | AGAAACTATGAACTTGACCT | 29 | 1739 |
| 1238552 | 2262 | 2281 | 18053 | 18072 | TTGTCTCCCTATTCTTTGAT | 38 | 1740 |
| 1238574 | 2295 | 2314 | 18086 | 18105 | TTCTGTCATCTCCAACCTAA | 41 | 1741 |
| 1238596 | 2318 | 2337 | 18109 | 18128 | TTTCCACTTCAAATCAATCA | 49 | 1742 |
| 1238618 | 2362 | 2381 | 18153 | 18172 | TTCAGGGAATAATTTTACTT | 48 | 1743 |
| 1238640 | 2399 | 2418 | 18190 | 18209 | AAGTAATACATATCTGCTAG | 47 | 1744 |
| 1238662 | 2503 | 2522 | 18294 | 18313 | TAAACAAAACTCCTAAGTCT | 111 | 1745 |
| 1238684 | 2558 | 2577 | 18349 | 18368 | GTATTCAGTACCTTACAAAA | 43 | 1746 |
| 1238706 | 2701 | 2720 | 18492 | 18511 | TGCAAAGTTACAAATATAGA | 85 | 1747 |
| 1238728 | N/A | N/A | 4709 | 4728 | AGATCCTCATCATTACAGCA | 87 | 1748 |
| 1238750 | N/A | N/A | 4809 | 4828 | CAGGAGTTTTCCCTAAGGAA | 48 | 1749 |
| 1238772 | N/A | N/A | 4848 | 4867 | TGATAATTATATTTGTAAAA | 108 | 1750 |
| 1238794 | N/A | N/A | 4889 | 4908 | GAAGTTTAACATATTTATCC | 38 | 1751 |
| 1238816 | N/A | N/A | 4945 | 4964 | CCACTGGTGATTTTTTCCTT | 36 | 1752 |
| 1238838 | N/A | N/A | 5006 | 5025 | TGGTTAGCTTTTTTTCACTG | 12 | 1753 |
| 1238860 | N/A | N/A | 5064 | 5083 | GTTAGATATAAATAACATAC | 48 | 1754 |
| 1238882 | N/A | N/A | 5116 | 5135 | GCCATTTATCTATTATAATC | 32 | 1755 |
| 1238904 | N/A | N/A | 5159 | 5178 | ATGCTCTAATTTGCATTTTA | 59 | 1756 |
| 1238926 | N/A | N/A | 5263 | 5282 | CCAGACACTTGAAAATGCCA | 75 | 1757 |
| 1238948 | N/A | N/A | 5394 | 5413 | CGCAGAAAGTAGCTATCATT | 33 | 1758 |
| 1238970 | N/A | N/A | 5480 | 5499 | CTTCCAGCTTCTTAATGCAT | 64 | 1759 |
| 1238992 | N/A | N/A | 5613 | 5632 | TGGTGTTATACATTTAGGCT | 20 | 1760 |

TABLE 24-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1239014 | N/A | N/A | 5680 | 5699 | CATGATTTTAGTGGTTACA | 11 | 1761 |
| 1239036 | N/A | N/A | 5732 | 5751 | AACCCACTTTTTACTTGTC | 55 | 1762 |
| 1239058 | N/A | N/A | 5829 | 5848 | ATCACCGACAATTTCAATGA | 77 | 1763 |
| 1239080 | N/A | N/A | 5960 | 5979 | TAGCAAATATAACAATCTCT | 48 | 1764 |
| 1239102 | N/A | N/A | 6268 | 6287 | TTGGTGACTTTCAACCTTCC | 93 | 1765 |
| 1239124 | N/A | N/A | 6416 | 6435 | AAATCTGTGGCCATTTCTCT | 61 | 1766 |
| 1239146 | N/A | N/A | 6493 | 6512 | CTGTTATGTTATTATTGTTA | 19 | 1767 |
| 1239168 | N/A | N/A | 6675 | 6694 | ACATGTTTTGAATGTTTAAT | 76 | 1768 |
| 1239190 | N/A | N/A | 6848 | 6867 | CTCCCTTAAAGTGATCACAC | 92 | 1769 |
| 1239212 | N/A | N/A | 7143 | 7162 | GCTGAAAAAATTTTGCACA | 86 | 1770 |
| 1239234 | N/A | N/A | 7432 | 7451 | CGTTCATCTTATTCCCATTT | 17 | 1771 |
| 1239256 | N/A | N/A | 8082 | 8101 | TGGCTAAATTTATTCTGAAA | 68 | 1772 |
| 1239278 | N/A | N/A | 8312 | 8331 | AAAGATGCCACCTTCACCCA | 89 | 1773 |
| 1239300 | N/A | N/A | 8616 | 8635 | AGATCATTTACTATGATACA | 109 | 1774 |
| 1239322 | N/A | N/A | 8975 | 8994 | CTTACACTTCACTTAGACCA | 70 | 1775 |
| 1239344 | N/A | N/A | 9351 | 9370 | GTAGTTTTTCAAATCAACAA | 54 | 1776 |
| 1239366 | N/A | N/A | 9520 | 9539 | GCCCAAGATATCATAATTTT | 74 | 1777 |
| 1239388 | N/A | N/A | 9786 | 9805 | CAGCACCCAACTTATTTTAA | 72 | 1778 |
| 1239410 | N/A | N/A | 10631 | 10650 | AAGGAGATCAAATCTGTGGA | 52 | 1779 |
| 1239432 | N/A | N/A | 10760 | 10779 | GGCACAATAATTTATTGATT | 92 | 1780 |
| 1239454 | N/A | N/A | 12311 | 12330 | TGCAGAGGAACAACACATAC | 109 | 1781 |
| 1239476 | N/A | N/A | 13492 | 13511 | GATAACATGAGAACCAACGC | 98 | 1782 |
| 1239498 | N/A | N/A | 13728 | 13747 | TTTCAAGATATCCTATTAAG | 85 | 1783 |
| 1239520 | N/A | N/A | 14118 | 14137 | CCAGCTAACATTTTCAATTC | 51 | 1784 |
| 1239542 | N/A | N/A | 14365 | 14384 | TTATTATTCATGTTCTCCAC | 79 | 1785 |
| 1239564 | N/A | N/A | 14529 | 14548 | TAGAAGGCTTTTCTTCCAGC | 60 | 1786 |
| 1239586 | N/A | N/A | 14901 | 14920 | ACATTGGATCTATCAGCAAA | 77 | 1787 |
| 1239608 | N/A | N/A | 15195 | 15214 | AGTTAAAGTACTCAGGTCAT | 66 | 1788 |
| 1239630 | N/A | N/A | 15300 | 15319 | AAATAAATTAACATCCTGTT | 97 | 1789 |
| 1239652 | N/A | N/A | 15399 | 15418 | AATTAGCTGCAAATTTTTCT | 78 | 1790 |
| 1239674 | N/A | N/A | 15445 | 15464 | TTTAGAACATTTTTGTGAAC | 82 | 1791 |
| 1239696 | N/A | N/A | 15648 | 15667 | GAAGTTAGTCTTGTCCTCAG | 31 | 1792 |
| 1239718 | N/A | N/A | 15721 | 15740 | CCCTAGGTCAAATCATAGGC | 99 | 1793 |
| 1239740 | N/A | N/A | 15810 | 15829 | ATTAAAGATCTCATTTACCC | 85 | 1794 |
| 1239762 | N/A | N/A | 15848 | 15867 | GAGAATGTACATTCATCAAA | 65 | 1795 |

TABLE 24-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1239784 | N/A | N/A | 15903 | 15922 | TGTACCAAAACAACAAACAG | 102 | 1796 |
| 1239806 | N/A | N/A | 16082 | 16101 | ACACTGTTGCCACCCTGTAC | 85 | 1797 |

TABLE 25

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1201142 | 1963 | 1982 | 17754 | 17773 | GCCACATATAGGGTCCTTTA | 12 | 66 |
| 1238135 | 68 | 87 | 3161 | 3180 | GGCTCATTGACTGTAAAAAT | 120 | 1798 |
| 1238157 | 140 | 159 | 3233 | 3252 | AAAACGAGTTGAGATTCGCT | 132 | 1799 |
| 1238179 | 601 625 | 620 644 | 16392 16416 | 16411 16435 | CCACCACCATGAGGCTGCCC | 84 | 1800 |
| 1238201 | 701 | 720 | 16492 | 16511 | ACTGTGGGTGCCACCTCCTT | 73 | 1801 |
| 1238223 | 1181 | 1200 | 16972 | 16991 | AGACCTTCCTCATCCCACTA | 107 | 1802 |
| 1238245 | 1341 | 1360 | 17132 | 17151 | TCTACTCTATGTTTTCCAGT | 27 | 1803 |
| 1238267 | 1485 | 1504 | 17276 | 17295 | TTGTTTTAGCCTCAACCTGT | 48 | 1804 |
| 1238289 | 1656 | 1675 | 17447 | 17466 | CATGTGGCCTCCTAACAAAC | 81 | 1805 |
| 1238311 | 1768 | 1787 | 17559 | 17578 | TGTGAAAAGTAAAACATCAC | 84 | 1806 |
| 1238333 | 1826 | 1845 | 17617 | 17636 | GAGGTTCAGTGTTGTGACAA | 34 | 1807 |
| 1238355 | 1870 | 1889 | 17661 | 17680 | ATATATGTTACAGTTATGTT | 82 | 1808 |
| 1238377 | 1906 | 1925 | 17697 | 17716 | TCCCAAACATTTGATTTCAA | 83 | 1809 |
| 1238399 | 1981 | 2000 | 17772 | 17791 | TAGTTTAAAGAAAGGAATGC | 129 | 1810 |
| 1238421 | 2023 | 2042 | 17814 | 17833 | TGTCTAGAAGGCAATTTACT | 120 | 1811 |
| 1238443 | 2078 | 2097 | 17869 | 17888 | TATGTCAAAATCATTCTGGT | 22 | 1812 |
| 1238465 | 2112 | 2131 | 17903 | 17922 | TGATGATGGTGCTTTCACAA | 25 | 1813 |
| 1238487 | 2142 | 2161 | 17933 | 17952 | CTGACCATTTTTAATTACA | 36 | 1814 |
| 1238509 | 2168 | 2187 | 17959 | 17978 | ATGCAAGCAGTTCTTTTCTT | 22 | 1815 |
| 1238531 | 2228 | 2247 | 18019 | 18038 | CAGAAACTATGAACTTGACC | 34 | 1816 |
| 1238553 | 2263 | 2282 | 18054 | 18073 | ATTGTCTCCCTATTCTTTGA | 44 | 1817 |
| 1238575 | 2296 | 2315 | 18087 | 18106 | TTTCTGTCATCTCCAACCTA | 61 | 1818 |
| 1238597 | 2319 | 2338 | 18110 | 18129 | TTTTCCACTTCAAATCAATC | 61 | 1819 |
| 1238619 | 2363 | 2382 | 18154 | 18173 | ATTCAGGGAATAATTTTACT | 75 | 1820 |
| 1238641 | 2401 | 2420 | 18192 | 18211 | AAAAGTAATACATATCTGCT | 72 | 1821 |
| 1238663 | 2507 | 2526 | 18298 | 18317 | GCTCTAAACAAAACTCCTAA | 61 | 1822 |
| 1238685 | 2559 | 2578 | 18350 | 18369 | AGTATTCAGTACCTTACAAA | 48 | 1823 |
| 1238707 | 2704 | 2723 | 18495 | 18514 | ACATGCAAAGTTACAAATAT | 82 | 1824 |

TABLE 25-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1238729 | N/A | N/A | 4712 | 4731 | TGAAGATCCTCATCATTACA | 102 | 1825 |
| 1238751 | N/A | N/A | 4810 | 4829 | CCAGGAGTTTTCCCTAAGGA | 66 | 1826 |
| 1238773 | N/A | N/A | 4849 | 4868 | TTGATAATTATATTTGTAAA | 114 | 1827 |
| 1238795 | N/A | N/A | 4890 | 4909 | AGAAGTTTAACATATTTATC | 103 | 1828 |
| 1238817 | N/A | N/A | 4946 | 4965 | TCCACTGGTGATTTTTCCT | 50 | 1829 |
| 1238839 | N/A | N/A | 5007 | 5026 | CTGGTTAGCTTTTTTTCACT | 17 | 1830 |
| 1238861 | N/A | N/A | 5065 | 5084 | TGTTAGATATAAATAACATA | 100 | 1831 |
| 1238883 | N/A | N/A | 5117 | 5136 | TGCCATTTATCTATTATAAT | 88 | 1832 |
| 1238905 | N/A | N/A | 5162 | 5181 | AACATGCTCTAATTTGCATT | 107 | 1833 |
| 1238927 | N/A | N/A | 5301 | 5320 | CAGAACCATCTTTGTGACCC | 72 | 1834 |
| 1238949 | N/A | N/A | 5410 | 5429 | AACTCATACATACAGACGCA | 37 | 1835 |
| 1238971 | N/A | N/A | 5481 | 5500 | GCTTCCAGCTTCTTAATGCA | 78 | 1836 |
| 1238993 | N/A | N/A | 5634 | 5653 | TAATTTTCTTAGCTACTGCC | 60 | 1837 |
| 1239015 | N/A | N/A | 5682 | 5701 | ATCATGATTTTAGTGGTTA | 26 | 1838 |
| 1239037 | N/A | N/A | 5733 | 5752 | TAACCCACTTTTTTACTTGT | 97 | 1839 |
| 1239059 | N/A | N/A | 5831 | 5850 | AGATCACCGACAATTTCAAT | 53 | 1840 |
| 1239081 | N/A | N/A | 5961 | 5980 | GTAGCAAATATAACAATCTC | 43 | 1841 |
| 1239103 | N/A | N/A | 6271 | 6290 | CATTTGGTGACTTTCAACCT | 65 | 1842 |
| 1239125 | N/A | N/A | 6423 | 6442 | ATTCTAAAAATCTGTGGCCA | 92 | 1843 |
| 1239147 | N/A | N/A | 6494 | 6513 | TCTGTTATGTTATTATTGTT | 38 | 1844 |
| 1239169 | N/A | N/A | 6683 | 6702 | AGATACAGACATGTTTTGAA | 30 | 1845 |
| 1239191 | N/A | N/A | 6854 | 6873 | GATTACCTCCCTTAAAGTGA | 78 | 1846 |
| 1239213 | N/A | N/A | 7186 | 7205 | GTTATATTTTAATTTTCTGA | 42 | 1847 |
| 1239235 | N/A | N/A | 7433 | 7452 | CCGTTCATCTTATTCCCATT | 28 | 1848 |
| 1239257 | N/A | N/A | 8085 | 8104 | TCTTGGCTAAATTTATTCTG | 37 | 1849 |
| 1239279 | N/A | N/A | 8313 | 8332 | CAAAGATGCCACCTTCACCC | 98 | 1850 |
| 1239301 | N/A | N/A | 8618 | 8637 | AAAGATCATTTACTATGATA | 115 | 1851 |
| 1239323 | N/A | N/A | 8976 | 8995 | ACTTACACTTCACTTAGACC | 64 | 1852 |
| 1239345 | N/A | N/A | 9353 | 9372 | TGGTAGTTTTTCAAATCAAC | 12 | 1853 |
| 1239367 | N/A | N/A | 9526 | 9545 | CACAAAGCCCAAGATATCAT | 81 | 1854 |
| 1239389 | N/A | N/A | 9846 | 9865 | CACACTTAGCCACCCTGCCA | 130 | 1855 |
| 1239411 | N/A | N/A | 10656 | 10675 | TAGCTTGGTGGGCTTAAGGA | 86 | 1856 |
| 1239433 | N/A | N/A | 10761 | 10780 | TGGCACAATAATTTATTGAT | 97 | 1857 |
| 1239455 | N/A | N/A | 12370 | 12389 | CCAATTCTACATGTTCTCAT | 60 | 1858 |
| 1239477 | N/A | N/A | 13521 | 13540 | GCACATAGAAAATCCAACAG | 61 | 1859 |
| 1239499 | N/A | N/A | 13734 | 13753 | GGCATATTTCAAGATATCCT | 34 | 1860 |
| 1239521 | N/A | N/A | 14119 | 14138 | GCCAGCTAACATTTTCAATT | 43 | 1861 |

TABLE 25-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1239543 | N/A | N/A | 14366 | 14385 | CTTATTATTCATGTTCTCCA | 46 | 1862 |
| 1239565 | N/A | N/A | 14531 | 14550 | CCTAGAAGGCTTTTCTTCCA | 80 | 1863 |
| 1239587 | N/A | N/A | 14902 | 14921 | TACATTGGATCTATCAGCAA | 68 | 1864 |
| 1239609 | N/A | N/A | 15197 | 15216 | AGAGTTAAAGTACTCAGGTC | 65 | 1865 |
| 1239631 | N/A | N/A | 15303 | 15322 | AATAAATAAATTAACATCCT | 109 | 1866 |
| 1239653 | N/A | N/A | 15409 | 15428 | TTTATCACCCAATTAGCTGC | 76 | 1867 |
| 1239675 | N/A | N/A | 15456 | 15475 | CTGTTGCCAATTTTAGAACA | 118 | 1868 |
| 1239697 | N/A | N/A | 15658 | 15677 | CTGGAACACTGAAGTTAGTC | 68 | 1869 |
| 1239719 | N/A | N/A | 15729 | 15748 | CTGCTGTACCCTAGGTCAAA | 66 | 1870 |
| 1239741 | N/A | N/A | 15816 | 15835 | TTTCAAATTAAAGATCTCAT | 103 | 1871 |
| 1239763 | N/A | N/A | 15849 | 15868 | GGAGAATGTACATTCATCAA | 82 | 1872 |
| 1239785 | N/A | N/A | 15904 | 15923 | TTGTACCAAAACAACAAACA | 105 | 1873 |
| 1239807 | N/A | N/A | 16094 | 16113 | TGCTCAGTAGAAACACTGTT | 85 | 1874 |

TABLE 26

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1201142 | 1963 | 1982 | 17754 | 17773 | GCCACATATAGGGTCCTTTA | 11 | 66 |
| 1238136 | 69 | 88 | 3162 | 3181 | TGGCTCATTGACTGTAAAAA | 111 | 1875 |
| 1238158 | 142 | 161 | 3235 | 3254 | AAAAAACGAGTTGAGATTCG | 105 | 1876 |
| 1238180 | 602 626 | 621 645 | 16393 16417 | 16412 16436 | GCCACCACCATGAGGCTGCC | 102 | 1877 |
| 1238202 | 722 | 741 | 16513 | 16532 | CTTACTCGGCTTGTTCCACT | 87 | 1878 |
| 1238224 | 1182 | 1201 | 16973 | 16992 | AAGACCTTCCTCATCCCACT | 87 | 1879 |
| 1238246 | 1345 | 1364 | 17136 | 17155 | CAGGTCTACTCTATGTTTTC | 24 | 1880 |
| 1238268 | 1490 | 1509 | 17281 | 17300 | GAGATTTGTTTTAGCCTCAA | 27 | 1881 |
| 1238290 | 1657 | 1676 | 17448 | 17467 | TCATGTGGCCTCCTAACAAA | 29 | 1882 |
| 1238312 | 1769 | 1788 | 17560 | 17579 | CTGTGAAAAGTAAACATCA | 53 | 1883 |
| 1238334 | 1829 | 1848 | 17620 | 17639 | CCAGAGGTTCAGTGTTGTGA | 13 | 1884 |
| 1238356 | 1873 | 1892 | 17664 | 17683 | TTCATATATGTTACAGTTAT | 26 | 1885 |
| 1238378 | 1909 | 1928 | 17700 | 17719 | CATTCCCAAACATTTGATTT | 82 | 1886 |
| 1238400 | 1985 | 2004 | 17776 | 17795 | CCTATAGTTTAAAGAAAGGA | 96 | 1887 |
| 1238422 | 2024 | 2043 | 17815 | 17834 | GTGTCTAGAAGGCAATTTAC | 70 | 1888 |
| 1238444 | 2079 | 2098 | 17870 | 17889 | GTATGTCAAAATCATTCTGG | 16 | 1889 |
| 1238466 | 2113 | 2132 | 17904 | 17923 | ATGATGATGGTGCTTTCACA | 19 | 1890 |

TABLE 26-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1238488 | 2143 | 2162 | 17934 | 17953 | ACTGACCATTTTTAATTAC | 32 | 1891 |
| 1238510 | 2172 | 2191 | 17963 | 17982 | AGAAATGCAAGCAGTTCTTT | 40 | 1892 |
| 1238532 | 2230 | 2249 | 18021 | 18040 | TACAGAAACTATGAACTTGA | 36 | 1893 |
| 1238554 | 2264 | 2283 | 18055 | 18074 | GATTGTCTCCCTATTCTTTG | 22 | 1894 |
| 1238576 | 2297 | 2316 | 18088 | 18107 | ATTTCTGTCATCTCCAACCT | 34 | 1895 |
| 1238598 | 2321 | 2340 | 18112 | 18131 | CTTTTTCCACTTCAAATCAA | 48 | 1896 |
| 1238620 | 2364 | 2383 | 18155 | 18174 | AATTCAGGGAATAATTTTAC | 79 | 1897 |
| 1238642 | 2402 | 2421 | 18193 | 18212 | GAAAAGTAATACATATCTGC | 72 | 1898 |
| 1238664 | 2509 | 2528 | 18300 | 18319 | CTGCTCTAAACAAAACTCCT | 61 | 1899 |
| 1238686 | 2560 | 2579 | 18351 | 18370 | AAGTATTCAGTACCTTACAA | 44 | 1900 |
| 1238708 | 2708 | 2727 | 18499 | 18518 | AAGAACATGCAAAGTTACAA | 82 | 1901 |
| 1238730 | N/A | N/A | 4713 | 4732 | ATGAAGATCCTCATCATTAC | 82 | 1902 |
| 1238752 | N/A | N/A | 4812 | 4831 | TACCAGGAGTTTTCCCTAAG | 73 | 1903 |
| 1238774 | N/A | N/A | 4850 | 4869 | TTTGATAATTATATTTGTAA | 123 | 1904 |
| 1238796 | N/A | N/A | 4891 | 4910 | CAGAAGTTTAACATATTTAT | 74 | 1905 |
| 1238818 | N/A | N/A | 4956 | 4975 | ATTGCTCCTTTCCACTGGTG | 32 | 1906 |
| 1238840 | N/A | N/A | 5008 | 5027 | ACTGGTTAGCTTTTTTTCAC | 29 | 1907 |
| 1238862 | N/A | N/A | 5066 | 5085 | GTGTTAGATATAAATAACAT | 94 | 1908 |
| 1238884 | N/A | N/A | 5118 | 5137 | TTGCCATTTATCTATTATAA | 47 | 1909 |
| 1238906 | N/A | N/A | 5163 | 5182 | AAACATGCTCTAATTTGCAT | 79 | 1910 |
| 1238928 | N/A | N/A | 5302 | 5321 | GCAGAACCATCTTTGTGACC | 51 | 1911 |
| 1238950 | N/A | N/A | 5413 | 5432 | AATAACTCATACATACAGAC | 60 | 1912 |
| 1238972 | N/A | N/A | 5490 | 5509 | TGGGTCACAGCTTCCAGCTT | 60 | 1913 |
| 1238994 | N/A | N/A | 5638 | 5657 | GTCATAATTTTCTTAGCTAC | 12 | 1914 |
| 1239016 | N/A | N/A | 5684 | 5703 | AAATCATGATTTTTAGTGGT | 55 | 1915 |
| 1239038 | N/A | N/A | 5735 | 5754 | AATAACCCACTTTTTTACTT | 80 | 1916 |
| 1239060 | N/A | N/A | 5839 | 5858 | GAAAATTAAGATCACCGACA | 26 | 1917 |
| 1239082 | N/A | N/A | 5974 | 5993 | TCTTTTATTCTAAGTAGCAA | 72 | 1918 |
| 1239104 | N/A | N/A | 6288 | 6307 | ACCCTCATTTTCTGTGACAT | 61 | 1919 |
| 1239126 | N/A | N/A | 6424 | 6443 | AATTCTAAAAATCTGTGGCC | 84 | 1920 |
| 1239148 | N/A | N/A | 6499 | 6518 | AAACTTCTGTTATGTTATTA | 75 | 1921 |
| 1239170 | N/A | N/A | 6684 | 6703 | TAGATACAGACATGTTTTGA | 58 | 1922 |
| 1239192 | N/A | N/A | 6855 | 6874 | GGATTACCTCCCTTAAAGTG | 62 | 1923 |
| 1239214 | N/A | N/A | 7189 | 7208 | CTTGTTATATTTTAATTTTC | 113 | 1924 |
| 1239236 | N/A | N/A | 7588 | 7607 | GAAGAAAATTTTTAATGAGA | 114 | 1925 |
| 1239258 | N/A | N/A | 8159 | 8178 | TATCTTTCTATTTGTGTCTC | 39 | 1926 |

TABLE 26-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1239280 | N/A | N/A | 8314 | 8333 | ACAAAGATGCCACCTTCACC | 82 | 1927 |
| 1239302 | N/A | N/A | 8639 | 8658 | GCAAATTCAACAGCTCATTA | 39 | 1928 |
| 1239324 | N/A | N/A | 8981 | 9000 | ATCAGACTTACACTTCACTT | 55 | 1929 |
| 1239346 | N/A | N/A | 9354 | 9373 | GTGGTAGTTTTTCAAATCAA | 12 | 1930 |
| 1239368 | N/A | N/A | 9536 | 9555 | CTGTCACAAACACAAAGCCC | 79 | 1931 |
| 1239390 | N/A | N/A | 9847 | 9866 | GCACACTTAGCCACCCTGCC | 112 | 1932 |
| 1239412 | N/A | N/A | 10675 | 10694 | CAGTTTTGAATAAGATACTT | 77 | 1933 |
| 1239434 | N/A | N/A | 10780 | 10799 | ATTATTGTGCCACCAAGCCT | 129 | 1934 |
| 1239456 | N/A | N/A | 12378 | 12397 | CAGAAAACCCAATTCTACAT | 107 | 1935 |
| 1239478 | N/A | N/A | 13522 | 13541 | TGCACATAGAAAATCCAACA | 70 | 1936 |
| 1239500 | N/A | N/A | 13735 | 13754 | TGGCATATTTCAAGATATCC | 44 | 1937 |
| 1239522 | N/A | N/A | 14135 | 14154 | AGTATTTTTGACAATGGCCA | 61 | 1938 |
| 1239544 | N/A | N/A | 14367 | 14386 | GCTTATTATTCATGTTCTCC | 13 | 1939 |
| 1239566 | N/A | N/A | 14579 | 14598 | TGACAAGCCCATCCTGTCTC | 102 | 1940 |
| 1239588 | N/A | N/A | 14918 | 14937 | ATTTCTCTCCCAGCATACA | 109 | 1941 |
| 1239610 | N/A | N/A | 15203 | 15222 | ACAAGCAGAGTTAAAGTACT | 77 | 1942 |
| 1239632 | N/A | N/A | 15332 | 15351 | CTGGATAATATTCATAAAAA | 95 | 1943 |
| 1239654 | N/A | N/A | 15410 | 15429 | CTTTATCACCCAATTAGCTG | 73 | 1944 |
| 1239676 | N/A | N/A | 15458 | 15477 | AACTGTTGCCAATTTTAGAA | 86 | 1945 |
| 1239698 | N/A | N/A | 15663 | 15682 | ATATACTGGAACACTGAAGT | 61 | 1946 |
| 1239720 | N/A | N/A | 15732 | 15751 | TACCTGCTGTACCCTAGGTC | 86 | 1947 |
| 1239742 | N/A | N/A | 15819 | 15838 | TCTTTTCAAATTAAAGATCT | 105 | 1948 |
| 1239764 | N/A | N/A | 15850 | 15869 | TGGAGAATGTACATTCATCA | 33 | 1949 |
| 1239786 | N/A | N/A | 15911 | 15930 | CTAATTTTTGTACCAAAACA | 106 | 1950 |
| 1239808 | N/A | N/A | 16116 | 16135 | AGTGCATAGCAATGGTATCA | 34 | 1951 |

TABLE 27

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1201142 | 1963 | 1982 | 17754 | 17773 | GCCACATATAGGGTCCTTTA | 8 | 66 |
| 1238119 | 48 | 67 | 3141 | 3160 | CATCTTTAATTGGAAATTCG | 98 | 1952 |
| 1238141 | 109 | 128 | 3202 | 3221 | ATCAGTTGATACCGCCTGCG | 120 | 1953 |
| 1238163 | 457 | 476 | 16248 | 16267 | CATGTGGCCACAAAGAGAAC | 54* | 1954 |
| 1238185 | 590 614 | 609 633 | 16381 16405 | 16400 16424 | AGGCTGCCCCCAGCCACCAC | 98 | 1955 |

TABLE 27-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1238207 | 789 | 808 | 16580 | 16599 | CGCCAAGGCCCCCCACCACT | 64 | 1956 |
| 1238229 | 1187 | 1206 | 16978 | 16997 | ACAGGAAGACCTTCCTCATC | 86 | 1957 |
| 1238251 | 1385 | 1404 | 17176 | 17195 | CTCATGATGAACTCAATCAA | 58 | 1958 |
| 1238273 | 1585 | 1604 | 17376 | 17395 | CTATGAAATCTCTACTAAGA | 66 | 1959 |
| 1238295 | 1666 | 1685 | 17457 | 17476 | GAATAAGTATCATGTGGCCT | 35 | 1960 |
| 1238317 | 1807 | 1826 | 17598 | 17617 | ATATTTACTCTTGTTGAACA | 55 | 1961 |
| 1238339 | 1851 | 1870 | 17642 | 17661 | TCACTGTGAATATGTCCTCT | 9 | 1962 |
| 1238361 | 1879 | 1898 | 17670 | 17689 | AAGCCTTTCATATATGTTAC | 18 | 1963 |
| 1238383 | 1917 | 1936 | 17708 | 17727 | AAGGGCACCATTCCCAAACA | 106 | 1964 |
| 1238405 | 2000 | 2019 | 17791 | 17810 | CAGCTGCCTTAATTACCTAT | 20 | 1965 |
| 1238427 | 2039 | 2058 | 17830 | 17849 | GGAGATTTGCCTTCAGTGTC | 29 | 1966 |
| 1238449 | 2088 | 2107 | 17879 | 17898 | AGCTCTCCTGTATGTCAAAA | 17 | 1967 |
| 1238471 | 2123 | 2142 | 17914 | 17933 | ATCATCCTCTATGATGATGG | 101 | 1968 |
| 1238493 | 2152 | 2171 | 17943 | 17962 | TCTTTGCACACTGACCATTT | 15 | 1969 |
| 1238515 | 2199 | 2218 | 17990 | 18009 | TTTTTGACAATTATGAGACA | 54 | 1970 |
| 1238537 | 2242 | 2261 | 18033 | 18052 | TCAAAAGCCAATTACAGAAA | 78 | 1971 |
| 1238559 | 2272 | 2291 | 18063 | 18082 | ATTTTTTAGATTGTCTCCCT | 43 | 1972 |
| 1238581 | 2302 | 2321 | 18093 | 18112 | ATCATATTTCTGTCATCTCC | 23 | 1973 |
| 1238603 | 2331 | 2350 | 18122 | 18141 | AACAGAATTTCTTTTTCCAC | 43 | 1974 |
| 1238625 | 2377 | 2396 | 18168 | 18187 | GACAATATCAAACAATTCAG | 22 | 1975 |
| 1238647 | 2425 | 2444 | 18216 | 18235 | TGCAAGCCAATAATAACATT | 25 | 1976 |
| 1238669 | 2521 | 2540 | 18312 | 18331 | TTCAGATGTTAACTGCTCTA | 35 | 1977 |
| 1238691 | 2579 | 2598 | 18370 | 18389 | AAAGGGTTTCCCACATATTA | 49 | 1978 |
| 1238713 | 2722 | 2741 | 18513 | 18532 | TTATATAACAAAACAAGAAC | 88 | 1979 |
| 1238735 | N/A | N/A | 4743 | 4762 | ATGCTCTCAGAACAAGAAAA | 53 | 1980 |
| 1238757 | N/A | N/A | 4824 | 4843 | TTAATCCTATTCTACCAGGA | 78 | 1981 |
| 1238779 | N/A | N/A | 4871 | 4890 | CCAATTCCCTGTTCCTATGT | 42 | 1982 |
| 1238801 | N/A | N/A | 4901 | 4920 | TTGATTTTTCCAGAAGTTTA | 36 | 1983 |
| 1238823 | N/A | N/A | 4963 | 4982 | AAGTAAAATTGCTCCTTTCC | 58 | 1984 |
| 1238845 | N/A | N/A | 5040 | 5059 | CACATCCTACCCCTCTGCCT | 95 | 1985 |
| 1238867 | N/A | N/A | 5096 | 5115 | TTAATATTTTCCTTTCGGTG | 33 | 1986 |
| 1238889 | N/A | N/A | 5124 | 5143 | ATCATTTTGCCATTTATCTA | 24 | 1987 |
| 1238911 | N/A | N/A | 5179 | 5198 | TGTAAAATGATAACCCAAAC | 63 | 1988 |
| 1238933 | N/A | N/A | 5324 | 5343 | GTCCAAGGTCACAAAATTGA | 74 | 1989 |
| 1238955 | N/A | N/A | 5425 | 5444 | CGAAATGCCCCCAATAACTC | 51 | 1990 |
| 1238977 | N/A | N/A | 5572 | 5591 | TAGATCATTCTGCTAGGAAT | 35 | 1991 |
| 1238999 | N/A | N/A | 5644 | 5663 | TAATGTGTCATAATTTTCTT | 64 | 1992 |

TABLE 27-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1239021 | N/A | N/A | 5703 | 5722 | CCACATATCACAGGCTCCAA | 31 | 1993 |
| 1239043 | N/A | N/A | 5742 | 5761 | TGCAGTTAATAACCCACTTT | 44 | 1994 |
| 1239065 | N/A | N/A | 5861 | 5880 | GAGAGCAATATATTCACCAA | 20 | 1995 |
| 1239087 | N/A | N/A | 6040 | 6059 | ACTAAATCATTAATCAACTA | 91 | 1996 |
| 1239109 | N/A | N/A | 6306 | 6325 | TGATCACAGCCTTTCCTGAC | 69 | 1997 |
| 1239131 | N/A | N/A | 6431 | 6450 | TCAGCATAATTCTAAAAATC | 95 | 1998 |
| 1239153 | N/A | N/A | 6507 | 6526 | TGGTGCAGAAACTTCTGTTA | 69 | 1999 |
| 1239175 | N/A | N/A | 6713 | 6732 | ATTTTATAATGCTGTAGCCA | 40 | 2000 |
| 1239197 | N/A | N/A | 6861 | 6880 | ACTGAAGGATTACCTCCCTT | 64 | 2001 |
| 1239219 | N/A | N/A | 7227 | 7246 | CATAATGTCCCTTGTCTCTT | 56 | 2002 |
| 1239241 | N/A | N/A | 7709 | 7728 | TCTAATTTTGTACACAATAC | 61 | 2003 |
| 1239263 | N/A | N/A | 8168 | 8187 | AGCACAGGCTATCTTTCTAT | 29 | 2004 |
| 1239285 | N/A | N/A | 8347 | 8366 | ATTGAGAGCTTTTCCTCTTA | 106 | 2005 |
| 1239307 | N/A | N/A | 8655 | 8674 | ACAAAATTCTAGCGAAGCAA | 75 | 2006 |
| 1239329 | N/A | N/A | 9039 | 9058 | GCTTTGGATCTCTTAGATTT | 14 | 2007 |
| 1239351 | N/A | N/A | 9417 | 9436 | TATAATTTTTTTACCTGGAA | 58 | 2008 |
| 1239373 | N/A | N/A | 9636 | 9655 | ATGAAAATCAATATCATTCC | 80 | 2009 |
| 1239395 | N/A | N/A | 10022 | 10041 | TAGACATGTAAACTTTGCCA | 37 | 2010 |
| 1239417 | N/A | N/A | 10722 | 10741 | AGTGTCAGAATTCTAAGGGT | 36 | 2011 |
| 1239439 | N/A | N/A | 10797 | 10816 | TAGGTGACCCACAACACATT | 96 | 2012 |
| 1239461 | N/A | N/A | 12469 | 12488 | AGTGTGGTACATATATGCTA | 50 | 2013 |
| 1239483 | N/A | N/A | 13544 | 13563 | CTATTTGCAATTAGTGTGAT | 84 | 2014 |
| 1239505 | N/A | N/A | 13778 | 13797 | CTAAGATACTCTCTGTCACC | 63 | 2015 |
| 1239527 | N/A | N/A | 14191 | 14210 | TACTAAATATTTATAATGGA | 103 | 2016 |
| 1239549 | N/A | N/A | 14372 | 14391 | TCTGTGCTTATTATTCATGT | 51 | 2017 |
| 1239571 | N/A | N/A | 14799 | 14818 | CCATCACTTCTCACCTGATT | 73 | 2018 |
| 1239593 | N/A | N/A | 14927 | 14946 | AGTGACTGAATTTTCTCTCC | 66 | 2019 |
| 1239615 | N/A | N/A | 15238 | 15257 | GTGGTCATAAGCAAATCAAA | 44 | 2020 |
| 1239637 | N/A | N/A | 15362 | 15381 | TTTTCATCTCCTTCAGAGCT | 60 | 2021 |
| 1239659 | N/A | N/A | 15417 | 15436 | CCCTTACCTTTATCACCCAA | 76 | 2022 |
| 1239681 | N/A | N/A | 15508 | 15527 | CCATGTACAGTTCAATGGTT | 102 | 2023 |
| 1239703 | N/A | N/A | 15683 | 15702 | GCCGTAAAACCTATAATGGC | 87 | 2024 |
| 1239725 | N/A | N/A | 15748 | 15767 | AATGATTGCTAAACAGTACC | 75 | 2025 |
| 1239747 | N/A | N/A | 15830 | 15849 | AATCAAAAATCTCTTTTCAA | 97 | 2026 |
| 1239769 | N/A | N/A | 15874 | 15893 | CCAGAATGACAATTTATGAC | 34 | 2027 |
| 1239791 | N/A | N/A | 15926 | 15945 | GTGAATTATTTTCTTCTAAT | 35 | 2028 |

TABLE 28

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1201142 | 1963 | 1982 | 17754 | 17773 | GCCACATATAGGGTCCTTTA | 11 | 66 |
| 1238120 | 49 | 68 | 3142 | 3161 | TCATCTTTAATTGGAAATTC | 95 | 2029 |
| 1238142 | 113 | 132 | 3206 | 3225 | TTGCATCAGTTGATACCGCC | 121 | 2030 |
| 1238164 | 458 | 477 | 16249 | 16268 | CCATGTGGCCACAAAGAGAA | 32* | 2031 |
| 1238186 | 591 | 610 | 16382 | 16401 | GAGGCTGCCCCCAGCCACCA | 79 | 2032 |
|  | 615 | 634 | 16406 | 16425 |  |  |  |
| 1238208 | 856 | 875 | 16647 | 16666 | TAACGGTCCTCATAGTCACT | 63 | 2033 |
| 1238230 | 1189 | 1208 | 16980 | 16999 | AAACAGGAAGACCTTCCTCA | 82 | 2034 |
| 1238252 | 1397 | 1416 | 17188 | 17207 | CATTAGCAACGGCTCATGAT | 75 | 2035 |
| 1238274 | 1586 | 1605 | 17377 | 17396 | GCTATGAAATCTCTACTAAG | 15 | 2036 |
| 1238296 | 1676 | 1695 | 17467 | 17486 | GGATTTTTTGAATAAGTAT | 31 | 2037 |
| 1238318 | 1808 | 1827 | 17599 | 17618 | AATATTTACTCTTGTTGAAC | 72 | 2038 |
| 1238340 | 1852 | 1871 | 17643 | 17662 | TTCACTGTGAATATGTCCTC | 20 | 2039 |
| 1238362 | 1881 | 1900 | 17672 | 17691 | AGAAGCCTTTCATATATGTT | 26 | 2040 |
| 1238384 | 1918 | 1937 | 17709 | 17728 | CAAGGGCACCATTCCCAAAC | 102 | 2041 |
| 1238406 | 2001 | 2020 | 17792 | 17811 | TCAGCTGCCTTAATTACCTA | 25 | 2042 |
| 1238428 | 2040 | 2059 | 17831 | 17850 | AGGAGATTTGCCTTCAGTGT | 35 | 2043 |
| 1238450 | 2090 | 2109 | 17881 | 17900 | GCAGCTCTCCTGTATGTCAA | 28 | 2044 |
| 1238472 | 2124 | 2143 | 17915 | 17934 | CATCATCCTCTATGATGATG | 104 | 2045 |
| 1238494 | 2153 | 2172 | 17944 | 17963 | TTCTTTGCACACTGACCATT | 31 | 2046 |
| 1238516 | 2200 | 2219 | 17991 | 18010 | GTTTTTGACAATTATGAGAC | 16 | 2047 |
| 1238538 | 2243 | 2262 | 18034 | 18053 | TTCAAAAGCCAATTACAGAA | 58 | 2048 |
| 1238560 | 2273 | 2292 | 18064 | 18083 | TATTTTTTAGATTGTCTCCC | 44 | 2049 |
| 1238582 | 2303 | 2322 | 18094 | 18113 | AATCATATTTCTGTCATCTC | 20 | 2050 |
| 1238604 | 2332 | 2351 | 18123 | 18142 | TAACAGAATTTCTTTTTCCA | 32 | 2051 |
| 1238626 | 2378 | 2397 | 18169 | 18188 | TGACAATATCAAACAATTCA | 48 | 2052 |
| 1238648 | 2427 | 2446 | 18218 | 18237 | AGTGCAAGCCAATAATAACA | 34 | 2053 |
| 1238670 | 2523 | 2542 | 18314 | 18333 | ACTTCAGATGTTAACTGCTC | 21 | 2054 |
| 1238692 | 2602 | 2621 | 18393 | 18412 | ATTGTAAGCCTAAGGACCAC | 49 | 2055 |
| 1238714 | 2723 | 2742 | 18514 | 18533 | TTTATATAACAAAACAAGAA | 89 | 2056 |
| 1238736 | N/A | N/A | 4744 | 4763 | GATGCTCTCAGAACAAGAAA | 49 | 2057 |
| 1238758 | N/A | N/A | 4826 | 4845 | CCTTAATCCTATTCTACCAG | 78 | 2058 |
| 1238780 | N/A | N/A | 4874 | 4893 | TATCCAATTCCCTGTTCCTA | 48 | 2059 |
| 1238802 | N/A | N/A | 4902 | 4921 | GTTGATTTTTCCAGAAGTTT | 9 | 2060 |
| 1238824 | N/A | N/A | 4964 | 4983 | TAAGTAAAATTGCTCCTTTC | 76 | 2061 |
| 1238846 | N/A | N/A | 5042 | 5061 | ATCACATCCTACCCCTCTGC | 77 | 2062 |
| 1238868 | N/A | N/A | 5097 | 5116 | CTTAATATTTTCCTTTCGGT | 37 | 2063 |

TABLE 28-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1238890 | N/A | N/A | 5125 | 5144 | CATCATTTGCCATTTATCT | 30 | 2064 |
| 1238912 | N/A | N/A | 5183 | 5202 | TAGATGTAAAATGATAACCC | 43 | 2065 |
| 1238934 | N/A | N/A | 5345 | 5364 | GATCAGGAAATTAGGTAGCC | 39 | 2066 |
| 1238956 | N/A | N/A | 5426 | 5445 | TCGAAATGCCCCCAATAACT | 59 | 2067 |
| 1238978 | N/A | N/A | 5577 | 5596 | AATTTTAGATCATTCTGCTA | 82 | 2068 |
| 1239000 | N/A | N/A | 5650 | 5669 | TTCAGTTAATGTGTCATAAT | 22 | 2069 |
| 1239022 | N/A | N/A | 5704 | 5723 | CCCACATATCACAGGCTCCA | 59 | 2070 |
| 1239044 | N/A | N/A | 5746 | 5765 | CAGGTGCAGTTAATAACCCA | 70 | 2071 |
| 1239066 | N/A | N/A | 5862 | 5881 | TGAGAGCAATATATTCACCA | 15 | 2072 |
| 1239088 | N/A | N/A | 6041 | 6060 | TACTAAATCATTAATCAACT | 117 | 2073 |
| 1239110 | N/A | N/A | 6307 | 6326 | GTGATCACAGCCTTTCCTGA | 83 | 2074 |
| 1239132 | N/A | N/A | 6432 | 6451 | TTCAGCATAATTCTAAAAAT | 102 | 2075 |
| 1239154 | N/A | N/A | 6508 | 6527 | GTGGTGCAGAAACTTCTGTT | 64 | 2076 |
| 1239176 | N/A | N/A | 6721 | 6740 | TAGGAGTTATTTTATAATGC | 39 | 2077 |
| 1239198 | N/A | N/A | 6872 | 6891 | TAATGCTTTTCACTGAAGGA | 57 | 2078 |
| 1239220 | N/A | N/A | 7254 | 7273 | ATGTCAAACAACCCCCGACC | 108 | 2079 |
| 1239242 | N/A | N/A | 7714 | 7733 | CTCTTTCTAATTTTGTACAC | 101 | 2080 |
| 1239264 | N/A | N/A | 8182 | 8201 | ATTATCCCCCATGAGCACA | 58 | 2081 |
| 1239286 | N/A | N/A | 8348 | 8367 | AATTGAGAGCTTTTCCTCTT | 99 | 2082 |
| 1239308 | N/A | N/A | 8660 | 8679 | TCTTAACAAAATTCTAGCGA | 107 | 2083 |
| 1239330 | N/A | N/A | 9064 | 9083 | AAGGTAATTTTATAACCCCC | 69 | 2084 |
| 1239352 | N/A | N/A | 9418 | 9437 | GTATAATTTTTTACCTGGA | 8 | 2085 |
| 1239374 | N/A | N/A | 9640 | 9659 | TTCAATGAAAATCAATATCA | 101 | 2086 |
| 1239396 | N/A | N/A | 10037 | 10056 | CCAAGAGTTTCAGTATAGAC | 16 | 2087 |
| 1239418 | N/A | N/A | 10734 | 10753 | ACACACATTTCAAGTGTCAG | 54 | 2088 |
| 1239440 | N/A | N/A | 10811 | 10830 | GCCACAGCTATATATAGGTG | 104 | 2089 |
| 1239462 | N/A | N/A | 12545 | 12564 | TCATTGCAAAACTATCCACA | 77 | 2090 |
| 1239484 | N/A | N/A | 13546 | 13565 | CACTATTTGCAATTAGTGTG | 82 | 2091 |
| 1239506 | N/A | N/A | 13779 | 13798 | TCTAAGATACTCTCTGTCAC | 79 | 2092 |
| 1239528 | N/A | N/A | 14210 | 14229 | AAGGAATAATCAAACTAAAT | 94 | 2093 |
| 1239550 | N/A | N/A | 14382 | 14401 | TGTTATTTCCTCTGTGCTTA | 33 | 2094 |
| 1239572 | N/A | N/A | 14802 | 14821 | CTTCCATCACTTCTCACCTG | 70 | 2095 |
| 1239594 | N/A | N/A | 14928 | 14947 | GAGTGACTGAATTTTCTCTC | 107 | 2096 |
| 1239616 | N/A | N/A | 15267 | 15286 | ACATTATTGAAATGGGAAGT | 50 | 2097 |
| 1239638 | N/A | N/A | 15363 | 15382 | TTTTTCATCTCCTTCAGAGC | 74 | 2098 |
| 1239660 | N/A | N/A | 15418 | 15437 | CCCCTTACCTTTATCACCCA | 119 | 2099 |
| 1239682 | N/A | N/A | 15516 | 15535 | ACCATATACCATGTACAGTT | 7 | 2100 |

TABLE 28-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) RTS 42354 | SEQ ID NO |
|---|---|---|---|---|---|---|---|
| 1239704 | N/A | N/A | 15686 | 15705 | TGTGCCGTAAAACCTATAAT | 69 | 2101 |
| 1239726 | N/A | N/A | 15749 | 15768 | AAATGATTGCTAAACAGTAC | 78 | 2102 |
| 1239748 | N/A | N/A | 15831 | 15850 | AAATCAAAAATCTCTTTTCA | 135 | 2103 |
| 1239770 | N/A | N/A | 15875 | 15894 | TCCAGAATGACAATTTATGA | 57 | 2104 |
| 1239792 | N/A | N/A | 15928 | 15947 | GAGTGAATTATTTTCTTCTA | 16 | 2105 |

TABLE 29

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5 to 3') | PRNP (% UTC) RTS 42354 | SEQ ID NO |
|---|---|---|---|---|---|---|---|
| 1201142 | 1963 | 1982 | 17754 | 17773 | GCCACATATAGGGTCCTTTA | 13 | 66 |
| 1238121 | 50 | 69 | 3143 | 3162 | ATCATCTTTAATTGGAAATT | 106 | 2106 |
| 1238143 | 117 | 136 | 3210 | 3229 | ACACTTGCATCAGTTGATAC | 126 | 2107 |
| 1238165 | 467 | 486 | 16258 | 16277 | CAGGTCACTCCATGTGGCCA | 91* | 2108 |
| 1238187 | 592 616 | 611 635 | 16383 16407 | 16402 16426 | TGAGGCTGCCCCCAGCCACC | 103 | 2109 |
| 1238209 | 857 | 876 | 16648 | 16667 | GTAACGGTCCTCATAGTCAC | 83 | 2110 |
| 1238231 | 1197 | 1216 | 16988 | 17007 | GATGGTGAAAACAGGAAGAC | 82 | 2111 |
| 1238253 | 1419 | 1438 | 17210 | 17229 | TGTTATACTTTTACTGGCCT | 57 | 2112 |
| 1238275 | 1588 | 1607 | 17379 | 17398 | TAGCTATGAAATCTCTACTA | 42 | 2113 |
| 1238297 | 1677 | 1696 | 17468 | 17487 | AGGATTTTTTTGAATAAGTA | 51 | 2114 |
| 1238319 | 1810 | 1829 | 17601 | 17620 | ACAATATTTACTCTTGTTGA | 31 | 2115 |
| 1238341 | 1853 | 1872 | 17644 | 17663 | GTTCACTGTGAATATGTCCT | 4 | 2116 |
| 1238363 | 1882 | 1901 | 17673 | 17692 | CAGAAGCCTTTCATATATGT | 25 | 2117 |
| 1238385 | 1919 | 1938 | 17710 | 17729 | CCAAGGGCACCATTCCCAAA | 87 | 2118 |
| 1238407 | 2002 | 2021 | 17793 | 17812 | TTCAGCTGCCTTAATTACCT | 38 | 2119 |
| 1238429 | 2041 | 2060 | 17832 | 17851 | AAGGAGATTTGCCTTCAGTG | 53 | 2120 |
| 1238451 | 2091 | 2110 | 17882 | 17901 | TGCAGCTCTCCTGTATGTCA | 32 | 2121 |
| 1238473 | 2125 | 2144 | 17916 | 17935 | ACATCATCCTCTATGATGAT | 107 | 2122 |
| 1238495 | 2154 | 2173 | 17945 | 17964 | TTTCTTTGCACACTGACCAT | 29 | 2123 |
| 1238517 | 2201 | 2220 | 17992 | 18011 | GGTTTTTGACAATTATGAGA | 4 | 2124 |
| 1238539 | 2245 | 2264 | 18036 | 18055 | GATTCAAAAGCCAATTACAG | 43 | 2125 |
| 1238561 | 2274 | 2293 | 18065 | 18084 | ATATTTTTAGATTGTCTCC | 52 | 2126 |
| 1238583 | 2304 | 2323 | 18095 | 18114 | CAATCATATTTCTGTCATCT | 26 | 2127 |
| 1238605 | 2333 | 2352 | 18124 | 18143 | TTAACAGAATTTCTTTTTCC | 58 | 2128 |
| 1238627 | 2379 | 2398 | 18170 | 18189 | GTGACAATATCAAACAATTC | 43 | 2129 |

TABLE 29-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5 to 3') | PRNP (% UTC) RTS 42354 | SEQ ID NO |
|---|---|---|---|---|---|---|---|
| 1238649 | 2429 | 2448 | 18220 | 18239 | AAAGTGCAAGCCAATAATAA | 60 | 2130 |
| 1238671 | 2525 | 2544 | 18316 | 18335 | ACACTTCAGATGTTAACTGC | 34 | 2131 |
| 1238693 | 2604 | 2623 | 18395 | 18414 | ACATTGTAAGCCTAAGGACC | 31 | 2132 |
| 1238715 | 2725 | 2744 | 18516 | 18535 | TTTTTATATAACAAAACAAG | 91 | 2133 |
| 1238737 | N/A | N/A | 4745 | 4764 | TGATGCTCTCAGAACAAGAA | 39 | 2134 |
| 1238759 | N/A | N/A | 4827 | 4846 | TCCTTAATCCTATTCTACCA | 92 | 2135 |
| 1238781 | N/A | N/A | 4875 | 4894 | TTATCCAATTCCCTGTTCCT | 67 | 2136 |
| 1238803 | N/A | N/A | 4903 | 4922 | TGTTGATTTTTCCAGAAGTT | 15 | 2137 |
| 1238825 | N/A | N/A | 4965 | 4984 | GTAAGTAAAATTGCTCCTTT | 35 | 2138 |
| 1238847 | N/A | N/A | 5044 | 5063 | AAATCACATCCTACCCCTCT | 80 | 2139 |
| 1238869 | N/A | N/A | 5098 | 5117 | TCTTAATATTTTCCTTTCGG | 30 | 2140 |
| 1238891 | N/A | N/A | 5131 | 5150 | ATGACTCATCATTTTGCCAT | 47 | 2141 |
| 1238913 | N/A | N/A | 5193 | 5212 | GTTATTTTAATAGATGTAAA | 106 | 2142 |
| 1238935 | N/A | N/A | 5379 | 5398 | TCATTTCCTCCATTCTATGA | 95 | 2143 |
| 1238957 | N/A | N/A | 5449 | 5468 | TTAACAAAATGTTTGTCACT | 71 | 2144 |
| 1238979 | N/A | N/A | 5579 | 5598 | CTAATTTTAGATCATTCTGC | 44 | 2145 |
| 1239001 | N/A | N/A | 5653 | 5672 | CATTTCAGTTAATGTGTCAT | 30 | 2146 |
| 1239023 | N/A | N/A | 5710 | 5729 | TTTTTCCCCACATATCACAG | 61 | 2147 |
| 1239045 | N/A | N/A | 5782 | 5801 | TCAGATTTTTCACATATGCG | 12 | 2148 |
| 1239067 | N/A | N/A | 5864 | 5883 | AGTGAGAGCAATATATTCAC | 70 | 2149 |
| 1239089 | N/A | N/A | 6054 | 6073 | CCAATACACAAATTACTAAA | 87 | 2150 |
| 1239111 | N/A | N/A | 6314 | 6333 | AGAGCTTGTGATCACAGCCT | 75 | 2151 |
| 1239133 | N/A | N/A | 6442 | 6461 | CCTTACATAATTCAGCATAA | 44 | 2152 |
| 1239155 | N/A | N/A | 6526 | 6545 | GCCATGTTCAGTGTCAGTGT | 34 | 2153 |
| 1239177 | N/A | N/A | 6723 | 6742 | CTTAGGAGTTATTTTATAAT | 81 | 2154 |
| 1239199 | N/A | N/A | 6874 | 6893 | TATAATGCTTTTCACTGAAG | 66 | 2155 |
| 1239221 | N/A | N/A | 7259 | 7278 | GGCAAATGTCAAACAACCCC | 80 | 2156 |
| 1239243 | N/A | N/A | 7715 | 7734 | TCTCTTTCTAATTTTGTACA | 97 | 2157 |
| 1239265 | N/A | N/A | 8187 | 8206 | CATTAATTATCCCCCCATGA | 65 | 2158 |
| 1239287 | N/A | N/A | 8393 | 8412 | CCACATATGACAAGGTCACA | 61 | 2159 |
| 1239309 | N/A | N/A | 8702 | 8721 | GCAGTATAGGCCAATATCCC | 47 | 2160 |
| 1239331 | N/A | N/A | 9065 | 9084 | AAAGGTAATTTTATAACCCC | 73 | 2161 |
| 1239353 | N/A | N/A | 9421 | 9440 | TAGGTATAATTTTTTTACCT | 111 | 2162 |
| 1239375 | N/A | N/A | 9650 | 9669 | TTGAAAAGTTTTCAATGAAA | 106 | 2163 |
| 1239397 | N/A | N/A | 10090 | 10109 | GCCATCTACTGAAATAGGAC | 105 | 2164 |
| 1239419 | N/A | N/A | 10735 | 10754 | AACACACATTTCAGTGTCA | 88 | 2165 |

TABLE 29-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5 to 3') | PRNP (% UTC) RTS 42354 | SEQ ID NO |
|---|---|---|---|---|---|---|---|
| 1239441 | N/A | N/A | 11088 | 11107 | GTACCATAACCTTTTTTTT | 40 | 2166 |
| 1239463 | N/A | N/A | 12638 | 12657 | CGGAAATATCATTCGACTCA | 47 | 2167 |
| 1239485 | N/A | N/A | 13548 | 13567 | GACACTATTTGCAATTAGTG | 91 | 2168 |
| 1239507 | N/A | N/A | 13780 | 13799 | ATCTAAGATACTCTCTGTCA | 120 | 2169 |
| 1239529 | N/A | N/A | 14213 | 14232 | CATAAGGAATAATCAAACTA | 102 | 2170 |
| 1239551 | N/A | N/A | 14383 | 14402 | ATGTTATTTCCTCTGTGCTT | 36 | 2171 |
| 1239573 | N/A | N/A | 14808 | 14827 | TCGGTGCTTCCATCACTTCT | 77 | 2172 |
| 1239595 | N/A | N/A | 14930 | 14949 | TAGAGTGACTGAATTTTCTC | 131 | 2173 |
| 1239617 | N/A | N/A | 15269 | 15288 | TAACATTATTGAAATGGGAA | 81 | 2174 |
| 1239639 | N/A | N/A | 15366 | 15385 | TTATTTTTCATCTCCTTCAG | 65 | 2175 |
| 1239661 | N/A | N/A | 15419 | 15438 | ACCCCTTACCTTTATCACCC | 75 | 2176 |
| 1239683 | N/A | N/A | 15517 | 15536 | CACCATATACCATGTACAGT | 22 | 2177 |
| 1239705 | N/A | N/A | 15687 | 15706 | GTGTGCCGTAAAACCTATAA | 51 | 2178 |
| 1239727 | N/A | N/A | 15761 | 15780 | ATGACAATAGTAAAATGATT | 98 | 2179 |
| 1239749 | N/A | N/A | 15832 | 15851 | CAAATCAAAAATCTCTTTTC | 97 | 2180 |
| 1239771 | N/A | N/A | 15877 | 15896 | CATCCAGAATGACAATTTAT | 95 | 2181 |
| 1239793 | N/A | N/A | 15932 | 15951 | TTATGAGTGAATTATTTTCT | 63 | 2182 |

TABLE 30

Reduction of PRNP RNA

| Compound ID | SEQ ID NO: 3 Start Site | SEQ ID NO: 3 Stop Site | Sequence (5' to 3') | PRNP (% UTC) | SEQ ID NO |
|---|---|---|---|---|---|
| 1238727 | 216 | 235 | TGCTCTGAAAAGCGAAGCCA | 97 | 2183 |

Example 2: Effect of 5-10-5 MOE Gapmers with Mixed Internucleoside Linkages on Human PRNP RNA In Vitro, Single Dose Modified oligonucleotides complementary to human PRNP nucleic acid were synthesized and tested for their effect on PRNP RNA levels in vitro.

The modified oligonucleotides in the tables below are 5-10-5 MOE gapmers with mixed internucleoside linkages.

The gapmers are 20 nucleosides in length, wherein the central gap segment consists of ten 2'-β-D-deoxynucleosides and the 3' and 5' wings each consist of five 2'-MOE modified nucleosides. The sugar motif of the gapmers is (from 5' to 3'): eeeeedddddddddeeeee; wherein "d" represents a 2'-β-D-deoxyribosyl sugar, and 'e' represents a 2'-MOE modified ribosyl sugar. The internucleoside linkage motif for the gapmers is (from 5' to 3'): sooossssssssssooss; wherein 'o' represents a phosphodiester internucleoside linkage and 's' represents a phosphorothioate internucleoside linkage. Each cytosine residue is a 5-methyl cytosine.

"Start site" indicates the 5'-most nucleoside to which the gapmer is complementary to in the human sequence. "Stop site" indicates the 3'-most nucleoside to which the gapmer is complementary to in the human sequence. Each modified oligonucleotide listed in the tables below is complementary to human PRNP nucleic acid sequences SEQ ID NO: 1 or SEQ ID NO: 2, as indicated. 'N/A' indicates that the modified oligonucleotide is not complementary to that particular nucleic acid with 100% complementarity. As shown below, modified oligonucleotides complementary to the nucleobase sequence of human PRNP reduced the amount of human PRNP RNA.

Cultured A-431 cells at a density of 20,000 cells per well were treated with 4,000 nM of modified oligonucleotide by free uptake. After a treatment period of approximately 48 hours, total RNA was isolated from the cells and PRNP RNA levels were measured by quantitative real-time RTPCR, using primer probe set RTS42354, as described in Example 1. PRNP RNA levels were normalized using RIBOGREENE. Results are presented in the tables below are normalized to PRNP RNA levels in untreated control cells (UTC). Values marked with an asterisk (*) result from oligonucleotides that are complementary to the amplicon region of the primer probe set. Additional assays may be used to measure the potency and efficacy of the modified oligonucleotides complementary to the amplicon region.

TABLE 31

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) | SEQ ID NO |
|---|---|---|---|---|---|---|---|
| 1201142 | 1963 | 1982 | 17754 | 17773 | GCCACATATAGGGTCCTTTA | 6 | 66 |
| 1270212 | 420 | 439 | 16211 | 16230 | GGTTCGCCATAATGACTGCT | 2* | 2184 |
| 1270213 | 423 | 442 | 16214 | 16233 | CAAGGTTCGCCATAATGACT | 23* | 2185 |
| 1270218 | 506 | 525 | 16297 | 16316 | GTTCCATCCTCCAGGCTTCG | 5* | 2186 |
| 1270219 | 507 | 526 | 16298 | 16317 | TGTTCCATCCTCCAGGCTTC | 11* | 2187 |
| 1270224 | 516 | 535 | 16307 | 16326 | TGCCCCCAGTGTTCCATCCT | 5* | 2188 |
| 1270225 | 517 | 536 | 16308 | 16327 | CTGCCCCCAGTGTTCCATCC | 5 | 2189 |
| 1270230 | 1335 | 1354 | 17126 | 17145 | CTATGTTTTCCAGTGCCCAT | 12 | 2190 |
| 1270231 | 1337 | 1356 | 17128 | 17147 | CTCTATGTTTTCCAGTGCCC | 4 | 2191 |
| 1270236 | 1425 | 1444 | 17216 | 17235 | ATTTGCTGTTATACTTTTAC | 6 | 2192 |
| 1270237 | 1426 | 1445 | 17217 | 17236 | TATTTGCTGTTATACTTTTA | 17 | 2193 |
| 1270242 | 1455 | 1474 | 17246 | 17265 | CCAAAAATAAGTCCAGATTA | 27 | 2194 |
| 1270243 | 1456 | 1475 | 17247 | 17266 | TCCAAAAATAAGTCCAGATT | 30 | 2195 |
| 1270248 | 1512 | 1531 | 17303 | 17322 | CAAAGGTATTTCAGACTGTT | 9 | 2196 |
| 1270249 | 1513 | 1532 | 17304 | 17323 | GCAAAGGTATTTCAGACTGT | 16 | 2197 |
| 1270254 | 1559 | 1578 | 17350 | 17369 | ATTAGTATACTGAGCTCTAG | 36 | 2198 |
| 1270255 | 1565 | 1584 | 17356 | 17375 | TAGGGCATTAGTATACTGAG | 3 | 2199 |
| 1270260 | 1618 | 1637 | 17409 | 17428 | GGTTTTCTTAAAATGGAAAA | 72 | 2200 |
| 1270261 | 1622 | 1641 | 17413 | 17432 | GTCGGGTTTTCTTAAAATGG | 10 | 2201 |
| 1270266 | 1827 | 1846 | 17618 | 17637 | AGAGGTTCAGTGTTGTGACA | 17 | 2202 |
| 1270267 | 1841 | 1860 | 17632 | 17651 | TATGTCCTCTAGCCAGAGGT | 75 | 2203 |
| 1270272 | 1856 | 1875 | 17647 | 17666 | TATGTTCACTGTGAATATGT | 26 | 2204 |
| 1270273 | 1871 | 1890 | 17662 | 17681 | CATATATGTTACAGTTATGT | 35 | 2205 |
| 1270278 | 1895 | 1914 | 17686 | 17705 | TGATTTCAAGTCCCAGAAGC | 23 | 2206 |
| 1270279 | 1960 | 1979 | 17751 | 17770 | ACATATAGGGTCCTTTAAAC | 55 | 2207 |
| 1270284 | 1971 | 1990 | 17762 | 17781 | AAAGGAATGCCACATATAGG | 16 | 2208 |
| 1270285 | 1973 | 1992 | 17764 | 17783 | AGAAAGGAATGCCACATATA | 32 | 2209 |
| 1270290 | 2006 | 2025 | 17797 | 17816 | ACTTTTCAGCTGCCTTAATT | 33 | 2210 |
| 1270291 | 2007 | 2026 | 17798 | 17817 | TACTTTTCAGCTGCCTTAAT | 30 | 2211 |
| 1270296 | 2072 | 2091 | 17863 | 17882 | AAAATCATTCTGGTTTCCAG | 22 | 2212 |
| 1270297 | 2073 | 2092 | 17864 | 17883 | CAAAATCATTCTGGTTTCCA | 20 | 2213 |
| 1270302 | 2150 | 2169 | 17941 | 17960 | TTTGCACACTGACCATTTTT | 42 | 2214 |
| 1270303 | 2151 | 2170 | 17942 | 17961 | CTTTGCACACTGACCATTTT | 26 | 2215 |
| 1270308 | 2202 | 2221 | 17993 | 18012 | TGGTTTTTGACAATTATGAG | 4 | 2216 |
| 1270309 | 2203 | 2222 | 17994 | 18013 | CTGGTTTTTGACAATTATGA | 2 | 2217 |
| 1270314 | 2290 | 2309 | 18081 | 18100 | TCATCTCCAACCTAAGATAT | 52 | 2218 |
| 1270315 | 2323 | 2342 | 18114 | 18133 | TTCTTTTTCCACTTCAAATC | 50 | 2219 |

TABLE 31-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) | SEQ ID NO |
|---|---|---|---|---|---|---|---|
| 1270320 | 2358 | 2377 | 18149 | 18168 | GGGAATAATTTTACTTTAAT | 26 | 2220 |
| 1270321 | 2359 | 2378 | 18150 | 18169 | AGGGAATAATTTTACTTTAA | 14 | 2221 |
| 1270326 | 2419 | 2438 | 18210 | 18229 | CCAATAATAACATTGCAGAA | 18 | 2222 |
| 1270327 | 2421 | 2440 | 18212 | 18231 | AGCCAATAATAACATTGCAG | 9 | 2223 |
| 1270332 | 2573 | 2592 | 18364 | 18383 | TTTCCCACATATTAAGTATT | 43 | 2224 |
| 1270333 | 2577 | 2596 | 18368 | 18387 | AGGGTTTCCCACATATTAAG | 33 | 2225 |
| 1270338 | 2612 | 2631 | 18403 | 18422 | TTCAGTGCACATTGTAAGCC | 13 | 2226 |
| 1270339 | N/A | N/A | 4894 | 4913 | TTCCAGAAGTTTAACATATT | 29 | 2227 |
| 1270344 | N/A | N/A | 4908 | 4927 | AGCGTTGTTGATTTTTCCAG | 9 | 2228 |
| 1270350 | N/A | N/A | 4998 | 5017 | TTTTTTTCACTGTAAGACCT | 31 | 2229 |
| 1270356 | N/A | N/A | 5072 | 5091 | AGACTTGTGTTAGATATAAA | 35 | 2230 |
| 1270362 | N/A | N/A | 5081 | 5100 | CGGTGTGGAAGACTTGTGTT | 15 | 2231 |
| 1270368 | N/A | N/A | 5190 | 5209 | ATTTTAATAGATGTAAAATG | 97 | 2232 |
| 1270374 | N/A | N/A | 5517 | 5536 | CAGGTAAGTTCTCAGGAGTG | 12 | 2233 |
| 1270380 | N/A | N/A | 5530 | 5549 | GTTTCTTCCATTGCAGGTAA | 2 | 2234 |
| 1270386 | N/A | N/A | 5538 | 5557 | GTTTGTTTGTTTCTTCCATT | 2 | 2235 |
| 1270392 | N/A | N/A | 5607 | 5626 | TATACATTTAGGCTCTTTTC | 22 | 2236 |
| 1270398 | N/A | N/A | 5636 | 5655 | CATAATTTTCTTAGCTACTG | 32 | 2237 |
| 1270404 | N/A | N/A | 5674 | 5693 | TTTTAGTGGTTACATAATGT | 66 | 2238 |
| 1270410 | N/A | N/A | 5779 | 5798 | GATTTTTCACATATGCGTTC | 8 | 2239 |
| 1270416 | N/A | N/A | 5794 | 5813 | GTGCTTTTCCTTTCAGATTT | 21 | 2240 |
| 1270422 | N/A | N/A | 5855 | 5874 | AATATATTCACCAAAGGAAA | 63 | 2241 |
| 1270428 | N/A | N/A | 6216 | 6235 | ATCTGTTGTGGTTCAGCTAA | 42 | 2242 |
| 1270434 | N/A | N/A | 6224 | 6243 | TATGTACAATCTGTTGTGGT | 19 | 2243 |
| 1270440 | N/A | N/A | 6496 | 6515 | CTTCTGTTATGTTATTATTG | 34 | 2244 |
| 1270446 | N/A | N/A | 7280 | 7299 | TAATTAGTTACATCGGGAAG | 64 | 2245 |
| 1270452 | N/A | N/A | 7387 | 7406 | TAGTAAGAACTTATCCCAAG | 59 | 2246 |
| 1270458 | N/A | N/A | 8039 | 8058 | ATGGCACTTTCTTTTTATTT | 20 | 2247 |
| 1270464 | N/A | N/A | 8166 | 8185 | CACAGGCTATCTTTCTATTT | 46 | 2248 |
| 1270470 | N/A | N/A | 9024 | 9043 | GATTTTGGACGGGAGATTT | 57 | 2249 |
| 1270476 | N/A | N/A | 9034 | 9053 | GGATCTCTTAGATTTTGGA | 40 | 2250 |
| 1270482 | N/A | N/A | 9042 | 9061 | TTTGCTTTGGATCTCTTAGA | 23 | 2251 |
| 1270488 | N/A | N/A | 9358 | 9377 | CAGGGTGGTAGTTTTTCAAA | 10 | 2252 |
| 1270494 | N/A | N/A | 9686 | 9705 | ATTAATAGGTTAGGAAGAAA | 91 | 2253 |
| 1270500 | N/A | N/A | 9694 | 9713 | GGAGCTCTATTAATAGGTTA | 63 | 2254 |
| 1270506 | N/A | N/A | 9984 | 10003 | GTGGGAGTATCAATTTAAGC | 46 | 2255 |

TABLE 31-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) | SEQ ID NO |
|---|---|---|---|---|---|---|---|
| 1270512 | N/A | N/A | 11334 | 11353 | TGTTGTTTCTTTTCTGGTAG | 12 | 2256 |
| 1270518 | N/A | N/A | 14380 | 14399 | TTATTTCCTCTGTGCTTATT | 54 | 2257 |
| 1270524 | N/A | N/A | 15164 | 15183 | TTTTTGGAGGCTCTTTTAGG | 53 | 2258 |
| 1270530 | N/A | N/A | 15515 | 15534 | CCATATACCATGTACAGTTC | 17 | 2259 |
| 1270536 | N/A | N/A | 15623 | 15642 | GGATGATCTGCAATTGTTTT | 24 | 2260 |

TABLE 32

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) | SEQ ID NO |
|---|---|---|---|---|---|---|---|
| 1201142 | 1963 | 1982 | 17754 | 17773 | GCCACATATAGGGTCCTTTA | 7 | 66 |
| 1270214 | 425 | 444 | 16216 | 16235 | GCCAAGGTTCGCCATAATGA | 10* | 2261 |
| 1270220 | 509 | 528 | 16300 | 16319 | AGTGTTCCATCCTCCAGGCT | 5* | 2262 |
| 1270226 | 518 | 537 | 16309 | 16328 | GCTGCCCCCAGTGTTCCATC | 12* | 2263 |
| 1270232 | 1338 | 1357 | 17129 | 17148 | ACTCTATGTTTTCCAGTGCC | 7 | 2264 |
| 1270238 | 1427 | 1446 | 17218 | 17237 | TTATTTGCTGTTATACTTTT | 31 | 2265 |
| 1270244 | 1458 | 1477 | 17249 | 17268 | AGTCCAAAAATAAGTCCAGA | 12 | 2266 |
| 1270250 | 1515 | 1534 | 17306 | 17325 | AGGCAAAGGTATTTCAGACT | 3 | 2267 |
| 1270256 | 1566 | 1585 | 17357 | 17376 | ATAGGGCATTAGTATACTGA | 5 | 2268 |
| 1270262 | 1623 | 1642 | 17414 | 17433 | TGTCGGGTTTTCTTAAAATG | 16 | 2269 |
| 1270268 | 1843 | 1862 | 17634 | 17653 | AATATGTCCTCTAGCCAGAG | 37 | 2270 |
| 1270274 | 1872 | 1891 | 17663 | 17682 | TCATATATGTTACAGTTATG | 22 | 2271 |
| 1270280 | 1961 | 1980 | 17752 | 17771 | CACATATAGGGTCCTTTAAA | 30 | 2272 |
| 1270286 | 1992 | 2011 | 17783 | 17802 | TTAATTACCTATAGTTTAAA | 42 | 2273 |
| 1270292 | 2008 | 2027 | 17799 | 17818 | TTACTTTTCAGCTGCCTTAA | 19 | 2274 |
| 1270298 | 2084 | 2103 | 17875 | 17894 | CTCCTGTATGTCAAAATCAT | 55 | 2275 |
| 1270304 | 2169 | 2188 | 17960 | 17979 | AATGCAAGCAGTTCTTTTCT | 14 | 2276 |
| 1270310 | 2204 | 2223 | 17995 | 18014 | TCTGGTTTTGACAATTATG | 3 | 2277 |
| 1270316 | 2324 | 2343 | 18115 | 18134 | TTTCTTTTTCCACTTCAAAT | 26 | 2278 |
| 1270322 | 2365 | 2384 | 18156 | 18175 | CAATTCAGGGAATAATTTTA | 61 | 2279 |
| 1270328 | 2423 | 2442 | 18214 | 18233 | CAAGCCAATAATAACATTGC | 28 | 2280 |
| 1270334 | 2605 | 2624 | 18396 | 18415 | CACATTGTAAGCCTAAGGAC | 20 | 2281 |
| 1270340 | N/A | N/A | 4897 | 4916 | TTTTTCCAGAAGTTAACAT | 69 | 2282 |
| 1270345 | N/A | N/A | 4910 | 4929 | AGAGCGTTGTTGATTTTTCC | 4 | 2283 |
| 1270346 | N/A | N/A | 4935 | 4954 | TTTTTTCCTTTCTTCTACAA | 117 | 2284 |
| 1270351 | N/A | N/A | 5000 | 5019 | GCTTTTTTTCACTGTAAGAC | 2 | 2285 |

TABLE 32-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) | SEQ ID NO |
|---|---|---|---|---|---|---|---|
| 1270352 | N/A | N/A | 5001 | 5020 | AGCTTTTTTTCACTGTAAGA | 8 | 2286 |
| 1270357 | N/A | N/A | 5073 | 5092 | AAGACTTGTGTTAGATATAA | 24 | 2287 |
| 1270358 | N/A | N/A | 5074 | 5093 | GAAGACTTGTGTTAGATATA | 10 | 2288 |
| 1270363 | N/A | N/A | 5126 | 5145 | TCATCATTTTGCCATTTATC | 10 | 2289 |
| 1270364 | N/A | N/A | 5127 | 5146 | CTCATCATTTTGCCATTTAT | 7 | 2290 |
| 1270369 | N/A | N/A | 5192 | 5211 | TTATTTTAATAGATGTAAAA | 83 | 2291 |
| 1270370 | N/A | N/A | 5194 | 5213 | GGTTATTTTAATAGATGTAA | 4 | 2292 |
| 1270375 | N/A | N/A | 5519 | 5538 | TGCAGGTAAGTTCTCAGGAG | 12 | 2293 |
| 1270376 | N/A | N/A | 5521 | 5540 | ATTGCAGGTAAGTTCTCAGG | 7 | 2294 |
| 1270381 | N/A | N/A | 5532 | 5551 | TTGTTTCTTCCATTGCAGGT | 17 | 2295 |
| 1270382 | N/A | N/A | 5533 | 5552 | TTTGTTTCTTCCATTGCAGG | 27 | 2296 |
| 1270387 | N/A | N/A | 5540 | 5559 | TTGTTTGTTTGTTTCTTCCA | 4 | 2297 |
| 1270388 | N/A | N/A | 5597 | 5616 | GGCTCTTTTCCAGGTGTTCT | 9 | 2298 |
| 1270393 | N/A | N/A | 5608 | 5627 | TTATACATTTAGGCTCTTTT | 21 | 2299 |
| 1270394 | N/A | N/A | 5610 | 5629 | TGTTATACATTTAGGCTCTT | 8 | 2300 |
| 1270399 | N/A | N/A | 5637 | 5656 | TCATAATTTTCTTAGCTACT | 32 | 2301 |
| 1270400 | N/A | N/A | 5640 | 5659 | GTGTCATAATTTTCTTAGCT | 7 | 2302 |
| 1270405 | N/A | N/A | 5711 | 5730 | GTTTTTCCCCACATATCACA | 21 | 2303 |
| 1270406 | N/A | N/A | 5715 | 5734 | GTCAGTTTTTCCCCACATAT | 7 | 2304 |
| 1270411 | N/A | N/A | 5780 | 5799 | AGATTTTTCACATATGCGTT | 12 | 2305 |
| 1270412 | N/A | N/A | 5781 | 5800 | CAGATTTTTCACATATGCGT | 11 | 2306 |
| 1270417 | N/A | N/A | 5796 | 5815 | CTGTGCTTTTCCTTTCAGAT | 18 | 2307 |
| 1270418 | N/A | N/A | 5798 | 5817 | TTCTGTGCTTTTCCTTTCAG | 29 | 2308 |
| 1270423 | N/A | N/A | 5856 | 5875 | CAATATATTCACCAAAGGAA | 45 | 2309 |
| 1270424 | N/A | N/A | 5858 | 5877 | AGCAATATATTCACCAAAGG | 13 | 2310 |
| 1270429 | N/A | N/A | 6217 | 6236 | AATCTGTTGTGGTTCAGCTA | 18 | 2311 |
| 1270430 | N/A | N/A | 6218 | 6237 | CAATCTGTTGTGGTTCAGCT | 11 | 2312 |
| 1270435 | N/A | N/A | 6488 | 6507 | ATGTTATTATTGTTATTTGA | 42 | 2313 |
| 1270436 | N/A | N/A | 6490 | 6509 | TTATGTTATTATTGTTATTT | 71 | 2314 |
| 1270441 | N/A | N/A | 6498 | 6517 | AACTTCTGTTATGTTATTAT | 33 | 2315 |
| 1270442 | N/A | N/A | 6565 | 6584 | CAGAGAATCTTTCACCTTGG | 21 | 2316 |
| 1270447 | N/A | N/A | 7281 | 7300 | TTAATTAGTTACATCGGGAA | 31 | 2317 |
| 1270448 | N/A | N/A | 7285 | 7304 | AAGCTTAATTAGTTACATCG | 32 | 2318 |
| 1270453 | N/A | N/A | 7391 | 7410 | GAGCTAGTAAGAACTTATCC | 50 | 2319 |
| 1270454 | N/A | N/A | 7393 | 7412 | CAGAGCTAGTAAGAACTTAT | 26 | 2320 |
| 1270459 | N/A | N/A | 8041 | 8060 | AAATGGCACTTTCTTTTTAT | 20 | 2321 |

TABLE 32-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) | SEQ ID NO |
|---|---|---|---|---|---|---|---|
| 1270460 | N/A | N/A | 8156 | 8175 | CTTTCTATTTGTGTCTCCTT | 22 | 2322 |
| 1270465 | N/A | N/A | 8167 | 8186 | GCACAGGCTATCTTTCTATT | 16 | 2323 |
| 1270466 | N/A | N/A | 8169 | 8188 | GAGCACAGGCTATCTTTCTA | 22 | 2324 |
| 1270471 | N/A | N/A | 9026 | 9045 | TAGATTTTTGGACGGGAGAT | 28 | 2325 |
| 1270472 | N/A | N/A | 9027 | 9046 | TTAGATTTTTGGACGGGAGA | 41 | 2326 |
| 1270477 | N/A | N/A | 9036 | 9055 | TTGGATCTCTTAGATTTTTG | 35 | 2327 |
| 1270483 | N/A | N/A | 9044 | 9063 | TGTTTGCTTTGGATCTCTTA | 20 | 2328 |
| 1270489 | N/A | N/A | 9413 | 9432 | ATTTTTTTACCTGGAAAATC | 72 | 2329 |
| 1270495 | N/A | N/A | 9687 | 9706 | TATTAATAGGTTAGGAAGAA | 70 | 2330 |
| 1270501 | N/A | N/A | 9696 | 9715 | CAGGAGCTCTATTAATAGGT | 24 | 2331 |
| 1270507 | N/A | N/A | 9985 | 10004 | AGTGGGAGTATCAATTTAAG | 42 | 2332 |
| 1270513 | N/A | N/A | 11337 | 11356 | TGTTGTTGTTTCTTTTCTGG | 7 | 2333 |
| 1270519 | N/A | N/A | 14381 | 14400 | GTTATTTCCTCTGTGCTTAT | 12 | 2334 |
| 1270525 | N/A | N/A | 15165 | 15184 | GTTTTTGGAGGCTCTTTTAG | 41 | 2335 |
| 1270531 | N/A | N/A | 15518 | 15537 | TCACCATATACCATGTACAG | 50 | 2336 |
| 1270537 | N/A | N/A | 15626 | 15645 | CTGGGATGATCTGCAATTGT | 40 | 2337 |

TABLE 33

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) | SEQ ID NO |
|---|---|---|---|---|---|---|---|
| 1201142 | 1963 | 1982 | 17754 | 17773 | GCCACATATAGGGTCCTTTA | 6 | 66 |
| 1270215 | 427 | 446 | 16218 | 16237 | CAGCCAAGGTTCGCCATAAT | 19* | 2338 |
| 1270216 | 503 | 522 | 16294 | 16313 | CCATCCTCCAGGCTTCGGGC | 13* | 2339 |
| 1270221 | 511 | 530 | 16302 | 16321 | CCAGTGTTCCATCCTCCAGG | 4* | 2340 |
| 1270222 | 514 | 533 | 16305 | 16324 | CCCCCAGTGTTCCATCCTCC | 6* | 2341 |
| 1270227 | 1331 | 1350 | 17122 | 17141 | GTTTTCCAGTGCCCATCAGT | 13 | 2342 |
| 1270228 | 1333 | 1352 | 17124 | 17143 | ATGTTTTCCAGTGCCCATCA | 9 | 2343 |
| 1270233 | 1339 | 1358 | 17130 | 17149 | TACTCTATGTTTTCCAGTGC | 19 | 2344 |
| 1270234 | 1422 | 1441 | 17213 | 17232 | TGCTGTTATACTTTTACTGG | 6 | 2345 |
| 1270239 | 1429 | 1448 | 17220 | 17239 | GGTTATTTGCTGTTATACTT | 3 | 2346 |
| 1270240 | 1452 | 1471 | 17243 | 17262 | AAAATAAGTCCAGATTAACC | 66 | 2347 |
| 1270245 | 1459 | 1478 | 17250 | 17269 | AAGTCCAAAATAAGTCCAG | 25 | 2348 |
| 1270246 | 1509 | 1528 | 17300 | 17319 | AGGTATTTCAGACTGTTCTG | 7 | 2349 |
| 1270251 | 1516 | 1535 | 17307 | 17326 | CAGGCAAAGGTATTTCAGAC | 14 | 2350 |
| 1270252 | 1517 | 1536 | 17308 | 17327 | CCAGGCAAAGGTATTTCAGA | 16 | 2351 |

TABLE 33-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) | SEQ ID NO |
|---|---|---|---|---|---|---|---|
| 1270257 | 1567 | 1586 | 17358 | 17377 | GATAGGGCATTAGTATACTG | 4 | 2352 |
| 1270258 | 1569 | 1588 | 17360 | 17379 | AAGATAGGGCATTAGTATAC | 28 | 2353 |
| 1270263 | 1625 | 1644 | 17416 | 17435 | GTTGTCGGGTTTTCTTAAAA | 12 | 2354 |
| 1270264 | 1820 | 1839 | 17611 | 17630 | CAGTGTTGTGACAATATTTA | 7 | 2355 |
| 1270269 | 1844 | 1863 | 17635 | 17654 | GAATATGTCCTCTAGCCAGA | 23 | 2356 |
| 1270270 | 1849 | 1868 | 17640 | 17659 | ACTGTGAATATGTCCTCTAG | 6 | 2357 |
| 1270275 | 1878 | 1897 | 17669 | 17688 | AGCCTTTCATATATGTTACA | 18 | 2358 |
| 1270276 | 1880 | 1899 | 17671 | 17690 | GAAGCCTTTCATATATGTTA | 8 | 2359 |
| 1270281 | 1964 | 1983 | 17755 | 17774 | TGCCACATATAGGGTCCTTT | 5 | 2360 |
| 1270287 | 1999 | 2018 | 17790 | 17809 | AGCTGCCTTAATTACCTATA | 14 | 2361 |
| 1270293 | 2011 | 2030 | 17802 | 17821 | AATTTACTTTTCAGCTGCCT | 10 | 2362 |
| 1270299 | 2105 | 2124 | 17896 | 17915 | GGTGCTTTCACAACTGCAGC | 37 | 2363 |
| 1270305 | 2171 | 2190 | 17962 | 17981 | GAAATGCAAGCAGTTCTTTT | 23 | 2364 |
| 1270311 | 2206 | 2225 | 17997 | 18016 | ATTCTGGTTTTTGACAATTA | 11 | 2365 |
| 1270317 | 2325 | 2344 | 18116 | 18135 | ATTTCTTTTTCCACTTCAAA | 15 | 2366 |
| 1270323 | 2415 | 2434 | 18206 | 18225 | TAATAACATTGCAGAAAAGT | 65 | 2367 |
| 1270329 | 2569 | 2588 | 18360 | 18379 | CCACATATTAAGTATTCAGT | 3 | 2368 |
| 1270335 | 2606 | 2625 | 18397 | 18416 | GCACATTGTAAGCCTAAGGA | 2 | 2369 |
| 1270341 | N/A | N/A | 4900 | 4919 | TGATTTTTCCAGAAGTTTAA | 42 | 2370 |
| 1270347 | N/A | N/A | 4936 | 4955 | ATTTTTTCCTTTCTTCTACA | 78 | 2371 |
| 1270353 | N/A | N/A | 5010 | 5029 | TTACTGGTTAGCTTTTTTTC | 44 | 2372 |
| 1270359 | N/A | N/A | 5075 | 5094 | GGAAGACTTGTGTTAGATAT | 7 | 2373 |
| 1270365 | N/A | N/A | 5129 | 5148 | GACTCATCATTTTGCCATTT | 10 | 2374 |
| 1270371 | N/A | N/A | 5197 | 5216 | TTTGGTTATTTTAATAGATG | 62 | 2375 |
| 1270377 | N/A | N/A | 5522 | 5541 | CATTGCAGGTAAGTTCTCAG | 9 | 2376 |
| 1270383 | N/A | N/A | 5534 | 5553 | GTTTGTTTCTTCCATTGCAG | 8 | 2377 |
| 1270389 | N/A | N/A | 5603 | 5622 | CATTTAGGCTCTTTTCCAGG | 20 | 2378 |
| 1270395 | N/A | N/A | 5615 | 5634 | CCTGGTGTTATACATTTAGG | 68 | 2379 |
| 1270401 | N/A | N/A | 5665 | 5684 | TTACATAATGTTCATTTCAG | 50 | 2380 |
| 1270407 | N/A | N/A | 5722 | 5741 | TTTACTTGTCAGTTTTTCCC | 26 | 2381 |
| 1270413 | N/A | N/A | 5787 | 5806 | TCCTTTCAGATTTTTCACAT | 38 | 2382 |
| 1270419 | N/A | N/A | 5800 | 5819 | TTTTCTGTGCTTTTCCTTTC | 20 | 2383 |
| 1270425 | N/A | N/A | 5863 | 5882 | GTGAGAGCAATATATTCACC | 69 | 2384 |
| 1270431 | N/A | N/A | 6220 | 6239 | TACAATCTGTTGTGGTTCAG | 19 | 2385 |
| 1270437 | N/A | N/A | 6491 | 6510 | GTTATGTTATTATTGTTATT | 25 | 2386 |
| 1270443 | N/A | N/A | 6566 | 6585 | TCAGAGAATCTTTCACCTTG | 21 | 2387 |

TABLE 33-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) | SEQ ID NO |
|---|---|---|---|---|---|---|---|
| 1270449 | N/A | N/A | 7288 | 7307 | TTGAAGCTTAATTAGTTACA | 22 | 2388 |
| 1270455 | N/A | N/A | 8035 | 8054 | CACTTTCTTTTTATTTCTTT | 23 | 2389 |
| 1270461 | N/A | N/A | 8158 | 8177 | ATCTTTCTATTTGTGTCTCC | 19

TABLE 34-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) | SEQ ID NO |
|---|---|---|---|---|---|---|---|
| 1270235 | 1423 | 1442 | 17214 | 17233 | TTGCTGTTATACTTTTACTG | 6 | 2418 |
| 1270241 | 1454 | 1473 | 17245 | 17264 | CAAAAATAAGTCCAGATTAA | 60 | 2419 |
| 1270247 | 1511 | 1530 | 17302 | 17321 | AAAGGTATTTCAGACTGTTC | 9 | 2420 |
| 1270253 | 1519 | 1538 | 17310 | 17329 | ATCCAGGCAAAGGTATTTCA | 13 | 2421 |
| 1270259 | 1615 | 1634 | 17406 | 17425 | TTTCTTAAAATGGAAAATAT | 77 | 2422 |
| 1270265 | 1822 | 1841 | 17613 | 17632 | TTCAGTGTTGTGACAATATT | 5 | 2423 |
| 1270271 | 1850 | 1869 | 17641 | 17660 | CACTGTGAATATGTCCTCTA | 7 | 2424 |
| 1270277 | 1894 | 1913 | 17685 | 17704 | GATTTCAAGTCCCAGAAGCC | 21 | 2425 |
| 1270282 | 1966 | 1985 | 17757 | 17776 | AATGCCACATATAGGGTCCT | 13 | 2426 |
| 1270283 | 1970 | 1989 | 17761 | 17780 | AAGGAATGCCACATATAGGG | 6 | 2427 |
| 1270288 | 2004 | 2023 | 17795 | 17814 | TTTTCAGCTGCCTTAATTAC | 72 | 2428 |
| 1270289 | 2005 | 2024 | 17796 | 17815 | CTTTTCAGCTGCCTTAATTA | 56 | 2429 |
| 1270294 | 2065 | 2084 | 17856 | 17875 | TTCTGGTTTCCAGGTAAATG | 19 | 2430 |
| 1270295 | 2067 | 2086 | 17858 | 17877 | CATTCTGGTTTCCAGGTAAA | 13 | 2431 |
| 1270300 | 2144 | 2163 | 17935 | 17954 | CACTGACCATTTTTAATTA | 55 | 2432 |
| 1270301 | 2146 | 2165 | 17937 | 17956 | CACACTGACCATTTTTAAT | 32 | 2433 |
| 1270306 | 2196 | 2215 | 17987 | 18006 | TTGACAATTATGAGACAGAA | 8 | 2434 |
| 1270307 | 2198 | 2217 | 17989 | 18008 | TTTTGACAATTATGAGACAG | 17 | 2435 |
| 1270312 | 2269 | 2288 | 18060 | 18079 | TTTTAGATTGTCTCCCTATT | 50 | 2436 |
| 1270313 | 2288 | 2307 | 18079 | 18098 | ATCTCCAACCTAAGATATTT | 57 | 2437 |
| 1270318 | 2329 | 2348 | 18120 | 18139 | CAGAATTTCTTTTTCCACTT | 13 | 2438 |
| 1270319 | 2355 | 2374 | 18146 | 18165 | AATAATTTTACTTTAATTAA | 110 | 2439 |
| 1270324 | 2417 | 2436 | 18208 | 18227 | AATAATAACATTGCAGAAAA | 92 | 2440 |
| 1270325 | 2418 | 2437 | 18209 | 18228 | CAATAATAACATTGCAGAAA | 72 | 2441 |
| 1270330 | 2571 | 2590 | 18362 | 18381 | TCCCACATATTAAGTATTCA | 22 | 2442 |
| 1270331 | 2572 | 2591 | 18363 | 18382 | TTCCCACATATTAAGTATTC | 36 | 2443 |
| 1270336 | 2608 | 2627 | 18399 | 18418 | GTGCACATTGTAAGCCTAAG | 44 | 2444 |
| 1270337 | 2610 | 2629 | 18401 | 18420 | CAGTGCACATTGTAAGCCTA | 24 | 2445 |
| 1270342 | N/A | N/A | 4906 | 4925 | CGTTGTTGATTTTTCCAGAA | 2 | 2446 |
| 1270343 | N/A | N/A | 4907 | 4926 | GCGTTGTTGATTTTTCCAGA | 2 | 2447 |
| 1270348 | N/A | N/A | 4938 | 4957 | TGATTTTTCCTTTCTTCTA | 61 | 2448 |
| 1270349 | N/A | N/A | 4944 | 4963 | CACTGGTGATTTTTCCTTT | 44 | 2449 |
| 1270354 | N/A | N/A | 5011 | 5030 | CTTACTGGTTAGCTTTTTTT | 70 | 2450 |
| 1270355 | N/A | N/A | 5071 | 5090 | GACTTGTGTTAGATATAAAT | 30 | 2451 |
| 1270360 | N/A | N/A | 5078 | 5097 | TGTGGAAGACTTGTGTTAGA | 10 | 2452 |
| 1270361 | N/A | N/A | 5079 | 5098 | GTGTGGAAGACTTGTGTTAG | 24 | 2453 |

TABLE 34-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) | SEQ ID NO |
|---|---|---|---|---|---|---|---|
| 1270366 | N/A | N/A | 5130 | 5149 | TGACTCATCATTTTGCCATT | 20 | 2454 |
| 1270367 | N/A | N/A | 5135 | 5154 | GTAAATGACTCATCATTTTG | 42 | 2455 |
| 1270372 | N/A | N/A | 5200 | 5219 | TATTTTGGTTATTTTAATAG | 122 | 2456 |
| 1270373 | N/A | N/A | 5515 | 5534 | GGTAAGTTCTCAGGAGTGGG | 22 | 2457 |
| 1270378 | N/A | N/A | 5523 | 5542 | CCATTGCAGGTAAGTTCTCA | 6 | 2458 |
| 1270379 | N/A | N/A | 5525 | 5544 | TTCCATTGCAGGTAAGTTCT | 24 | 2459 |
| 1270384 | N/A | N/A | 5536 | 5555 | TTGTTTGTTTCTTCCATTGC | 10 | 2460 |
| 1270385 | N/A | N/A | 5537 | 5556 | TTTGTTTGTTTCTTCCATTG | 7 | 2461 |
| 1270390 | N/A | N/A | 5604 | 5623 | ACATTTAGGCTCTTTTCCAG | 25 | 2462 |
| 1270391 | N/A | N/A | 5605 | 5624 | TACATTTAGGCTCTTTTCCA | 27 | 2463 |
| 1270396 | N/A | N/A | 5616 | 5635 | CCCTGGTGTTATACATTTAG | 73 | 2464 |
| 1270397 | N/A | N/A | 5618 | 5637 | TGCCCTGGTGTTATACATTT | 82 | 2465 |
| 1270402 | N/A | N/A | 5671 | 5690 | TAGTGGTTACATAATGTTCA | 12 | 2466 |
| 1270403 | N/A | N/A | 5673 | 5692 | TTTAGTGGTTACATAATGTT | 49 | 2467 |
| 1270408 | N/A | N/A | 5777 | 5796 | TTTTTCACATATGCGTTCAC | 24 | 2468 |
| 1270409 | N/A | N/A | 5778 | 5797 | ATTTTTCACATATGCGTTCA | 26 | 2469 |
| 1270414 | N/A | N/A | 5790 | 5809 | TTTTCCTTTCAGATTTTTCA | 46 | 2470 |
| 1270415 | N/A | N/A | 5793 | 5812 | TGCTTTTCCTTTCAGATTTT | 20 | 2471 |
| 1270420 | N/A | N/A | 5852 | 5871 | ATATTCACCAAAGGAAAATT | 68 | 2472 |
| 1270426 | N/A | N/A | 5867 | 5886 | CTTAGTGAGAGCAATATATT | 62 | 2473 |
| 1270432 | N/A | N/A | 6221 | 6240 | GTACAATCTGTTGTGGTTCA | 12 | 2474 |
| 1270438 | N/A | N/A | 6492 | 6511 | TGTTATGTTATTATTGTTAT | 34 | 2475 |
| 1270444 | N/A | N/A | 6571 | 6590 | GAAGTTCAGAGAATCTTTCA | 85 | 2476 |
| 1270450 | N/A | N/A | 7383 | 7402 | AAGAACTTATCCCAAGGTTG | 30 | 2477 |
| 1270456 | N/A | N/A | 8036 | 8055 | GCACTTTCTTTTTATTTCTT | 3 | 2478 |
| 1270462 | N/A | N/A | 8164 | 8183 | CAGGCTATCTTTCTATTTGT | 47 | 2479 |
| 1270468 | N/A | N/A | 8171 | 8190 | ATGAGCACAGGCTATCTTTC | 54 | 2480 |
| 1270474 | N/A | N/A | 9030 | 9049 | CTCTTAGATTTTGGACGGG | 6 | 2481 |
| 1270480 | N/A | N/A | 9040 | 9059 | TGCTTTGGATCTCTTAGATT | 11 | 2482 |
| 1270486 | N/A | N/A | 9352 | 9371 | GGTAGTTTTCAAATCAACA | 8 | 2483 |
| 1270492 | N/A | N/A | 9419 | 9438 | GGTATAATTTTTTTACCTGG | 54 | 2484 |
| 1270498 | N/A | N/A | 9690 | 9709 | CTCTATTAATAGGTTAGGAA | 60 | 2485 |
| 1270504 | N/A | N/A | 9980 | 9999 | GAGTATCAATTTAAGCAATT | 45 | 2486 |
| 1270510 | N/A | N/A | 11331 | 11350 | TGTTTCTTTTCTGGTAGAGA | 7 | 2487 |
| 1270516 | N/A | N/A | 14377 | 14396 | TTTCCTCTGTGCTTATTATT | 54 | 2488 |
| 1270522 | N/A | N/A | 15160 | 15179 | TGGAGGCTCTTTTAGGTGGG | 46 | 2489 |

TABLE 34-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) | SEQ ID NO |
|---|---|---|---|---|---|---|---|
| 1270528 | N/A | N/A | 15513 | 15532 | ATATACCATGTACAGTTCAA | 40 | 2490 |
| 1270534 | N/A | N/A | 15619 | 15638 | GATCTGCAATTGTTTTCTC | 42 | 2491 |

TABLE 35

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) | SEQ ID NO |
|---|---|---|---|---|---|---|---|
| 1201142 | 1963 | 1982 | 17754 | 17773 | GCCACATATAGGGTCCTTTA | 6 | 66 |
| 1270421 | N/A | N/A | 5854 | 5873 | ATATATTCACCAAAGGAAAA | 73 | 2492 |
| 1270427 | N/A | N/A | 6214 | 6233 | CTGTTGTGGTTCAGCTAAAC | 32 | 2493 |
| 1270433 | N/A | N/A | 6222 | 6241 | TGTACAATCTGTTGTGGTTC | 24 | 2494 |
| 1270439 | N/A | N/A | 6495 | 6514 | TTCTGTTATGTTATTATTGT | 45 | 2495 |
| 1270445 | N/A | N/A | 6573 | 6592 | CTGAAGTTCAGAGAATCTTT | 50 | 2496 |
| 1270451 | N/A | N/A | 7386 | 7405 | AGTAAGAACTTATCCCAAGG | 28 | 2497 |
| 1270457 | N/A | N/A | 8037 | 8056 | GGCACTTTCTTTTTATTTCT | 8 | 2498 |
| 1270463 | N/A | N/A | 8165 | 8184 | ACAGGCTATCTTTCTATTTG | 27 | 2499 |
| 1270469 | N/A | N/A | 8173 | 8192 | CCATGAGCACAGGCTATCTT | 59 | 2500 |
| 1270475 | N/A | N/A | 9032 | 9051 | ATCTCTTAGATTTTGGACG | 38 | 2501 |
| 1270481 | N/A | N/A | 9041 | 9060 | TTGCTTTGGATCTCTTAGAT | 29 | 2502 |
| 1270487 | N/A | N/A | 9356 | 9375 | GGGTGGTAGTTTTTCAAATC | 30 | 2503 |
| 1270493 | N/A | N/A | 9420 | 9439 | AGGTATAATTTTTTTACCTG | 123 | 2504 |
| 1270499 | N/A | N/A | 9693 | 9712 | GAGCTCTATTAATAGGTTAG | 26 | 2505 |
| 1270505 | N/A | N/A | 9981 | 10000 | GGAGTATCAATTTAAGCAAT | 26 | 2506 |
| 1270511 | N/A | N/A | 11333 | 11352 | GTTGTTTCTTTTCTGGTAGA | 16 | 2507 |
| 1270517 | N/A | N/A | 14379 | 14398 | TATTTCCTCTGTGCTTATTA | 56 | 2508 |
| 1270523 | N/A | N/A | 15163 | 15182 | TTTTGGAGGCTCTTTTAGGT | 30 | 2509 |
| 1270529 | N/A | N/A | 15514 | 15533 | CATATACCATGTACAGTTCA | 48 | 2510 |
| 1270535 | N/A | N/A | 15621 | 15640 | ATGATCTGCAATTGTTTTTC | 37 | 2511 |
| 1270540 | 1560 | 1579 | 17351 | 17370 | CATTAGTATACTGAGCTCTA | 39 | 2512 |
| 1270541 | 1842 | 1861 | 17633 | 17652 | ATATGTCCTCTAGCCAGAGG | 81 | 2513 |
| 1270542 | 1959 | 1978 | 17750 | 17769 | CATATAGGGTCCTTTAAACA | 61 | 2514 |
| 1270543 | 2603 | 2622 | 18394 | 18413 | CATTGTAAGCCTAAGGACCA | 52 | 2515 |
| 1270544 | N/A | N/A | 6215 | 6234 | TCTGTTGTGGTTCAGCTAAA | 30 | 2516 |
| 1270545 | N/A | N/A | 7279 | 7298 | AATTAGTTACATCGGGAAGG | 50 | 2517 |
| 1270546 | N/A | N/A | 9025 | 9044 | AGATTTTGGACGGGAGATT | 38 | 2518 |
| 1270547 | 504 | 523 | 16295 | 16314 | TCCATCCTCCAGGCTTCGGG | 4* | 2519 |

TABLE 35-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) | SEQ ID NO |
|---|---|---|---|---|---|---|---|
| 1270548 | 1332 | 1351 | 17123 | 17142 | TGTTTTCCAGTGCCCATCAG | 14 | 2520 |
| 1270549 | 1453 | 1472 | 17244 | 17263 | AAAAATAAGTCCAGATTAAC | 84 | 2521 |
| 1270550 | 1510 | 1529 | 17301 | 17320 | AAGGTATTTCAGACTGTTCT | 6 | 2522 |
| 1270551 | 1809 | 1828 | 17600 | 17619 | CAATATTTACTCTTGTTGAA | 54 | 2523 |
| 1270552 | 1993 | 2012 | 17784 | 17803 | CTTAATTACCTATAGTTTAA | 60 | 2524 |
| 1270553 | 2066 | 2085 | 17857 | 17876 | ATTCTGGTTTCCAGGTAAAT | 17 | 2525 |
| 1270554 | 2197 | 2216 | 17988 | 18007 | TTTGACAATTATGAGACAGA | 16 | 2526 |
| 1270555 | 2356 | 2375 | 18147 | 18166 | GAATAATTTTACTTTAATTA | 106 | 2527 |
| 1270556 | 2416 | 2435 | 18207 | 18226 | ATAATAACATTGCAGAAAAG | 63 | 2528 |
| 1270557 | 2570 | 2589 | 18361 | 18380 | CCCACATATTAAGTATTCAG | 19 | 2529 |
| 1270558 | N/A | N/A | 4898 | 4917 | ATTTTTCCAGAAGTTTAACA | 52 | 2530 |
| 1270559 | N/A | N/A | 5120 | 5139 | TTTTGCCATTTATCTATTAT | 53 | 2531 |
| 1270560 | N/A | N/A | 5516 | 5535 | AGGTAAGTTCTCAGGAGTGG | 14 | 2532 |
| 1270561 | N/A | N/A | 5531 | 5550 | TGTTTCTTCCATTGCAGGTA | 4 | 2533 |
| 1270562 | N/A | N/A | 5598 | 5617 | AGGCTCTTTTCCAGGTGTTC | 7 | 2534 |
| 1270563 | N/A | N/A | 5609 | 5628 | GTTATACATTTAGGCTCTTT | 2 | 2535 |
| 1270564 | N/A | N/A | 5635 | 5654 | ATAATTTTCTTAGCTACTGC | 37 | 2536 |
| 1270565 | N/A | N/A | 5791 | 5810 | CTTTTCCTTTCAGATTTTTC | 28 | 2537 |
| 1270566 | N/A | N/A | 5853 | 5872 | TATATTCACCAAAGGAAAAT | 89 | 2538 |
| 1270567 | N/A | N/A | 6489 | 6508 | TATGTTATTATTGTTATTTG | 79 | 2539 |
| 1270568 | N/A | N/A | 7384 | 7403 | TAAGAACTTATCCCAAGGTT | 29 | 2540 |
| 1270569 | N/A | N/A | 9035 | 9054 | TGGATCTCTTAGATTTTTGG | 26 | 2541 |
| 1270570 | N/A | N/A | 9979 | 9998 | AGTATCAATTTAAGCAATTG | 51 | 2542 |
| 1270571 | N/A | N/A | 14378 | 14397 | ATTTCCTCTGTGCTTATTAT | 40 | 2543 |
| 1270572 | N/A | N/A | 15512 | 15531 | TATACCATGTACAGTTCAAT | 33 | 2544 |
| 1270573 | 426 | 445 | 16217 | 16236 | AGCCAAGGTTCGCCATAATG | 20* | 2545 |
| 1270574 | 1568 | 1587 | 17359 | 17378 | AGATAGGGCATTAGTATACT | 21 | 2546 |
| 1270575 | 1972 | 1991 | 17763 | 17782 | GAAAGGAATGCCACATATAG | 33 | 2547 |
| 1270576 | 2611 | 2630 | 18402 | 18421 | TCAGTGCACATTGTAAGCCT | 11 | 2548 |
| 1270577 | N/A | N/A | 6223 | 6242 | ATGTACAATCTGTTGTGGTT | 10 | 2549 |
| 1270578 | N/A | N/A | 7287 | 7306 | TGAAGCTTAATTAGTTACAT | 38 | 2550 |
| 1270579 | 1340 | 1359 | 17131 | 17150 | CTACTCTATGTTTTCCAGTG | 5 | 2551 |
| 1270580 | 1428 | 1447 | 17219 | 17238 | GTTATTTGCTGTTATACTTT | 5 | 2552 |
| 1270581 | 1461 | 1480 | 17252 | 17271 | CTAAGTCCAAAAATAAGTCC | 54 | 2553 |
| 1270582 | 1518 | 1537 | 17309 | 17328 | TCCAGGCAAAGGTATTTCAG | 28 | 2554 |
| 1270583 | 1624 | 1643 | 17415 | 17434 | TTGTCGGGTTTTCTTAAAAT | 47 | 2555 |

TABLE 35-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) | SEQ ID NO |
|---|---|---|---|---|---|---|---|
| 1270584 | 1828 | 1847 | 17619 | 17638 | CAGAGGTTCAGTGTTGTGAC | 5 | 2556 |
| 1270585 | 1857 | 1876 | 17648 | 17667 | TTATGTTCACTGTGAATATG | 31 | 2557 |
| 1270586 | 1883 | 1902 | 17674 | 17693 | CCAGAAGCCTTTCATATATG | 8 | 2558 |
| 1270587 | 1905 | 1924 | 17696 | 17715 | CCCAAACATTTGATTTCAAG | 67 | 2559 |
| 1270588 | 2083 | 2102 | 17874 | 17893 | TCCTGTATGTCAAAATCATT | 59 | 2560 |
| 1270589 | 2170 | 2189 | 17961 | 17980 | AAATGCAAGCAGTTCTTTTC | 44 | 2561 |
| 1270590 | 2424 | 2443 | 18215 | 18234 | GCAAGCCAATAATAACATTG | 9 | 2562 |
| 1270591 | 2578 | 2597 | 18369 | 18388 | AAGGGTTTCCCACATATTAA | 46 | 2563 |
| 1270592 | N/A | N/A | 4896 | 4915 | TTTTCCAGAAGTTTAACATA | 74 | 2564 |
| 1270593 | N/A | N/A | 5524 | 5543 | TCCATTGCAGGTAAGTTCTC | 28 | 2565 |
| 1270594 | N/A | N/A | 5606 | 5625 | ATACATTTAGGCTCTTTTCC | 22 | 2566 |
| 1270595 | N/A | N/A | 5617 | 5636 | GCCCTGGTGTTATACATTTA | 89 | 2567 |
| 1270596 | N/A | N/A | 5799 | 5818 | TTTCTGTGCTTTTCCTTTCA | 12 | 2568 |

TABLE 36

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) | SEQ ID NO |
|---|---|---|---|---|---|---|---|
| 1201142 | 1963 | 1982 | 17754 | 17773 | GCCACATATAGGGTCCTTTA | 6 | 66 |
| 1270597 | N/A | N/A | 5866 | 5885 | TTAGTGAGAGCAATATATTC | 63 | 2569 |
| 1270598 | N/A | N/A | 6497 | 6516 | ACTTCTGTTATGTTATTATT | 32 | 2570 |
| 1270599 | N/A | N/A | 6572 | 6591 | TGAAGTTCAGAGAATCTTTC | 110 | 2571 |
| 1270600 | N/A | N/A | 7392 | 7411 | AGAGCTAGTAAGAACTTATC | 49 | 2572 |
| 1270601 | N/A | N/A | 9043 | 9062 | GTTTGCTTTGGATCTCTTAG | 15 | 2573 |
| 1270602 | N/A | N/A | 9357 | 9376 | AGGGTGGTAGTTTTTCAAAT | 6 | 2574 |
| 1270603 | N/A | N/A | 9987 | 10006 | CAAGTGGGAGTATCAATTTA | 40 | 2575 |
| 1270604 | N/A | N/A | 15166 | 15185 | GGTTTTTGGAGGCTCTTTTA | 13 | 2576 |
| 1270605 | N/A | N/A | 15628 | 15647 | TGCTGGGATGATCTGCAATT | 69 | 2577 |
| 1270606 | 415 | 434 | N/A | N/A | GCCATAATGACTGCTCTGCC | 13* | 2578 |
| 1270607 | 1956 | 1975 | 17747 | 17766 | ATAGGGTCCTTTAAACATCT | 13 | 2579 |
| 1270608 | N/A | N/A | 6212 | 6231 | GTTGTGGTTCAGCTAAACTA | 66 | 2580 |
| 1270609 | N/A | N/A | 9022 | 9041 | TTTTTGGACGGGAGATTTAG | 73 | 2581 |
| 1270610 | N/A | N/A | 9684 | 9703 | TAATAGGTTAGGAAGAAAAG | 105 | 2582 |
| 1270611 | N/A | N/A | 9685 | 9704 | TTAATAGGTTAGGAAGAAAA | 88 | 2583 |
| 1270612 | 501 | 520 | 16292 | 16311 | ATCCTCCAGGCTTCGGGCGC | 16* | 2584 |
| 1270613 | 1417 | 1436 | 17208 | 17227 | TTATACTTTTACTGGCCTGG | 51 | 2585 |

TABLE 36-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) | SEQ ID NO |
|---|---|---|---|---|---|---|---|
| 1270614 | 1450 | 1469 | 17241 | 17260 | AATAAGTCCAGATTAACCAA | 57 | 2586 |
| 1270615 | 1507 | 1526 | 17298 | 17317 | GTATTTCAGACTGTTCTGAG | 4 | 2587 |
| 1270616 | 1806 | 1825 | 17597 | 17616 | TATTTACTCTTGTTGAACAG | 40 | 2588 |
| 1270617 | 1891 | 1910 | 17682 | 17701 | TTCAAGTCCCAGAAGCCTTT | 20 | 2589 |
| 1270618 | 1892 | 1911 | 17683 | 17702 | TTTCAAGTCCCAGAAGCCTT | 18 | 2590 |
| 1270619 | 1990 | 2009 | 17781 | 17800 | AATTACCTATAGTTTAAAGA | 65 | 2591 |
| 1270620 | 2063 | 2082 | 17854 | 17873 | CTGGTTTCCAGGTAAATGGA | 21 | 2592 |
| 1270621 | 2100 | 2119 | 17891 | 17910 | TTTCACAACTGCAGCTCTCC | 41 | 2593 |
| 1270622 | 2194 | 2213 | 17985 | 18004 | GACAATTATGAGACAGAAAT | 11 | 2594 |
| 1270623 | 2286 | 2305 | 18077 | 18096 | CTCCAACCTAAGATATTTTT | 38 | 2595 |
| 1270624 | 2413 | 2432 | 18204 | 18223 | ATAACATTGCAGAAAAGTAA | 79 | 2596 |
| 1270625 | N/A | N/A | 4996 | 5015 | TTTTTCACTGTAAGACCTTC | 38 | 2597 |
| 1270626 | N/A | N/A | 4997 | 5016 | TTTTTTCACTGTAAGACCTT | 72 | 2598 |
| 1270627 | N/A | N/A | 5069 | 5088 | CTTGTGTTAGATATAAATAA | 74 | 2599 |
| 1270628 | N/A | N/A | 5070 | 5089 | ACTTGTGTTAGATATAAATA | 75 | 2600 |
| 1270629 | N/A | N/A | 5528 | 5547 | TTCTTCCATTGCAGGTAAGT | 19 | 2601 |
| 1270630 | N/A | N/A | 5595 | 5614 | CTCTTTTCCAGGTGTTCTAA | 12 | 2602 |
| 1270631 | N/A | N/A | 5632 | 5651 | ATTTTCTTAGCTACTGCCCT | 42 | 2603 |
| 1270632 | N/A | N/A | 5660 | 5679 | TAATGTTCATTTCAGTTAAT | 58 | 2604 |
| 1270633 | N/A | N/A | 5709 | 5728 | TTTTCCCCACATATCACAGG | 39 | 2605 |
| 1270634 | N/A | N/A | 5850 | 5869 | ATTCACCAAAGGAAAATTAA | 58 | 2606 |
| 1270635 | N/A | N/A | 6561 | 6580 | GAATCTTTCACCTTGGTTTG | 41 | 2607 |
| 1270636 | N/A | N/A | 7381 | 7400 | GAACTTATCCCAAGGTTGTA | 55 | 2608 |
| 1270637 | N/A | N/A | 8154 | 8173 | TTCTATTTGTGTCTCCTTGA | 32 | 2609 |
| 1270638 | N/A | N/A | 9411 | 9430 | TTTTTTACCTGGAAAATCTC | 84 | 2610 |
| 1270639 | N/A | N/A | 9976 | 9995 | ATCAATTTAAGCAATTGTTA | 58 | 2611 |
| 1270640 | N/A | N/A | 14375 | 14394 | TCCTCTGTGCTTATTATTCA | 50 | 2612 |
| 1270641 | N/A | N/A | 15509 | 15528 | ACCATGTACAGTTCAATGGT | 79 | 2613 |
| 1270642 | 1571 | 1590 | 17362 | 17381 | CTAAGATAGGGCATTAGTAT | 30 | 2614 |
| 1270643 | 1975 | 1994 | 17766 | 17785 | AAAGAAAGGAATGCCACATA | 30 | 2615 |
| 1270644 | 2614 | 2633 | 18405 | 18424 | GATTCAGTGCACATTGTAAG | 10 | 2616 |
| 1270645 | N/A | N/A | 6226 | 6245 | GATATGTACAATCTGTTGTG | 22 | 2617 |
| 1270646 | N/A | N/A | 9698 | 9717 | ATCAGGAGCTCTATTAATAG | 39 | 2618 |
| 1270647 | N/A | N/A | 9699 | 9718 | AATCAGGAGCTCTATTAATA | 55 | 2619 |
| 1270648 | 519 | 538 | 16310 | 16329 | GGCTGCCCCCAGTGTTCCAT | 27* | 2620 |
| 1270649 | 520 | 539 | 16311 | 16330 | CGGCTGCCCCCAGTGTTCCA | 36* | 2621 |

TABLE 36-continued

Reduction of PRNP RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PRNP (% UTC) | SEQ ID NO |
|---|---|---|---|---|---|---|---|
| 1270650 | 1343 | 1362 | 17134 | 17153 | GGTCTACTCTATGTTTTCCA | 51 | 2622 |
| 1270651 | 1431 | 1450 | 17222 | 17241 | ATGGTTATTTGCTGTTATAC | 8 | 2623 |
| 1270652 | 1627 | 1646 | 17418 | 17437 | ATGTTGTCGGGTTTTCTTAA | 3 | 2624 |
| 1270653 | 1831 | 1850 | 17622 | 17641 | AGCCAGAGGTTCAGTGTTGT | 32 | 2625 |
| 1270654 | 1908 | 1927 | 17699 | 17718 | ATTCCCAAACATTTGATTTC | 83 | 2626 |
| 1270655 | 2086 | 2105 | 17877 | 17896 | CTCTCCTGTATGTCAAAATC | 66 | 2627 |
| 1270656 | 2114 | 2133 | 17905 | 17924 | TATGATGATGGTGCTTTCAC | 11 | 2628 |
| 1270657 | 2208 | 2227 | 17999 | 18018 | TAATTCTGGTTTTTGACAAT | 47 | 2629 |
| 1270658 | 2271 | 2290 | 18062 | 18081 | TTTTTTAGATTGTCTCCCTA | 56 | 2630 |
| 1270659 | 2581 | 2600 | 18372 | 18391 | CAAAAGGGTTTCCCACATAT | 27 | 2631 |
| 1270660 | N/A | N/A | 4947 | 4966 | TTCCACTGGTGATTTTTCC | 35 | 2632 |
| 1270661 | N/A | N/A | 4948 | 4967 | TTTCCACTGGTGATTTTTC | 52 | 2633 |
| 1270662 | N/A | N/A | 5012 | 5031 | CCTTACTGGTTAGCTTTTTT | 40 | 2634 |
| 1270663 | N/A | N/A | 5013 | 5032 | CCCTTACTGGTTAGCTTTTT | 49 | 2635 |
| 1270664 | N/A | N/A | 5083 | 5102 | TTCGGTGTGGAAGACTTGTG | 37 | 2636 |
| 1270665 | N/A | N/A | 5084 | 5103 | TTTCGGTGTGGAAGACTTGT | 41 | 2637 |
| 1270666 | N/A | N/A | 5527 | 5546 | TCTTCCATTGCAGGTAAGTT | 34 | 2638 |
| 1270667 | N/A | N/A | 5620 | 5639 | ACTGCCCTGGTGTTATACAT | 61 | 2639 |
| 1270668 | N/A | N/A | 5646 | 5665 | GTTAATGTGTCATAATTTTC | 23 | 2640 |
| 1270669 | N/A | N/A | 5675 | 5694 | TTTTTAGTGGTTACATAATG | 59 | 2641 |
| 1270670 | N/A | N/A | 5676 | 5695 | ATTTTTAGTGGTTACATAAT | 55 | 2642 |
| 1270671 | N/A | N/A | 5723 | 5742 | TTTTACTTGTCAGTTTTTCC | 16 | 2643 |
| 1270672 | N/A | N/A | 5724 | 5743 | TTTTTACTTGTCAGTTTTTC | 33 | 2644 |
| 1270673 | N/A | N/A | 5789 | 5808 | TTTCCTTTCAGATTTTTCAC | 47 | 2645 |

Example 3: Effect of Modified Oligonucleotides on Human PRNP RNA In Vitro, Multiple Doses Modified oligonucleotides selected from the examples above were tested at various doses in A-431 cells. Cells were plated at a density of 10,000 cells per well and treated with modified oligonucleotide at various doses by free uptake, as specified in the tables below. After a treatment period of approximately 48 hours, total RNA was isolated from the cells and PRNP RNA levels were measured by quantitative real-time PCR using primer probe set RTS42354 as described in Example 1. PRNP RNA levels were normalized with RIBOGREEN®. Results are presented in the tables below as percent PRNP RNA relative to untreated control cells (UTC). The half maximal inhibitory concentration (IC$_{50}$) of each modified oligonucleotide is also presented. IC$_{50}$ was calculated using a linear regression on a log/linear plot of the data in Excel. The modified oligonucleotides marked with an asterisk (*) are complementary to the amplicon region of the primer probe set. Additional assays may be used to measure the potency and efficacy of the modified oligonucleotides complementary to the amplicon region.

TABLE 37

Dose-dependent reduction of human PRNP RNA expression in A-431 cells

| Compound ID | % UTC | | | | | IC50 (µM) |
|---|---|---|---|---|---|---|
| | 23 nM | 94 nM | 375 nM | 1500 nM | 6000 nM | |
| 1201120 | 98 | 51 | 18 | 6 | 2 | 0.2 |
| 1201138 | 98 | 93 | 36 | 19 | 15 | 0.4 |
| 1201142 | 84 | 58 | 30 | 13 | 8 | 0.2 |
| 1201145 | 92 | 88 | 70 | 34 | 13 | 0.7 |
| 1201154 | 68 | 42 | 19 | 7 | 4 | 0.1 |
| 1201255 | 64 | 55 | 31 | 15 | 8 | 0.1 |
| 1201276 | 75 | 46 | 15 | 5 | 3 | 0.1 |

TABLE 37-continued

Dose-dependent reduction of human PRNP RNA expression in A-431 cells

| Compound ID | 23 nM | 94 nM | 375 nM | 1500 nM | 6000 nM | IC50 (µM) |
|---|---|---|---|---|---|---|
| 1201288 | 101 | 62 | 31 | 22 | 13 | 0.3 |
| 1201293 | 80 | 57 | 21 | 7 | 4 | 0.1 |
| 1201294 | 84 | 64 | 37 | 19 | 11 | 0.2 |
| 1238797 | 100 | 77 | 45 | 27 | 14 | 0.4 |
| 1238863 | 64 | 38 | 8 | 2 | 1 | 0.04 |
| 1238864 | 74 | 27 | 8 | 3 | 1 | 0.04 |
| 1238995 | 103 | 59 | 32 | 21 | 11 | 0.3 |
| 1200977* | 92 | 68 | 46 | 27 | 21 | 0.4 |

TABLE 38

Dose-dependent reduction of human PRNP RNA expression in A-431 cells

| Compound ID | 23 nM | 94 nM | 375 nM | 1500 nM | 6000 nM | IC50 (µM) |
|---|---|---|---|---|---|---|
| 1201142 | 82 | 58 | 30 | 13 | 7 | 0.2 |
| 1238270 | 77 | 57 | 30 | 12 | 8 | 0.1 |
| 1238359 | 83 | 57 | 31 | 12 | 4 | 0.2 |
| 1238360 | 102 | 65 | 41 | 22 | 13 | 0.4 |
| 1238490 | 79 | 53 | 36 | 12 | 7 | 0.1 |
| 1238491 | 95 | 77 | 46 | 41 | 17 | 0.5 |
| 1238600 | 93 | 76 | 55 | 29 | 16 | 0.5 |
| 1238645 | 92 | 65 | 57 | 32 | 20 | 0.5 |
| 1238688 | 87 | 81 | 96 | 32 | 31 | 1.4 |
| 1238974 | 50 | 48 | 17 | 8 | 4 | <0.02 |
| 1238975 | 82 | 67 | 41 | 22 | 11 | 0.3 |
| 1239062 | 87 | 76 | 56 | 28 | 13 | 0.4 |
| 1239063 | 179 | 72 | 37 | 16 | 5 | 0.6 |
| 1239064 | 96 | 95 | 59 | 27 | 10 | 0.6 |
| 1239260 | 98 | 79 | 56 | 35 | 26 | 0.7 |

TABLE 39

Dose-dependent reduction of human PRNP RNA expression in A-431 cells

| Compound ID | 23 nM | 94 nM | 375 nM | 1500 nM | 6000 nM | IC50 (µM) |
|---|---|---|---|---|---|---|
| 1201142 | 84 | 56 | 26 | 11 | 8 | 0.1 |
| 1238341 | 72 | 46 | 15 | 4 | 2 | 0.1 |
| 1238404 | 94 | 80 | 58 | 37 | 21 | 0.7 |
| 1238517 | 81 | 44 | 16 | 6 | 3 | 0.1 |
| 1238582 | 95 | 67 | 54 | 33 | 23 | 0.5 |
| 1238802 | 98 | 71 | 46 | 17 | 6 | 0.3 |
| 1238892 | 104 | 101 | 74 | 49 | 36 | 2 |
| 1238914 | 97 | 86 | 72 | 36 | 13 | 0.7 |
| 1239045 | 82 | 75 | 38 | 18 | 9 | 0.3 |
| 1239046 | 91 | 65 | 50 | 25 | 13 | 0.3 |
| 1239066 | 81 | 79 | 48 | 20 | 10 | 0.3 |
| 1239352 | 94 | 71 | 37 | 16 | 7 | 0.3 |
| 1239394 | 88 | 86 | 44 | 28 | 15 | 0.4 |
| 1239550 | 87 | 85 | 69 | 53 | 39 | 2.2 |
| 1239682 | 108 | 58 | 34 | 13 | 5 | 0.3 |

TABLE 40

Dose-dependent reduction of human PRNP RNA expression in A-431 cells

| Compound ID | 23 nM | 94 nM | 375 nM | 1500 nM | 6000 nM | IC50 (µM) |
|---|---|---|---|---|---|---|
| 1201142 | 83 | 55 | 23 | 17 | 7 | 0.1 |
| 1238167* | 63 | 41 | 18 | 13 | 9 | 0.04 |
| 1238168* | 72 | 44 | 17 | 17 | 12 | 0.1 |
| 1238169* | 76 | 41 | 21 | 17 | 11 | 0.1 |
| 1238170* | 69 | 35 | 18 | 10 | 8 | 0.05 |
| 1238255 | 91 | 59 | 29 | 15 | 9 | 0.2 |
| 1238322 | 67 | 31 | 9 | 4 | 1 | 0.03 |
| 1238324 | 91 | 69 | 32 | 13 | 5 | 0.2 |
| 1238409 | 72 | 61 | 40 | 14 | 8 | 0.2 |
| 1238410 | 87 | 67 | 33 | 18 | 8 | 0.2 |
| 1238497 | 86 | 65 | 31 | 14 | 8 | 0.2 |
| 1238498 | 81 | 65 | 34 | 16 | 9 | 0.2 |
| 1238500 | 82 | 36 | 15 | 5 | 2 | 0.1 |
| 1238805 | 85 | 58 | 30 | 12 | 5 | 0.2 |
| 1239027 | 67 | 60 | 33 | 17 | 13 | 0.1 |

TABLE 41

Dose-dependent reduction of human PRNP RNA expression in A-431 cells

| Compound ID | 23 nM | 94 nM | 375 nM | 1500 nM | 6000 nM | IC50 (µM) |
|---|---|---|---|---|---|---|
| 1201142 | 87 | 61 | 25 | 14 | 9 | 0.2 |
| 1238259 | 86 | 59 | 26 | 9 | 3 | 0.2 |
| 1238325 | 56 | 40 | 17 | 6 | 2 | 0.03 |
| 1238327 | 72 | 51 | 22 | 8 | 4 | 0.1 |
| 1238370 | 84 | 54 | 24 | 9 | 2 | 0.1 |
| 1238371 | 93 | 80 | 43 | 17 | 8 | 0.3 |
| 1238437 | 88 | 79 | 36 | 20 | 11 | 0.3 |
| 1238501 | 71 | 36 | 17 | 7 | 3 | 0.1 |
| 1238502 | 91 | 62 | 32 | 16 | 8 | 0.2 |
| 1239009 | 71 | 39 | 16 | 5 | 3 | 0.1 |
| 1239028 | 77 | 66 | 44 | 29 | 17 | 0.3 |
| 1239052 | 89 | 54 | 34 | 19 | 12 | 0.2 |
| 1239162 | 89 | 73 | 47 | 34 | 15 | 0.4 |
| 1239250 | 89 | 64 | 38 | 24 | 16 | 0.3 |
| 1239448 | 76 | 44 | 25 | 9 | 5 | 0.1 |

TABLE 42

Dose-dependent reduction of human PRNP RNA expression in A-431 cells

| Compound ID | 23 nM | 94 nM | 375 nM | 1500 nM | 6000 nM | IC50 (µM) |
|---|---|---|---|---|---|---|
| 1201142 | 90 | 52 | 33 | 12 | 8 | 0.2 |
| 1238285 | 97 | 84 | 55 | 36 | 14 | 0.6 |
| 1238329 | 90 | 49 | 25 | 12 | 6 | 0.1 |
| 1238373 | 75 | 60 | 11 | 9 | 4 | 0.1 |
| 1238440 | 74 | 61 | 26 | 12 | 8 | 0.1 |
| 1238460 | 85 | 77 | 46 | 30 | 13 | 0.4 |
| 1238572 | 96 | 82 | 60 | 39 | 29 | 0.9 |
| 1238812 | 100 | 51 | 34 | 11 | 6 | 0.2 |
| 1238813 | 88 | 64 | 41 | 21 | 17 | 0.3 |
| 1238835 | 109 | 80 | 43 | 20 | 8 | 0.4 |
| 1238836 | 78 | 61 | 35 | 11 | 6 | 0.2 |
| 1238990 | 81 | 62 | 33 | 15 | 7 | 0.2 |
| 1239010 | 76 | 38 | 15 | 6 | 1 | 0.1 |
| 1239011 | 97 | 68 | 36 | 16 | 7 | 0.3 |
| 1239231 | 85 | 96 | 76 | 52 | 30 | 1.8 |

TABLE 43

Dose-dependent reduction of human PRNP RNA expression in A-431 cells

| Compound ID | \% UTC | | | | | | IC50 (µM) |
|---|---|---|---|---|---|---|---|
| | 6 nM | 23 nM | 94 nM | 375 nM | 1500 nM | 6000 nM | |
| 1201142 | 94 | 97 | 62 | 27 | 14 | 7 | 0.2 |
| 1238244 | 92 | 106 | 61 | 31 | 15 | 12 | 0.2 |
| 1238331 | 107 | 116 | 64 | 28 | 14 | 8 | 0.3 |
| 1238507 | 92 | 66 | 39 | 25 | 9 | 5 | 0.1 |
| 1238616 | 109 | 91 | 70 | 56 | 35 | 29 | 0.7 |
| 1238837 | 90 | 70 | 50 | 15 | 9 | 4 | 0.1 |
| 1238838 | 88 | 92 | 53 | 31 | 18 | 9 | 0.2 |
| 1239146 | 109 | 100 | 61 | 44 | 23 | 11 | 0.3 |
| 1239607 | 97 | 86 | 66 | 39 | 23 | 18 | 0.3 |
| 1239694 | 110 | 108 | 84 | 76 | 48 | 28 | 1.5 |

TABLE 44

Dose-dependent reduction of human PRNP RNA expression in A-431 cells

| Compound ID | \% UTC | | | | | | IC50 (µM) |
|---|---|---|---|---|---|---|---|
| | 6 nM | 23 nM | 94 nM | 375 nM | 1500 nM | 6000 nM | |
| 1201142 | 105 | 98 | 69 | 27 | 20 | 10 | 0.3 |
| 1238361 | 88 | 86 | 53 | 31 | 20 | 10 | 0.5 |
| 1238444 | 107 | 96 | 83 | 51 | 39 | 21 | 0.6 |
| 1238554 | 96 | 91 | 85 | 67 | 44 | 31 | 1.3 |
| 1238889 | 99 | 85 | 88 | 61 | 59 | 39 | 2.6 |
| 1238992 | 84 | 101 | 73 | 51 | 31 | 20 | 0.5 |
| 1239263 | 89 | 100 | 92 | 69 | 48 | 32 | 1.8 |
| 1239329 | 106 | 96 | 80 | 47 | 39 | 31 | 0.8 |
| 1239345 | 120 | 113 | 90 | 49 | 30 | 19 | 0.6 |

Example 4: Design and Synthesis of MOE Gapmer Modified Oligonucleotides Complementary to a Human PRNP Nucleic Acid Modified oligonucleotides complementary to human PRNP nucleic acid were designed and synthesized.

"Start site" indicates the 5'-most nucleoside to which the gapmer is complementary to in the human gene sequence. "Stop site" indicates the 3'-most nucleoside to which the gapmer is complementary to in the human gene sequence. Most of the modified oligonucleotides listed in the Tables below are complementary to the human PRNP mRNA sequence, designated herein as SEQ ID NO: 1 (described here in above) and/or the human PRNP genomic sequence, designated herein as SEQ ID NO: 2 (described herein above). In addition, certain modified oligonucleotides are complementary to the human PRNP mRNA designated herein as SEQ ID NO: 4 (ENSEMBL Accession NO: ENST00000424424.1). 'N/A' indicates that the modified oligonucleotide is not complementary to that particular gene sequence with 100% complementarity.

The modified oligonucleotides in the table below are 3-10-7 MOE gapmers with mixed PO/PS internucleoside linkages. The gapmers are 20 nucleosides in length and have a central gap segment that consists of ten 2'-β-D-deoxynucleosides, a 5' wing segment that consists of three 2'-MOE nucleosides, and a 3' wing segment that consists of seven 2-MOE nucleosides. The sugar motif of the gapmers is (from 5' to 3'): eeedddddddddddeeeeeee; wherein 'd' represents a 2'-β-D-deoxyribosyl sugar, and 'e' represents a 2'-MOE modified ribosyl sugar. The gapmers have an internucleoside linkage motif of (from 5' to 3'): soossssssss-sooooss; wherein each "s" represents a phosphorothioate internucleoside linkage and each "o" represents a phosphodiester internucleoside linkage. Each cytosine nucleoside is a 5-methyl cytosine.

TABLE 45

3-10-7 MOE gapmers with mixed PO/PS internucleoside linkages complementary to human PRNP

| Compound Number | Sequence (5' to 3') | SEQ ID NO: 1 Start Site | SEQ ID NO: 1 Stop Site | SEQ ID NO: 2 Start Site | SEQ ID NO: 2 Start Site | SEQ ID NO. |
|---|---|---|---|---|---|---|
| 1373041 | GTCAGTTTTTCCCCACATAT | N/A | N/A | 5715 | 5734 | 2304 |
| 1373042 | ACTCTATGTTTTCCAGTGCC | 1338 | 1357 | 17129 | 17148 | 2264 |
| 1373043 | CTCTATGTTTTCCAGTGCCC | 1337 | 1356 | 17128 | 17147 | 2191 |
| 1373044 | CTATGTTTTCCAGTGCCCAT | 1335 | 1354 | 17126 | 17145 | 2190 |
| 1393331 | ACTGAATTTTCTCTCCCAGC | N/A | N/A | 14923 | 14942 | 2646 |
| 1393332 | GCCACATATAGGGTCCTTTA | 1963 | 1982 | 17754 | 17773 | 66 |
| 1411007 | CGTCCATTTTCTGTGCTTTT | N/A | N/A | 5806 | 5825 | 2647 |

The modified oligonucleotides in the table below are 4-10-6 MOE gapmers with mixed PO/PS internucleoside linkages. The gapmers are 20 nucleosides in length and have a central gap segment that consists of ten 2'-β-D-deoxynucleosides, a 5' wing segment that consists of four 2'-MOE nucleosides, and a 3' wing segment that consists of six 2'-MOE nucleosides. The sugar motif of the gapmers is (from 5' to 3'): eeeeddddddddddeeeeee; wherein 'd' represents a 2'-β-D-deoxyribosyl sugar, and 'e' represents a 2'-MOE modified ribosyl sugar. The gapmers have an internucleoside linkage motif of (from 5' to 3'): sooosssssssss-soooss; wherein each "s" represents a phosphorothioate internucleoside linkage and each "o" represents a phosphodiester internucleoside linkage. Each cytosine nucleoside is a 5-methyl cytosine.

TABLE 46

4-10-6 MOE gapmers with mixed PO/PS internucleoside linkages complementary to human PRNP

| Compound Number | Sequence (5' to 3') | SEQ ID NO: 1 Start Site | SEQ ID NO: 1 Stop Site | SEQ ID NO: 2 Start Site | SEQ ID NO: 2 Start Site | SEQ ID NO. |
|---|---|---|---|---|---|---|
| 1373029 | CTATGTTTTCCAGTGCCCAT | 1335 | 1354 | 17126 | 17145 | 2190 |
| 1373030 | ACTCTATGTTTTCCAGTGCC | 1338 | 1357 | 17129 | 17148 | 2264 |
| 1373031 | GCTTATTATTCATGTTCTCC | N/A | N/A | 14367 | 14386 | 1939 |
| 1373032 | GTCATAATTTTCTTAGCTAC | N/A | N/A | 5638 | 5657 | 1914 |
| 1373033 | GCTTACTCGGCTTGTTCCAC | 723 | 742 | 16514 | 16533 | 351 |
| 1373034 | GTGTCATAATTTTCTTAGCT | N/A | N/A | 5640 | 5659 | 2302 |
| 1373035 | GCACACTGACCATTTTTAA | 2147 | 2166 | 17938 | 17957 | 584 |
| 1373036 | TCTATGTTTTCCAGTGCCCA | 1336 | 1355 | 17127 | 17146 | 1726 |
| 1373037 | CTCTATGTTTTCCAGTGCCC | 1337 | 1356 | 17128 | 17147 | 2191 |
| 1373038 | GTCAGTTTTTCCCCACATAT | N/A | N/A | 5715 | 5734 | 2304 |
| 1373039 | ACTTGTCAGTTTTTCCCCAC | N/A | N/A | 5719 | 5738 | 1301 |
| 1373040 | TGTCAGTTTTTCCCCACATA | N/A | N/A | 5716 | 5735 | 1070 |
| 1373078 | GCCACATATAGGGTCCTTTA | 1963 | 1982 | 17754 | 17773 | 66 |
| 1393327 | ACTGAATTTTCTCTCCCAGC | N/A | N/A | 14923 | 14942 | 2646 |
| 1411005 | CGTCCATTTTCTGTGCTTTT | N/A | N/A | 5806 | 5825 | 2647 |

The modified oligonucleotides in Table 47 and 48 below are 5-10-5 MOE gapmers with mixed PO/PS internucleoside linkages. The gapmers are 20 nucleosides in length and have a central gap segment that consists of ten 2'-β-D-deoxynucleosides, a 5' wing segment that consists of five 2'-MOE nucleosides, and a 3' wing segment that consists of five 2'-MOE nucleosides. The sugar motif of the gapmers is (from 5' to 3'): eeeeedddddddddddeeeee; wherein 'd' represents a 2'-β-D-deoxyribosyl sugar, and 'e' represents a 2'-MOE modified ribosyl sugar. The gapmers have an internucleoside linkage motif of (from 5' to 3'): sooossssssssss-sooss; wherein each "s" represents a phosphorothioate internucleoside linkage and each "o" represents a phosphodiester internucleoside linkage. Each cytosine nucleoside is a 5-methyl cytosine.

TABLE 47

5-10-5 MOE gapmers with mixed PO/PS internucleoside linkages complementary to human PRNP

| Compound Number | Sequence (5' to 3') | SEQ ID NO: 1 Start Site | SEQ ID NO: 1 Stop Site | SEQ ID NO: 2 Start Site | SEQ ID NO: 2 Start Site | SEQ ID NO. |
|---|---|---|---|---|---|---|
| 1355702 | CATAATGACTGCTCTGCAAA | N/A | N/A | 16204 | 16223 | 2651 |
| 1355704 | CCATAATGACTGCTCTGCAA | N/A | N/A | 16205 | 16224 | 2653 |
| 1355710 | ATTAGTGTGATCATGCACAT | N/A | N/A | 13535 | 13554 | 2655 |
| 1355711 | ACAGCCATGTTCAGTGTCAG | N/A | N/A | 6529 | 6548 | 2656 |
| 1355712 | TTGATTGTGATATTGACGCA | 964 | 983 | 16755 | 16774 | 2657 |
| 1355713 | CATGTTTTCACGATAGTAAC | 872 | 891 | 16663 | 16682 | 2658 |
| 1355714 | TATTCATGTTCTCCACGGGA | N/A | N/A | 14361 | 14380 | 2659 |
| 1355715 | AAAATGTTTGTCACTGGTTC | N/A | N/A | 5444 | 5463 | 2660 |
| 1355716 | AGAAGATAATCAAGGGTGCA | N/A | N/A | 7571 | 7590 | 2661 |
| 1355717 | ATCCTGATGTCAAAGTCCCA | N/A | N/A | 8742 | 8761 | 2662 |
| 1355718 | AGGTGCTGTCCAAGGCCATA | N/A | N/A | 13615 | 13634 | 2663 |
| 1355719 | TTAGTCTTGTCCTCAGTGCT | N/A | N/A | 15644 | 15663 | 2664 |
| 1355720 | CGTCCATTTTCTGTGCTTTT | N/A | N/A | 5806 | 5825 | 2647 |
| 1355721 | ACTGAATTTTCTCTCCCAGC | N/A | N/A | 14923 | 14942 | 2646 |
| 1355722 | TGGTTGCTGTACTCATCCAT | 925 | 944 | 16716 | 16735 | 2665 |
| 1355723 | GCATGTTTTCACGATAGTAA | 873 | 892 | 16664 | 16683 | 2666 |
| 1355724 | AACTGTGGGTCCATTTCATC | N/A | N/A | 5924 | 5943 | 2667 |
| 1355725 | TGACCATCTTATTCGGTGCT | N/A | N/A | 14820 | 14839 | 2668 |
| 1355726 | TCTATGGAATCTGTAGGTCA | N/A | N/A | 8234 | 8253 | 2669 |
| 1355727 | CAATTAGTGTGATCATGCAC | N/A | N/A | 13537 | 13556 | 2670 |
| 1355728 | TTTTCTGTGACATTTGGTGA | N/A | N/A | 6281 | 6300 | 2671 |
| 1355729 | GCTTCCATCACTTCTCACCT | N/A | N/A | 14803 | 14822 | 2672 |
| 1355730 | TTTCTGTGACATTTGGTGAC | N/A | N/A | 6280 | 6299 | 2673 |
| 1355731 | GACAGCCATGTTCAGTGTCA | N/A | N/A | 6530 | 6549 | 2674 |
| 1355732 | GGTTTCTGGGTCACAGCTTC | N/A | N/A | 5496 | 5515 | 2675 |
| 1355733 | AAGGTGCTGTCCAAGGCCAT | N/A | N/A | 13616 | 13635 | 2676 |
| 1355734 | TTCCTCTGTGCTTATTATTC | N/A | N/A | 14376 | 14395 | 2677 |
| 1355735 | GGTTGTTCTATAAATTCATC | N/A | N/A | 9441 | 9460 | 2678 |
| 1355736 | ACATTTATTTCATGTGCCAG | N/A | N/A | 14088 | 14107 | 2679 |
| 1355737 | CAAGGTGCTGTCCAAGGCCA | N/A | N/A | 13617 | 13636 | 2680 |
| 1355738 | CTGAAGTTAGTCTTGTCCTC | N/A | N/A | 15650 | 15669 | 2681 |
| 1355739 | GTTAGTCTTGTCCTCAGTGC | N/A | N/A | 15645 | 15664 | 2682 |
| 1355740 | CTCAAGGTGCTGTCCAAGGC | N/A | N/A | 13619 | 13638 | 2683 |
| 1355741 | TTAGTGTGATCATGCACATA | N/A | N/A | 13534 | 13553 | 2684 |
| 1355742 | CATTTATTTCATGTGCCAGC | N/A | N/A | 14087 | 14106 | 2685 |
| 1355743 | AAGTTAGTCTTGTCCTCAGT | N/A | N/A | 15647 | 15666 | 2686 |

TABLE 47-continued 5-10-5 MOE gapmers with mixed PO/PS internucleoside linkages complementary to human PRNP

| Compound Number | Sequence (5' to 3') | SEQ ID NO: 1 Start Site | SEQ ID NO: 1 Stop Site | SEQ ID NO: 2 Start Site | SEQ ID NO: 2 Start Site | SEQ ID NO. |
|---|---|---|---|---|---|---|
| 1355744 | CCCCACATATCACAGGCTCC | N/A | N/A | 5705 | 5724 | 2687 |
| 1355745 | CTTTCCTGATAGTTCACTGT | N/A | N/A | 8019 | 8038 | 2688 |
| 1355746 | AGATTCTTGTTCAGCACGAT | N/A | N/A | 12108 | 12127 | 2689 |
| 1355747 | CGGTGCATGTTTTCACGATA | 877 | 896 | 16668 | 16687 | 2690 |
| 1355748 | TTGACAGCCATGTTCAGTGT | N/A | N/A | 6532 | 6551 | 2691 |
| 1355749 | GTGCATGTTTTCACGATAGT | 875 | 894 | 16666 | 16685 | 2692 |
| 1355750 | TGCTTCCATCACTTCTCACC | N/A | N/A | 14804 | 14823 | 2693 |
| 1355751 | TTTCTAGAACTTGCAAGGAA | N/A | N/A | 12006 | 12025 | 2694 |
| 1355752 | CCTGATAGTTCACTGTTGGC | N/A | N/A | 8015 | 8034 | 2695 |
| 1355753 | TCTATTTGTGTCTCCTTGAA | N/A | N/A | 8153 | 8172 | 2696 |
| 1355754 | TTCTTAGCTACTGCCCTGGT | N/A | N/A | 5629 | 5648 | 2697 |
| 1355755 | TTTTTAGATTGTCTCCCTAT | 2270 | 2289 | 18061 | 18080 | 2698 |
| 1355756 | ATTTTTCCAACATGACCATC | N/A | N/A | 14832 | 14851 | 2699 |
| 1355757 | CACAACTGCAGCTCTCCTGT | 2097 | 2116 | 17888 | 17907 | 2700 |
| 1394116 | GCTCCTCAAACTGACAAGCC | N/A | N/A | 14590 | 14609 | 2701 |
| 1394117 | TTGCTCCTTTCCACTGGTGA | N/A | N/A | 4955 | 4974 | 2702 |
| 1394118 | GCACCTTCTCCATTCGCTGC | N/A | N/A | 14977 | 14996 | 2703 |
| 1394119 | GGTGCTTCCATCACTTCTCA | N/A | N/A | 14806 | 14825 | 2704 |
| 1394120 | GCTCATGGCACTTCCCAGCA | 815 | 834 | 16606 | 16625 | 2705 |
| 1394121 | GCCACCTTCACCCAATTTTA | N/A | N/A | 8306 | 8325 | 2706 |
| 1394122 | GAGCCTGCATCCCAAGAGCT | 1707 | 1726 | 17498 | 17517 | 2707 |
| 1394123 | GGGCACCATCCCCTCAGTCA | N/A | N/A | 15028 | 15047 | 2708 |
| 1394124 | GCTTGACCAGCATCTCAGGT | 1360 | 1379 | 17151 | 17170 | 2709 |
| 1394125 | CTGTAGCCATCACTGGGTTA | N/A | N/A | 6702 | 6721 | 2710 |
| 1394126 | CTGACAAGCCCATCCTGTCT | N/A | N/A | 14580 | 14599 | 2711 |
| 1394127 | TCCTCATCCCACTATCAGGA | 1175 | 1194 | 16966 | 16985 | 2712 |
| 1394128 | CCTCCATTCTATGAATGGAC | N/A | N/A | 5373 | 5392 | 2713 |
| 1394129 | CCCCCAATAACTCATACATA | N/A | N/A | 5418 | 5437 | 2714 |
| 1394130 | CGGTGCTTCCATCACTTCTC | N/A | N/A | 14807 | 14826 | 2715 |
| 1394131 | TCTCAGGTCTACTCTATGTT | 1348 | 1367 | 17139 | 17158 | 2716 |
| 1394132 | GTTCAGGCCTCCCACTGCTC | N/A | N/A | 14606 | 14625 | 2717 |
| 1394133 | CCAAGAGCTAAGAATCTCTA | 1696 | 1715 | 17487 | 17506 | 2718 |
| 1394134 | GTGAACAATAATCTATTGCT | N/A | N/A | 9473 | 9492 | 2719 |
| 1394135 | CTGTACTCATCCATGGGCCT | 919 | 938 | 16710 | 16729 | 2720 |
| 1394136 | GTGACTTTCAACCTTCCTAA | N/A | N/A | 6265 | 6284 | 2721 |

TABLE 47-continued 5-10-5 MOE gapmers with mixed PO/PS internucleoside linkages complementary to human PRNP

| Compound Number | Sequence (5' to 3') | SEQ ID NO: 1 Start Site | SEQ ID NO: 1 Stop Site | SEQ ID NO: 2 Start Site | SEQ ID NO: 2 Start Site | SEQ ID NO. |
|---|---|---|---|---|---|---|
| 1394137 | TCAGGTCTACTCTATGTTTT | 1346 | 1365 | 17137 | 17156 | 2722 |
| 1394138 | CTCAGGTCTACTCTATGTTT | 1347 | 1366 | 17138 | 17157 | 2723 |
| 1394139 | TTCCAGCTTCTTAATGCATC | N/A | N/A | 5479 | 5498 | 2724 |
| 1406230 | CTCCTTGAATTTCTTTCATC | N/A | N/A | 8142 | 8161 | 2725 |
| 1406232 | GCTTCTCAATTTTTCCAACA | N/A | N/A | 14840 | 14859 | 2726 |
| 1406236 | TCTTTCTAATTTTGTACACA | N/A | N/A | 7713 | 7732 | 2727 |
| 1406238 | GTTGTTCTATAAATTCATCT | N/A | N/A | 9440 | 9459 | 2728 |
| 1406243 | TCCTTGAATTTCTTTCATCA | N/A | N/A | 8141 | 8160 | 2729 |
| 1406250 | CCATTTTTAATTACATCAT | 2138 | 2157 | 17929 | 17948 | 2730 |
| 1406254 | TCTCCTTGAATTTCTTTCAT | N/A | N/A | 8143 | 8162 | 2731 |
| 1406261 | TCTGAGATTTGTTTTAGCCT | 1493 | 1512 | 17284 | 17303 | 2732 |
| 1406262 | CAATTGTTTTCTCTCTC | N/A | N/A | 15613 | 15632 | 2733 |
| 1406264 | TCTCAATTTTTGAGAAGTT | N/A | N/A | 13161 | 13180 | 2734 |
| 1406267 | TCTCAATTTTTCCAACATGA | N/A | N/A | 14837 | 14856 | 2735 |
| 1411013 | CCATTTTCTGTGCTTTTCCT | N/A | N/A | 5803 | 5822 | 2736 |
| 1411014 | TCCATTTTCTGTGCTTTTCC | N/A | N/A | 5804 | 5823 | 2737 |
| 1411015 | GTCCATTTTCTGTGCTTTTC | N/A | N/A | 5805 | 5824 | 2738 |
| 1411016 | ACGTCCATTTTCTGTGCTTT | N/A | N/A | 5807 | 5826 | 2739 |
| 1411017 | AACGTCCATTTTCTGTGCTT | N/A | N/A | 5808 | 5827 | 2740 |
| 1411018 | AAACGTCCATTTTCTGTGCT | N/A | N/A | 5809 | 5828 | 2741 |

TABLE 48

5-10-5 MOE gapmers with mixed PO/PS internucleoside linkages complementary to human PRNP

| Compound Number | Sequence (5' to 3') | SEQ ID NO: 4 Start Site | SEQ ID NO: 4 Stop Site | SEQ ID NO. |
|---|---|---|---|---|
| 1355700 | ATAATGACTGCCTCGGTCGT | 42 | 61 | 2649 |
| 1355701 | CCATAATGACTGCCTCGGTC | 44 | 63 | 2650 |
| 1355703 | TTCGCCATAATGACTGCCTC | 48 | 67 | 2652 |
| 1355705 | GTTCGCCATAATGACTGCCT | 49 | 68 | 2654 |

The modified oligonucleotides in the table below are 6-10-4 MOE gapmers with mixed PO/PS internucleoside linkages. The gapmers are 20 nucleosides in length and have a central gap segment that consists of ten 2'-β-D-deoxynucleosides, a 5' wing segment that consists of six 2'-MOE nucleosides, and a 3' wing segment that consists of four 2'-MOE nucleosides. The sugar motif of the gapmers is (from 5' to 3'): eeeeeedddddddddeeee; wherein 'd' represents a 2'-β-D-deoxyribosyl sugar, and 'e' represents a 2'-MOE modified ribosyl sugar. The gapmers have an internucleoside linkage motif of (from 5' to 3'): sooooossssssss-soss; wherein each "s" represents a phosphorothioate internucleoside linkage and each "o" represents a phosphodiester internucleoside linkage. Each cytosine nucleoside is a 5-methyl cytosine.

TABLE 49

6-10-4 MOE gapmers with mixed PO/PS internucleoside linkages complementary to human PRNP

| Compound Number | Sequence (5' to 3') | SEQ ID NO: 1 Start Site | SEQ ID NO: 1 Stop Site | SEQ ID NO: 2 Start Site | SEQ ID NO: 2 Start Site | SEQ ID NO. |
|---|---|---|---|---|---|---|
| 1335684 | TGGCACTTTCTTTTTATTTC | N/A | N/A | 8038 | 8057 | 1311 |
| 1335686 | GCACACTGACCATTTTTTAA | 2147 | 2166 | 17938 | 17957 | 584 |
| 1335687 | AAGGTTCGCCATAATGACTG | 422 | 441 | 16213 | 16232 | 38 |
| 1335688 | TGTCAGTTTTTCCCCACATA | N/A | N/A | 5716 | 5735 | 1070 |
| 1355706 | GCCACATATAGGGTCCTTTA | 1963 | 1982 | 17754 | 17773 | 66 |
| 1355707 | GTGACAATATTTACTCTTGT | 1813 | 1832 | 17604 | 17623 | 961 |
| 1355708 | GGTTACATAATGTTCATTTC | N/A | N/A | 5667 | 5686 | 1377 |
| 1355709 | TCGCCATAATGACTGCTCTG | 417 | 436 | 16208 | 16227 | 192 |
| 1373020 | CTATGTTTTCCAGTGCCCAT | 1335 | 1354 | 17126 | 17145 | 2190 |
| 1373021 | GTCATAATTTTCTTAGCTAC | N/A | N/A | 5638 | 5657 | 1914 |
| 1373022 | GCTTATTATTCATGTTCTCC | N/A | N/A | 14367 | 14386 | 1939 |
| 1373023 | GTGTCATAATTTTCTTAGCT | N/A | N/A | 5640 | 5659 | 2302 |
| 1373024 | GCTTACTCGGCTTGTTCCAC | 723 | 742 | 16514 | 16533 | 351 |
| 1373025 | ACTTGTCAGTTTTTCCCCAC | N/A | N/A | 5719 | 5738 | 1301 |
| 1373026 | ACTCTATGTTTTCCAGTGCC | 1338 | 1357 | 17129 | 17148 | 2264 |
| 1373027 | CTCTATGTTTTCCAGTGCCC | 1337 | 1356 | 17128 | 17147 | 2191 |
| 1373028 | GTCAGTTTTTCCCCACATAT | N/A | N/A | 5715 | 5734 | 2304 |
| 1393324 | ACTGAATTTTCTCTCCCAGC | N/A | N/A | 14923 | 14942 | 2646 |
| 1411004 | CGTCCATTTTCTGTGCTTTT | N/A | N/A | 5806 | 5825 | 2647 |
| 1423120 | CCATTTTCTGTGCTTTTCCT | N/A | N/A | 5803 | 5822 | 2736 |
| 1423121 | TCCATTTTCTGTGCTTTTCC | N/A | N/A | 5804 | 5823 | 2737 |
| 1423122 | GTCCATTTTCTGTGCTTTTC | N/A | N/A | 5805 | 5824 | 2738 |
| 1423123 | ACGTCCATTTTCTGTGCTTT | N/A | N/A | 5807 | 5826 | 2739 |
| 1423124 | AACGTCCATTTTCTGTGCTT | N/A | N/A | 5808 | 5827 | 2740 |
| 1423125 | AAACGTCCATTTTCTGTGCT | N/A | N/A | 5809 | 5828 | 2741 |

The modified oligonucleotides in the table below are 7-10-3 MOE gapmers with mixed PO/PS internucleoside linkages. The gapmers are 20 nucleosides in length and have a central gap segment that consists of ten 2'-β-D-deoxynucleosides, a 5' wing segment that consists of seven 2'-MOE nucleosides, and a 3' wing segment that consists of three 2'-MOE nucleosides. The sugar motif of the gapmers is (from 5' to 3'): eeeeeeedddddddddddeee; wherein 'd' represents a 2'-β-D-deoxyribosyl sugar, and 'e' represents a 2'-MOE modified ribosyl sugar. The gapmers have an internucleoside linkage motif of (from 5' to 3'): ssooooosssssssssos; wherein each "s" represents a phosphothioate internucleoside linkage and each "o" represents a phosphodiester internucleoside linkage. Each cytosine nucleoside is a 5-methyl cytosine.

TABLE 50

7-10-3 MOE gapmers with mixed PO/PS internucleoside linkages complementary to human PRNP

| Compound Number | Sequence (5' to 3') | SEQ ID NO: 1 Start Site | SEQ ID NO: 1 Stop Site | SEQ ID NO: 2 Start Site | SEQ ID NO: 2 Start Site | SEQ ID NO. |
|---|---|---|---|---|---|---|
| 1373045 | ACTCTATGTTTTCCAGTGCC | 1338 | 1357 | 17129 | 17148 | 2264 |
| 1373046 | CTATGTTTTCCAGTGCCCAT | 1335 | 1354 | 17126 | 17145 | 2190 |
| 1373047 | GTCAGTTTTTCCCCACATAT | N/A | N/A | 5715 | 5734 | 2304 |
| 1373048 | CTCTATGTTTTCCAGTGCCC | 1337 | 1356 | 17128 | 17147 | 2191 |
| 1393329 | ACTGAATTTTCTCTCCCAGC | N/A | N/A | 14923 | 14942 | 2646 |
| 1393330 | GCCACATATAGGGTCCTTTA | 1963 | 1982 | 17754 | 17773 | 66 |
| 1411006 | CGTCCATTTTCTGTGCTTTT | N/A | N/A | 5806 | 5825 | 2647 |

The modified oligonucleotides in the table below are 5-10-5 MOE gapmers with a 2'-OMe modified nucleoside at position 2 of the gap and mixed PO/PS internucleoside linkages. The gapmers are 20 nucleosides in length, wherein the 5' wing segment consists of five 2'-MOE nucleosides and the 3' wing segment consists of five 2'-MOE nucleosides. The gap is ten nucleosides in length, and has a nucleoside comprising a 2'-β-D-deoxyribosyl sugar moiety at positions 1, 3, 4, 5, 6, 7, 8, 9 and 10 of the gap (counting from the 5' end) and 2'-OMe nucleoside at position 2 of the gap (counting from the 5' end). The sugar motif of the mixed, altered gapmers is (from 5' to 3'): eeeeedydddddddeeeee; wherein 'd' represents a 2'-β-D-deoxyribosyl sugar, 'y' represents a 2'-O-methyl ribosyl sugar, 'k' represents a cEt sugar, and 'e' represents a 2'-MOE sugar. The gapmers have an internucleoside linkage motif of (from 5' to 3'): sooossssssssss-sooss; wherein "s" represents a phosphorothioate internucleoside linkage and "o" represents a phosphodiester internucleoside linkage. All cytosine residues are 5-methylcytosines.

TABLE 51

5-10-5 MOE gapmers having a 2'-OMe at position 2 of the gap with mixed PO/PS internucleoside linkages complementary to human PRNP

| Compound Number | SEQUENCE | SEQ ID NO: 1 Start Site | SEQ ID NO: 1 Stop Site | SEQ ID NO: 2 Start Site | SEQ ID NO: 2 Start Site | SEQ ID NO. |
|---|---|---|---|---|---|---|
| 1418386 | CTCTATGTTTTCCAGTGCCC | 1337 | 1356 | 17128 | 17147 | 2191 |
| 1418387 | GTCAGTUTTTCCCCACATAT | N/A | N/A | 5715 | 5734 | 2648 |
| 1423126 | CGTCCAUTTTCTGTGCTTTT | N/A | N/A | 5806 | 5825 | 2744 |

The modified oligonucleotides in the table below are 5-10-5 mixed MOE/cEt gapmer with mixed PO/PS internucleoside linkages. The gapmers are 20 nucleosides in length, wherein the central gap segment consists of ten 2'-β-D-deoxynucleosides, a 5' wing segment that consists of five 2'-MOE nucleosides, and a 3' wing segment that consists of two cEt nucleosides and three 2'-MOE nucleosides. The sugar motif of the gapmers is (from 5' to 3'): eeeeedddddddddkkeee; wherein 'd' represents a 2'-Q-D-deoxyribosyl sugar, 'k' represents a cEt sugar, and 'c' represents a 2'-MOE modified ribosyl sugar. The gapmers have an internucleoside linkage motif of (from 5' to 3'): sooossssssssssooss; wherein "s" represents a phosphorothioate internucleoside linkage and "o" represents a phosphodiester internucleoside linkage. All cytosine residues are 5-methylcytosines.

TABLE 52

5-10-5 MOE/cEt mixed wing gapmers with mixed PO/PS internucleoside linkages complementary to human PRNP

| Compound Number | SEQUENCE | SEQ ID NO: 1 Start Site | SEQ ID NO: 1 Stop Site | SEQ ID NO: 2 Start Site | SEQ ID NO: 2 Start Site | SEQ ID NO. |
|---|---|---|---|---|---|---|
| 1418416 | ACTCTATGTTTTCCAGTGCC | 1338 | 1357 | 17129 | 17148 | 2264 |
| 1418417 | GCCACATATAGGGTCCTTTA | 1963 | 1982 | 17754 | 17773 | 66 |
| 1418418 | GTCATAATTTTCTTAGCTAC | N/A | N/A | 5638 | 5657 | 1914 |
| 1418419 | GTGTCATAATTTTCTTAGCT | N/A | N/A | 5640 | 5659 | 2302 |
| 1418421 | GCTTATTATTCATGTTCTCC | N/A | N/A | 14367 | 14386 | 1939 |
| 1418426 | CGTCCATTTTCTGTGCTTTT | N/A | N/A | 5806 | 5825 | 2647 |

The modified oligonucleotides in the table below are 6-10-4 mixed MOE/cEt gapmer with mixed PO/PS internucleoside linkages. The gapmers are 20 nucleosides in length, wherein the central gap segment consists of ten 2'-β-D-deoxynucleosides, a 5' wing segment that consists of six 2'-MOE nucleosides, and a 3' wing segment that consists of two cEt nucleosides and two 2'-MOE nucleosides. The sugar motif of the gapmers is (from 5' to 3'): eeeeeedddddddddddkkee; wherein 'd' represents a 2'-D-D-deoxyribosyl sugar, 'k' represents a cEt sugar, and 'e' represents a 2'-MOE modified ribosyl sugar. The gapmers have an internucleoside linkage motif of (from 5' to 3'): sooooosssssssssssoss; wherein "s" represents a phosphorothioate internucleoside linkage and "o" represents a phosphodiester internucleoside linkage. All cytosine residues are 5-methylcytosines.

TABLE 53

6-10-4 MOE/cEt mixed wing gapmers with mixed PO/PS internucleoside linkages complementary to human PRNP

| Compound Number | SEQUENCE | SEQ ID NO: 1 Start Site | SEQ ID NO: 1 Stop Site | SEQ ID NO: 2 Start Site | SEQ ID NO: 2 Start Site | SEQ ID NO. |
|---|---|---|---|---|---|---|
| 1418420 | GTCATAATTTTCTTAGCTAC | N/A | N/A | 5638 | 5657 | 1914 |
| 1418422 | GCCACATATAGGGTCCTTTA | 1963 | 1982 | 17754 | 17773 | 66 |
| 1418424 | GCTTATTATTCATGTTCTCC | N/A | N/A | 14367 | 14386 | 1939 |
| 1418425 | GTGTCATAATTTTCTTAGCT | N/A | N/A | 5640 | 5659 | 2302 |

The modified oligonucleotides in the table below are 6-10-4 mixed MOE gapmers with a 2'-OMe modified nucleoside at position 2 of the gap and mixed PO/PS internucleoside linkages. The gapmers are 20 nucleosides in length, wherein the 5' wing segment consists of six 2'-MOE nucleosides, and the 3' wing segment consists of four 2'-MOE nucleosides. The gap is ten nucleosides in length, and has a nucleoside comprising a 2'-β-D-deoxyribosyl sugar moiety at positions 1, 3, 4, 5, 6, 7, 8, 9 and 10 of the gap (counting from the 5' end) and a 2'-OMe nucleoside at position 2 of the gap (counting from the 5' end). The sugar motif of the mixed, altered gapmers is (from 5' to 3'): eeeeeedydddddddddeeee; wherein 'd' represents a 2'-β-D-deoxyribosyl sugar, 'y' represents a 2'-O-methyl ribosyl sugar, 'k' represents a cEt sugar, and 'e' represents a 2'-MOE sugar. The gapmers have an internucleoside linkage motif of (from 5' to 3'): sooooosssssssssssoss; wherein "s" represents a phosphorothioate internucleoside linkage and "o" represents a phosphodiester internucleoside linkage. All cytosine residues are 5-methylcytosines.

TABLE 54

6-10-4 MOE gapmers having a 2'-OMe at position 2 of the gap with mixed PO/PS internucleoside linkages complementary to human PRNP

| Compound Number | SEQUENCE | SEQ ID NO: 1 Start Site | SEQ ID NO: 1 Stop Site | SEQ ID NO: 2 Start Site | SEQ ID NO: 2 Start Site | SEQ ID NO. |
|---|---|---|---|---|---|---|
| 1418389 | TGGCACTUTCTTTTTATTTC | N/A | N/A | 8038 | 8057 | 2743 |
| 1423127 | GGTTACAUAATGTTCATTTC | N/A | N/A | 5667 | 5686 | 2742 |

The modified oligonucleotides in the table below are 5-9-5 MOE gapmers with mixed PO/PS internucleoside linkages. The gapmers are 19 nucleosides in length and have a central gap segment that consists of nine 2'-β-D-deoxynucleosides, a 5' wing segment that consists of five 2'-MOE nucleosides, and a 3' wing segment that consists of five 2'-MOE nucleosides. The sugar motif of the gapmers is (from 5' to 3'): eeeeeddddddddddeeeee; wherein 'd' represents a 2'-R-D-deoxyribosyl sugar, and 'e' represents a 2'-MOE modified ribosyl sugar. The gapmers have an internucleoside linkage motif of (from 5' to 3'): soooossssssss-soos; wherein each "s" represents a phosphorothioate internucleoside linkage and each "o" represents a phosphodiester internucleoside linkage. Each cytosine nucleoside is a 5-methyl cytosine.

TABLE 55

5-9-5 MOE gapmers with mixed PO/PS internucleoside linkages complementary to human PRNP

| Compound Number | Sequence (5' to 3') | SEQ ID NO: 1 Start Site | SEQ ID NO: 1 Stop Site | SEQ ID NO: 2 Start Site | SEQ ID NO: 2 Start Site | SEQ ID NO. |
|---|---|---|---|---|---|---|
| 1373049 | GTCAGTTTTCCCCACATA | N/A | N/A | 5716 | 5734 | 2745 |
| 1373050 | GTGTCATAATTTTCTTAGC | N/A | N/A | 5641 | 5659 | 2764 |
| 1373051 | GCTTATTATTCATGTTCTC | N/A | N/A | 14368 | 14386 | 2765 |
| 1373052 | GCTTACTCGGCTTGTTCCA | 724 | 742 | 16515 | 16533 | 2766 |
| 1373053 | CTCTATGTTTTCCAGTGCC | 1338 | 1356 | 17129 | 17147 | 2746 |
| 1373054 | GCACACTGACCATTTTTTA | 2148 | 2166 | 17939 | 17957 | 2747 |
| 1373055 | ACTCTATGTTTTCCAGTGC | 1339 | 1357 | 17130 | 17148 | 2748 |
| 1373056 | TGTCAGTTTTCCCCACAT | N/A | N/A | 5717 | 5735 | 2749 |
| 1373057 | GTCATAATTTTCTTAGCTA | N/A | N/A | 5639 | 5657 | 2750 |
| 1373058 | CTATGTTTTCCAGTGCCCA | 1336 | 1354 | 17127 | 17145 | 2751 |
| 1373059 | TCTATGTTTTCCAGTGCCC | 1337 | 1355 | 17128 | 17146 | 2752 |
| 1393333 | CTGAATTTTCTCTCCCAGC | N/A | N/A | 14923 | 14941 | 2753 |
| 1393334 | CCACATATAGGGTCCTTTA | 1963 | 1981 | 17754 | 17772 | 2754 |
| 1393335 | GCCACATATAGGGTCCTTT | 1964 | 1982 | 17755 | 17773 | 2755 |
| 1393336 | ACTGAATTTTCTCTCCCAG | N/A | N/A | 14924 | 14942 | 2756 |

The modified oligonucleotides in the table below are 5-9-5 MOE gapmers with mixed PO/PS internucleoside linkages. The gapmers are 19 nucleosides in length and have a central gap segment that consists of nine 2'-β-D-deoxynucleosides, a 5' wing segment that consists of five 2'-MOE nucleosides, and a 3' wing segment that consists of five 2'-MOE nucleosides. The sugar motif of the gapmers is (from 5' to 3'): eeeeeddddddddddeeeee; wherein 'd' represents a 2'-β-D-deoxyribosyl sugar, and 'e' represents a 2'-MOE modified ribosyl sugar. The gapmers have an internucleoside linkage motif of (from 5' to 3'): soooossssssss-sooss; wherein each "s" represents a phosphorothioate internucleoside linkage and each "o" represents a phosphodiester internucleoside linkage. Each cytosine nucleoside is a 5-methyl cytosine.

TABLE 56

5-9-5 MOE gapmers with mixed PO/PS internucleoside linkages complementary to human PRNP

| Compound Number | Sequence (5' to 3') | SEQ ID NO: 1 Start Site | SEQ ID NO: 1 Stop Site | SEQ ID NO: 2 Start Site | SEQ ID NO: 2 Start Site | SEQ ID NO. |
|---|---|---|---|---|---|---|
| 1373060 | CTATGTTTTCCAGTGCCCA | 1336 | 1354 | 17127 | 17145 | 2751 |
| 1373061 | CTTATTATTCATGTTCTCC | N/A | N/A | 14367 | 14385 | 2757 |
| 1373062 | CTTACTCGGCTTGTTCCAC | 723 | 741 | 16514 | 16532 | 2758 |
| 1373063 | TGTCATAATTTTCTTAGCT | N/A | N/A | 5640 | 5658 | 2759 |
| 1373064 | TCTATGTTTTCCAGTGCCC | 1337 | 1355 | 17128 | 17146 | 2752 |
| 1373065 | TCATAATTTTCTTAGCTAC | N/A | N/A | 5638 | 5656 | 2760 |
| 1373066 | CACACTGACCATTTTTAA | 2147 | 2165 | 17938 | 17956 | 2761 |
| 1373067 | CTCTATGTTTTCCAGTGCC | 1338 | 1356 | 17129 | 17147 | 2746 |
| 1373068 | GTCAGTTTTTCCCCACATA | N/A | N/A | 5716 | 5734 | 2745 |
| 1373069 | TCAGTTTTTCCCCACATAT | N/A | N/A | 5715 | 5733 | 2762 |
| 1373070 | TATGTTTTCCAGTGCCCAT | 1335 | 1353 | 17126 | 17144 | 2763 |

The modified oligonucleotide in the table below is a 5-9-5 mixed MOE/cEt gapmer with mixed PO/PS internucleoside linkages. The gapmer is 19 nucleosides in length, wherein the central gap segment consists of nine 2'-β-D-deoxynucleosides, a 5' wing segment that consists of five 2'-MOE nucleosides, and a 3' wing segment that consists of two cEt nucleosides and three 2'-MOE nucleosides. The sugar motif of the gapmers is (from 5' to 3'): eeeeedddddddddkkeee; wherein 'd' represents a 2'-O-D-deoxyribosyl sugar, 'k' represents a cEt sugar, and 'e' represents a 2'-MOE modified ribosyl sugar. The gapmers have an internucleoside linkage motif of (from 5' to 3'):soooosssssssssssoos; wherein "s" represents a phosphorothioate internucleoside linkage and "o" represents a phosphodiester internucleoside linkage. All cytosine residues are 5-methylcytosines.

TABLE 57

5-9-5 MOE/cEt mixed wing gapmers with mixed PO/PS internucleoside linkages complementary to human PRNP

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1418423 | GTCATAATTTTCTTAGCTA | N/A | N/A | 5639 | 5657 | 2750 |

The modified oligonucleotides in the table below are 5-8-5 MOE gapmers with mixed PO/PS internucleoside linkages. The gapmers are 18 nucleosides in length and have a central gap segment that consists of eight 2'-β-D-deoxynucleosides, a 5' wing segment that consists of five 2'-MOE nucleosides, and a 3' wing segment that consists of five 2'-MOE nucleosides. The sugar motif of the gapmers is (from 5' to 3'): eeeeeddddddddeeeee; wherein 'd' represents a 2'-β-D-deoxyribosyl sugar, and 'e' represents a 2'-MOE modified ribosyl sugar. The gapmers have an internucleoside linkage motif of (from 5' to 3'): sooossssssssssooss; wherein each "s" represents a phosphorothioate internucleoside linkage and each "o" represents a phosphodiester internucleoside linkage. Each cytosine nucleoside is a 5-methyl cytosine.

TABLE 58

5-8-5 MOE gapmers with mixed PO/PS internucleoside linkages complementary to human PRNP

| Compound Number | Sequence (5' to 3') | SEQ ID NO: 1 Start Site | SEQ ID NO: 1 Stop Site | SEQ ID NO: 2 Start Site | SEQ ID NO: 2 Start Site | SEQ ID NO. |
|---|---|---|---|---|---|---|
| 1373071 | CAGTTTTTCCCCACATAT | N/A | N/A | 5715 | 5732 | 2767 |
| 1373072 | ACTCTATGTTTTCCAGTG | 1340 | 1357 | 17131 | 17148 | 2777 |
| 1373073 | TCTATGTTTTCCAGTGCC | 1338 | 1355 | 17129 | 17146 | 2778 |
| 1373074 | CTCTATGTTTTCCAGTGC | 1339 | 1356 | 17130 | 17147 | 2779 |
| 1373075 | CTATGTTTTCCAGTGCCC | 1337 | 1354 | 17128 | 17145 | 2768 |
| 1373076 | GTCAGTTTTTCCCCACAT | N/A | N/A | 5717 | 5734 | 2769 |
| 1373077 | TCAGTTTTTCCCCACATA | N/A | N/A | 5716 | 5733 | 2770 |
| 1393337 | CCACATATAGGGTCCTTT | 1964 | 1981 | 17755 | 17772 | 2771 |
| 1393338 | CACATATAGGGTCCTTTA | 1963 | 1980 | 17754 | 17771 | 2772 |
| 1393339 | ACTGAATTTTCTCTCCCA | N/A | N/A | 14925 | 14942 | 2773 |
| 1393340 | TGAATTTTCTCTCCCAGC | N/A | N/A | 14923 | 14940 | 2774 |
| 1393341 | CTGAATTTTCTCTCCCAG | N/A | N/A | 14924 | 14941 | 2775 |
| 1393342 | GCCACATATAGGGTCCTT | 1965 | 1982 | 17756 | 17773 | 2776 |

The modified oligonucleotide in the table below is a 5-8-5 MOE gapmer with a 2'-OMe modified nucleoside at position 2 of the gap and mixed PO/PS internucleoside linkages. The gapmers are 18 nucleosides in length, wherein the 5' wing segment consists of five 2'-MOE nucleosides and the 3' wing segment consists of five 2'-MOE nucleosides. The gap is eight nucleosides in length, and has a nucleoside comprising a 2'-D-D-deoxyribosyl sugar moiety at positions 1, 3, 4, 5, 6, 7, and 8 of the gap (counting from the 5' end) and 2'-OMe nucleoside at position 2 of the gap (counting from the 5' end). The sugar motif of the gapmer is (from 5' to 3'): eeeeedyddddddeeeee; wherein 'd' represents a 2'-β-D-deoxyribosyl sugar, 'y' represents a 2'-O-methyl ribosyl sugar, and 'e' represents a 2'-MOE sugar. The gapmers have an internucleoside linkage motif of (from 5' to 3'): sooosssssssssooss; wherein "s" represents a phosphorothioate internucleoside linkage and "o" represents a phosphodiester internucleoside linkage. All cytosine residues are 5-methylcytosines.

TABLE 59

5-8-5 MOE gapmers having a 2'-OMe at position 2 of the gap with mixed PO/PS internucleoside linkages complementary to human PRNP

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1418388 | CTATGTUTTCCAGTGCCC | 1337 | 1354 | 17128 | 17145 | 2780 |

The modified oligonucleotides in the table below are 4-8-5 mixed MOE/cEt gapmers with mixed PO/PS internucleoside linkages. The gapmers are 17 nucleosides in length, wherein the central gap segment consists of eight 2'-β-D-deoxynucleosides, a 5' wing segment that consists of four 2'-MOE nucleosides, and a 3' wing segment that consists of two cEt nucleosides and three 2'-MOE nucleosides. The sugar motif of the gapmers is (from 5' to 3'): eeeedddddddddkkeee; wherein 'd' represents a 2'-β-D-deoxyribosyl sugar, 'k' represents a cEt sugar, and 'e' represents a 2'-MOE modified ribosyl sugar. The gapmers have an internucleoside linkage motif of (from 5' to 3'): soosssssssssooss; wherein "s" represents a phosphorothioate internucleoside linkage and "o" represents a phosphodiester internucleoside linkage. All cytosine residues are 5-methylcytosines.

TABLE 60

4-8-5 MOE/cEt mixed wing gapmers with mixed PO/PS internucleoside linkages complementary to human PRNP

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1418390 | CTATGTTTTCCAGTGCC | 1338 | 1354 | 17129 | 17145 | 2802 |
| 1418391 | ACTCTATGTTTTCCAGT | 1341 | 1357 | 17132 | 17148 | 2781 |
| 1418392 | TCTATGTTTTCCAGTGC | 1339 | 1355 | 17130 | 17146 | 2782 |
| 1418393 | CTCTATGTTTTCCAGTG | 1340 | 1356 | 17131 | 17147 | 2783 |
| 1418394 | ACATATAGGGTCCTTTA | 1963 | 1979 | 17754 | 17770 | 2784 |
| 1418395 | GCCACATATAGGGTCCT | 1966 | 1982 | 17757 | 17773 | 2785 |
| 1418396 | CACATATAGGGTCCTTT | 1964 | 1980 | 17755 | 17771 | 2786 |
| 1418397 | CCACATATAGGGTCCTT | 1965 | 1981 | 17756 | 17772 | 2787 |
| 1418398 | ATAATTTTCTTAGCTAC | N/A | N/A | 5638 | 5654 | 2788 |
| 1418399 | GTCATAATTTTCTTAGC | N/A | N/A | 5641 | 5657 | 2789 |
| 1418400 | CATAATTTTCTTAGCTA | N/A | N/A | 5639 | 5655 | 2790 |
| 1418401 | TCATAATTTTCTTAGCT | N/A | N/A | 5640 | 5656 | 2791 |
| 1418402 | GTGTCATAATTTTCTTA | N/A | N/A | 5643 | 5659 | 2792 |
| 1418403 | TGTCATAATTTTCTTAG | N/A | N/A | 5642 | 5658 | 2793 |
| 1418404 | TATTATTCATGTTCTCC | N/A | N/A | 14367 | 14383 | 2794 |
| 1418405 | GCTTATTATTCATGTTC | N/A | N/A | 14370 | 14386 | 2795 |
| 1418406 | TTATTATTCATGTTCTC | N/A | N/A | 14368 | 14384 | 2796 |
| 1418407 | CTTATTATTCATGTTCT | N/A | N/A | 14369 | 14385 | 2797 |
| 1418412 | CCATTTTCTGTGCTTTT | N/A | N/A | 5806 | 5822 | 2798 |
| 1418413 | CGTCCATTTTCTGTGCT | N/A | N/A | 5809 | 5825 | 2799 |
| 1418414 | TCCATTTTCTGTGCTTT | N/A | N/A | 5807 | 5823 | 2800 |
| 1418415 | GTCCATTTTCTGTGCTT | N/A | N/A | 5808 | 5824 | 2801 |

The modified oligonucleotides in the table below are 4-8-4 mixed MOE/cEt gapmers with mixed PO/PS internucleoside linkages. The gapmers are 17 nucleotides in length, wherein the central gap segment consists of eight 2'-β-D-deoxynucleosides, a 5' wing segment that consists of four 2'-MOE nucleosides, and a 3' wing segment that consists of two cEt nucleosides and two 2'-MOE nucleosides. The sugar motif of the gapmers is (from 5' to 3'): eeeedddddddddkkee; wherein 'd' represents a 2'-D-D-deoxyribosyl sugar, 'k' represents a cEt sugar, and 'e' represents a 2'-MOE modified ribosyl sugar. The gapmers have an internucleoside linkage motif of (from 5' to 3'): soossssssssssoos; wherein "s" represents a phosphorothioate internucleoside linkage and "o" represents a phosphodiester internucleoside linkage. All cytosine residues are 5-methylcytosines.

TABLE 61

4-8-4 MOE/cEt mixed wing gapmers with mixed PO/PS internucleoside linkages complementary to human PRNP

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1418408 | ATAATTTTCTTAGCTA | N/A | N/A | 5639 | 5654 | 2806 |
| 1418409 | GTCATAATTTTCTTAG | N/A | N/A | 5642 | 5657 | 2803 |

TABLE 61-continued 4-8-4 MOE/cEt mixed wing gapmers with mixed PO/PS internucleoside linkages complementary to human PRNP

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1418410 | CATAATTTTCTTAGCT | N/A | N/A | 5640 | 5655 | 2804 |
| 1418411 | TCATAATTTTCTTAGC | N/A | N/A | 5641 | 5656 | 2805 |

Example 5: Activity of Modified Oligonucleotides Complementary to Human PRNP in Transgenic Mice Modified oligonucleotides described above were tested in human PRNP knock-in mouse model. Humanization of PRNP gene was done via CRISPR/Cas-9-mediated gene editing, allowing for generation of a model with constitutive expression of human PRNP gene. Targeting strategy was based on NCBI transcripts NM_011170.3 (mouse) and NM_000311.1 (human). Mouse genomic sequence from exon 1 (5' untranslated region, UTR) to exon 3 (3' UTR) were replaced with its human counterpart. A plasmid allowing expression of Cas9 mRNA and specific gRNA, plasmid containing the puromycin resistance cassette, and a plasmid containing the homology regions of the mouse PRNP gene and the replaced human region were co-transfected into the Taconic Biosciences C57BL/6N Tac ES cell line. Homologous recombination clones were isolated using positive puromycin selection, and humanized allele was obtained after Cas9-mediated gene editing. Line C57BL/6NTac-Pmp<em5804_E-D05(PRNP) was used in these experiments. Human PRNP RNA expression is found in the brain and spinal cord.

Treatment

The PRNP knock-in mice were divided into groups of 2-3 mice each. Each mouse received a single ICV bolus of 300 µg of a modified oligonucleotide described above. A group of 2-4 mice received PBS as a negative control within each study. Also tested in one study were comparator compounds 169746, 169750, 169753, and 169764, described herein above and in WO2010/019270.

RNA Analysis

Two weeks post treatment, mice were sacrificed and RNA was extracted from cortical brain tissue and spinal cord for RTPCR analysis to measure amount of PRNP RNA using human primer probe sets RTS42354 (described herein above) and primer probe set RTS42356 (forward sequence GGTGGTGTCTCACTCTTTCTTC, designated herein as SEQ ID NO: 12; reverse sequence CCAG-CATCTCAGGTCTACTCTA, designated herein as SEQ ID NO: 13; probe sequence AATACCCTTGGCACT-GATGGGCA, designated herein as SEQ ID NO: 14). Results are presented as percent human PRNP RNA relative to PBS control, normalized to mouse cyclophilin A. Each study is represented in a separate table. Cyclophilin A was amplified using primer probe set m_cyclo24 (forward sequence TCGCCGCTTGCTGCA, designated herein as SEQ ID NO: 18; reverse sequence ATCGGCCGT-GATGTCGA, designated herein as SEQ ID NO: 19; probe sequence CCATGGTCAACCCCACCGTGTTC, designated herein as SEQ ID NO: 20). In some cases, RTPCR value is not defined for a certain sample, and is labeled N.D. (Not Defined). The values marked with a (*) symbol indicate that the modified oligonucleotide is complementary to the amplicon region of the primer probe set. Additional assays may be used to measure the potency and efficacy of the modified oligonucleotides complementary to the amplicon region, including testing with a second primer probe set.

As shown in the table below, treatment with modified oligonucleotides resulted in reduction of PRNP RNA in comparison to the PBS control.

TABLE 62

Reduction of human PRNP RNA in knock-in mice

| | PRNP RNA (% control) | | | |
|---|---|---|---|---|
| Compound | RTS42354 | | RTS42356 | |
| Number | Cortex | Spinal Cord | Cortex | Spinal Cord |
| PBS | 100 | 100 | 100 | 100 |
| 169746 | 67 | 52 | 72 | 46 |
| 169750 | 73‡ | 61‡ | 78‡ | 52‡ |
| 169753 | 37 | 32 | 37 | 29 |
| 169764 | 77 | 61 | 80 | 57 |
| 1201071 | 80 | 67 | 83 | 54 |
| 1201142 | 29‡ | 30‡ | 35‡ | 28‡ |
| 1238171 | 62* | 71* | 83 | 74 |
| 1238195 | 90 | 67 | 87 | 64 |
| 1238240 | 63 | 46 | 8* | 6* |
| 1238320 | 83 | 71 | 93 | 60 |
| 1238321 | 73 | 73 | 82 | 69 |
| 1239027 | 28 | 25 | 29 | 20 |
| 1239250 | 32 | 20 | 32 | 16 |
| 1239696 | 88 | 73 | 90 | 65 |
| 1270230 | 48 | 44 | 33* | 21* |
| 1270231 | 15 | 22 | 13* | 10* |
| 1270232 | 29 | 29 | 28* | 20* |
| 1270293 | 64 | 64 | 63 | 54 |
| 1270406 | 16 | 19 | 18 | 12 |
| 1270457 | 42 | 26 | 46 | 22 |
| 1270458 | 44 | 36 | 47 | 30 |
| 1335684 | 30 | 28 | 30 | 20 |
| 1335686 | 47 | 37 | 46 | 27 |
| 1335688 | 34 | 22 | 35 | 16 |

‡Notes value is based on a single animal and is not an average.

TABLE 63

Reduction of human PRNP RNA in knock-in mice

| | PRNP RNA (% control) | | | |
|---|---|---|---|---|
| Compound | RTS42354 | | RTS42356 | |
| Number | Cortex | Spinal Cord | Cortex | Spinal Cord |
| PBS | 100 | 100 | 100 | 100 |
| 1200973 | 12* | 10* | 94 | 73 |
| 1201005 | 52 | 30 | 53 | 33 |
| 1201142 | 61 | 16 | 43 | 18 |
| 1238167 | 44* | 6* | 104 | 74 |
| 1238168 | 52* | 8* | 103 | 74 |

TABLE 63-continued

Reduction of human PRNP RNA in knock-in mice

| | PRNP RNA (% control) | | | |
|---|---|---|---|---|
| Compound | RTS42354 | | RTS42356 | |
| Number | Cortex | Spinal Cord | Cortex | Spinal Cord |
| 1238169 | 42* | 6* | 88 | 52 |
| 1238170 | 39* | 6* | 76 | 51 |
| 1238322 | 61 | 21 | 63 | 30 |
| 1238325 | 84 | 30 | 70 | 35 |
| 1238490 | 60 | 26 | 43 | 28 |
| 1238498 | 97 | 48 | 68 | 54 |
| 1238507 | 104 | 48 | 74 | 50 |
| 1238517 | 104 | 45 | 67 | 44 |
| 1238812 | 72 | 40 | 48 | 35 |
| 1238863 | 119 | 46 | 76 | 41 |
| 1238987 | 88 | 35 | 57 | 34 |
| 1239009 | 68 | 34 | 44 | 31 |
| 1239027 | 49 | 24 | 33 | 23 |
| 1239052 | 94 | 40 | 60 | 38 |
| 1239234 | 70 | 29 | 44 | 28 |
| 1239250 | 54 | 19 | 36 | 18 |
| 1239544 | 80 | 29 | 55 | 27 |
| 1201143 | 123 | 40 | 83 | 37 |
| 1201154 | 100 | 36 | 66 | 34 |
| 1201157 | 111 | 49 | 74 | 42 |
| 1201255 | 142 | 66 | 93 | 59 |
| 1238580 | 80 | 48 | 53 | 47 |
| 1238582 | 130 | 67 | 83 | 65 |
| 1238600 | 123 | 57 | 80 | 56 |
| 1238632 | 115 | 60 | 74 | 57 |

TABLE 64

Reduction of human PRNP RNA in knock-in mice

| | PRNP RNA (% control) | | | |
|---|---|---|---|---|
| Compound | RTS42354 | | RTS42356 | |
| Number | Cortex | Spinal Cord | Cortex | Spinal Cord |
| PBS | 100 | 100 | 100 | 100 |
| 1201142 | 44 | 29 | 44 | 32 |
| 1200974 | 37* | 46* | 96 | 96 |
| 1200975 | 43* | 21* | 101 | 85 |
| 1200976 | 67* | 47* | 102 | 86 |
| 1200978 | 33* | 26* | 105 | 104 |
| 1201143 | 77 | 38 | 73 | 41 |
| 1238339 | 81 | 50 | 78 | 53 |
| 1238404 | 86 | 49 | 80 | 57 |
| 1238410 | 56 | 38 | 55 | 43 |
| 1238489 | 93 | 70 | 89 | 73 |
| 1238491 | 65 | 49 | 58 | 47 |
| 1238492 | 66 | 53 | 61 | 53 |
| 1238500 | 69 | 44 | 61 | 45 |
| 1238501 | 59 | 49 | 53 | 50 |
| 1238600 | 83 | 67 | 78 | 70 |
| 1238814 | 83 | 51 | 76 | 53 |
| 1238837 | 64 | 48 | 60 | 50 |
| 1238947 | 80 | 41 | 80 | 49 |
| 1238990 | 86 | 48 | 84 | 54 |
| 1238996 | 64 | 42 | 60 | 46 |
| 1239010 | 76 | 37 | 71 | 39 |
| 1239024 | 93 | 72 | 91 | 77 |
| 1239025 | 89 | 52 | 79 | 54 |
| 1239026 | 91 | 67 | 84 | 64 |
| 1239028 | 59 | 38 | 58 | 40 |
| 1239029 | 65 | 40 | 64 | 42 |
| 1239030 | 47 | 34 | 43 | 37 |
| 1239031 | 68 | 44 | 66 | 49 |
| 1239045 | 80 | 51 | 79 | 55 |
| 1239062 | 97 | 68 | 97 | 79 |
| 1239063 | 88 | 39 | 87 | 43 |
| 1239293 | 91 | 40 | 90 | 42 |

TABLE 64-continued

Reduction of human PRNP RNA in knock-in mice

| | PRNP RNA (% control) | | | |
|---|---|---|---|---|
| Compound | RTS42354 | | RTS42356 | |
| Number | Cortex | Spinal Cord | Cortex | Spinal Cord |
| 1239448 | 13 | 180 | 8 | 111 |
| 1270213 | 43* | 66* | 92 | 98 |
| 1270228 | 65 | 39 | 43* | 32* |
| 1270229 | 39 | 27 | 32* | 22* |
| 1270230 | 32 | 39 | 18* | 26* |
| 1270231 | 42 | 21 | 27* | 16* |
| 1270232 | 50 | 22 | 35* | 18* |
| 1270233 | 70 | 46 | 56* | 47* |
| 1270301 | 78 | 58 | 70 | 60 |
| 1270302 | 81 | 61 | 73 | 60 |
| 1270303 | 97 | 58 | 90 | 60 |
| 1270405 | 72 | 49 | 64 | 53 |
| 1270406 | 25 | 19 | 22 | 20 |
| 1270457 | 37 | 27 | 35 | 30 |
| 1270458 | 40 | 33 | 36 | 34 |
| 1335684 | 32 | 31 | 25 | 30 |
| 1335686 | 39 | 36 | 32 | 34 |
| 1335687 | 44* | 58* | 83 | 79 |
| 1335688 | 34 | 19 | 31 | 18 |

TABLE 65

Reduction of human PRNP RNA in knock-in mice

| | PRNP RNA (% control) | | | |
|---|---|---|---|---|
| Compound | RTS42354 | | RTS42356 | |
| Number | Cortex | Spinal Cord | Cortex | Spinal Cord |
| PBS | 100 | 100 | 100 | 100 |
| 1201142 | 31 | 33 | 29 | 31 |
| 1201144 | 114 | 80 | 102 | 66 |
| 1238319 | 91 | 79 | 97 | 80 |
| 1238326 | 88 | 70 | 84 | 56 |
| 1238328 | ‡93 | ‡86 | ‡85 | ‡63 |
| 1238335 | 80 | 61 | 69 | 57 |
| 1238397 | 110 | 100 | 97 | 90 |
| 1238398 | 104 | 79 | 96 | 72 |
| 1238994 | 41 | 32 | 39 | 29 |
| 1238998 | 87 | 86 | 80 | 77 |
| 1239003 | 98 | 85 | 94 | 76 |
| 1239004 | 62 | 47 | 95 | 91 |
| 1239005 | 57 | 72 | 88 | 81 |
| 1239007 | 92 | 75 | 86 | 66 |
| 1239008 | 62 | 67 | 61 | 59 |
| 1239012 | 100 | 82 | 92 | 69 |
| 1239013 | 96 | 97 | 91 | 86 |
| 1239015 | 73 | 69 | 62 | 61 |
| 1270212 | 26* | 47* | 96 | 88 |
| 1270265 | 63 | 57 | 60 | 50 |
| 1270279 | 108 | 92 | 93 | 85 |
| 1270280 | 77 | 80 | 71 | 71 |
| 1270281 | 56 | 38 | 55 | 41 |
| 1270282 | 83 | 52 | 75 | 46 |
| 1270400 | 41 | 33 | 38 | 27 |
| 1270401 | 106 | 100 | 89 | 79 |
| 1270402 | 107 | 82 | 93 | 67 |
| 1270542 | 100 | 100 | 83 | 82 |
| 1270551 | 115 | 105 | 105 | 88 |
| 1270584 | 100 | 91 | 85 | 76 |
| 1270616 | 120 | 108 | 105 | 88 |
| 1355700 | 111* | 112* | 108 | 98 |
| 1355701 | 36* | 54* | 103 | 96 |
| 1355702 | 113* | 103* | 105 | 93 |
| 1355703 | 43* | 64* | 89 | 87 |
| 1355704 | 70* | 81* | 98 | 96 |
| 1355705 | 67* | 83* | 96 | 99 |
| 1355706 | 32 | 30 | 29 | 25 |

TABLE 65-continued

Reduction of human PRNP RNA in knock-in mice

| Compound | PRNP RNA (% control) | | | |
|---|---|---|---|---|
| | RTS42354 | | RTS42356 | |
| Number | Cortex | Spinal Cord | Cortex | Spinal Cord |
| 1355707 | 70 | 55 | 60 | 48 |
| 1355708 | 40 | 40 | 37 | 35 |
| 1355709 | 16* | 17* | 78 | 70 |

‡Notes value is based on a single animal and is not an average.

TABLE 66

Reduction of human PRNP RNA in knock-in mice

| Compound | PRNP RNA (% control) | | | |
|---|---|---|---|---|
| | RTS42354 | | RTS42356 | |
| Number | Cortex | Spinal Cord | Cortex | Spinal Cord |
| PBS | 100 | 100 | 100 | 100 |
| 1201142 | 37 | 69 | 40 | 98 |
| 1201004 | 90 | 61 | 90 | 116 |
| 1201006 | 68 | 58 | 70 | 123 |
| 1201007 | 76 | 60 | 76 | 91 |
| 1201141 | 62 | 55 | 64 | 92 |
| 1238202 | 91 | 82 | 92 | 109 |
| 1239543 | 68 | 74 | 69 | 92 |
| 1239545 | 81 | 81 | 79 | 88 |
| 1239546 | 90 | 87 | 88 | 71 |
| 1239547 | 91 | 113 | 93 | 86 |
| 1373020 | 60 | 65 | 18* | 25* |
| 1373021 | 31 | 32 | 26 | 35 |
| 1373022 | 36 | 43 | 37 | 40 |
| 1373023 | 28 | 28 | 28 | 35 |
| 1373024 | 62 | 59 | 60 | 50 |
| 1373025 | 57 | 45 | 59 | 43 |
| 1373026 | 57 | 48 | 44* | 28* |
| 1373027 | 53 | 56 | 31* | 21* |
| 1373028 | 72 | 61 | 68 | 56 |
| 1373029 | 73 | 68 | 61* | 35* |
| 1373030 | 73 | 60 | 66* | 40* |
| 1373031 | 68 | 63 | 56 | 44 |
| 1373032 | 59 | 43 | 57 | 50 |
| 1373033 | 83 | 55 | 82 | 70 |
| 1373034 | 56 | 48 | 57 | 79 |
| 1373035 | 64 | 48 | 64 | 81 |
| 1373036 | 41 | 33 | 40* | 45* |
| 1373037 | 35 | 37 | 32* | 53* |
| 1373038 | 41 | 31 | 41 | 51 |
| 1373039 | 51 | 51 | 50 | 70 |
| 1373040 | 34 | 34 | 35 | 56 |
| 1373041 | 32 | 44 | 29 | 51 |
| 1373042 | 57 | 59 | 56* | 41* |
| 1373043 | 39 | 48 | 37* | 32* |
| 1373044 | 36 | 42 | 26* | 28* |
| 1373045 | 49 | 59 | 31* | 29* |
| 1373046 | 52 | 57 | 15* | 16* |
| 1373047 | 56 | 58 | 44 | 42 |
| 1373048 | 46 | 67 | 21* | 22* |
| 1373049 | 59 | 48 | 51 | 40 |
| 1373050 | 65 | 66 | 44 | 44 |
| 1373051 | 59 | 72 | 57 | 61 |
| 1373052 | 59 | 68 | 48 | 56 |
| 1373053 | 44 | 50 | 35* | 38* |
| 1373054 | 53 | 64 | 46 | 59 |
| 1373055 | 75 | 78 | 668 | 518 |
| 1373056 | 39 | 33 | 43 | 32 |
| 1373057 | 41 | 25 | 29 | 24 |
| 1373058 | 45 | 42 | 24* | 19* |
| 1373059 | 31 | 22 | 20* | 15* |
| 1373060 | 42 | 43 | 24* | 19* |
| 1373061 | 46 | 64 | 45 | 59 |
| 1373062 | 62 | 89 | 90 | 85 |

TABLE 66-continued

Reduction of human PRNP RNA in knock-in mice

| Compound | PRNP RNA (% control) | | | |
|---|---|---|---|---|
| | RTS42354 | | RTS42356 | |
| Number | Cortex | Spinal Cord | Cortex | Spinal Cord |
| 1373063 | 43 | 52 | 74 | 43 |
| 1373064 | 71 | 92 | 89* | 81* |
| 1373065 | 93 | 93 | 94 | 83 |
| 1373066 | 95 | 94 | 77 | 82 |
| 1373067 | 64 | 34 | 46* | 20* |
| 1373068 | 53 | 36 | 55 | 31 |
| 1373069 | 57 | 51 | 66 | 49 |
| 1373070 | 66 | 55 | 62* | 56* |
| 1373071 | 70 | 70 | 73 | 67 |
| 1373072 | 62 | 58 | 55* | 52* |
| 1373073 | 51 | 46 | 45* | 40* |
| 1373074 | 63 | 47 | 56* | 41* |
| 1373075 | 31 | 27 | 25* | 14* |
| 1373076 | 30 | 23 | 29 | 16 |
| 1373077 | 80 | 71 | 76 | 66 |
| 1373078 | 54 | 36 | 53 | 35 |

TABLE 67

Reduction of human PRNP RNA in knock-in mice

| Compound | PRNP RNA (% control) | | | |
|---|---|---|---|---|
| | RTS42354 | | RTS42356 | |
| Number | Cortex | Spinal Cord | Cortex | Spinal Cord |
| PBS | 100 | 100 | 100 | 100 |
| 1201263 | 62 | 45 | 64 | 44 |
| 1201324 | 86 | 63 | 92 | 66 |
| 1238739 | 74 | 45 | 74 | 47 |
| 1238741 | 91 | 56 | 93 | 60 |
| 1238816 | 72 | 48 | 74 | 52 |
| 1238818 | 97 | 63 | 97 | 71 |
| 1238867 | 87 | 68 | 91 | 69 |
| 1238940 | 87 | 48 | 88 | 50 |
| 1239047 | 91 | 63 | 96 | 66 |
| 1239048 | 84 | 67 | 91 | 70 |
| 1239073 | 66 | 41 | 67 | 43 |
| 1239079 | 71 | 50 | 73 | 52 |
| 1239086 | 82 | 60 | 85 | 64 |
| 1239138 | 77 | 39 | 76 | 41 |
| 1239159 | 101 | 64 | 100 | 62 |
| 1239185 | 92 | 58 | 99 | 60 |
| 1239235 | 56 | 32 | 60 | 35 |
| 1239272 | 79 | 45 | 86 | 49 |
| 1239346 | 61 | 40 | 62 | 44 |
| 1239347 | 71 | 45 | 74 | 48 |
| 1239370 | 87 | 60 | 91 | 65 |
| 1239419 | 107 | 80 | 111 | 83 |
| 1239452 | 71 | 44 | 72 | 46 |
| 1239460 | 84 | 64 | 80 | 61 |
| 1239514 | 101 | 75 | 98 | 74 |
| 1239541 | 80 | 50 | 84 | 51 |
| 1239547 | 81 | 63 | 82 | 65 |
| 1239598 | 94 | 63 | 93 | 64 |
| 1270345 | 79 | 56 | 82 | 60 |
| 1270411 | 74 | 47 | 75 | 52 |
| 1270412 | 75 | 38 | 81 | 41 |

TABLE 68

Reduction of human PRNP RNA in knock-in mice

| Compound Number | PRNP RNA (% control) | | | |
|---|---|---|---|---|
| | RTS42354 | | RTS42356 | |
| | Cortex | Spinal Cord | Cortex | Spinal Cord |
| PBS | 100 | 100 | 100 | 100 |
| 1355710 | 105 | 89 | 97 | 98 |
| 1355711 | 93 | 57 | 80 | 72 |
| 1355712 | 122 | 79 | 91 | 96 |
| 1355713 | 114 | 86 | 97 | 100 |
| 1355714 | 116 | 70 | 94 | 87 |
| 1355715 | 102 | 54 | 75 | 63 |
| 1355716 | 117 | 79 | 83 | 93 |
| 1355717 | 108 | 63 | 68 | 75 |
| 1355718 | 150 | 74 | 100 | 95 |
| 1355719 | 185 | 68 | 114 | 86 |
| 1355720 | 51 | 32 | 26 | 33 |
| 1355721 | 119 | 65 | 63 | 67 |
| 1355722 | 119 | 67 | 64 | 70 |
| 1355723 | 130 | 72 | 73 | 78 |
| 1355724 | 120 | 60 | 68 | 65 |
| 1355725 | 116 | 56 | 64 | 58 |
| 1355726 | 128 | 63 | 85 | 68 |
| 1355727 | 186 | 83 | 112 | 89 |
| 1355728 | 74 | 49 | 60 | 53 |
| 1355729 | 171 | 73 | 117 | 85 |
| 1355730 | 179 | 82 | 115 | 94 |
| 1355731 | 149 | 66 | 104 | 84 |
| 1355732 | 79 | 62 | 83 | 47 |
| 1355733 | 92 | 84 | 92 | 87 |
| 1355734 | 62 | 54 | 59 | 58 |
| 1355735 | 55 | 51 | 51 | 58 |
| 1355736 | 82 | 66 | 82 | 71 |
| 1355737 | 86 | 71 | 89 | 86 |
| 1355738 | 95 | 53 | 77 | 64 |
| 1355739 | 92 | 58 | 74 | 74 |
| 1355740 | 98 | 67 | 81 | 81 |
| 1355741 | 119 | 85 | 91 | 97 |
| 1355742 | 105 | 66 | 75 | 77 |
| 1355743 | 117 | 72 | 88 | 86 |
| 1355744 | 64 | 43 | 44 | 57 |
| 1355745 | 130 | 69 | 93 | 92 |
| 1355746 | 110 | 79 | 67 | 83 |
| 1355747 | 117 | 69 | 63 | 70 |
| 1355748 | 128 | 80 | 71 | 87 |
| 1355749 | 135 | 69 | 78 | 78 |
| 1355750 | 146 | 77 | 90 | 83 |
| 1355751 | 146 | 81 | 92 | 91 |
| 1355752 | 109 | 50 | 67 | 53 |
| 1355753 | 146 | 68 | 94 | 76 |
| 1355754 | 152 | 81 | 107 | 84 |
| 1355755 | 141 | 79 | 96 | 85 |
| 1355756 | 177 | 78 | 118 | 87 |
| 1355757 | 196 | 72 | 129 | 92 |

TABLE 69

Reduction of human PRNP RNA in knock-in mice

| Compound Number | PRNP RNA (% control) | | | |
|---|---|---|---|---|
| | RTS42354 | | RTS42356 | |
| | Cortex | Spinal Cord | Cortex | Spinal Cord |
| PBS | 100 | 100 | 100 | 100 |
| 1393324 | 82 | 56 | 83 | 47 |
| 1393327 | 85 | 55 | 87 | 49 |
| 1393329 | 94 | 56 | 96 | 53 |
| 1393330 | 44 | 30 | 49 | 29 |
| 1393331 | 78 | 57 | 89 | 54 |
| 1393332 | 57 | 29 | 62 | 28 |
| 1393333 | 79 | 64 | 86 | 59 |
| 1393334 | 63 | 41 | 68 | 35 |
| 1393335 | 50 | 30 | 54 | 27 |
| 1393336 | 86 | 84 | 98 | 71 |
| 1393337 | 67 | 56 | 69 | 43 |
| 1393338 | 81 | 76 | 90 | 70 |
| 1393339 | 78 | 65 | 86 | 52 |
| 1393340 | 79 | 79 | 87 | 66 |
| 1393341 | 86 | 85 | 94 | 69 |
| 1393342 | 58 | 46 | 64 | 39 |
| 1394116 | 85 | 80 | 93 | 69 |
| 1394117 | 74 | 60 | 83 | 49 |
| 1394118 | 65 | 51 | 74 | 44 |
| 1394119 | 64 | 51 | 71 | 44 |
| 1394120 | 65 | 50 | 77 | 45 |
| 1394121 | 66 | 54 | 71 | 46 |
| 1394122 | 83 | 53 | 98 | 59 |
| 1394123 | 62 | 45 | 76 | 49 |
| 1394124 | 73 | 35 | 62* | 34* |
| 1394125 | 72 | 55 | 84 | 68 |
| 1394126 | 81 | 72 | 94 | 74 |
| 1394127 | 79 | 58 | 98 | 76 |
| 1394128 | 86 | 61 | 104 | 77 |
| 1394129 | 60 | 51 | 77 | 55 |
| 1394130 | 66 | 40 | 60 | 46 |
| 1394131 | 67 | 47 | 24* | 19* |
| 1394132 | 71 | 55 | 47 | 46 |
| 1394133 | 87 | 72 | 87 | 62 |
| 1394134 | 75 | 51 | 72 | 46 |
| 1394135 | 79 | 60 | 52 | 46 |
| 1394136 | 45 | 32 | 47 | 30 |
| 1394137 | 76 | 66 | 59* | 36* |
| 1394138 | 73 | 62 | 24* | 18* |
| 1394139 | 68 | 58 | 35 | 42 |

TABLE 70

Reduction of human PRNP RNA in knock-in mice

| Compound Number | PRNP RNA (% control) | | | |
|---|---|---|---|---|
| | RTS42354 | | RTS42356 | |
| | Cortex | Spinal Cord | Cortex | Spinal Cord |
| PBS | 100 | 100 | 100 | 100 |
| 1238414 | 90 | 75 | 89 | 72 |
| 1238503 | 68 | 43 | 68 | 42 |
| 1238550 | 58 | 41 | 55 | 41 |
| 1238882 | 71 | 35 | 68 | 38 |
| 1238982 | 86 | 61 | 82 | 57 |
| 1239136 | 59 | 56 | 58 | 57 |
| 1239202 | 77 | 66 | 76 | 64 |
| 1239559 | 70 | 47 | 70 | 47 |
| 1239560 | 81 | 68 | 81 | 65 |
| 1239661 | 63 | 39 | 62 | 38 |
| 1406230 | 77 | 59 | 73 | 52 |
| 1406232 | 50 | 33 | 49 | 32 |
| 1406236 | 86 | 70 | 85 | 66 |
| 1406238 | 65 | 40 | 61 | 39 |
| 1406243 | 54 | 50 | 51 | 48 |
| 1406250 | 99 | 93 | 63 | 91 |
| 1406254 | 60 | 49 | 58 | 44 |
| 1406261 | 56 | 52 | 54 | 47 |
| 1406262 | 38 | 34 | 36 | 31 |
| 1406264 | 85 | 84 | 85 | 80 |
| 1406267 | 69 | 56 | 64 | 49 |
| 1238358 | 63 | 55 | 60 | 51 |
| 1238374 | 51 | 73 | 45 | 64 |
| 1238441 | 89 | 73 | 83 | 70 |
| 1238638 | 81 | 66 | 80 | 66 |

TABLE 70-continued

Reduction of human PRNP RNA in knock-in mice

| Compound | RTS42354 | | RTS42356 | |
|---|---|---|---|---|
| Number | Cortex | Spinal Cord | Cortex | Spinal Cord |
| 1238803 | 72 | 62 | 67 | 60 |
| 1238896 | 51 | 47 | 58 | 46 |
| 1239049 | 68 | 64 | 60 | 60 |
| 1239179 | 78 | 52 | 66 | 49 |
| 1239223 | 79 | 70 | 76 | 67 |
| 1239326 | 68 | 49 | 60 | 49 |
| 1270309 | 68 | 43 | 60 | 36 |
| 1270317 | 66 | 56 | 61 | 56 |
| 1270318 | 62 | 48 | 63 | 46 |
| 1238240 | 54 | 47 | 1* | 4* |
| 1270342 | 54 | 46 | 46 | 43 |

TABLE 71

Reduction of human PRNP RNA in knock-in mice

| Compound | RTS42354 | | RTS42356 | |
|---|---|---|---|---|
| Number | Cortex | Spinal Cord | Cortex | Spinal Cord |
| PBS | 100 | 100 | 100 | 100 |
| 1270363 | 39 | 29 | 31 | 31 |
| 1411004 | 21 | 13 | 13 | 13 |
| 1411005 | 30 | 20 | 19 | 19 |
| 1411006 | 28 | 14 | 15 | 15 |
| 1411007 | 32 | 21 | 19 | 19 |
| 1411013 | 38 | 26 | 26 | 26 |
| 1411014 | 28 | 13 | 13 | 13 |
| 1411015 | 22 | 13 | 12 | 12 |
| 1411016 | 29 | 22 | 21 | 21 |
| 1270381 | 77 | 51 | 45 | 45 |
| 1270459 | 62 | 52 | 46 | 46 |
| 1270530 | 67 | 55 | 43 | 43 |

TABLE 72

Reduction of human PRNP RNA in knock-in mice

| Compound | RTS42354 | | RTS42356 | |
|---|---|---|---|---|
| Number | Cortex | Spinal Cord | Cortex | Spinal Cord |
| PBS | 100 | 100 | 100 | 100 |
| 1270342 | 75 | 47 | 73 | 47 |
| 1270363 | 71 | 37 | 76 | 35 |
| 1406232 | 59 | 37 | 60 | 34 |
| 1406254 | 66 | 71 | 69 | 75 |
| 1406261 | 52 | 35 | 51 | 34 |
| 1406262 | 56 | 43 | 54 | 41 |
| 1411004 | 30 | 17 | 29 | 17 |
| 1411005 | 44 | 24 | 46 | 23 |
| 1411006 | 30 | 18 | 31 | 18 |
| 1411007 | 36 | 26 | 38 | 24 |
| 1411013 | 44 | 28 | 44 | 27 |
| 1411014 | 33 | 25 | 34 | 23 |
| 1411015 | 25 | 21 | 24 | 18 |
| 1411016 | 42 | 25 | 44 | 21 |
| 1411017 | 80 | 38 | 76 | 35 |
| 1411018 | 81 | 56 | 79 | 52 |

TABLE 73

Reduction of human PRNP RNA in knock-in mice

| Compound | RTS42354 | | RTS42356 | |
|---|---|---|---|---|
| Number | Cortex | Spinal Cord | Cortex | Spinal Cord |
| PBS | 100 | 100 | 100 | 100 |
| 1418386 | 35 | 19 | 13* | 8* |
| 1418387 | 53 | 29 | 46 | 28 |
| 1418388 | 68 | 58 | 16* | 15* |
| 1418389 | 76 | 48 | 54 | 46 |
| 1418390 | 68 | 34 | 36* | 20* |
| 1418391 | 67 | 38 | 60* | 35* |
| 1418392 | 63 | 27 | 52* | 25* |
| 1418393 | 68 | 34 | 48* | 25* |
| 1418394 | 97 | 81 | 69 | 66 |
| 1418395 | 74 | 48 | 77 | 49 |
| 1418396 | 84 | 60 | 80 | 49 |
| 1418397 | 87 | 61 | 76 | 57 |
| 1418398 | 95 | 80 | 89 | 73 |
| 1418399 | 93 | 64 | 90 | 62 |
| 1418400 | 99 | 71 | 94 | 66 |
| 1418401 | 94 | 68 | 91 | 65 |
| 1418402 | 93 | 54 | 84 | 54 |
| 1418403 | 114 | 94 | 105 | 89 |
| 1418404 | 82 | 60 | 85 | 57 |
| 1418405 | 103 | 71 | 92 | 69 |
| 1418406 | 91 | 77 | 79 | 69 |
| 1418416 | 60 | 35 | 37* | 25* |
| 1418417 | 62 | 43 | 62 | 48 |
| 1418418 | 44 | 26 | 41 | 26 |
| 1418419 | 57 | 34 | 52 | 32 |
| 1418420 | 19 | 12 | 18 | 14 |
| 1418421 | 45 | 34 | 45 | 33 |
| 1418422 | 50 | 27 | 50 | 29 |

TABLE 74

Reduction of human PRNP RNA in knock-in mice

| Compound | RTS42354 | | RTS42356 | |
|---|---|---|---|---|
| Number | Cortex | Spinal Cord | Cortex | Spinal Cord |
| PBS | 100 | 100 | 100 | 100 |
| 1418407 | 82 | 68 | 91 | 72 |
| 1418408 | 86 | 85 | 101 | 91 |
| 1418409 | 94 | 95 | 105 | 86 |
| 1418410 | 92 | 85 | 98 | 80 |
| 1418411 | 85 | 67 | 84 | 65 |
| 1418412 | 55 | 39 | 56 | 40 |
| 1418413 | 78 | 45 | 82 | 44 |
| 1418414 | 69 | 44 | 70 | 45 |
| 1418415 | 76 | 45 | 79 | 43 |
| 1418423 | 70 | 38 | 75 | 36 |
| 1418424 | 33 | 21 | 32 | 20 |
| 1418425 | 39 | 22 | 37 | 21 |
| 1418426 | 36 | 31 | 35 | 29 |
| 1423120 | 45 | 29 | 43 | 30 |
| 1423121 | 28 | 23 | 27 | 22 |
| 1423122 | 31 | 14 | 29 | 15 |
| 1423123 | 30 | 20 | 30 | 19 |
| 1423124 | 46 | 28 | 43 | 27 |
| 1423125 | 79 | 48 | 82 | 51 |
| 1423126 | 39 | 29 | 38 | 28 |
| 1423127 | 58 | 40 | 56 | 39 |

TABLE 75

Reduction of human PRNP RNA in knock-in mice

| Compound Number | PRNP RNA (% control) | | | |
|---|---|---|---|---|
| | RTS42354 | | RTS42356 | |
| | Cortex | Spinal Cord | Cortex | Spinal Cord |
| PBS | 100 | 100 | 100 | 100 |
| 1201005 | 56 | 32 | 57 | 24 |
| 1238994 | 46 | 21 | 48 | 22 |
| 1239544 | 52 | 28 | 34 | 17 |
| 1270400 | 57 | 34 | 59 | 28 |
| 1355706 | 55 | 12 | 35 | 12 |
| 1355721 | 98 | 59 | 90 | 57 |
| 1355745 | 83 | 96 | 90 | 65 |
| 1373021 | 36 | 17 | 26 | 14 |
| 1373022 | 33 | 16 | 28 | 16 |
| 1373023 | 27 | 8 | 17 | 10 |
| 1373043 | 43 | 17 | 20* | 9* |
| 1373045 | 66 | 50 | 24* | 13* |
| 1373050 | 62 | 50 | 45 | 32 |
| 1373053 | 32 | 18 | 16* | 10* |
| 1373054 | 72 | 38 | 35 | 13 |
| 1373057 | 62 | 24 | 49 | 12 |
| 1373061 | 94 | 77 | 60 | 43 |

Example 6: Potency of Modified Oligonucleotides Complementary to Human PRNP in Knock-In Mice Modified oligonucleotides described above were tested in human PRNP knock-in mouse model as described above.

Treatment

The PRNP knock-in mice were divided into groups of 3-4 mice each. Each mouse received a single ICV bolus of modified oligonucleotide at the doses indicated in tables below. A group of 4 mice received PBS as a negative control for each study. Each table below represents an independent study.

RNA Analysis

Two weeks post treatment, mice were sacrificed and RNA was extracted from cortical brain tissue, spinal cord, and brain stem for RTPCR analysis to measure amount of PRNP RNA using human primer probe set RTS42356 (described herein above). In some cases, levels of PRNP RNA in hippocampus were examined as well. Results are presented as percent human PRNP RNA relative to PBS control, normalized to mouse cyclophilin A. Cyclophilin A was amplified using primer probe set m_cyclo24 (described herein above). N/A indicates that a value is not available.

As shown in the table below, treatment with modified oligonucleotides resulted in reduction of PRNP RNA in comparison to the PBS control.

TABLE 76

Reduction of human PRNP RNA in knock-in mice

| Compound No. | Dose (µg) | CORTEX | | SPINAL CORD | | BRAIN STEM | |
|---|---|---|---|---|---|---|---|
| | | PRNP RNA (% control) | ED50 (µg) | PRNP RNA (% control) | ED50 (µg) | PRNP RNA (% control) | ED50 (µg) |
| 1201142 | 10 | 94 | 196 | 87 | 37 | 81 | 46 |
| | 30 | 97 | | 51 | | 66 | |
| | 100 | 70 | | 34 | | 44 | |
| | 300 | 44 | | 24 | | 26 | |
| | 700 | 39 | | 21 | | 23 | |
| 1270232 | 10 | 89 | 102 | 68 | 22 | 80 | 36 |
| | 30 | 69 | | 49 | | 62 | |
| | 100 | 65 | | 32 | | 39 | |
| | 300 | 29 | | 16 | | 18 | |
| | 700 | 19 | | 15 | | 19 | |
| 1270458 | 10 | 89 | 143 | 87 | 36 | 82 | 57 |
| | 30 | 82 | | 45 | | 61 | |
| | 100 | 56 | | 41 | | 45 | |
| | 300 | 45 | | 25 | | 34 | |
| | 700 | 27 | | 24 | | 27 | |

TABLE 77

Reduction of human PRNP RNA in knock-in mice

| Compound No. | Dose (µg) | CORTEX | | SPINAL CORD | | BRAIN STEM | |
|---|---|---|---|---|---|---|---|
| | | PRNP RNA (% control) | ED50 (µg) | PRNP RNA (% control) | ED50 (µg) | PRNP RNA (% control) | ED50 (µg) |
| 1238994 | 10 | 95 | 124 | 82 | 44 | 73 | 33 |
| | 30 | 73 | | 64 | | 57 | |
| | 100 | 63 | | 33 | | 39 | |
| | 300 | 37 | | 28 | | 25 | |
| | 700 | 28 | | 22 | | 18 | |
| 1270400 | 10 | 89 | 262 | 63 | 24 | 65 | 29 |
| | 30 | 94 | | 55 | | 60 | |
| | 100 | 62 | | 40 | | 38 | |
| | 300 | 48 | | 22 | | 24 | |
| | 700 | 47 | | 20 | | 23 | |
| 1355721 | 10 | 104 | >700 | 86 | 374 | 78 | 637 |
| | 30 | 84 | | 74 | | 78 | |
| | 100 | 84 | | 66 | | 73 | |
| | 300 | 75 | | 58 | | 60 | |
| | 700 | 75 | | 50 | | 52 | |

TABLE 78

Reduction of human PRNP RNA in knock-in mice

| Compound No. | Dose (µg) | CORTEX | | SPINAL CORD | | BRAIN STEM | |
|---|---|---|---|---|---|---|---|
| | | PRNP RNA (% control) | ED50 (µg) | PRNP RNA (% control) | ED50 (µg) | PRNP RNA (% control) | ED50 (µg) |
| 1239544 | 10 | 103 | 310 | 77 | 70 | 90 | 91 |
| | 30 | 105 | | 76 | | 74 | |
| | 100 | 75 | | 46 | | 50 | |
| | 300 | 62 | | 32 | | 35 | |
| | 700 | 34 | | 24 | | 27 | |
| 1355706 | 10 | 95 | 105 | 75 | 45 | 76 | 33 |
| | 30 | 81 | | 78 | | 61 | |
| | 100 | 59 | | 28 | | 38 | |
| | 300 | 28 | | 17 | | 14 | |
| | 700 | 19 | | 14 | | 11 | |
| 1373021 | 10 | 99 | 118 | 98 | 53 | 85 | 40 |
| | 30 | 82 | | 65 | | 60 | |
| | 100 | 62 | | 40 | | 34 | |
| | 300 | 30 | | 17 | | 18 | |
| | 700 | 18 | | 9 | | 12 | |

TABLES 79

Reduction of human PRNP RNA in knock-in mice

| Compound No. | Dose (µg) | CORTEX PRNP RNA (% control) | ED50 (µg) | SPINAL CORD PRNP RNA (% control) | ED50 (µg) | BRAIN STEM PRNP RNA (% control) | ED50 (µg) | HIPPOCAMPUS PRNP RNA (% control) | ED50 (µg) |
|---|---|---|---|---|---|---|---|---|---|
| 1355720 | 30 | 84 | 88 | 54 | 27 | 53 | 27 | 68 | 57 |
|  | 100 | 49 |  | 29 |  | 39 |  | 43 |  |
|  | 300 | 27 |  | 19 |  | 23 |  | 25 |  |
|  | 700 | 17 |  | 17 |  | 21 |  | 21 |  |
| 1373022 | 10 | 95 | 126 | 79 | 50 | 79 | 41 | N/A | 98 |
|  | 30 | 77 |  | 61 |  | 64 |  | 75 |  |
|  | 100 | 67 |  | 40 |  | 45 |  | 59 |  |
|  | 300 | 34 |  | 23 |  | 27 |  | 30 |  |
|  | 700 | 20 |  | 14 |  | 19 |  | 22 |  |
| 1373023 | 10 | 72 | 69 | 88 | 27 | 76 | 30 | N/A | 49 |
|  | 30 | 73 |  | 59 |  | 56 |  | 69 |  |
|  | 100 | 49 |  | 26 |  | 32 |  | 36 |  |
|  | 300 | 25 |  | 14 |  | 17 |  | 21 |  |
|  | 700 | 11 |  | 10 |  | 13 |  | 12 |  |
| 1373057 | 10 | 88 | 98 | 100 | 44 | 86 | 51 | N/A | 55 |
|  | 30 | 74 |  | 65 |  | 68 |  | 65 |  |
|  | 100 | 55 |  | 33 |  | 38 |  | 46 |  |
|  | 300 | 34 |  | 19 |  | 24 |  | 27 |  |
|  | 700 | 18 |  | 16 |  | 17 |  | 20 |  |

TABLES 80

Reduction of human PRNP RNA in knock-in mice

| Compound No. | Dose (µg) | CORTEX PRNP RNA (% control) | ED50 (µg) | SPINAL CORD PRNP RNA (% control) | ED50 (µg) | BRAIN STEM PRNP RNA (% control) | ED50 (µg) | HIPPOCAMPUS PRNP RNA (% control) | ED50 (µg) |
|---|---|---|---|---|---|---|---|---|---|
| 1411016 | 10 | 95 | 80 | 86 | 44 | 85 | 51 | N/A | 82 |
|  | 30 | 84 |  | 56 |  | 62 |  | 99 |  |
|  | 100 | 45 |  | 41 |  | 42 |  | 81 |  |
|  | 300 | 29 |  | 26 |  | 27 |  | 39 |  |
|  | 700 | 26 |  | 23 |  | 22 |  | 31 |  |

Example 7: Tolerability of Modified Oligonucleotides Complementary to Human PRNP in Wild-Type Mice, 3-Hour Study Modified oligonucleotides described above were tested in wild-type female C57/B16 mice to assess the tolerability of the oligonucleotides. Also tested in one study was Comparator Compound No. 169753, described herein above and in WO2010/019270. Wild-type female C57/B16 mice each received a single 1CV dose of 700 gig of modified oligonucleotide listed in the table below. Each treatment group consisted of 2-4 mice. A group of 4 mice received PBS as a negative control for each study (identified in separate tables below). At 3 hours post-injection, mice were evaluated according to seven different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing. For each of the 7 criteria, a mouse was given a sub-score of 0 if it met the criteria and 1 if it did not (the functional observational battery score or FOB). After all 7 criteria were evaluated, the scores were summed for each mouse and the summed scores for each animal are reported individually. The results are presented in the tables below.

TABLE 81

Tolerability scores in mice at 700 µg dose

| Compound Number | 3 hr. FOB |
|---|---|
| PBS | 0, 0, 0, 0 |
| 1238169 | 1, 3, 1, 3 |
| 1200973 | 4, 4, 5, 5 |
| 1201005 | 5, 5, 7, 4 |
| 1201010 | 4, 4, 4, 4 |
| 1201142 | 1, 1, 2, 2 |
| 1201293 | 4, 4, 3, 6 |
| 1238167 | 1, 1, 1, 1 |
| 1238168 | 1, 1, 1, 1 |
| 1238339 | 5, 5, 5, 5 |
| 1238467 | 6, 6, 6, 6 |
| 1238497 | 4, 4, 4, 4 |
| 1238498 | 3, 3, 3, 3 |
| 1238507 | 6, 6, 6, 6 |
| 1238517 | 5, 5, 5, 5 |
| 1238812 | 1, 1, 1, 1 |
| 1238814 | 0, 0, 0, 0 |
| 1238987 | 1, 1, 1, 1 |
| 1238996 | 1, 1, 1, 1 |
| 1239009 | 5, 5, 5, 5 |
| 1239031 | 4, 4, 5, 5 |
| 1239234 | 1, 1, 1, 1 |
| 1239293 | 5, 4, 4, 5 |
| 1239544 | 3, 4, 4, 3 |

TABLE 82

Tolerability scores in mice at 700 µg dose

| Compound Number | 3 hr. FOB |
|---|---|
| PBS | 0, 0, 0, 0 |
| 1239030 | 1, 1, 1, 1 |
| 1270228 | 6, 6, 6, 5 |
| 1270230 | 3, 3, 3, 3 |
| 1270231 | 1, 1, 1, 1 |
| 1270232 | 2, 2, 2, 2 |
| 1270406 | 1, 1, 1, 1 |
| 1270457 | 1, 1, 1, 1 |
| 1270458 | 1, 1, 1, 1 |
| 1335684 | 1, 0, 0, 0 |
| 1335686 | 0, 0, 0, 0 |
| 1335688 | 1, 1, 0, 0 |

TABLE 83

Tolerability scores in mice at 700 µg dose

| Compound Number | 3 hr. FOB |
|---|---|
| PBS | 0, 0, 0, 0 |
| 169753 | 6, 3, 4, 4 |
| 1238994 | 0, 0, 0, 0 |
| 1239235 | 0, 0, 0, 0 |
| 1270233 | 2, 1, 1, 3 |
| 1270281 | 4, 4, 3, 1 |
| 1270400 | 0, 1, 0, 1 |
| 1355706 | 4, 5, 4, 3 |
| 1355708 | 3, 5, 4, 3 |

TABLE 84

Tolerability scores in mice at 700 µg dose

| Compound Number | 3 hr. FOB |
|---|---|
| PBS | 0, 0, 0, 0 |
| 1201004 | 3, 3, 2, 2 |
| 1201006 | 3, 4, 4, 4 |
| 1201007 | 4, 3, 4, 4 |
| 1201141 | 1, 2, 1, 2 |
| 1238202 | 0, 0, 0, 0 |
| 1239543 | 1, 1, 2, 1 |
| 1239545 | 0, 0, 0, 0 |
| 1239546 | 1, 0, 1, 0 |
| 1239547 | 0, 0, 0, 0 |
| 1373020 | 4, 4, 4, 3 |
| 1373021 | 3, 3, 2, 2 |
| 1373022 | 2, 2, 2, 1 |
| 1373023 | 0, 0, 0, 0 |
| 1373024 | 1, 1, 1, 0 |
| 1373025 | 0, 0, 0, 1 |
| 1373026 | 2, 1, 1, 1 |
| 1373027 | 1, 2, 3, 2 |
| 1373028 | 0, 0, 0, 0 |
| 1373029 | 1, 2, 1, 1 |
| 1373030 | 1, 2, 2, 1 |
| 1373031 | 1, 1, 1, 1 |
| 1373032 | 0, 0, 1, 0 |
| 1373033 | 3, 2, 4, 4 |

TABLE 85

Tolerability scores in mice at 700 µg dose

| Compound Number | 3 hr. FOB |
|---|---|
| PBS | 0, 0, 0, 0 |
| 1373057 | 0, 0, 0, 0 |
| 1373058 | 0, 0, 3, 0 |
| 1373059 | 0, 0, 0, 0 |
| 1373060 | 0, 0, 0, 4 |
| 1373061 | 0, 0, 0, 0 |
| 1373062 | 1, 4, 1, 1 |
| 1373063 | 0, 0, 0, 0 |
| 1373064 | 0, 0, 0, 0 |
| 1373065 | 0, 0, 0, 0 |
| 1373066 | 0, 0, 0, 0 |
| 1373067 | 0, 1, 0, 0 |
| 1373068 | 0, 0, 0, 0 |
| 1373069 | 0, 0, 0, 0 |
| 1373070 | 6, 5, 5, 5 |
| 1373071 | 0, 0, 0, 0 |
| 1373072 | 6, 4, 4, 4 |
| 1373073 | 0, 0, 0, 0 |
| 1373074 | 1, 1, 0, 1 |
| 1373075 | 0, 0, 0, 0 |
| 1373076 | 0, 0, 0, 0 |
| 1373077 | 0, 0, 0, 0 |
| 1373078 | 4, 3, 4, 4 |

TABLE 86

Tolerability scores in mice at 700 µg dose

| Compound Number | 3 hr. FOB |
|---|---|
| PBS | 0, 0, 0, 0 |
| 1201157 | 3, 3, 3, 1 |
| 1201255 | 7, 6, 6, 7 |
| 1201288 | 3, 6, 6, 3 |
| 1201294 | 6, 7, 4, 5 |
| 1238259 | 1, 1, 1, 1 |
| 1238264 | 1, 1, 1, 1 |
| 1238270 | 6, 7, 7, 6 |
| 1238274 | 3, 3, 3, 1 |
| 1238323 | 1, 3, 3, 2 |
| 1238329 | 4, 4, 4, 5 |
| 1238330 | 7, 6, 7, 7 |
| 1238331 | 7, 7, 7, 7 |
| 1238341 | 4, 4, 6, 3 |
| 1238437 | 0, 1, 0, 1 |
| 1238440 | 1, 1, 1, 1 |
| 1238449 | 4, 5, 4, 6 |
| 1238580 | 2, 5, 3, 2 |
| 1238688 | 1, 1, 1, 1 |
| 1238914 | 1, 1, 1, 1 |
| 1200977 | 6, 4, 7, 4 |
| 1201138 | 1, 3, 4, 2 |
| 1201145 | 3, 3, 4, 6 |
| 1238170 | 0, 0, 0, 0 |

TABLE 87

Tolerability scores in mice at 700 µg dose

| Compound Number | 3 hr. FOB |
|---|---|
| PBS | 0, 0, 0, 0 |
| 1238600 | 0, 0, 0, 0 |
| 1238491 | 1, 1, 1, 1 |
| 1239162 | 0, 0, 0, 0 |

TABLE 87-continued

Tolerability scores in mice at 700 μg dose

| Compound Number | 3 hr. FOB |
|---|---|
| 1238813 | 0, 0, 0, 0 |
| 1238889 | 4, 1, 4, 4 |
| 1238892 | 0, 0, 0, 0 |
| 1238975 | 1, 1, 1, 1 |
| 1238992 | 1, 1, 1, 1 |
| 1239046 | 1, 1, 1, 1 |
| 1239146 | 4, 4, 3, 4 |
| 1239260 | 1, 1, 1, 1 |
| 1239263 | 5, 5, 5, 5 |
| 1239448 | 6, 6, 6, 6 |
| 1239682 | 7, 4, 4, 4 |
| 1239694 | 4, 4, 4, 4 |
| 1238322 | 1, 1, 1, 1 |
| 1238324 | 0, 0, 0, 0 |
| 1238327 | 1, 1, 1, 1 |
| 1238359 | 5, 5, 5, 5 |
| 1238373 | 3, 3, 3, 1 |
| 1238460 | 1, 1, 1, 1 |
| 1238554 | 6, 6, 5, 5 |
| 1238572 | 1, 1, 1, 1 |

TABLE 88

Tolerability scores in mice at 700 μg dose

| Compound Number | 3 hr. FOB |
|---|---|
| PBS | 0, 0, 0, 0 |
| 1238255 | 2, 1, 1, 1 |
| 1238285 | 1, 1, 3, 3 |
| 1238325 | 0, 0, 0, 0 |
| 1238361 | 0, 0, 0, 0 |
| 1238370 | 7, 7, 4, 5 |
| 1238404 | 0, 0, 1, 0 |
| 1238409 | 6, 6, 6, 6 |
| 1238444 | 7, 5, 6, 6 |
| 1238500 | 6, 6, 7, 6 |
| 1238582 | 5, 5, 5, 5 |
| 1238616 | 0, 0, 0, 0 |
| 1238645 | 0, 0, 0, 0 |
| 1238797 | 0, 0, 0, 0 |
| 1238802 | 1, 3, 6, 3 |
| 1238837 | 4, 7, 4, 4 |
| 1238838 | 6, 7, 6, 6 |
| 1238863 | 7, 7, 6, 6 |
| 1238990 | 7, 4, 4, 4 |
| 1239052 | 1, 1, 1, 0 |
| 1239063 | 2, 3, 2, 3 |
| 1239064 | 0, 0, 0, 0 |
| 1239550 | 4, 4, 4, 3 |
| 1239607 | 4, 4, 4, 4 |

TABLE 89

Tolerability scores in mice at 700 μg dose

| Compound Number | 3 hr. FOB |
|---|---|
| PBS | 0, 0, 0, 0 |
| 1238244 | 0, 0, 0, 0 |
| 1238410 | 4, 4, 4, 0 |
| 1238490 | 0, 0, 0, 0 |
| 1238632 | 0, 0, 0, 0 |

TABLE 89-continued

Tolerability scores in mice at 700 μg dose

| Compound Number | 3 hr. FOB |
|---|---|
| 1238836 | 1, 1, 0, 0 |
| 1239027 | 0, 0, 0, 0 |
| 1239231 | 0, 0, 0, 0 |
| 1239250 | 0, 0, 0, 0 |
| 1239329 | 0, 0, 0, 0 |
| 1239345 | 0, 0, 0, 0 |
| 1239352 | 0, 0, 0, 0 |
| 1239394 | 0, 0, 0, 0 |

TABLE 90

Tolerability scores in mice at 700 μg dose

| Compound Number | 3 hr. FOB |
|---|---|
| PBS | 0, 0, 0, 0 |
| 1201095 | 4, 4, 3, 3 |
| 1201124 | 6, 5, 5, 6 |
| 1201276 | 6, 4, 4, 4 |
| 1238293 | 5, 6, 6, 6 |
| 1238316 | 4, 4, 3, 4 |
| 1238334 | 6, 6, 7, 6 |
| 1238351 | 2, 3, 3, 2 |
| 1238369 | 3, 2, 2, 2 |
| 1238371 | 3, 4, 2, 3 |
| 1238402 | 1, 1, 1, 1 |
| 1238501 | 5, 5, 6, 5 |
| 1238506 | 2, 2, 2, 3 |
| 1238805 | 4, 5, 4, 6 |
| 1238864 | 6, 5, 5, 5 |
| 1238947 | 4, 4, 4, 5 |
| 1238974 | 5, 6, 6, 4 |
| 1238981 | 2, 2, 2, 2 |
| 1239010 | 4, 4, 4, 4 |
| 1239222 | 4, 6, 4, 4 |
| 1239792 | 2, 2, 2, 2 |
| 1201098 | 4, 3, 3, 4 |
| 1201120 | 2, 4, 3, 2 |
| 1201143 | 3, 3, 3, 3 |

TABLE 91

Tolerability scores in mice at 700 μg dose

| Compound Number | 3 hr. FOB |
|---|---|
| PBS | 0, 0, 0, 0 |
| 1355721 | 0, 0, 0, 0 |
| 1355745 | 2, 2, 3, 3 |
| 1355736 | 3, 3, 3, 3 |

TABLE 92

Tolerability scores in mice at 700 μg dose

| Compound Number | 3 hr. FOB |
|---|---|
| PBS | 0, 0, 0, 0 |
| 1373034 | 0, 0, 0, 0 |
| 1373035 | 3, 1, 1, 4 |
| 1373036 | 0, 4, 0, 0 |
| 1373037 | 5, 4, 1, 3 |
| 1373038 | 0, 0, 0, 0 |
| 1373039 | 1, 4, 1, 4 |
| 1373040 | 0, 0, 0, 0 |
| 1373041 | 0, 0, 0, 0 |
| 1373042 | 3, 1, 1, 1 |
| 1373043 | 3, 4, 4, 1 |
| 1373044 | 1, 0, 0, 0 |

TABLE 92-continued

Tolerability scores in mice at 700 µg dose

| Compound Number | 3 hr. FOB |
|---|---|
| 1373045 | 4, 4, 5, 4 |
| 1373046 | 6, 4, 5, 4 |
| 1373047 | 0, 0, 0, 0 |
| 1373048 | 6, 6, 6, 6 |
| 1373049 | 0, 0, 0, 0 |
| 1373050 | 0, 0, 0, 0 |
| 1373051 | 0, 2, 2, 0 |
| 1373052 | 6, 5, 3, 4 |
| 1373053 | 4, 0, 0, 0 |
| 1373054 | 0, 0, 0, 0 |
| 1373055 | 3, 4, 1, 1 |
| 1373056 | 0, 0, 0, 0 |

TABLE 93

Tolerability scores in mice at 700 µg dose

| Compound Number | 3 hr. FOB |
|---|---|
| PBS | 0, 0, 0, 0 |
| 1394131 | 1, 2, 1, 1 |
| 1394138 | 0, 0, 0, 0 |
| 1394139 | 0, 0, 0, 0 |

TABLE 94

Tolerability scores in mice at 700 µg dose

| Compound Number | 3 hr. FOB |
|---|---|
| PBS | 0, 0, 0, 0 |
| 1411017 | 0, 0, 0, 0 |
| 1411018 | 0, 0, 0, 0 |
| 1406232 | 0, 0, 0, 0 |
| 1406254 | 0, 0, 0, 0 |
| 1406261 | 3, 3, 3, 3 |
| 1406262 | 0, 0, 0, 0 |
| 1270342 | 2, 3, 1, 1 |
| 1270363 | 6, 6, 6, 6 |
| 1411004 | 7, 6, 6, 6 |
| 1411005 | 3, 3, 3, 3 |
| 1411006 | 6, 6, 5, 5 |
| 1411007 | 0, 0, 0, 0 |
| 1411013 | 4, 4, 4, 4 |
| 1411014 | 3, 4, 4, 4 |
| 1411015 | 4, 4, 5, 5 |
| 1411016 | 2, 1, 2, 2 |

Example 8: Tolerability of Modified Oligonucleotides Complementary to Human PRNP in Rats at 3 Hours Post Dosing, 3 mg Dose Modified oligonucleotides described above were tested in rats to assess the tolerability of the oligonucleotides. Sprague Dawley rats each received a single intrathecal (IT) dose of 3 mg of oligonucleotide listed in the table below. Also tested in one study was Comparator Compound No. 169753, described herein above and in WO2010/019270. Each treatment group consisted of 2-4 rats. A group of 4 rats received PBS as a negative control in each study (represented in separate tables below). At 3 hours post-injection, movement in 7 different parts of the body were evaluated for each rat. The 7 body parts are (1) the rat's tail; (2) the rat's posterior posture; (3) the rat's hind limbs; (4) the rat's hind paws; (5) the rat's forepaws; (6) the rat's anterior posture; (7) the rat's head. For each of the 7 different body parts, each rat was given a sub-score of 0 if the body part was moving or 1 if the body part was paralyzed (the functional observational battery score or FOB). After each of the 7 body parts were evaluated, the sub-scores were summed for each rat and then summed scores were reported for each individual animal. For example, if a rat's tail, head, and all other evaluated body parts were moving 3 hours after the 3 mg IT dose, it would get a summed score of 0. If another rat was not moving its tail 3 hours after the 3 mg IT dose but all other evaluated body parts were moving, it would receive a score of 1.

TABLE 95

Tolerability scores in rats at 3 mg dose

| Compound Number | 3 hr. FOB |
|---|---|
| PBS | 0, 0, 0, 0 |
| 1200973 | 4, 4, 5, 5 |
| 1201005 | 4, 4, 5, 4 |
| 1201142 | 1, 4, 2, 2 |
| 1238167 | 4, 1, 4, 4 |
| 1238168 | 2, 2, 3, 1 |
| 1238169 | 5, 5, 4, 4 |
| 1238325 | 0, 0, 0, 0 |
| 1238498 | 5, 5, 2, 5 |
| 1238507 | 5, 6, 5, 6 |
| 1238517 | 6, 5, 6, 6 |
| 1238797 | 0, 2, 1, 1 |
| 1238802 | 5, 4, 6, 5 |
| 1238812 | 3, 2, 1, 1 |
| 1238837 | 0, 3, 0, 5 |
| 1238838 | 6, 6, 6, 6 |
| 1238863 | 6, 6, 6, 6 |
| 1238987 | 5, 4, 5, 5 |
| 1239009 | 5, 5, 4, 5 |
| 1239052 | 2, 3, 3, 3 |
| 1239234 | 2, 1, 1, 2 |
| 1239544 | 5, 4, 2, 0 |
| 1239682 | 0, 2, 2, 2 |
| 1239694 | 5, 2, 3, 3 |

TABLE 96

Tolerability scores in rats at 3 mg dose

| Compound Number | 3 hr. FOB |
|---|---|
| PBS | 0, 0, 1, 0 |
| 1239030 | 1, 0, 0, 0 |
| 1270228 | 5, 5, 4, 4 |
| 1270230 | 0, 0, 1, 3 |
| 1270231 | 0, 1, 3, 3 |
| 1270232 | 3, 3, 3, 3 |
| 1270406 | 0, 2, 0, 0 |
| 1270457 | 3, 2, 2, 0 |
| 1270458 | 0, 1, 0, 0 |
| 1335684 | 3, 2, 0, 2 |
| 1335686 | 0, 0, 0, 0 |
| 1335688 | 0, 0, 0, 0 |

TABLE 97

Tolerability scores in rats at 3 mg dose

| Compound Number | 3 hr. FOB |
|---|---|
| PBS | 0, 0, 0, 0 |
| 1201004 | 4, 4, 4, 4 |
| 1201006 | 5, 0, 6, 0 |
| 1201007 | 6, 5, 5, 5 |
| 1201141 | 0, 4, 4, 4 |
| 1238202 | 3, 3, 2, 0 |
| 1239543 | 3, 3, 3, 3 |
| 1239545 | 1, 1, 1, 2 |
| 1239546 | 2, 2, 2, 1 |
| 1239547 | 1, 0, 1, 1 |
| 1373020 | 5, 5, 5, 4 |
| 1373021 | 4, 4, 0, 4 |
| 1373022 | 3, 3, 0, 0 |
| 1373023 | 1, 1, 2, 1 |
| 1373024 | 1, 1, 0, 0 |
| 1373025 | 1, 0, 0, 0 |
| 1373026 | 1, 1, 2, 1 |
| 1373027 | 2, 2, 2, 0 |
| 1373028 | 0, 0, 0, 0 |
| 1373029 | 2, 2, 2, 3 |
| 1373030 | 2, 2, 3, 2 |

TABLE 98

Tolerability scores in rats at 3 mg dose

| Compound Number | 3 hr. FOB |
|---|---|
| PBS | 0, 0, 0, 0 |
| 1373057 | 0, 2, 1, 0 |
| 1373058 | 2, 3, 3, 3 |
| 1373059 | 3, 3, 3, 0 |
| 1373060 | 3, 3, 3, 2 |
| 1373061 | 3, 2, 3, 3 |
| 1373062 | 0, 3, 3, 3 |
| 1373063 | 0, 0, 0, 1 |
| 1373064 | 2, 2, 2, 2 |
| 1373065 | 1, 2, 2, 2 |
| 1373066 | 0, 0, 0, 0 |
| 1373067 | 0, 2, 2, 2 |
| 1373068 | 0, 0, 0, 0 |
| 1373069 | 0, 0, 0, 0 |
| 1373071 | 0, 0, 0, 0 |
| 1373073 | 0, 0, 0, 0 |
| 1373074 | 3, 3, 2, 0 |
| 1373075 | 2, 2, 3, 3 |
| 1373076 | 0, 0, 0, 0 |
| 1373077 | 0, 0, 0, 0 |
| 1373078 | 4, 4, 3, 2 |

TABLE 99

Tolerability scores in rats at 3 mg dose

| Compound Number | 3 hr. FOB |
|---|---|
| PBS | 0, 0, 0, 0 |
| 1201154 | 6, 6, 4, 0 |
| 1201293 | 4, 4, 4, 4 |
| 1238339 | 0, 3, 0, 3 |
| 1238351 | 0, 3, 2, 0 |
| 1238361 | 0, 0, 1, 1 |

TABLE 99-continued

Tolerability scores in rats at 3 mg dose

| Compound Number | 3 hr. FOB |
|---|---|
| 1238402 | 0, 1, 1, 1 |
| 1238404 | 1, 1, 1, 1 |
| 1238500 | 6, 4, 4, 3 |
| 1238501 | 3, 4, 5, 0 |
| 1238506 | 3, 3, 3, 3 |
| 1238805 | 6, 3, 4, 5 |
| 1238814 | 1, 1 |
| 1238864 | 4, 3, 3, 3 |
| 1238947 | 6, 0, 0, 7 |
| 1238974 | 4, 5, 0, 4 |
| 1238990 | 5, 3, 4, 0 |
| 1238996 | 0, 4, 5, 3 |
| 1239010 | 4, 5, 5, 5 |
| 1239031 | 3, 2, 3, 2 |
| 1239063 | 4, 4, 3, 1 |
| 1239222 | 6, 6, 6, 5 |
| 1239293 | 5, 0, 0, 6 |
| 1239396 | 4, 3, 5, 3 |

TABLE 100

Tolerability scores in rats at 3 mg dose

| Compound Number | 3 hr. FOB |
|---|---|
| PBS | 0, 0, 0, 0 |
| 1201255 | 6, 5, 5, 6 |
| 1201288 | 5, 5, 5, 5 |
| 1238264 | 4, 5, 5, 5 |
| 1238270 | 7, 6, 0, 6 |
| 1238274 | 5, 5, 5, 5 |
| 1238293 | 5, 6, 6, 6 |
| 1238316 | 0, 5, 0, 5 |
| 1238323 | 1, 5, 5, 5 |
| 1238329 | 6, 6, 5, 6 |
| 1238330 | 6, 5, 6, 6 |
| 1238331 | 2, 6, 6, 6 |
| 1238341 | 6, 6, 5, 6 |
| 1238369 | 5, 5, 3, 5 |
| 1238437 | 4, 4, 4, 0 |
| 1238449 | 6, 0, 6, 0 |
| 1238580 | 3, 0, 2, 0 |
| 1238914 | 4, 0, 3, 3 |
| 1239064 | 0, 2, 2, 2 |
| 1239329 | 3, 3, 0, 3 |
| 1239352 | 4, 2, 4, 3 |
| 1239607 | 5, 5, 0, 0 |

TABLE 101

Tolerability scores in rats at 3 mg dose

| Compound Number | 3 hr. FOB |
|---|---|
| PBS | 0, 0, 0, 0 |
| 1200977 | 2, 6, 6, 6 |
| 1238170 | 3, 2, 0, 2 |

TABLE 101-continued

Tolerability scores in rats at 3 mg dose

| Compound Number | 3 hr. FOB |
|---|---|
| 1238244 | 0, 4, 4, 3 |
| 1238410 | 3, 3, 3, 3 |
| 1238490 | 2, 2, 2, 2 |
| 1239027 | 2, 2, 2, 2 |
| 1239250 | 2, 2, 2, 2 |

TABLE 102

Tolerability scores in rats at 3 mg dose

| Compound Number | 3 hr. FOB |
|---|---|
| PBS | 0, 0, 0, 1 |
| 1238322 | 3, 3, 3, 3 |
| 1238324 | 0, 0, 0, 0 |
| 1238327 | 2, 2, 3, 0 |
| 1238359 | 0, 0, 0, 0 |
| 1238373 | 2, 2, 1, 1 |
| 1238460 | 2, 2, 2, 2 |
| 1238491 | 2, 0, 1, 1 |
| 1238554 | 2, 4, 4, 3 |
| 1238572 | 2, 2, 2, 2 |
| 1238600 | 0, 0, 0, 0 |
| 1238813 | 0, 1, 0, 0 |
| 1238889 | 0, 4, 1, 3 |
| 1238892 | 0, 0, 0, 0 |
| 1238975 | 0, 3, 2, 2 |
| 1238992 | 1, 2, 2, 1 |
| 1239046 | 2, 1, 1, 1 |
| 1239146 | 3, 3, 4, 1 |
| 1239162 | 1, 0, 1, 2 |
| 1239260 | 3, 3, 3, 2 |
| 1239263 | 3, 3, 4, 4 |
| 1239448 | 4, 0, 4, 3 |

TABLE 103

Tolerability scores in rats at 3 mg dose

| Compound Number | 3 hr. FOB |
|---|---|
| PBS | 0, 0, 0, 0 |
| 1201010 | 5, 4, 6, 6 |
| 1201095 | 6, 6, 6, 6 |
| 1201098 | 5, 6, 5, 6 |
| 1201120 | 4, 4, 6 |
| 1201124 | 6, 4, 6, 6 |
| 1201276 | 6, 6, 2 |
| 1201294 | 5, 5, 5, 4 |
| 1238259 | 3, 3, 3, 3 |
| 1238285 | 3, 3, 4, 3 |
| 1238334 | 6, 6, 6, 6 |
| 1238370 | 3, 3, 3, 3 |
| 1238371 | 3, 4 |
| 1238409 | 4, 4, 3, 4 |
| 1238440 | 3, 3, 3, 3 |
| 1238444 | 6, 5, 5, 6 |
| 1238467 | 6, 6, 6 |
| 1238497 | 4, 4, 4, 3 |
| 1238582 | 2, 3, 2, 3 |
| 1238645 | 2, 2 |
| 1238688 | 1, 1, 0, 0 |
| 1238981 | 1, 1, 0, 0 |
| 1239045 | 0, 0, 0, 0 |
| 1239792 | 3, 2, 3 |

TABLE 104

Tolerability scores in rats at 3 mg dose

| Compound Number | 3 hr. FOB |
|---|---|
| PBS | 0, 0, 0, 0 |
| 1355721 | 1, 2, 0, 1 |
| 1355745 | 3, 3, 0, 3 |
| 1355736 | 3, 0 |

TABLE 105

Tolerability scores in rats at 3 mg dose

| Compound Number | 3 hr. FOB |
|---|---|
| PBS | 0, 0, 0, 0 |
| 1373031 | 3, 3, 0, 3 |
| 1373032 | 0, 0, 0, 0 |
| 1373033 | 4, 3, 3, 4 |
| 1373034 | 1, 1, 1, 1 |
| 1373035 | 3, 3, 3, 3 |
| 1373036 | 3, 3, 2, 2 |
| 1373037 | 3, 0, 3, 2 |
| 1373038 | 1, 0, 1, 0 |
| 1373039 | 2, 2, 2, 3 |
| 1373040 | 1, 1, 1, 1 |
| 1373041 | 2, 2, 2, 2 |
| 1373042 | 0, 0, 1, 1 |
| 1373043 | 2, 3, 3, 3 |
| 1373044 | 2, 3, 2, 2 |
| 1373047 | 0, 2, 2, 0 |
| 1373049 | 1, 2, 2, 1 |
| 1373050 | 2, 2, 2, 3 |
| 1373051 | 3, 3, 3, 3 |
| 1373052 | 3, 0, 3, 3 |
| 1373054 | 0, 1, 2, 2 |
| 1373055 | 4, 2, 2, 3 |
| 1373056 | 1, 1, 0, 0 |

TABLE 106

Tolerability scores in rats at 3 mg dose

| Compound Number | 3 hr. FOB |
|---|---|
| PBS | 0, 0, 0, 0 |
| 169753 | 6, 5, 5, 6 |
| 1239235 | 0, 0, 0, 0 |
| 1270233 | 5, 5, 5, 3 |
| 1270281 | 4, 5 |
| 1270400 | 1, 2, 1, 1 |
| 1355708 | 4, 4, 4, 4 |

TABLE 107

Tolerability scores in rats at 3 mg dose

| Compound Number | 3 hr. FOB |
|---|---|
| PBS | 0, 0, 0, 0 |
| 1238994 | 1, 1, 1, 1 |
| 1373053 | 2, 2, 2, 2 |

TABLE 108

Tolerability scores in rats at 3 mg dose

| Compound Number | 3 hr. FOB |
|---|---|
| PBS | 0, 0, 0, 0 |
| 1411017 | 0, 2, 2, 2 |
| 1411018 | 1, 1, 0, 1 |
| 1406232 | 0, 0, 0, 0 |
| 1406254 | 0, 0, 0, 0 |
| 1406261 | 3, 0, 0, 3 |
| 1406262 | 0, 0, 0, 0 |
| 1270342 | 3, 3, 3, 3 |
| 1270363 | 3, 4, 4, 1 |
| 1411004 | 5, 5, 4, 4 |
| 1411005 | 3, 3, 4, 4 |
| 1411006 | 5, 5, 4, 5 |
| 1411007 | 3, 3, 3, 3 |
| 1411013 | 4, 3, 4, 4 |
| 1411014 | 4, 0, 4, 4 |
| 1411015 | 5, 5, 5, 5 |
| 1411016 | 3, 3, 3, 4 |

TABLE 109

Tolerability scores in rats at 3 mg dose

| Compound Number | 3 hr. FOB |
|---|---|
| PBS | 0, 0, 0, 0 |
| 1355720 | 4, 4, 4 |
| 1373045 | 2, 3, 2, 0 |
| 1373046 | 4, 3 |
| 1373048 | 3, 3, 0, 3 |
| 1373053 | 2, 0, 2, 2 |
| 1394131 | 3, 3, 3, 3 |
| 1394138 | 0, 0, 0, 0 |
| 1394139 | 0, 0, 0, 0 |

TABLE 110

Tolerability scores in rats at 3 mg dose

| Compound Number | 3 hr. FOB |
|---|---|
| PBS | 0, 0, 0, 0 |
| 1355706 | 4, 3, 4, 3 |
| 1406262 | 1, 1, 1, 1 |

Example 9: Tolerability of Modified Oligonucleotides Complementary to Human PRNP in Rats, Long-Term Assessment In separate studies run under the same conditions, modified oligonucleotides described above were tested in Sprague Dawley rats to assess the long-term tolerability of the oligonucleotides. Also tested was Comparator Compound No. 169753, described herein above and in WO2010/019270. Sprague Dawley rats each received a single intrathecal (IT) delivered dose of 3 mg of oligonucleotide or PBS. Each animal was weighed and evaluated weekly by a trained observer for adverse events. Adverse events were defined as neurological dysfunction not typical in PBS-treated control animals, including, but not limited to: abnormal limb splay, abnormal gait, tremors, abnormal respiration, paralysis, and spasticity. The onset of an adverse event is defined as the week post-dosing when the dysfunction was first recorded. Onset of adverse events typically correlates with a failure to thrive as defined by a lack of body weight gain/maintenance similar to PBS-treated animals. Animals treated with Compound No. 1238994, Compound No. 1373021, Compound No. 1373022, Compound No. 1373023, Compound No. 1373057, and Compound No. 1411016 achieved no adverse events for the duration of the study. In contrast, each animal treated with comparator Compound No. 169753 experienced one or more adverse events by five weeks post treatment.

Example 10: Human Clinical Trial with Modified Oligonucleotides Complementary to Human PRNP Safety, tolerability, pharmacokinetics, pharmacodynamics and efficacy of modified oligonucleotide complementary to human PRNP will be evaluated in a clinical trial setting. Patient safety will be monitored closely during the study. Safety and tolerability evaluations will include: physical examination, standard neurological assessment, vital signs, ECG, AEs and concomitant medications, CSF safety labs, plasma laboratory tests and urinalysis.

SEQUENCE LISTING

The patent contains a lengthy sequence listing. A copy of the sequence listing is available in electronic form from the USPTO web site (https://seqdata.uspto.gov/?pageRequest=docDetail&DocID=US12281305B2). An electronic copy of the sequence listing will also be available from the USPTO upon request and payment of the fee set forth in 37 CFR 1.19(b)(3).

The invention claimed is:
1. A modified oligonucleotide according to the following chemical structure:

(SEQ ID NO: 2302)

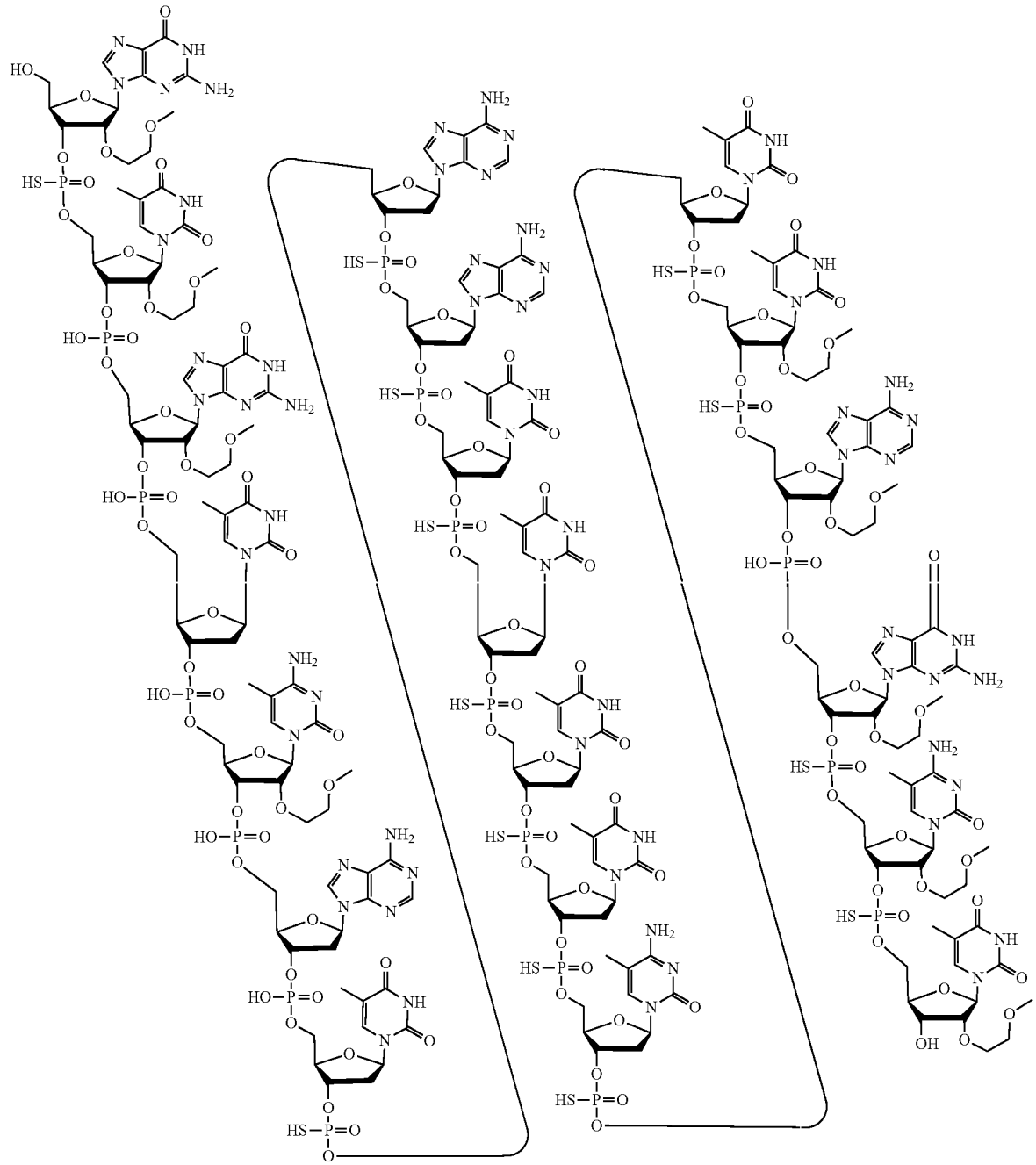

or a salt thereof.

2. The modified oligonucleotide of claim 1, which is the sodium salt of the potassium salt.

3. A pharmaceutical composition comprising the modified oligonucleotide of claim 1, and a pharmaceutically acceptable diluent.

4. The pharmaceutical composition of claim 3, wherein the pharmaceutically acceptable diluent is artificial cerebrospinal fluid.

5. The pharmaceutical composition of claim 4, wherein the pharmaceutical composition consists essentially of the modified oligonucleotide and artificial cerebrospinal fluid.

6. A population of modified oligonucleotides of claim 1, wherein all of the phosphorothioate internucleoside linkages of the modified oligonucleotide are stereorandom.

7. A pharmaceutical composition comprising the population of modified oligonucleotides of claim 6, and a pharmaceutically acceptable diluent.

8. The pharmaceutical composition of claim 7, wherein the pharmaceutically acceptable diluent is artificial cerebrospinal fluid.

9. The pharmaceutical composition of claim 8, wherein the pharmaceutical composition consists essentially of the population of modified oligonucleotides and artificial cerebrospinal fluid.

10. A modified oligonucleotide according to the following chemical structure:

12. The pharmaceutical composition of claim 11, wherein the pharmaceutically acceptable diluent is artificial cerebrospinal fluid.

13. The pharmaceutical composition of claim 12, wherein the pharmaceutical composition consists essentially of the modified oligonucleotide and artificial cerebrospinal fluid.

(SEQ ID NO: 2302)

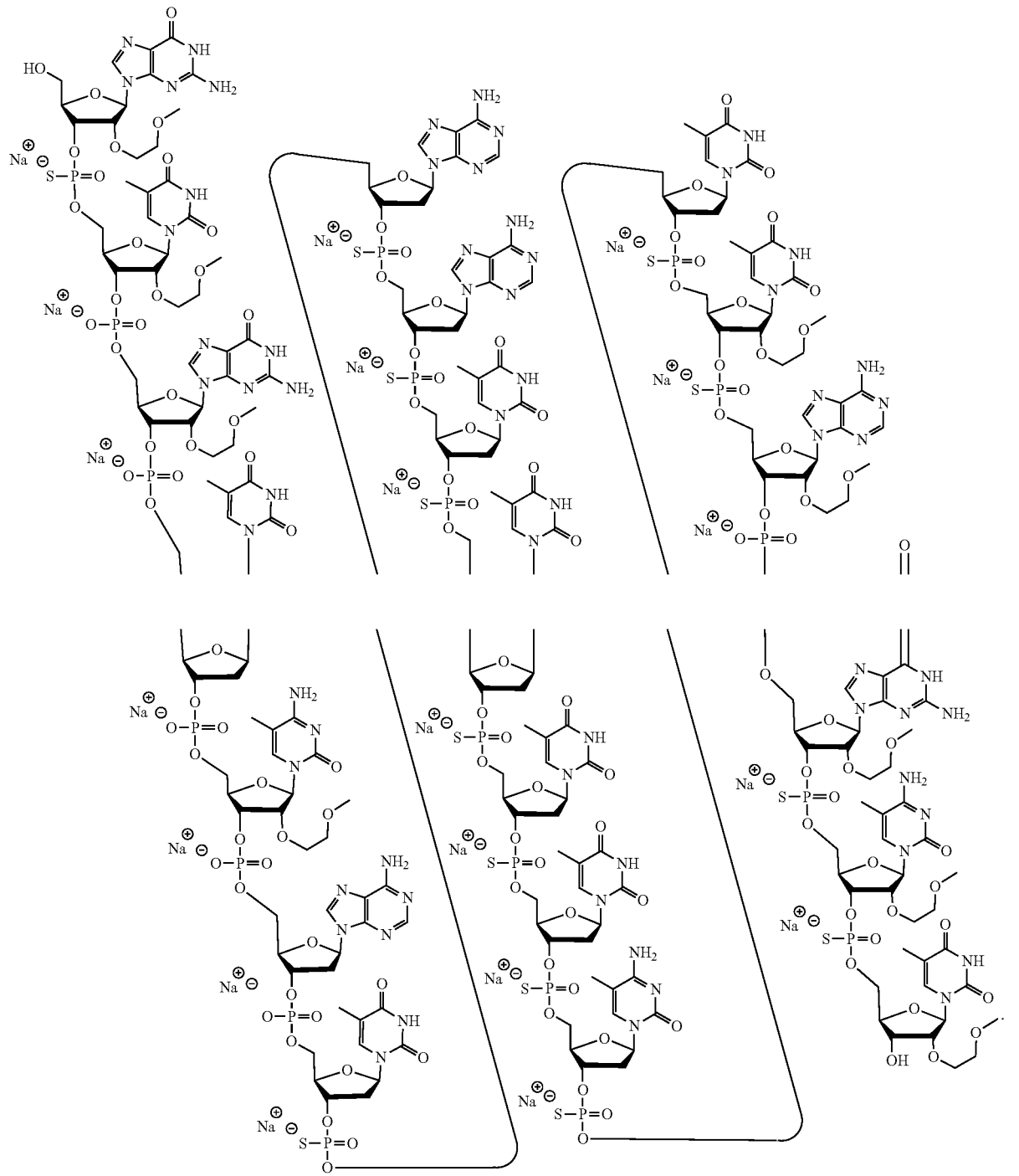

11. A pharmaceutical composition comprising the modified oligonucleotide of claim 10 and a pharmaceutically acceptable diluent.

14. A population of modified oligonucleotides of claim 10, wherein all of the phosphorothioate internucleoside linkages of the modified oligonucleotide are stereorandom.

15. A pharmaceutical composition comprising the population of modified oligonucleotides of claim 14, and a pharmaceutically acceptable diluent.

16. The pharmaceutical composition of claim 15, wherein the pharmaceutically acceptable diluent is artificial cerebrospinal fluid.

17. The pharmaceutical composition of claim 16, wherein the pharmaceutical composition consists essentially of the population of modified oligonucleotides and artificial cerebrospinal fluid.

18. A compound comprising a modified oligonucleotide according to the following chemical notation: Ges Teo Geo Teo $^m$Ceo Aeo Tds Ads Ads Tds Tds Tds Tds $^m$Cds Tds Tds Aeo Ges $^m$Ces Te (SEQ ID NO: 2302), wherein,
   A=an adenine nucleobase,
   mC=a 5-methylcytosine nucleobase,
   G=a guanine nucleobase,
   T=a thymine nucleobase,
   e=a 2'-MOE modified sugar,
   d=a 2'-β-D deoxyribosyl sugar,
   s=a phosphorothioate internucleoside linkage, and
   o=a phosphodiester internucleoside linkage.

19. A pharmaceutical composition comprising a compound of claim 18, and a pharmaceutically acceptable diluent.

20. The pharmaceutical composition of claim 19, wherein the pharmaceutically acceptable diluent is artificial cerebrospinal fluid.

21. The pharmaceutical composition of claim 20, wherein the pharmaceutical composition consists essentially of the compound and artificial cerebrospinal fluid.

22. The compound of claim 18, comprising the modified oligonucleotide covalently linked to a conjugate group.

23. A pharmaceutical composition comprising a compound of claim 22, and a pharmaceutically acceptable diluent.

24. The pharmaceutical composition of claim 23, wherein the pharmaceutically acceptable diluent is artificial cerebrospinal fluid.

25. The pharmaceutical composition of claim 24, wherein the pharmaceutical composition consists essentially of the compound and artificial cerebrospinal fluid.

26. A population of compounds of claim 18, wherein all of the phosphorothioate internucleoside linkages of the compound are stereorandom.

27. A pharmaceutical composition comprising the population of compounds of claim 26, and a pharmaceutically acceptable diluent.

28. The pharmaceutical composition of claim 27, wherein the pharmaceutically acceptable diluent is artificial cerebrospinal fluid.

29. The pharmaceutical composition of claim 28, wherein the pharmaceutical composition consists essentially of the population of compounds and artificial cerebrospinal fluid.

\* \* \* \* \*